US011332743B2

(12) United States Patent
Bettencourt et al.

(10) Patent No.: US 11,332,743 B2
(45) Date of Patent: May 17, 2022

(54) ANGIOPOIETIN-LIKE 3 (ANGPTL3) IRNA COMPOSITIONS AND METHODS OF USE THEREOF

(71) Applicant: Alnylam Pharmaceuticals, Inc., Cambridge, MA (US)

(72) Inventors: Brian Bettencourt, Groton, MA (US); William Querbes, Boston, MA (US); Kevin Fitzgerald, Brookline, MA (US); Maria Frank-Kamenetsky, Brookline, MA (US); Stuart Milstein, Arlington, MA (US); Svetlana Shulga Morskaya, Sudbury, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 17/089,854

(22) Filed: Nov. 5, 2020

(65) Prior Publication Data

US 2021/0171954 A1    Jun. 10, 2021

Related U.S. Application Data

(63) Continuation of application No. 16/411,261, filed on May 14, 2019, now Pat. No. 10,934,545, which is a continuation of application No. 15/683,999, filed on Aug. 23, 2017, now Pat. No. 10,337,010, which is a continuation of application No. 15/068,912, filed on Mar. 14, 2016, now Pat. No. 9,771,591, which is a continuation of application No. 14/132,999, filed on Dec. 18, 2013, now Pat. No. 9,322,018, which is a continuation of application No. PCT/US2012/043378, filed on Jun. 20, 2012.

(60) Provisional application No. 61/638,288, filed on Apr. 25, 2012, provisional application No. 61/499,620, filed on Jun. 21, 2011.

(51) Int. Cl.
*C12N 15/113* (2010.01)
*A61K 31/713* (2006.01)
*A61K 31/7105* (2006.01)
*C12Q 1/68* (2018.01)

(52) U.S. Cl.
CPC ........ *C12N 15/1136* (2013.01); *A61K 31/713* (2013.01); *A61K 31/7105* (2013.01); *C12N 15/113* (2013.01); *C12N 2310/14* (2013.01); *C12N 2310/315* (2013.01); *C12N 2310/321* (2013.01); *C12N 2310/322* (2013.01); *C12N 2310/3515* (2013.01)

(58) Field of Classification Search
None
See application file for complete search history.

(56) References Cited

U.S. PATENT DOCUMENTS

| | | |
|---|---|---|
| 7,935,796 B2 | 5/2011 | Lee et al. |
| 9,322,018 B2 | 4/2016 | Bettencourt et al. |
| 9,708,607 B2 | 7/2017 | Rajeev et al. |
| 9,771,591 B2 | 9/2017 | Bettencourt et al. |
| 9,796,974 B2 | 10/2017 | Rajeev et al. |
| 10,337,010 B2 | 7/2019 | Bettencourt et al. |
| 10,550,390 B2 | 2/2020 | Bettencourt et al. |
| 10,557,139 B2 | 2/2020 | Bettencourt et al. |
| 10,570,393 B2 | 2/2020 | Querbes et al. |
| 2004/0259247 A1 | 12/2004 | Tuschl et al. |
| 2005/0246794 A1 | 11/2005 | Khvorova et al. |
| 2005/0255487 A1 | 11/2005 | Khvorova et al. |
| 2008/0177045 A1 | 7/2008 | Lee et al. |
| 2010/0010066 A1 | 1/2010 | Fitzgerald et al. |
| 2013/0023579 A1 | 1/2013 | Crooke et al. |
| 2014/0179768 A1 | 6/2014 | Bettencourt et al. |
| 2015/0315594 A1 | 11/2015 | Prakash et al. |
| 2017/0275626 A1 | 9/2017 | Maier et al. |
| 2017/0355994 A1 | 12/2017 | Bettencourt et al. |
| 2018/0008724 A1 | 1/2018 | Rajeev et al. |
| 2020/0224201 A1 | 7/2020 | Querbes et al. |

FOREIGN PATENT DOCUMENTS

| | | |
|---|---|---|
| WO | WO-2008/073300 A2 | 6/2008 |
| WO | WO-2009/073809 A2 | 6/2009 |
| WO | WO-2009/134487 A2 | 11/2009 |
| WO | WO-2010/036962 A1 | 4/2010 |
| WO | WO-2010/048228 A2 | 4/2010 |
| WO | WO-2010/068816 A1 | 6/2010 |
| WO | WO-2010/144740 A1 | 12/2010 |
| WO | WO-2010148013 A2 | 12/2010 |
| WO | WO-2012177784 A2 | 12/2012 |
| WO | WO-2013/074974 A2 | 5/2013 |
| WO | WO-2013/165816 A2 | 11/2013 |
| WO | WO-2014/182661 A2 | 11/2014 |
| WO | WO-2016/028649 A1 | 2/2016 |
| WO | WO-2016/168286 A1 | 10/2016 |

OTHER PUBLICATIONS

International Preliminary Report on Patentability from PCT/US2012/043378, dated Jul. 29, 2013.

(Continued)

*Primary Examiner* — Sean McGarry

(74) *Attorney, Agent, or Firm* — McCarter & English, LLP; Maria Laccotripe Zacharakis; Deborah L. Nagle

(57) ABSTRACT

The invention relates to double-stranded ribonucleic acid (dsRNA) compositions targeting the ANGPTL3 gene, as well as methods of inhibiting expression of ANGPTL3 and methods of treating subjects having a disorder of lipid metabolism, such as hyperlipidemia or hypertriglyceridemia, using such dsRNA compositions.

26 Claims, 7 Drawing Sheets

Specification includes a Sequence Listing.

(56) References Cited

OTHER PUBLICATIONS

Gao et al., "Angiopoietin-like protein 3 regulates the motility and permeability of podocytes by alterning nephrin expression in vitro", Biochemical and Biophysical Research Communications, 2010, pp. 31 -36, vol. 399:1.
English translation of a Chinese Office Action and Chinese Search Report issued by the Chinese Intellectual Property Office dated Feb. 16, 2015.
Watts et al., "Gene silencing by siRNAs and antisense oligonucleotides in the laboratory and the clinic", J Pathol 2012; 226: 365-379.
GaLNAc-siRNA with Enhanced Stabilization chemistry:ESC-GaLNAc-siRNA, Muthiah Manoharan TIDES, (Mar. 14, 2014). Retrieved from the Internet: URL: http://www.alnylam.com/web/assets/ALNY-ESC-GalNAc-siRNA-TIDES-May2014-Capella.pdf.
International Search Report and Written Opinion from PCT/US2016/027271 dated Sep. 8, 2016.
International Search Report and Written Opinion from PCT/US2012/043378, dated Dec. 17, 2012.
Reynolds et al., "Rational siRNA design for RNA interference," Nature Biotechnology, vol. 22, pp. 326-330, 2004.
Ando et al, "A decreased expression of angiopoietin-like 3 is protective against atherosclerosis in apoE-deficient mice," J. Lipid Res., vol. 44, pp. 1216-1223 (2003).
Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.
Comparative In Vitro Studies cited in Notice of Opposition to European Patent No. EP 2 723 758 B1, dated Mar. 19, 2019.
The Dharmacon Story cited in Opposition to European Patent No. EP 2 723 758 B1, dated Feb. 17, 2021.
Comparative in vitro Studies on ANGPTL3 inhibition of the top 10 ANGPTL3 sequences disclosed in U.S. Patent Publication 2005/0255487 cited in Opposition to European Patent No. EP 2 723 758 B1, dated Feb. 17, 2021.
Ambion Product Information Sheet cited in Opposition to European Patent No. EP 2 723 758 B1 dated Feb. 17, 2021.
Dharmacon Press Release cited in Opposition to European Patent No. EP 2 723 758 B1 dated Feb. 17, 2021.
Excerpt from WO 2009-082817 cited in Opposition to European Patent No. EP 2 723 758 B1 dated Feb. 17, 2021.
Excerpt from WO 2008-011431 cited in Opposition to European Patent No. EP 2 723 758 B1 dated Feb. 17, 2021.
Excerpt from WO2007056861 cited in Opposition to European Patent No. EP 2 723 758 B1 dated Feb. 17, 2021.

mANGPTL3 protein in WT mice mANGPTL3 protein in ob/ob mice

LDL-c in WT mice

Panel B. LDL-c in ob/ob mice

HDL-c levels in WT mice

Panel B. HDL-c levels in ob/ob mice mANGPTL3 protein in Human PCS transgenic mice after a single dose of AD-52981

SEQUENCE LISTING

<160> NUMBER OF SEQ ID NOS: 1729

<210> SEQ ID NO 1
<211> LENGTH: 2126
<212> TYPE: DNA
<213> ORGANISM: Homo sapiens

<400> SEQUENCE: 1

| | | | | | |
|---|---|---|---|---|---|
| ttccagaaga | aaacagttcc | acgttgcttg | aaattgaaaa | tcaagataaa | aatgttcaca | 60 |
| attaagctcc | ttcttttat | tgttcctcta | gttatttcct | ccagaattga | tcaagacaat | 120 |
| tcatcatttg | attctctatc | tccagagcca | aaatcaagat | ttgctatgtt | agacgatgta | 180 |
| aaaattttag | ccaatggcct | ccttcagttg | ggacatggtc | ttaaagactt | tgtccataag | 240 |
| acgaagggcc | aaattaatga | catatttcaa | aaactcaaca | tatttgatca | gtcttttat | 300 |
| gatctatcgc | tgcaaaccag | tgaaatcaaa | gaagaagaaa | aggaactgag | aagaactaca | 360 |
| tataaactac | aagtcaaaaa | tgaagaggta | aagaatatgt | cacttgaact | caactcaaaa | 420 |
| cttgaaagcc | tcctagaaga | aaaaattcta | cttcaacaaa | aagtgaaata | tttagaagag | 480 |
| caactaacta | acttaattca | aaatcaacct | gaaactccag | aacacccaga | agtaacttca | 540 |
| cttaaaactt | ttgtagaaaa | acaagataat | agcatcaaag | accttctcca | gaccgtggaa | 600 |
| gaccaatata | aacaattaaa | ccaacagcat | agtcaaataa | aagaaataga | aaatcagctc | 660 |
| agaaggacta | gtattcaaga | acccacagaa | atttctctat | cttccaagcc | aagagcacca | 720 |
| agaactactc | cctttcttca | gttgaatgaa | ataagaaatg | taaacatga | tggcattcct | 780 |
| gctgaatgta | ccaccattta | taacagaggt | gaacatacaa | gtggcatgta | tgccatcaga | 840 |
| cccagcaact | ctcaagtttt | tcatgtctac | tgtgatgtta | tcaggtag | tccatggaca | 900 |
| ttaattcaac | atcgaataga | tggatcacaa | aacttcaatg | aaacgtggga | gaactacaaa | 960 |
| tatggttttg | ggaggcttga | tggagaattt | tggttgggcc | tagagaagat | atactccata | 1020 |
| gtgaagcaat | ctaattatgt | tttacgaatt | gagttggaag | actggaaaga | caacaaacat | 1080 |
| tatattgaat | attcttttta | cttgggaaat | cacgaaacca | actatacgct | acatctagtt | 1140 |
| gcgattactg | gcaatgtccc | caatgcaatc | ccggaaaaca | aagatttggt | gttttctact | 1200 |
| tgggatcaca | aagcaaaagg | acacttcaac | tgtccagagg | gttattcagg | aggctggtgg | 1260 |
| tggcatgatg | agtgtggaga | aaacaaccta | aatggtaaat | ataacaaacc | aagagcaaaa | 1320 |
| tctaagccag | agaggagaag | aggattatct | tggaagtctc | aaaatggaag | gttatactct | 1380 |
| ataaaatcaa | ccaaaatgtt | gatccatcca | acagattcag | aaagctttga | atgaactgag | 1440 |
| gcaaatttaa | aaggcaataa | tttaaacatt | aacctcattc | caagttaatg | tggtctaata | 1500 |
| atctggtatt | aaatccttaa | gagaaagctt | gagaaataga | tttttttat | cttaaagtca | 1560 |
| ctgtctattt | aagattaaac | atacaatcac | ataaccttaa | agaataccgt | ttacatttct | 1620 |
| caatcaaaat | tcttataata | ctatttgttt | taaattttgt | gatgtgggaa | tcaatttag | 1680 |
| atggtcacaa | tctagattat | aatcaatagg | tgaacttatt | aaataacttt | tctaaataaa | 1740 |
| aaatttagag | acttttattt | taaaaggcat | catatgagct | aatatcacaa | ctttcccagt | 1800 |
| ttaaaaaact | agtactcttg | ttaaaactct | aaacttgact | aaatacagag | gactggtaat | 1860 |
| tgtacagttc | ttaaatgttg | tagtattaat | ttcaaaacta | aaatcgtca | gcacagagta | 1920 |
| tgtgtaaaaa | tctgtaatac | aaattttaa | actgatgctt | cattttgcta | caaataatt | 1980 |
| tggagtaaat | gtttgatatg | atttattat | gaaacctaat | gaagcagaat | taaatactgt | 2040 |
| attaaaataa | gttcgctgtc | tttaaacaaa | tggagatgac | tactaagtca | cattgacttt | 2100 |

```
aacatgaggt atcactatac cttatt                                        2126

<210> SEQ ID NO 2
<211> LENGTH: 2149
<212> TYPE: DNA
<213> ORGANISM: Macaca mulatta

<400> SEQUENCE: 2
atatatagag ttaagaagtc taggtctgct tccagaagaa cacagttcca cgttgcttga     60
aattgaaaat caggataaaa atgttcacaa ttaagctcct tcttttatt gttcctctag    120 ttatttcctc cagaattgac caagacaatt catcatttga ttctgtatct ccagagccaa    180
aatcaagatt tgctatgtta gacgatgtaa aaattttagc caatggcctc cttcagttgg    240
gacatggtct taaagacttt gtccataaga ctaagggcca aattaatgac atatttcaaa    300
aactcaacat atttgatcag tcttttttatg atctatcact gcaaaccagt gaaatcaaag    360
aagaagaaaa ggaactgaga agaactacat ataaactaca agtcaaaaat gaagaggtaa    420
agaatatgtc acttgaactc aactcaaaac ttgaaagcct cctagaagaa aaaattctac    480
ttcaacaaaa agtgaaatat ttagaagagc aactaactaa cttaattcaa atcaacctg     540 aaactccaga acatccagaa gtaacttcac ttaaaagttt tgtagaaaaa caagataata    600
gcatcaaaga ccttctccag actgtggaag aacaatataa gcaattaaac caacagcaca    660
gtcaaataaa agaaatagaa aatcagctca gaatgactaa tattcaagaa cccacagaaa    720
tttctctatc ttccaagcca agagcaccaa gaactactcc ctttcttcag ctgaatgaaa    780
taagaaatgt aaaacatgat ggcattcctg ctgattgtac caccatttac aatagaggtg    840
aacatataag tggcatgtat gccatcagac ccagcaactc tcaagttttt catgtctact    900
gtgatgttgt atcaggtaaa acctgtctaa ggagaataga tggatcacaa aacttcaatg    960
aaacgtggga gaactacaaa tatggtttcg ggaggcttga tggagaattc tggttgggcc   1020
tagagaagat atactccata gtgaagcaat ctaattacgt tttacgaatt gagttggaag   1080
actggaaaga caacaaacat tatattgaat attcttttta cttgggaaat cacgaaacca   1140
actatacgct acatgtagtt aagattactg gcaatgtccc caatgcaatc ccggaaaaca   1200
aagatttggt gttttctact tgggatcaca aagcaaaagg acacttcagc tgtccagaga   1260
gttattcagg aggctggtgg tggcatgatg agtgtggaga aaacaaccta aatggtaaat   1320
ataacaaacc aagaacaaaa tctaagccag agcggagaag aggattatcc tggaagtctc   1380
aaaatggaag gttatactct ataaaatcaa ccaaaatgtt gatccatcca acagattcag   1440
aaagctttga atgaactgag gcaaatttaa aaggcaataa attaaacatt aaactcattc   1500
caagttaatg tggtttaata atctggtatt aaatccttaa gagaaggctt gagaaataga   1560
tttttttatc ttaaagtcac tgtcaattta agattaaaca tacaatcaca taaccttaaa   1620
gaataccatt tacatttctc aatcaaaatt cctacaacac tatttgtttt atattttgtg   1680
atgtgggaat caattttaga tggtcgcaat ctaaattata atcaacaggt gaacttacta   1740
aataactttt ctaaataaaa aacttagaga ctttaatttt aaaagtcatc atatgagcta   1800
atatcacaat tttcccagtt taaaaaacta gttttcttgt taaaactcta aacttgacta   1860
aataaagagg actgataatt atacagttct taaatttgtt gtaatattaa tttcaaaact   1920
aaaaattgtc agcacagagt atgtgtaaaa atctgtaata taaattttta aactgatgcc   1980
tcattttgct acaaaataat ctggagtaaa tttttgatag gatttatttta tgaaacctaa   2040
```

| | |
|---|---|
| tgaagcagga ttaaatactg tattaaaata ggttcgctgt cttttaaaca aatggagatg | 2100 |
| atgattacta agtcacattg actttaatat gaggtatcac tataccttta | 2149 |

<210> SEQ ID NO 3
<211> LENGTH: 1598
<212> TYPE: DNA
<213> ORGANISM: Mus musculus

<400> SEQUENCE: 3

| | |
|---|---|
| caggagggag aagttccaaa ttgcttaaaa ttgaataatt gagacaaaaa atgcacacaa | 60 |
| ttaaattatt cctttttgtt gttcctttag taattgcatc cagagtggat ccagaccttt | 120 |
| catcatttga ttctgcacct tcagagccaa atcaagatt tgctatgttg gatgatgtca | 180 |
| aaattttagc gaatggcctc ctgcagctgg gtcatggact taaagatttt gtccataaga | 240 |
| ctaagggaca aattaacgac atatttcaga agctcaacat atttgatcag tctttttatg | 300 |
| acctatcact tcgaaccaat gaaatcaaag aagaggaaaa ggagctaaga agaactacat | 360 |
| ctacactaca agttaaaaac gaggaggtga agaacatgtc agtagaactg aactcaaagc | 420 |
| ttgagagtct gctggaagag aagacagccc ttcaacacaa ggtcagggct ttggaggagc | 480 |
| agctaaccaa cttaattcta agcccagctg ggctcagga gcacccagaa gtaacatcac | 540 |
| tcaaaagttt tgtagaacag caagacaaca gcataagaga actcctccag agtgtggaag | 600 |
| aacagtataa acaattaagt caacagcaca tgcagataaa agaaatagaa aagcagctca | 660 |
| gaaagactgg tattcaagaa ccctcagaaa attctctttc ttctaaatca agagcaccaa | 720 |
| gaactactcc ccctcttcaa ctgaacgaaa cagaaaatac agaacaagat gaccttcctg | 780 |
| ccgactgctc tgccgtttat aacagaggcg aacatacaag tggcgtgtac actattaaac | 840 |
| caagaaactc ccaagggttt aatgtctact gtgatacccca atcaggcagt ccatggacat | 900 |
| taattcaaca ccggaaagat ggctcacagg acttcaacga acatgggaa aactacgaaa | 960 |
| agggctttgg gaggctcgat ggagaatttt ggttgggcct agagaagatc tatgctatag | 1020 |
| tccaacagtc taactacatt ttacgactcg agctacaaga ctggaaagac agcaagcact | 1080 |
| acgttgaata ctccttttcac ctgggcagtc acgaaaccaa ctacacgcta catgtggctg | 1140 |
| agattgctgg caatatccct ggggcccctcc cagagcacac agacctgatg ttttctacat | 1200 |
| ggaatcacag agcaaaggga cagctctact gtccagaaag ttactcaggt ggctggtggt | 1260 |
| ggaatgacat atgtggagaa acaacctaa atggaaaata caacaaaccc agaaccaaat | 1320 |
| ccagaccaga gagaagaaga gggatctact ggagacctca gagcagaaag ctctatgcta | 1380 |
| tcaaatcatc caaaatgatg ctccagccca ccacctaaga gcttcaact gaactgagac | 1440 |
| aaaataaaag atcaataaat taatattaa agtcctcccg atcactgtag taatctggta | 1500 |
| ttaaaatttt aatggaaagc ttgagaattg aatttcaatt aggtttaaac tcattgttaa | 1560 |
| gatcagatat caccgaatca acgtaaacaa aatttatc | 1598 |

<210> SEQ ID NO 4
<211> LENGTH: 1785
<212> TYPE: DNA
<213> ORGANISM: Rattus norvegicus

<400> SEQUENCE: 4

| | |
|---|---|
| gacgttccaa attgcttgaa attgaataat tgaaacaaaa atgcacacaa ttaagctgct | 60 |
| cctttttgtt gttcctctag taatttcgtc cagagttgat ccagaccttt cgccatttga | 120 |
| ttctgtaccg tcagagccaa atcaagatt tgctatgttg gatgatgtca aaattttagc | 180 |

-continued

| | |
|---|---|
| caatggcctc ctgcagctgg gtcatggtct taaagatttt gtccataaga caaagggaca | 240 |
| aattaatgac atatttcaga agctcaacat atttgatcag tgtttttatg acctatcact | 300 |
| tcaaaccaat gaaatcaaag aagaggaaaa ggagctaaga agaaccacat ctaaactaca | 360 |
| agttaaaaac gaagaggtga agaatatgtc acttgaactg aactcaaagc ttgaaagtct | 420 |
| actggaggag aagatggcgc tccaacacag agtcagggct ttggaggaac agctgaccag | 480 |
| cttggttcag aacccgcctg gggctcggga gcacccagag gtaacgtcac ttaaaagttt | 540 |
| tgtagaacag caagataaca gcataagaga actcctccag agtgtggaag aacaatataa | 600 |
| acaactaagt caacagcaca ttcagataaa agaaatagaa aatcagctca gaaagactgg | 660 |
| cattcaagaa cccactgaaa attctcttta ttctaaacca agagcaccaa gaactactcc | 720 |
| ccctcttcat ctgaaggaag caaaaaatat agaacaagat gatctgcctg ctgactgctc | 780 |
| tgccatttat aacagaggtg aacatacaag tggcgtgtat actattagac caagcagctc | 840 |
| tcaagtgttt aatgtctact gtgacaccca atcaggcact ccacggacat taattcaaca | 900 |
| ccggaaagat ggctctcaaa acttcaacca aacgtgggaa aactacgaaa agggttttgg | 960 |
| gaggcttgat ggtaaagtga tttccttgca tcactcactt atctgttgat ttaatagtat | 1020 |
| tagttgggtg tgttgacaca ggcctgagac catagcgctt ttgggcaagg ggggaggagg | 1080 |
| agcagcaggt gaattgaaag ttcaagacca gtctgggcca cacattgata ctccttctcg | 1140 |
| acattaagaa ttataaatta agcagcaatt ataaaatggg ctgtggaaat gtaacaataa | 1200 |
| gcaaaagcag accccagtct tcataaaact gattggtaaa tattatccat gatagcaact | 1260 |
| gcaatgatct cattgtactt atcactactg catgcctgca gtatgcttgt tgaaacttaa | 1320 |
| ttctatagtt catggttatc ataagtctta ttaaggaaca tagtatacgc cattggctct | 1380 |
| agtgaggggc catgctacaa atgagctgca aagatagcag tatagagctc tttcagtgat | 1440 |
| atcctaagca caacgtaaca caggtgaaat gggctggagg cacagttgtg gtggaacacg | 1500 |
| cggccagcag gacactggga ctgatcccca gcagcacaaa gaaagtgata ggaacacaga | 1560 |
| gcgagagtta aagggacag ggtcaccgtc agagatacgg tgtctaactc ctgcaaccct | 1620 |
| acctgtaatt attccatatt ataaacatat actatataac tgtgggtctc tgcatgttct | 1680 |
| agaatatgaa ttctatttga ttgtaaaaca aaactataaa aataagtaaa aaaataaaaa | 1740 |
| ataaacagat acttaaaatc aaaaaaaaaa aaaaaaaaaa aaaaa | 1785 |

<210> SEQ ID NO 5
<211> LENGTH: 2126
<212> TYPE: DNA
<213> ORGANISM: Homo sapiens

<400> SEQUENCE: 5

| | |
|---|---|
| aataaggtat agtgatacct catgttaaag tcaatgtgac ttagtagtca tctccatttg | 60 |
| tttaaagaca gcgaacttat tttaatacag tatttaattc tgcttcatta ggtttcataa | 120 |
| ataaatcata tcaaacattt actccaaatt attttgtagc aaaatgaagc atcagtttaa | 180 |
| aaatttgtat tacagatttt tacacatact ctgtgctgac gatttttagt tttgaaatta | 240 |
| atactacaac atttaagaac tgtacaatta ccagtcctct gtatttagtc aagtttagag | 300 |
| ttttaacaag agtactagtt ttttaaactg ggaaagttgt gatattagct catatgatgc | 360 |
| cttttaaaat aaaagtctct aaatttttta tttagaaaag ttatttaata agttcaccta | 420 |
| ttgattataa tctagattgt gaccatctaa aattgattcc cacatcacaa aatttaaaac | 480 |

```
aaatagtatt ataagaattt tgattgagaa atgtaaacgg tattctttaa ggttatgtga      540
ttgtatgttt aatcttaaat agacagtgac tttaagataa aaaaaatcta tttctcaagc      600
tttctcttaa ggatttaata ccagattatt agaccacatt aacttggaat gaggttaatg      660
tttaaattat tgccttttaa atttgcctca gttcattcaa agctttctga atctgttgga      720
tggatcaaca ttttggttga ttttatagag tataaccttc cattttgaga cttccaagat      780
aatcctcttc tcctctctgg cttagatttt gctcttggtt tgttatattt accatttagg      840
ttgttttctc cacactcatc atgccaccac cagcctcctg aataaccctc tggacagttg      900
aagtgtcctt ttgctttgtg atcccaagta gaaaacacca aatctttgtt ttccgggatt      960
gcattgggga cattgccagt aatcgcaact agatgtagcg tatagttggt ttcgtgattt     1020
cccaagtaaa aagaatattc aatataatgt tgttgtctt tccagtcttc caactcaatt      1080
cgtaaaacat aattagattg cttcactatg gagtatatct tctctaggcc caaccaaaat     1140
tctccatcaa gcctcccaaa accatatttg tagttctccc acgtttcatt gaagttttgt     1200
gatccatcta ttcgatgttg aattaatgtc catggactac ctgatataac atcacagtag     1260
acatgaaaaa cttgagagtt gctgggtctg atggcataca tgccacttgt atgttcacct     1320
ctgttataaa tggtggtaca ttcagcagga atgccatcat gttttacatt tcttatttca     1380
ttcaactgaa gaaagggagt agttcttggt gctcttggct tggaagatag agaaatttct     1440
gtgggttctt gaatactagt ccttctgagc tgattttcta tttctttat ttgactatgc      1500 tgttggttta attgtttata ttggtcttcc acggtctgga gaaggtcttt gatgctatta     1560
tcttgttttt ctacaaaagt tttaagtgaa gttacttctg ggtgttctgg agtttcaggt     1620
tgattttgaa ttaagttagt tagttgctct tctaaatatt tcacttttg ttgaagtaga      1680 atttttcttt ctaggaggct ttcaagtttt gagttgagtt caagtgacat attcttacc      1740 tcttcatttt tgacttgtag tttatatgta gttcttctca gttccttttc ttcttctttg     1800
atttcactgg tttgcagcga tagatcataa aaagactgat caaatatgtt gagttttga      1860 aatatgtcat taatttggcc cttcgtctta tggacaaagt ctttaagacc atgtcccaac     1920
tgaaggaggc cattggctaa aattttaca tcgtctaaca tagcaaatct tgattttggc      1980
tctggagata gagaatcaaa tgatgaattg tcttgatcaa ttctggagga ataactaga      2040 ggaacaataa aaagaaggag cttaattgtg aacattttta tcttgatttt caatttcaag     2100
caacgtggaa ctgttttctt ctggaa                                          2126

<210> SEQ ID NO 6
<211> LENGTH: 2149
<212> TYPE: DNA
<213> ORGANISM: Macaca mulatta

<400> SEQUENCE: 6
taaggtatag tgatacctca tattaaagtc aatgtgactt agtaatcatc atctccattt       60
gtttaaaaga cagcgaacct atttaatac agtatttaat cctgcttcat taggtttcat       120
aaataaatcc tatcaaaaat ttactccaga ttattttgta gcaaaatgag gcatcagttt      180
aaaaatttat attacagatt tttacacata ctctgtgctg acaattttta gttttgaaat      240
taatattaca acaaatttaa gaactgtata attatcagtc ctctttattt agtcaagttt      300
agagttttaa caagaaaact agtttttaa actgggaaaa ttgtgatatt agctcatatg      360
atgactttta aaattaaagt ctctaagttt tttatttaga aaagttattt agtaagttca      420
cctgttgatt ataatttaga ttgcgaccat ctaaaattga ttcccacatc acaaaatata      480
```

-continued

```
aaacaaatag tgttgtagga attttgattg agaaatgtaa atggtattct ttaaggttat      540
gtgattgtat gtttaatctt aaattgacag tgactttaag ataaaaaaat ctatttctca      600
agccttctct taaggattta ataccagatt attaaaccac attaacttgg aatgagttta      660
atgtttaatt tattgccttt taaatttgcc tcagttcatt caaagctttc tgaatctgtt      720
ggatggatca acattttggt tgattttata gagtataacc ttccattttg agacttccag      780
gataatcctc ttctccgctc tggcttagat tttgttcttg gtttgttata tttaccattt      840
aggttgtttt ctccacactc atcatgccac caccagcctc tgaataact ctctggacag       900 ctgaagtgtc cttttgcttt gtgatcccaa gtagaaaaca ccaaatcttt gttttccggg      960
attgcattgg ggacattgcc agtaatctta actacatgta gcgtatagtt ggtttcgtga     1020
tttcccaagt aaaagaata ttcaatataa tgtttgttgt ctttccagtc ttccaactca      1080
attcgtaaaa cgtaattaga ttgcttcact atggagtata tcttctctag gcccaaccag     1140
aattctccat caagcctccc gaaccatat ttgtagttct cccacgtttc attgaagttt      1200
tgtgatccat ctattctcct tagacaggtt ttacctgata caacatcaca gtagacatga     1260
aaaacttgag agttgctggg tctgatggca tacatgccac ttatatgttc acctctattg     1320
taaatggtgg tacaatcagc aggaatgcca tcatgtttta catttcttat ttcattcagc     1380
tgaagaaagg gagtagttct tggtgctctt ggcttggaag atagagaaat ttctgtgggt     1440
tcttgaatat tagtcattct gagctgattt tctatttctt ttatttgact gtgctgttgg     1500
tttaattgct tatattgttc ttccacagtc tggagaaggt ctttgatgct attatcttgt     1560
ttttctacaa aacttttaag tgaagttact tctggatgtt ctggagtttc aggttgattt     1620
tgaattaagt tagttagttg ctcttctaaa tatttcactt tttgttgaag tagaattttt     1680
tcttctagga ggctttcaag ttttgagttg agttcaagtg acatattctt tacctcttca     1740
tttttgactt gtagtttata tgtagttctt ctcagttcct tttcttcttc tttgatttca     1800
ctggtttgca gtgatagatc ataaaaagac tgatcaaata tgttgagttt ttgaaatatg     1860
tcattaattt ggcccttagt cttatggaca aagtctttaa gaccatgtcc caactgaagg     1920
aggccattgg ctaaaatttt tacatcgtct aacatagcaa atcttgattt tggctctgga     1980
gatacagaat caaatgatga attgtcttgg tcaattctgg aggaaataac tagaggaaca     2040
ataaaaagaa ggagcttaat tgtgaacatt tttatcctga ttttcaattt caagcaacgt     2100
ggaactgtgt tcttctggaa gcagacctag acttcttaac tctatatat                 2149
```

<210> SEQ ID NO 7
<211> LENGTH: 1598
<212> TYPE: DNA
<213> ORGANISM: Mus musculus

<400> SEQUENCE: 7

```
caggagggag aagttccaaa ttgcttaaaa ttgaataatt gagacaaaaa atgcacacaa       60
ttaaattatt ccttttttgtt gttcctttag taattgcatc cagagtggat ccagaccttt      120
catcatttga ttctgcacct tcagagccaa aatcaagatt tgctatgttg gatgatgtca      180 aaatttttagc gaatggcctc ctgcagctgg gtcatggact taaagatttt gtccataaga     240
ctaagggaca aattaacgac atatttcaga agctcaacat atttgatcag tcttttttatg     300 acctatcact tcgaaccaat gaaatcaaag aagaggaaaa ggagctaaga agaactacat      360
ctacactaca agttaaaaac gaggaggtga agaacatgtc agtagaactg aactcaaagc     420
```

| | |
|---|---|
| ttgagagtct gctggaagag aagacagccc ttcaacacaa ggtcagggct ttggaggagc | 480 |
| agctaaccaa cttaattcta agcccagctg gggctcagga gcacccagaa gtaacatcac | 540 |
| tcaaaagttt tgtagaacag caagacaaca gcataagaga actcctccag agtgtggaag | 600 |
| aacagtataa acaattaagt caacagcaca tgcagataaa agaaatagaa aagcagctca | 660 |
| gaaagactgg tattcaagaa ccctcagaaa attctctttc ttctaaatca agagcaccaa | 720 |
| gaactactcc ccctcttcaa ctgaacgaaa cagaaaatac agaacaagat gaccttcctg | 780 |
| ccgactgctc tgccgtttat aacagaggcg aacatacaag tggcgtgtac actattaaac | 840 |
| caagaaactc ccaagggttt aatgtctact gtgatacccca atcaggcagt ccatggacat | 900 |
| taattcaaca ccggaaagat ggctcacagg acttcaacga acatgggaa aactacgaaa | 960 |
| agggctttgg gaggctcgat ggagaatttt ggttgggcct agagaagatc tatgctatag | 1020 |
| tccaacagtc taactacatt ttacgactcg agctacaaga ctggaaagac agcaagcact | 1080 |
| acgttgaata ctccttcac ctgggcagtc acgaaaccaa ctacacgcta catgtggctg | 1140 |
| agattgctgg caatatccct ggggcccctcc cagagcacac agacctgatg tttttctacat | 1200 |
| ggaatcacag agcaaaggga cagctctact gtccagaaag ttactcaggt ggctggtggt | 1260 |
| ggaatgacat atgtggagaa aacaacctaa atggaaaata caacaaaccc agaaccaaat | 1320 |
| ccagaccaga gagaagaaga gggatctact ggagacctca gagcagaaag ctctatgcta | 1380 |
| tcaaatcatc caaaatgatg ctccagccca ccacctaaga agcttcaact gaactgagac | 1440 |
| aaaataaaag atcaataaat taaatattaa agtcctcccg atcactgtag taatctggta | 1500 |
| ttaaaatttt aatggaaagc ttgagaattg aatttcaatt aggtttaaac tcattgttaa | 1560 |
| gatcagatat caccgaatca acgtaaacaa aatttatc | 1598 |

<210> SEQ ID NO 8
<211> LENGTH: 1785
<212> TYPE: DNA
<213> ORGANISM: Rattus norvegicus

<400> SEQUENCE: 8

| | |
|---|---|
| tttttttttt tttttttttt tttttgattt taagtatctg tttatttttt attttttac | 60 |
| ttatttttat agttttgttt tacaatcaaa tagaattcat attctagaac atgcagagac | 120 |
| ccacagttat atagtatatg tttataatat ggataatta caggtagggt tgcaggagtt | 180 |
| agacaccgta tctctgacgg tgaccctgtc ccttctaact ctcgctctgt gttcctatca | 240 |
| ctttctttgt gctgctgggg atcagtccca gtgtcctgct ggccgcgtgt tccaccacaa | 300 |
| ctgtgcctcc agcccatttc acctgtgtta cgttgtgctt aggatatcac tgaaagagct | 360 |
| ctatactgct atctttgcag ctcatttgta gcatggcccc tcactagagc caatggcgta | 420 |
| tactatgttc cttaataaga cttatgataa ccatgaacta tagaattaag tttcaacaag | 480 |
| catactgcag gcatgcagta gtgataagta caatgagatc attgcagttg ctatcatgga | 540 |
| taatatttac caatcagttt tatgaagact ggggtctgct tttgcttatt gttacatttc | 600 |
| cacagcccat tttataattg ctgcttaatt tataattctt aatgtcgaga aggagtatca | 660 |
| atgtgtggcc cagactggtc ttgaactttc aattcacctg ctgctcctcc tcccccttg | 720 |
| cccaaaagcg ctatggtctc aggcctgtgt caacacaccc aactaatact attaaatcaa | 780 |
| cagataagtg agtgatgcaa ggaaatcact ttaccatcaa gcctcccaaa acccttttcg | 840 |
| tagttttccc acgtttggtt gaagttttga gagccatctt tccggtgttg aattaatgtc | 900 |
| cgtggagtgc ctgattgggt gtcacagtag acattaaaca cttgagagct gcttggtcta | 960 |

```
atagtataca cgccacttgt atgttcacct ctgttataaa tggcagagca gtcagcaggc    1020
agatcatctt gttctatatt tttgcttcc ttcagatgaa gagggggagt agttcttggt    1080
gctcttggtt tagaataaag agaattttca gtgggttctt gaatgccagt ctttctgagc    1140
tgattttcta tttctttat ctgaatgtgc tgttgactta gttgtttata ttgttcttcc    1200
acactctgga ggagttctct tatgctgtta tcttgctgtt ctacaaaact tttaagtgac    1260
gttacctctg ggtgctcccg agccccaggc gggttctgaa ccaagctggt cagctgttcc    1320
tccaaagccc tgactctgtg ttggagcgcc atcttctcct ccagtagact ttcaagcttt    1380
gagttcagtt caagtgacat attcttcacc tcttcgtttt taacttgtag tttagatgtg    1440
gttcttctta gctccttttc ctcttctttg atttcattgg tttgaagtga taggtcataa    1500
aaacactgat caaatatgtt gagcttctga aatatgtcat taatttgtcc ctttgtctta    1560
tggacaaaat ctttaagacc atgacccagc tgcaggaggc cattggctaa aattttgaca    1620
tcatccaaca tagcaaatct tgattttggc tctgacggta cagaatcaaa tggcgaaagg    1680
tctggatcaa ctctggacga aattactaga ggaacaacaa aaaggagcag cttaattgtg    1740 tgcattttg tttcaattat tcaatttcaa gcaatttgga acgtc                    1785

<210> SEQ ID NO 9
<211> LENGTH: 2201
<212> TYPE: DNA
<213> ORGANISM: Macaca fascicularis

<400> SEQUENCE: 9
gggtagtata tagagttaag aagtctaggt ctgcttccag aagaacacag ttccacgctg     60
cttgaaattg aaaatcagga taaaaatgtt cacaattaag ctccttcttt ttattgttcc    120
tctagttatt tcctccagaa ttgaccaaga caattcatca tttgattctg tatctccaga    180
gccaaaatca agatttgcta tgttagcga tgtaaaaatt ttagccaatg gcctccttca    240
gttgggacat ggtcttaaag actttgtcca taagactaag ggccaaatta atgacatatt    300
tcaaaaactc aacatatttg atcagtcttt ttatgatcta tcactgcaaa ccagtgaaat    360
caaagaagaa gaaaaggaac tgagaagaac tacatataaa ctacaagtca aaatgaaga    420 ggtaaagaat atgtcacttg aactcaactc aaaacttgaa agcctcctag aagaaaaaat    480
tctacttcaa caaaaagtga aatatttaga agagcaacta actaacttaa ttcaaaatca    540
acctgcaact ccagaacatc cagaagtaac ttcacttaaa agttttgtag aaaaacaaga    600
taatagcatc aaagaccttc tccagactgt ggaagaacaa tataagcaat taaccaaca    660 gcatagtcaa ataaagaaa tagaaaatca gctcagaatg actaatattc aagaacccac    720
agaaatttct ctatcttcca agccaagagc accaagaact actcccttc ttcagctgaa    780 tgaaataaga aatgtaaaac atgatggcat tcctgctgat tgtaccacca tttacaatag    840
aggtgaacat ataagtggca cgtatgccat cagacccagc aactctcaag ttttcatgt    900 ctactgtgat gttgtatcag gtagtccatg gacattaatt caacatcgaa tagatggatc    960
acaaaacttc aatgaaacgt gggagaacta caaatatggt ttcgggaggc ttgatggaga   1020
attctggttg ggcctagaga agatatactc catagtgaag caatctaatt acgttttacg   1080
aattgagttg gaagactgga agacaacaa acattatatt gaatattctt ttacttggg    1140 aaatcacgaa accaactata cgctacatgt agttaagatt actggcaatg tccccaatgc   1200
aatcccggaa aacaaagatt tggtgttttc tacttgggat cacaaagcaa aaggacactt   1260
```

```
cagctgtcca gagagttatt caggaggctg gtggtggcat gatgagtgtg gagaaaacaa    1320
cctaaatggt aaatataaca aaccaagaac aaaatctaag ccagagcgga gaagaggatt    1380
atcctggaag tctcaaaatg gaaggttata ctctataaaa tcaaccaaaa tgttgatcca    1440
tccaacagat tcagaaagct ttgaatgaac tgaggcaaat ttaaaaggca ataaattaaa    1500
cattaaactc attccaagtt aatgtggttt aataatctgg tattaaatcc ttaagagaag    1560
gcttgagaaa tagattttt tatcttaaag tcactgtcaa tttaagatta aacatacaat     1620
cacataacct taagaatac catttacatt tctcaatcaa aattcttaca acactatttg     1680
ttttatattt tgtgatgtgg gaatcaattt tagatggtcg caatctaaat tataatcaac    1740
aggtgaactt actaaataac ttttctaaat aaaaaactta gagactttaa ttttaaaagt    1800
catcatatga gctaatgtca caatttccc agtttaaaaa actagttttc ttgttaaaac     1860
tctaaacttg actaaataaa gaggactgat aattatacag ttcttaaatt tgttgtaata    1920
ttaatttcaa aactaaaaat tgtcagcaca gagtatgtgt aaaaatctgt aatataaatt    1980
tttaaactga tgcctcattt tgctacaaaa taatctggag taaattttg ataggattta    2040 tttatgaaac ctaatgaagc aggattaaat actgtattaa aataggttcg ctgtctttta    2100
aacaaatgga gatgatgatt actaagtcac attgacttta atatgaggta tcactatacc    2160
ttaacatatt tgttaaaacg tatactgtat acattttgtg t                         2201

<210> SEQ ID NO 10
<211> LENGTH: 11
<212> TYPE: PRT
<213> ORGANISM: Unknown
<220> FEATURE:
<223> OTHER INFORMATION: Description of Unknown: Hydrophobic
      membrane translocation peptide

<400> SEQUENCE: 10

Ala Ala Leu Leu Pro Val Leu Leu Ala Ala Pro
1               5                   10

<210> SEQ ID NO 11
<211> LENGTH: 13
<212> TYPE: PRT
<213> ORGANISM: Human immunodeficiency virus

<400> SEQUENCE: 11

Gly Arg Lys Lys Arg Arg Gln Arg Arg Pro Pro Gln
1               5                   10

<210> SEQ ID NO 12
<211> LENGTH: 16
<212> TYPE: PRT
<213> ORGANISM: Drosophila sp.

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 16
<212> TYPE: PRT
<213> ORGANISM: Unknown
<220> FEATURE:
<223> OTHER INFORMATION: Description of Unknown: Hydrophobic
      membrane translocation peptide

<400> SEQUENCE: 13
```

Ala Ala Val Ala Leu Leu Pro Ala Val Leu Leu Ala Leu Leu Ala Pro
1               5                   10                  15

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
cuuacgcuga guacuucgat t                                            21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 15
ucgaaguacu cagcguaagt t                                            21

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uauuugauca gucuuuuua                                               19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gagcaacuaa cuaacuuaa                                               19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ggccaaauua augacauau                                               19

<210> SEQ ID NO 19
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 19
cgaauugagu uggaagacu                                                    19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ccuccuucag uugggacau                                                    19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
cacuugaacu caacucaaa                                                    19

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
guccauggac auuaauuca                                                    19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
aaucaagauu ugcuauguu                                                    19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
cuagagaaga uauacucca                                                    19

<210> SEQ ID NO 25
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 25
cuaacuaacu uaauucaaa                                                    19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
cuaacuaacu uaauucaaa                                                    19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
cauuaauuca acaucgaau                                                    19

<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
caaaauguug auccaucca                                                    19

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
cauauaaacu acaagucaa                                                    19

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
gacccagcaa cucucaagu                                                    19

<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 31
gguugggccu agagaagau                                                    19

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
guguggagaa aacaaccua                                                    19

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
gacauuaauu caacaucga                                                    19

<210> SEQ ID NO 34
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
cauagugaag caaucuaau                                                    19

<210> SEQ ID NO 35
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
cuauguuaga cgauguaaa                                                    19

<210> SEQ ID NO 36
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
cacagaaauu ucucuaucu                                                    19

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 37
guugggccua gagaagaua                                                     19

<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
gccaaaauca agauuugcu                                                     19

<210> SEQ ID NO 39
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
acauauuuga ucagucuuu                                                     19

<210> SEQ ID NO 40
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
acauauuuga ucagucuuu                                                     19

<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
cuuaaagacu uuguccaua                                                     19

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
ccauagugaa gcaaucuaa                                                     19

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 43
caaccaaaau guugaucca                                                    19

<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
cuacauauaa acuacaagu                                                    19

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
gggaggcuug auggagaau                                                    19

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
gguguuuucu acuugggau                                                    19

<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
aagagcacca agaacuacu                                                    19

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
uggagaaaac aaccuaaau                                                    19

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
```
gcaacuaacu aacuuaauu                                              19

<210> SEQ ID NO 50
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
caaccuaaau gguaaauau                                              19

<210> SEQ ID NO 51
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
gcuauguuag acgauguaa                                              19

<210> SEQ ID NO 52
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
cccacagaaa uuucucuau                                              19

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
gauuuggugu uuucuacuu                                              19

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
cagagccaaa aucaagauu                                              19

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
aaaucaagau uugcuaugu                                                  19

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
cauggacauu aauucaaca                                                  19

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
gauuugcuau guuagacga                                                  19

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
gaacuacaua uaaacuaca                                                  19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
cgaauagaug gaucacaaa                                                  19

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
cuuguuaaaa cucuaaacu                                                  19

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
auuugaucag ucuuuuuau                                                  19

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
uccauggaca uuaauucaa                                                19

<210> SEQ ID NO 63
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
cacaauuaag cuccuucuu                                                19

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
caacauauuu gaucagucu                                                19

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
cuccauagug aagcaaucu                                                19

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
gccaaauuaa ugacauauu                                                19

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
caacagcaua gucaaauaa                                                19

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
ggaaaucacg aaaccaacu                                              19

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
caguugggac auggucuua                                              19

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
gacauggucu uaaagacuu                                              19

<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
uguggagaaa acaaccuaa                                              19

<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
guggagaaaa caaccuaaa                                              19

<210> SEQ ID NO 73
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
ccaacagcau agucaaaua                                              19

```
<210> SEQ ID NO 74
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
caacaucgaa uagauggau                                                    19

<210> SEQ ID NO 75
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
gcaaauuuaa aaggcaaua                                                    19

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
caaaaucaag auuugcuau                                                    19

<210> SEQ ID NO 77
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
agagccaaaa ucaagauuu                                                    19

<210> SEQ ID NO 78
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
uaaaaagacu gaucaaaua                                                    19

<210> SEQ ID NO 79
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
uuaaguuagu uaguugcuc                                                    19

<210> SEQ ID NO 80
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
auaugucauu aauuuggcc                                                  19

<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
agucuuccaa cucaauucg                                                  19

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82 augcccaac ugaaggagg                                                   19

<210> SEQ ID NO 83
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
uuugaguuga guucaagug                                                  19

<210> SEQ ID NO 84
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
ugaauuaaug uccauggac                                                  19

<210> SEQ ID NO 85
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
aacauagcaa aucuugauu                                                  19

<210> SEQ ID NO 86
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
uggaguauau cuucucuag                                                    19

<210> SEQ ID NO 87
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
uuugaauuaa guaguuag                                                     19

<210> SEQ ID NO 88
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
uuugaauuaa guaguuag                                                     19

<210> SEQ ID NO 89
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
auucgauguu gaauuaaug                                                    19

<210> SEQ ID NO 90
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
uggauggauc aacauuuug                                                    19

<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
uugacuugua guuuauaug                                                    19

<210> SEQ ID NO 92
<211> LENGTH: 19
<212> TYPE: RNA
```

-continued

```
<213> ORGANISM: Artificial Sequence
<220> FEATURE:
<223> OTHER INFORMATION: Description of Artificial Sequence: Synthetic
      oligonucleotide

<400> SEQUENCE: 92
acuugagagu ugcuggguc                                               19

<210> SEQ ID NO 93
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
aucuucucua ggcccaacc                                               19

<210> SEQ ID NO 94
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
uagguuguuu ucuccacac                                               19

<210> SEQ ID NO 95
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
ucgauguuga auuaauguc                                               19

<210> SEQ ID NO 96
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
auuagauugc uucacuaug                                               19

<210> SEQ ID NO 97
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
uuuacaucgu cuaacauag                                               19

<210> SEQ ID NO 98
<211> LENGTH: 19
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 98
agauagagaa auuucugug                                            19

<210> SEQ ID NO 99
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
uaucuucucu aggcccaac                                            19

<210> SEQ ID NO 100
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
agcaaaucuu gauuuuggc                                            19

<210> SEQ ID NO 101
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
aaagacugau caaauaugu                                            19

<210> SEQ ID NO 102
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
aaagacugau caaauaugu                                            19

<210> SEQ ID NO 103
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
uauggacaaa gucuuuaag                                            19

<210> SEQ ID NO 104
<211> LENGTH: 19
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 104
uuagauugcu ucacuaugg                                              19

<210> SEQ ID NO 105
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
uggaucaaca uuuugguug                                              19

<210> SEQ ID NO 106
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
acuuguaguu uauauguag                                              19

<210> SEQ ID NO 107
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
auucuccauc aagccuccc                                              19

<210> SEQ ID NO 108
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
aucccaagua gaaaacacc                                              19

<210> SEQ ID NO 109
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
aguaguucuu ggugcucuu                                              19

<210> SEQ ID NO 110
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 110
auuuagguug uuucucca                                                        19

<210> SEQ ID NO 111
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
aauuaaguua guuaguugc                                                       19

<210> SEQ ID NO 112
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
auauuuacca uuuagguug                                                       19

<210> SEQ ID NO 113
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
uuacaucguc uaacauagc                                                       19

<210> SEQ ID NO 114
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
auagagaaau uucuguggg                                                       19

<210> SEQ ID NO 115
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
aaguagaaaa caccaaauc                                                       19

<210> SEQ ID NO 116
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 116
aaucuugauu uuggcucug                                              19

<210> SEQ ID NO 117
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
acauagcaaa ucuugauuu                                              19

<210> SEQ ID NO 118
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
uguugaauua auguccaug                                              19

<210> SEQ ID NO 119
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
ucgucuaaca uagcaaauc                                              19

<210> SEQ ID NO 120
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
uguaguuuau auguaguuc                                              19

<210> SEQ ID NO 121
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
uuugugaucc aucuauucg                                              19

<210> SEQ ID NO 122
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 122
aguuuagagu uuuaacaag                                                19

<210> SEQ ID NO 123
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
auaaaaagac ugaucaaau                                                19

<210> SEQ ID NO 124
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
uugaauuaau guccaugga                                                19

<210> SEQ ID NO 125
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
aagaaggagc uuaauugug                                                19

<210> SEQ ID NO 126
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
agacugauca aauauguug                                                19

<210> SEQ ID NO 127
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
agauugcuuc acuauggag                                                19

<210> SEQ ID NO 128
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
```
aauaugucau uaauuuggc                                            19

<210> SEQ ID NO 129
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
uuauuugacu augcuguug                                            19

<210> SEQ ID NO 130
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
aguugguuuc gugauuucc                                            19

<210> SEQ ID NO 131
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
uaagaccaug ucccaacug                                            19

<210> SEQ ID NO 132
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
aagucuuuaa gaccauguc                                            19

<210> SEQ ID NO 133
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
uuagguuguu uucuccaca                                            19

<210> SEQ ID NO 134
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
uuuagguugu uuucuccac                                           19

<210> SEQ ID NO 135
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
uauuugacua ugcuguugg                                           19

<210> SEQ ID NO 136
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
auccaucuau ucgauguug                                           19

<210> SEQ ID NO 137
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
uauugccuuu uaaauuugc                                           19

<210> SEQ ID NO 138
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
auagcaaauc uugauuuug                                           19

<210> SEQ ID NO 139
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
aaaucuugau uuuggcucu                                           19

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 140
uauuugauca gucuuuuuat t                                              21

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 141
gagcaacuaa cuaacuuaat t                                              21

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 142
ggccaaauua augacauaut t                                              21

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 143
cgaauugagu uggaagacut t                                              21

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 144
ccuccuucag uugggacaut t                                              21

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 145
cacuugaacu caacucaaat t                                              21

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 146
guccauggac auuaauucat t                                              21

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 147
aaucaagauu ugcuauguut t                                              21

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 148
cuagagaaga uauacuccat t                                              21

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 149
cuaacuaacu uaauucaaat t                                              21

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 150
cuaacuaacu uaauucaaat t                                              21

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 151
cauuaauuca acaucgaaut t                                              21

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 152
caaaauguug auccauccat t                                              21

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 153
cauauaaacu acaagucaat t                                              21

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 154
gacccagcaa cucucaagut t                                              21

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 155
gguugggccu agagaagaut t                                              21

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 156
guguggagaa aacaaccuat t                                              21

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 157
gacauuaauu caacaucgat t                                              21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 158
cauagugaag caaucuaaut t                                              21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 159
cuauguuaga cgauguaaat t                                              21

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<223> OTHER INFORMATION: Description of Combined DNA/RNA Molecule:
      Synthetic oligonucleotide

<400> SEQUENCE: 160
cacagaaauu ucucuaucut t                                              21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 161
guugggccua gagaagauat t                                              21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 162
gccaaaauca agauuugcut t                                              21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 163
acauauuuga ucagucuuut t                                              21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 164
acauauuuga ucagucuuut t                                              21

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic

```
            oligonucleotide
<220> FEATURE:
<223> OTHER INFORMATION: Description of Combined DNA/RNA Molecule:
      Synthetic oligonucleotide

<400> SEQUENCE: 165
cuuaaagacu uuguccauat t                                              21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 166
ccauagugaa gcaaucuaat t                                              21

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 167
caaccaaaau guugauccat t                                              21

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 168
cuacauauaa acuacaagut t                                              21

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 169
gggaggcuug auggagaaut t                                              21

<210> SEQ ID NO 170
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 170
gguguuuucu acuugggaut t                                               21

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 171
aagagcacca agaacuacut t                                               21

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 172
uggagaaaac aaccuaaaut t                                               21

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 173
gcaacuaacu aacuuaauut t                                               21

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 174
caaccuaaau gguaaauaut t                                               21

<210> SEQ ID NO 175
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 175
gcuauguuag acgauguaat t                                              21

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 176
cccacagaaa uuucucuaut t                                              21

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 177
gauuuggugu uuucuacuut t                                              21

<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 178
cagagccaaa aucaagauut t                                              21

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 179
aaaucaagau uugcuaugut t                                              21

<210> SEQ ID NO 180
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 180
cauggacauu aauucaacat t                                           21

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 181
gauuugcuau guuagacgat t                                           21

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 182
gaacuacaua uaaacuacat t                                           21

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 183
cgaauagaug gaucacaaat t                                           21

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 184
cuuguuaaaa cucuaaacut t                                           21

<210> SEQ ID NO 185
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 185
auuugaucag ucuuuuuaut t                                           21

<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 186
uccauggaca uuaauucaat t                                           21

<210> SEQ ID NO 187
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 187
cacaauuaag cuccuucuut t                                           21

<210> SEQ ID NO 188
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 188
caacauauuu gaucagucut t                                           21

<210> SEQ ID NO 189
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 189
cuccauagug aagcaaucut t                                           21

<210> SEQ ID NO 190
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 190
gccaaauuaa ugacauauut t                                           21

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 191
caacagcaua gucaaauaat t                                           21

<210> SEQ ID NO 192
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 192
ggaaaucacg aaaccaacut t                                           21

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 193
caguugggac auggucuuat t                                           21

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 194
gacauggucu uaaagacuut t                                           21
```

```
<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 195
uguggagaaa acaaccuaat t                                            21

<210> SEQ ID NO 196
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 196
guggagaaaa caaccuaaat t                                            21

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 197
ccaacagcau agucaaauat t                                            21

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 198
caacaucgaa uagauggaut t                                            21

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 199
gcaaauuuaa aaggcaauat t                                            21
```

```
<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 200
caaaaucaag auuugcuaut t                                              21

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 201
agagccaaaa ucaagauuut t                                              21

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 202
uaaaaagacu gaucaaauat t                                              21

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 203
uuaaguuagu uaguugcuct t                                              21

<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 204
auaugucauu aauuuggcct t                                              21
```

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 205
agucuuccaa cucaauucgt t                                           21

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 206
augucccaac ugaaggaggt t                                           21

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 207
uuugaguuga guucaagugt t                                           21

<210> SEQ ID NO 208
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 208
ugaauuaaug uccauggact t                                           21

<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 209
aacauagcaa aucuugauut t                                              21

<210> SEQ ID NO 210
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 210
uggaguauau cuucucuagt t                                              21

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 211
uuugaauuaa guuaguuagt t                                              21

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 212
uuugaauuaa guuaguuagt t                                              21

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 213
auucgauguu gaauuaaugt t                                              21

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 214
uggauggauc aacauuuugt t                                              21

<210> SEQ ID NO 215
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 215
uugacuugua guuuauaugt t                                              21

<210> SEQ ID NO 216
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 216
acuugagagu ugcuggguct t                                              21

<210> SEQ ID NO 217
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 217
aucuucucua ggcccaacct t                                              21

<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 218
uagguuguuu ucuccacact t                                              21

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 219
ucgauguuga auuaauguct t                                              21

<210> SEQ ID NO 220
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 220
auuagauugc uucacuaugt t                                              21

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 221
uuuacaucgu cuaacauagt t                                              21

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 222
agauagagaa auuucugugt t                                              21

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 223
uaucuucucu aggcccaact t                                              21

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 224
agcaaaucuu gauuuuggct t                                              21

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 225
aaagacugau caaauaugut t                                              21

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 226
aaagacugau caaauaugut t                                              21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 227
uauggacaaa gucuuuaagt t                                              21

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 228
uuagauugcu ucacuauggt t                                              21

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 229
uggaucaaca uuuugguugt t                                              21

<210> SEQ ID NO 230
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 230
acuuguaguu uauauguagt t                                              21

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 231
auucuccauc aagccuccct t                                              21

<210> SEQ ID NO 232
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 232
aucccaagua gaaaacacct t                                              21

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 233
aguaguucuu ggugcucuut t                                              21

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 234
auuuagguug uuucuccat t                                               21

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 235
aauuaaguua guaguugct t                                               21

<210> SEQ ID NO 236
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 236
auauuuacca uuuaggung t                                               21

<210> SEQ ID NO 237
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 237
uuacaucguc uaacauagct t                                              21

<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 238
auagagaaau uucugugggt t                                              21

<210> SEQ ID NO 239
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<223> OTHER INFORMATION: Description of Combined DNA/RNA Molecule:
      Synthetic oligonucleotide

<400> SEQUENCE: 239
aaguagaaaa caccaaauct t                                                   21

<210> SEQ ID NO 240
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 240
aaucuugauu uuggcucugt t                                                   21

<210> SEQ ID NO 241
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 241
acauagcaaa ucuugauuut t                                                   21

<210> SEQ ID NO 242
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 242
uguugaauua auguccaugt t                                                   21

<210> SEQ ID NO 243
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 243
ucgucuaaca uagcaaauct t                                                   21

<210> SEQ ID NO 244
<211> LENGTH: 21
<212> TYPE: DNA
<213> ORGANISM: Artificial Sequence
<220> FEATURE:
<223> OTHER INFORMATION: Description of Artificial Sequence: Synthetic

```
                            oligonucleotide
<220> FEATURE:
<223> OTHER INFORMATION: Description of Combined DNA/RNA Molecule:
      Synthetic oligonucleotide

<400> SEQUENCE: 244
uguaguuuau auguaguuct t                                            21

<210> SEQ ID NO 245
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 245
uuugugaucc aucuauucgt t                                            21

<210> SEQ ID NO 246
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 246
aguuuagagu uuuaacaagt t                                            21

<210> SEQ ID NO 247
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 247
auaaaaagac ugaucaaaut t                                            21

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 248
uugaauuaau guccauggat t                                            21

<210> SEQ ID NO 249
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 249
aagaaggagc uuaauugugt t                                              21

<210> SEQ ID NO 250
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 250
agacugauca aauauguugt t                                              21

<210> SEQ ID NO 251
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 251
agauugcuuc acuauggagt t                                              21

<210> SEQ ID NO 252
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 252
aauaugucau uaauuuggct t                                              21

<210> SEQ ID NO 253
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 253
uuauuugacu augcuguugt t                                              21

<210> SEQ ID NO 254
<211> LENGTH: 21
<212> TYPE: DNA
<213> ORGANISM: Artificial Sequence -continued

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 254
aguugguuuc gugauuucct t                                              21

<210> SEQ ID NO 255
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 255
uaagaccaug ucccaacugt t                                              21

<210> SEQ ID NO 256
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 256
aagucuuuaa gaccauguct t                                              21

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 257
uuagguuguu uucuccacat t                                              21

<210> SEQ ID NO 258
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 258
uuuagguugu uuucuccact t                                              21

<210> SEQ ID NO 259
<211> LENGTH: 21
<212> TYPE: DNA
```

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 259
uauuugacua ugcuguuggt t                                              21

<210> SEQ ID NO 260
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 260
auccaucuau ucgauguugt t                                              21

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 261
uauugccuuu uaaauuugct t                                              21

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 262
auagcaaauc uugauuuugt t                                              21

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 263
aaaucuugau uuuggcucut t                                              21

<210> SEQ ID NO 264
<211> LENGTH: 21

-continued

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
aaagacaaca aacauuauau u                                          21

<210> SEQ ID NO 265
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
acaauuaagc uccuucuuuu u                                          21

<210> SEQ ID NO 266
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
ugucacuuga acucaacuca a                                          21

<210> SEQ ID NO 267
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
ucacaauuaa gcuccuucuu u                                          21

<210> SEQ ID NO 268
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
cuugaacuca acucaaaacu u                                          21

<210> SEQ ID NO 269
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
cuccauagug aagcaaucua a                                          21

<210> SEQ ID NO 270
<211> LENGTH: 21
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 270
caauuaagcu ccuucuuuuu a                                              21

<210> SEQ ID NO 271
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
acccagcaac ucucaaguuu u                                              21

<210> SEQ ID NO 272
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
gaauauguca cuugaacuca a                                              21

<210> SEQ ID NO 273
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
aauuaagcuc cuucuuuuua u                                              21

<210> SEQ ID NO 274
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
cauuauauug aauauucuuu u                                              21

<210> SEQ ID NO 275
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
acuaacuaac uuaauucaaa a                                              21

<210> SEQ ID NO 276
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 276
uuauuguucc ucuaguuauu u                                               21

<210> SEQ ID NO 277
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
cauagugaag caaucuaauu a                                               21

<210> SEQ ID NO 278
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
ccauagugaa gcaaucuaau u                                               21

<210> SEQ ID NO 279
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
gaucacaaaa cuucaaugaa a                                               21

<210> SEQ ID NO 280
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
auggaagguu auacucuaua a                                               21

<210> SEQ ID NO 281
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
uccauaguga agcaaucuaa u                                               21

<210> SEQ ID NO 282
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 282
cuauguuaga cgauguaaaa a                                              21

<210> SEQ ID NO 283
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
auuaagcucc uucuuuuuau u                                              21

<210> SEQ ID NO 284
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
aacuaacuaa cuuaauucaa a                                              21

<210> SEQ ID NO 285
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
ggccaaauua augacauauu u                                              21

<210> SEQ ID NO 286
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
uuuuauuguu ccucuaguua u                                              21

<210> SEQ ID NO 287
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
acauauuuga ucagucuuuu u                                              21

<210> SEQ ID NO 288
<211> LENGTH: 21
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 288
cccagcaacu cucaaguuuu u                                              21

<210> SEQ ID NO 289
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
cagguagucc auggacauua a                                              21

<210> SEQ ID NO 290
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
acugagaaga acuacauaua a                                              21

<210> SEQ ID NO 291
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
gagcaacuaa cuaacuuaau u                                              21

<210> SEQ ID NO 292
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
aacaaccuaa augguaaaua u                                              21

<210> SEQ ID NO 293
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
ccuagagaag auauacucca u                                              21

<210> SEQ ID NO 294
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
caacauauuu gaucagucuu u                                      21

<210> SEQ ID NO 295
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
acaacaaaca uuauauugaa u                                      21

<210> SEQ ID NO 296
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
acauauaaac uacaagucaa a                                      21

<210> SEQ ID NO 297
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
cuaguuauuu ccuccagaau u                                      21

<210> SEQ ID NO 298
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
aagagcaacu aacuaacuua a                                      21

<210> SEQ ID NO 299
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
uuuauuguuc cucuaguuau u                                      21

<210> SEQ ID NO 300
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 300
cuccuagaag aaaaaauucu a                                              21

<210> SEQ ID NO 301
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
aacaaacauu auauugaaua u                                              21

<210> SEQ ID NO 302
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
ggaaaucacg aaaccaacua u                                              21

<210> SEQ ID NO 303
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
aacauauuug aucagucuuu u                                              21

<210> SEQ ID NO 304
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
uggaagguua uacucuauaa a                                              21

<210> SEQ ID NO 305
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
ggagaacuac aaauaugguu u                                              21

<210> SEQ ID NO 306
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
```

```
gaaaacaaag auuugguguu u                                              21

<210> SEQ ID NO 307
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
aguguggaga aaacaaccua a                                              21

<210> SEQ ID NO 308
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
gucacuugaa cucaacucaa a                                              21

<210> SEQ ID NO 309
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
gauggaucac aaaacuucaa u                                              21

<210> SEQ ID NO 310
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
acaaacauua uauugaauau u                                              21

<210> SEQ ID NO 311
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
uguggagaaa acaaccuaaa u                                              21

<210> SEQ ID NO 312
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
```
aucagucuuu uuaugaucua u                                          21

<210> SEQ ID NO 313
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
gacaacaaac auuauauuga a                                          21

<210> SEQ ID NO 314
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
caacagcaua gucaaauaaa a                                          21

<210> SEQ ID NO 315
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
cugagaagaa cuacauauaa a                                          21

<210> SEQ ID NO 316
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
ugcuauguua gacgauguaa a                                          21

<210> SEQ ID NO 317
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
aacccacaga aauuucucua u                                          21

<210> SEQ ID NO 318
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
cuucaacaaa aagugaaaua u                                          21

<210> SEQ ID NO 319
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
ucacuugaac ucaacucaaa a                                              21

<210> SEQ ID NO 320
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
cauagucaaa uaaaagaaau a                                              21

<210> SEQ ID NO 321
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
caaaaacuca acauauuuga u                                              21

<210> SEQ ID NO 322
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
uacuucaaca aaaagugaaa u                                              21

<210> SEQ ID NO 323
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
gacccagcaa cucucaaguu u                                              21

<210> SEQ ID NO 324
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
uugaaugaac ugaggcaaau u                                              21

<210> SEQ ID NO 325
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
uauaaacuac aagucaaaaa u                                                 21

<210> SEQ ID NO 326
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
aaacaagaua auagcaucaa a                                                 21

<210> SEQ ID NO 327
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
caacuaacua acuuaauuca a                                                 21

<210> SEQ ID NO 328
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
gcuauguuag acgauguaaa a                                                 21

<210> SEQ ID NO 329
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
acuugggauc acaaagcaaa a                                                 21

<210> SEQ ID NO 330
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
uugcuauguu agacgaugua a                                                 21

<210> SEQ ID NO 331
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
aacugagaag aacuacauau a                                                21

<210> SEQ ID NO 332
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
gauguaaaaa uuuuagccaa u                                                21

<210> SEQ ID NO 333
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
acuccauagu gaagcaaucu a                                                21

<210> SEQ ID NO 334
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
uucaacaaaa agugaaauau u                                                21

<210> SEQ ID NO 335
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
cuagagaaga uauacuccau a                                                21

<210> SEQ ID NO 336
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
caaccuaaau gguaaauaua a                                                21

<210> SEQ ID NO 337

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
gaaaucacga aaccaacuau a                                              21

<210> SEQ ID NO 338
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338
ccacagaaau uucucuaucu u                                              21

<210> SEQ ID NO 339
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
aaaucaagau uugcuauguu a                                              21

<210> SEQ ID NO 340
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
acauuaauuc aacaucgaau a                                              21

<210> SEQ ID NO 341
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
ccagagccaa aaucaagauu u                                              21

<210> SEQ ID NO 342
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
cuacuucaac aaaaagugaa a                                              21

<210> SEQ ID NO 343
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
gacauuaauu caacaucgaa u                                              21

<210> SEQ ID NO 344
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
ggacauuaau ucaacaucga a                                              21

<210> SEQ ID NO 345
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
gcauagucaa auaaaagaaa u                                              21

<210> SEQ ID NO 346
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
cucucaaguu uuucaugucu a                                              21

<210> SEQ ID NO 347
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
aucgaauaga uggaucacaa a                                              21

<210> SEQ ID NO 348
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
acauuauauu gaauauucuu u                                              21

<210> SEQ ID NO 349
<211> LENGTH: 21
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 349
uuaauucaac aucgaauaga u                                              21

<210> SEQ ID NO 350
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
gauaauagca ucaaagaccu u                                              21

<210> SEQ ID NO 351
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
ugacauauuu caaaaacuca a                                              21

<210> SEQ ID NO 352
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
aaauuaauga cauauuucaa a                                              21

<210> SEQ ID NO 353
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
gaagauauac uccauaguga a                                              21

<210> SEQ ID NO 354
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
aauauuuaga agagcaacua a                                              21

<210> SEQ ID NO 355
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 355
cgauguaaaa auuuuagcca a                                              21

<210> SEQ ID NO 356
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
uucaacaucg aauagaugga u                                              21

<210> SEQ ID NO 357
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
guguggagaa aacaaccuaa a                                              21

<210> SEQ ID NO 358
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
ucaacauauu ugaucagucu u                                              21

<210> SEQ ID NO 359
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
ucagguaguc cauggacauu a                                              21

<210> SEQ ID NO 360
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
uuuagaagag caacuaacua a                                              21

<210> SEQ ID NO 361
<211> LENGTH: 21
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 361
uacauauaaa cuacaaguca a                                              21

<210> SEQ ID NO 362
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
ggaucacaaa acuucaauga a                                              21

<210> SEQ ID NO 363
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
agagcaacua acuaacuuaa u                                              21

<210> SEQ ID NO 364
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
accaacagca uagucaaaua a                                              21

<210> SEQ ID NO 365
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
aaccaacagc auagucaaau a                                              21

<210> SEQ ID NO 366
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
gaacucaacu caaaacuuga a                                              21

<210> SEQ ID NO 367
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 367
uacucuauaa aaucaaccaa a                           21

<210> SEQ ID NO 368
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
cagcauaguc aaauaaaaga a                           21

<210> SEQ ID NO 369
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
gaaauaagaa auguaaaaca u                           21

<210> SEQ ID NO 370
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
cuaacuaacu uaauucaaaa u                           21

<210> SEQ ID NO 371
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
augaacugag gcaaauuuaa a                           21

<210> SEQ ID NO 372
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
ugaacugagg caaauuuaaa a                           21

<210> SEQ ID NO 373
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 373
aaacaaccua aaugguaaau a                                              21

<210> SEQ ID NO 374
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
acaaccuaaa ugguaaauau a                                              21

<210> SEQ ID NO 375
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
aacgugggag aacuacaaau a                                              21

<210> SEQ ID NO 376
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
aaugaacuga ggcaaauuua a                                              21

<210> SEQ ID NO 377
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
guuggaagac uggaaagaca a                                              21

<210> SEQ ID NO 378
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
uggcaauguc cccaaugcaa u                                              21

<210> SEQ ID NO 379
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 379
gguaguccau ggacauuaau u                                              21

<210> SEQ ID NO 380
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
cauauaaacu acaagucaaa a                                              21

<210> SEQ ID NO 381
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
aaucccggaa aacaaagauu u                                              21

<210> SEQ ID NO 382
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
cuacuuggga ucacaaagca a                                              21

<210> SEQ ID NO 383
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
ugaaugaacu gaggcaaauu u                                              21

<210> SEQ ID NO 384
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
agcauaguca aauaaagaa a                                               21

<210> SEQ ID NO 385
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
```
auuuagaaga gcaacuaacu a                                              21

<210> SEQ ID NO 386
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
aggcaaauuu aaaaggcaau a                                              21

<210> SEQ ID NO 387
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
cauauuugau cagucuuuuu a                                              21

<210> SEQ ID NO 388
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388 aaacaaaga uuugguguuu u                                               21

<210> SEQ ID NO 389
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
caaucccgga aaacaaagau u                                              21

<210> SEQ ID NO 390
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
caacaaacau uauauugaau a                                              21

<210> SEQ ID NO 391
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
ggaaaacaaa gauuuggugu u                                      21

<210> SEQ ID NO 392
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
acaaagauuu gguguuuucu a                                      21

<210> SEQ ID NO 393
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
gaaugaacug aggcaaauuu a                                      21

<210> SEQ ID NO 394
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
ccauggacau uaauucaaca u                                      21

<210> SEQ ID NO 395
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
aacucaacuc aaaacuugaa a                                      21

<210> SEQ ID NO 396
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
caguugggac auggucuuaa a                                      21

<210> SEQ ID NO 397
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
aacauuauau ugaauauucu u                                      21

<210> SEQ ID NO 398
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
accagugaaa ucaaagaaga a                                             21

<210> SEQ ID NO 399
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
guugggccua gagaagauau a                                             21

<210> SEQ ID NO 400
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
cuccagagcc aaaaucaaga u                                             21

<210> SEQ ID NO 401
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
ggcaaauuua aaaggcaaua a                                             21

<210> SEQ ID NO 402
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
uacuugggau cacaaagcaa a                                             21

<210> SEQ ID NO 403
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
gaucagucuu uuuaugaucu a                                             21

-continued

<210> SEQ ID NO 404
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
gaaagccucc uagaagaaaa a                                          21

<210> SEQ ID NO 405
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
agucaaauaa aagaaauaga a                                          21

<210> SEQ ID NO 406
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
auacucuaua aaaucaacca a                                          21

<210> SEQ ID NO 407
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
gaacugaggc aaauuuaaaa a                                          21

<210> SEQ ID NO 408
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
agacccagca acucucaagu u                                          21

<210> SEQ ID NO 409
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
auauaaacua caagucaaaa a                                          21

```
<210> SEQ ID NO 410
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
ugaaagccuc cuagaagaaa a                                              21

<210> SEQ ID NO 411
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
gggagaacua caaauauggu u                                              21

<210> SEQ ID NO 412
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
agauuugcua uguuagacga u                                              21

<210> SEQ ID NO 413
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
gaacccacag aaauuucucu a                                              21

<210> SEQ ID NO 414
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
acuucaacaa aaagugaaau a                                              21

<210> SEQ ID NO 415
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 415
aguccaugga cauuaauuca a                                              21

<210> SEQ ID NO 416
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
aacugaggca aauuuaaaag a                                              21

<210> SEQ ID NO 417
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
gggccaaauu aaugacauau u                                              21

<210> SEQ ID NO 418
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
auccauccaa cagauucaga a                                              21

<210> SEQ ID NO 419
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
aagauuuggu guuuucuacu u                                              21

<210> SEQ ID NO 420
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
gucucaaaau ggaagguuau a                                              21

<210> SEQ ID NO 421
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
acugaggcaa auuuaaaagg a                                              21

<210> SEQ ID NO 422
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
gggacauggu cuuaaagacu u                                              21

<210> SEQ ID NO 423
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
augguaaaua uaacaaacca a                                              21

<210> SEQ ID NO 424
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
gggaaaucac gaaaccaacu a                                              21

<210> SEQ ID NO 425
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
ccaacagcau agucaaauaa a                                              21

<210> SEQ ID NO 426
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
uuuucuacuu gggaucacaa a                                              21

<210> SEQ ID NO 427
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
agaacuacau auaaacuaca a                                              21

<210> SEQ ID NO 428
<211> LENGTH: 21
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 428
agaguaugug uaaaaaucug u                                              21

<210> SEQ ID NO 429
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
aaaacaagau aauagcauca a                                              21

<210> SEQ ID NO 430
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
aguaugugua aaaaucugua a                                              21

<210> SEQ ID NO 431
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
agucaaaaau gaagagguaa a                                              21

<210> SEQ ID NO 432
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
ggacaugguc uuaaagacuu u                                              21

<210> SEQ ID NO 433
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
gaggcaaauu uaaaaggcaa u                                              21

<210> SEQ ID NO 434
<211> LENGTH: 21
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 434
gucuuaaaga cuuuguccau a                                              21

<210> SEQ ID NO 435
<211> LENGTH: 21
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 435
cugaggcaaa uuuaaaaggc a                                              21

<210> SEQ ID NO 436
<211> LENGTH: 21
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 436
gcaaucccgg aaaacaaaga u                                              21

<210> SEQ ID NO 437
<211> LENGTH: 21
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 437
ugaggcaaau uuaaaaggca a                                              21

<210> SEQ ID NO 438
<211> LENGTH: 21
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 438
ucuacuucaa caaaaaguga a                                              21

<210> SEQ ID NO 439
<211> LENGTH: 21
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 439
uauguguaaa aaucuguaau a                                              21

<210> SEQ ID NO 440
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 440
aaugcaaucc cggaaaacaa a                                              21

<210> SEQ ID NO 441
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 441
cuugaaagcc uccuagaaga a                                              21

<210> SEQ ID NO 442
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 442
guauguguaa aaaucuguaa u                                              21

<210> SEQ ID NO 443
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
cagaguaugu guaaaaaucu u                                              21

<210> SEQ ID NO 444
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 444
gaguaugugu aaaaaucugu a                                              21

<210> SEQ ID NO 445
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
ucaguuggga cauggucuua a                                              21

<210> SEQ ID NO 446
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 446
ggucuuaaag acuuugucca u                                              21

<210> SEQ ID NO 447
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
ucuuaaagac uuuguccaua a                                              21

<210> SEQ ID NO 448
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
uucaguuggg acauggucuu a                                              21

<210> SEQ ID NO 449
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
aauauaaugu uuguugucuu ucc                                            23

<210> SEQ ID NO 450
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 450
aaaaagaagg agcuuaauug uga                                            23

<210> SEQ ID NO 451
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
uugaguugag uucaagugac aua                                            23

<210> SEQ ID NO 452
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 452
aaagaaggag cuuaauugug aac                                         23

<210> SEQ ID NO 453
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
aaguuuugag uugaguucaa gug                                         23

<210> SEQ ID NO 454
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
uuagauugcu ucacuaugga gua                                         23

<210> SEQ ID NO 455
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
uaaaaagaag gagcuuaauu gug                                         23

<210> SEQ ID NO 456
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
aaaacuugag aguugcuggg ucu                                         23

<210> SEQ ID NO 457
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
uugaguucaa gugacauauu cuu                                         23

<210> SEQ ID NO 458
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 458
auaaaaagaa ggagcuuaau ugu                                            23

<210> SEQ ID NO 459
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
aaaagaauau ucaauauaau guu                                            23

<210> SEQ ID NO 460
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
uuuugaauua aguuaguuag uug                                            23

<210> SEQ ID NO 461
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
aaauaacuag aggaacaaua aaa                                            23

<210> SEQ ID NO 462
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
uaauuagauu gcuucacuau gga                                            23

<210> SEQ ID NO 463
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
aauuagauug cuucacuaug gag                                            23

<210> SEQ ID NO 464
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
``` uucauugaa guuugugau cca                                          23

<210> SEQ ID NO 465
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 465
uuauagagua uaaccuucca uuu                                        23

<210> SEQ ID NO 466
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 466
auuagauugc uucacuaugg agu                                        23

<210> SEQ ID NO 467
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 467
uuuuuacauc gucuaacaua gca                                        23

<210> SEQ ID NO 468
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 468
aauaaaaaga aggagcuuaa uug                                        23

<210> SEQ ID NO 469
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 469
uuugaauuaa guuaguuagu ugc                                        23

<210> SEQ ID NO 470
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 470
aaauauguca uuaauuuggc ccu                                              23

<210> SEQ ID NO 471
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 471
auaacuagag gaacaauaaa aag                                              23

<210> SEQ ID NO 472
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 472
aaaaagacug aucaaauaug uug                                              23

<210> SEQ ID NO 473
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 473
aaaaacuuga gaguugcugg guc                                              23

<210> SEQ ID NO 474
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 474
uuaaugucca uggacuaccu gau                                              23

<210> SEQ ID NO 475
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 475
uuauauguag uucuucucag uuc                                              23

<210> SEQ ID NO 476
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 476
aauuaaguua guuaguugcu cuu                                              23

<210> SEQ ID NO 477
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 477
auauuuacca uuuagguugu uuu                                            23

<210> SEQ ID NO 478
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 478
auggaguaua ucuucucuag gcc                                            23

<210> SEQ ID NO 479
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 479
aaagacugau caaauauguu gag                                            23

<210> SEQ ID NO 480
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 480
auucaauaua auguuguug ucu                                             23

<210> SEQ ID NO 481
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 481
uuugacuugu aguuuauaug uag                                            23

<210> SEQ ID NO 482
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 482
aauucuggag gaaauaacua gag                                            23

<210> SEQ ID NO 483
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 483
uuaaguuagu uaguugcucu ucu                                                23

<210> SEQ ID NO 484
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 484
aauaacuaga ggaacaauaa aaa                                                23

<210> SEQ ID NO 485
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 485
uagaauuuuu ucuucuagga ggc                                                23

<210> SEQ ID NO 486
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 486
auauucaaua uaauguuugu ugu                                                23

<210> SEQ ID NO 487
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 487
auaguugguu ucgugauuuc cca                                                23

<210> SEQ ID NO 488
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 488
aaaagacuga ucaaauaugu uga                                                23

```
<210> SEQ ID NO 489
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 489
uuuauagagu auaaccuucc auu                                              23

<210> SEQ ID NO 490
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 490
aaaccauauu uguaguucuc cca                                              23

<210> SEQ ID NO 491
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 491
aaacaccaaa ucuuuguuuu ccg                                              23

<210> SEQ ID NO 492
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 492
uuagguuguu uucuccacac uca                                              23

<210> SEQ ID NO 493
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 493
uuugaguuga guucaaguga cau                                              23

<210> SEQ ID NO 494
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 494
auugaaguuu ugugauccau cua                                              23

<210> SEQ ID NO 495
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495
aauauucaau auaauguuug uug                                             23

<210> SEQ ID NO 496
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 496
auuuagguug uuuucuccac acu                                             23

<210> SEQ ID NO 497
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 497
auagaucaua aaaagacuga uca                                             23

<210> SEQ ID NO 498
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 498
uucaauauaa uguuuguugu cuu                                             23

<210> SEQ ID NO 499
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 499
uuuuauuuga cuaugcuguu ggu                                             23

<210> SEQ ID NO 500
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 500
uuuauaugua guucuucuca guu                                             23

<210> SEQ ID NO 501
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 501
uuuacaucgu cuaacauagc aaa                                              23

<210> SEQ ID NO 502
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 502
auagagaaau uucugugggu ucu                                              23

<210> SEQ ID NO 503
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 503
auauuucacu uuuguugaa gua                                               23

<210> SEQ ID NO 504
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 504
uuuugaguug aguucaagug aca                                              23

<210> SEQ ID NO 505
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 505
uauuucuuuu auuugacuau gcu                                              23

<210> SEQ ID NO 506
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 506
aucaaauaug uugaguuuuu gaa                                              23

<210> SEQ ID NO 507
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 507
auuucacuuu uuguugaagu aga                                                 23

<210> SEQ ID NO 508
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 508
aaacuugaga guugcugggu cug                                                 23

<210> SEQ ID NO 509
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 509
aauuugccuc aguucauuca aag                                                 23

<210> SEQ ID NO 510
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 510
auuuuugacu uguaguuuau aug                                                 23

<210> SEQ ID NO 511
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 511
uuugaugcua uuaucuuguu uuu                                                 23

<210> SEQ ID NO 512
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 512
uugaauuaag uuaguuaguu gcu                                                 23

<210> SEQ ID NO 513
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 513
uuuuacaucg ucuaacauag caa                                               23

<210> SEQ ID NO 514
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 514
uuuugcuuug ugaucccaag uag                                               23

<210> SEQ ID NO 515
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 515
uuacaucguc uaacauagca aau                                               23

<210> SEQ ID NO 516
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 516
uauauguagu ucuucucagu ucc                                               23

<210> SEQ ID NO 517
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 517
auuggcuaaa auuuuacau cgu                                                23

<210> SEQ ID NO 518
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 518
uagauugcuu cacuauggag uau                                               23

<210> SEQ ID NO 519
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 519
aauauuucac uuuuuguuga agu                                            23

<210> SEQ ID NO 520
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 520
uauggaguau aucuucucua ggc                                            23

<210> SEQ ID NO 521
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 521
uuauauuuac cauuuagguu guu                                            23

<210> SEQ ID NO 522
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 522
uauaguuggu uucgugauuu ccc                                            23

<210> SEQ ID NO 523
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 523
aagauagaga aauuucugug ggu                                            23

<210> SEQ ID NO 524
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 524
uaacauagca aaucuugauu uug                                            23

<210> SEQ ID NO 525
<211> LENGTH: 23
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 525
uauucgaugu ugaauuaaug ucc                                          23

<210> SEQ ID NO 526
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 526
aaaucuugau uuuggcucug gag                                          23

<210> SEQ ID NO 527
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 527
uuucacuuuu uguugaagua gaa                                          23

<210> SEQ ID NO 528
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 528
auucgauguu gaauuaaugu cca                                          23

<210> SEQ ID NO 529
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 529
uucgauguug aauuaauguc cau                                          23

<210> SEQ ID NO 530
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 530
auuucuuuua uuugacuaug cug                                          23

<210> SEQ ID NO 531
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 531
uagacaugaa aaacuugaga guu                                          23

<210> SEQ ID NO 532
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 532
uuugugaucc aucuauucga ugu                                          23

<210> SEQ ID NO 533
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 533
aaagaauauu caauauaaug uuu                                          23

<210> SEQ ID NO 534
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 534
aucuauucga uguugaauua aug                                          23

<210> SEQ ID NO 535
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 535
aaggucuuug augcuauuau cuu                                          23

<210> SEQ ID NO 536
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 536
uugaguuuuu gaaauauguc auu                                          23

<210> SEQ ID NO 537
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 537
uuugaaauau gucauuaauu ugg                                    23

<210> SEQ ID NO 538
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 538
uucacuaugg aguauaucuu cuc                                    23

<210> SEQ ID NO 539
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 539
uuaguugcuc uucuaaauau uuc                                    23

<210> SEQ ID NO 540
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 540
uuggcuaaaa uuuuuacauc guc                                    23

<210> SEQ ID NO 541
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 541
auccaucuau ucgauguuga auu                                    23

<210> SEQ ID NO 542
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 542
uuuagguugu uuucuccaca cuc                                    23

<210> SEQ ID NO 543
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 543
aagacugauc aaauauguug agu                                              23

<210> SEQ ID NO 544
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 544
uaauguccau ggacuaccug aua                                              23

<210> SEQ ID NO 545
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 545
uuaguuaguu gcucuucuaa aua                                              23

<210> SEQ ID NO 546
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 546
uugacuugua guuuauaugu agu                                              23

<210> SEQ ID NO 547
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 547
uucauugaag uuuugugauc cau                                              23

<210> SEQ ID NO 548
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 548
auuaaguuag uuaguugcuc uuc                                              23

<210> SEQ ID NO 549
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 549

```
uuauuugacu augcuguugg uuu                                            23
```

<210> SEQ ID NO 550
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 550

```
uauuugacua ugcuguuggu uua                                            23
```

<210> SEQ ID NO 551
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 551

```
uucaaguuuu gaguugaguu caa                                            23
```

<210> SEQ ID NO 552
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 552

```
uuugguugau uuuauagagu aua                                            23
```

<210> SEQ ID NO 553
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 553

```
uucuuuuauu ugacuaugcu guu                                            23
```

<210> SEQ ID NO 554
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 554

```
auguuuuaca uuucuuauuu cau                                            23
```

<210> SEQ ID NO 555
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 555

```
auuuugaauu aaguuaguua guu                                            23
```

<210> SEQ ID NO 556
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 556
uuuaaauuug ccucaguuca uuc                                              23

<210> SEQ ID NO 557
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 557
uuuuaaauuu gccucaguuc auu                                              23

<210> SEQ ID NO 558
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 558
uauuuaccau uuagguuguu uuc                                              23

<210> SEQ ID NO 559
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 559
uauauuuacc auuuagguug uuu                                              23

<210> SEQ ID NO 560
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 560
uauuuguagu ucucccacgu uuc                                              23

<210> SEQ ID NO 561
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 561
uuaaauuugc cucaguucau uca                                              23

```
<210> SEQ ID NO 562
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 562
uugucuuucc agucuuccaa cuc                                               23

<210> SEQ ID NO 563
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 563
auugcauugg ggacauugcc agu                                               23

<210> SEQ ID NO 564
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 564
aauuaauguc cauggacuac cug                                               23

<210> SEQ ID NO 565
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 565
uuuugacuug uaguuuauau gua                                               23

<210> SEQ ID NO 566
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 566
aaaucuuugu uuccgggau ugc                                                23

<210> SEQ ID NO 567
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 567
uugcuuugug aucccaagua gaa                                               23
```

```
<210> SEQ ID NO 568
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 568
aaauuugccu caguucauuc aaa                                              23

<210> SEQ ID NO 569
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 569
uuucuuuuau uugacuaugc ugu                                              23

<210> SEQ ID NO 570
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 570
uaguuaguug cucuucuaaa uau                                              23

<210> SEQ ID NO 571
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 571
uauugccuuu uaaauuugcc uca                                              23

<210> SEQ ID NO 572
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 572
uaaaaagacu gaucaaauau guu                                              23

<210> SEQ ID NO 573
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 573
aaaacaccaa aucuuuguuu ucc                                              23

<210> SEQ ID NO 574
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 574
aaucuuuguu uuccgggauu gca                                          23

<210> SEQ ID NO 575
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 575
uauucaauau aauguuuguu guc                                          23

<210> SEQ ID NO 576
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 576
aacaccaaau cuuuguuuuc cgg                                          23

<210> SEQ ID NO 577
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 577
uagaaaacac caaaucuuug uuu                                          23

<210> SEQ ID NO 578
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 578
uaaauuugcc ucaguucauu caa                                          23

<210> SEQ ID NO 579
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 579
auguugaauu aauguccaug gac                                          23

<210> SEQ ID NO 580
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 580
uuucaaguuu ugaguugagu uca                                              23

<210> SEQ ID NO 581
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 581
uuuaagacca ugucccaacu gaa                                              23

<210> SEQ ID NO 582
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 582
aagaauauuc aauauaaugu uug                                              23

<210> SEQ ID NO 583
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 583
uucuucuuug auuucacugg uuu                                              23

<210> SEQ ID NO 584
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 584
uauaucuucu cuaggcccaa cca                                              23

<210> SEQ ID NO 585
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 585
aucuugauuu uggcucugga gau                                              23

<210> SEQ ID NO 586
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 586
uuauugccuu uaaauuugc cuc                                              23

<210> SEQ ID NO 587
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 587
uuugcuuugu gaucccaagu aga                                             23

<210> SEQ ID NO 588
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 588
uagaucauaa aaagacugau caa                                             23

<210> SEQ ID NO 589
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 589
uuuuucuucu aggaggcuuu caa                                             23

<210> SEQ ID NO 590
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 590
uucuauuucu uuuauuugac uau                                             23

<210> SEQ ID NO 591
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 591
uugguugauu uuauagagua uaa                                             23

<210> SEQ ID NO 592
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 592
uuuuuaaauu ugccucaguu cau                                              23

<210> SEQ ID NO 593
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 593
aacuugagag uugcuggguc uga                                              23

<210> SEQ ID NO 594
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 594
uuuuugacuu guaguuuaua ugu                                              23

<210> SEQ ID NO 595
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 595
uuuucuucua ggaggcuuuc aag                                              23

<210> SEQ ID NO 596
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 596
aaccauauuu guaguucucc cac                                              23

<210> SEQ ID NO 597
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 597
aucgucuaac auagcaaauc uug                                              23

<210> SEQ ID NO 598
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 598
uagagaaauu ucugugggu cuu                                              23

<210> SEQ ID NO 599
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 599
uauuucacuu uuuguugaag uag                                             23

<210> SEQ ID NO 600
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 600
uugaauuaau guccauggac uac                                             23

<210> SEQ ID NO 601
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 601
ucuuuuaaau uugccucagu uca                                             23

<210> SEQ ID NO 602
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 602
aauaugucau uaauuuggcc cuu                                             23

<210> SEQ ID NO 603
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 603
uucugaaucu guuggaugga uca                                             23

<210> SEQ ID NO 604
<211> LENGTH: 23
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 604
aaguagaaaa caccaaaucu uug                                              23

<210> SEQ ID NO 605
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 605
uauaaccuuc cauuugaga cuu                                               23

<210> SEQ ID NO 606
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 606
uccuuuuaaa uuugccucag uuc                                              23

<210> SEQ ID NO 607
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 607
aagucuuuaa gaccaugucc caa                                              23

<210> SEQ ID NO 608
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 608
uugguuuguu auauuuacca uuu                                              23

<210> SEQ ID NO 609
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 609
uaguugguuu cgugauuucc caa                                              23

<210> SEQ ID NO 610
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 610
uuuauuugac uaugcuguug guu                                              23

<210> SEQ ID NO 611
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 611
uuugugaucc caaguagaaa aca                                              23

<210> SEQ ID NO 612
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 612
uuguaguuua uauguaguuc uuc                                              23

<210> SEQ ID NO 613
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 613
acagauuuuu acacauacuc ugu                                              23

<210> SEQ ID NO 614
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 614
uugaugcuau uaucuuguuu uuc                                              23

<210> SEQ ID NO 615
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 615
uuacagauuu uuacacauac ucu                                              23

<210> SEQ ID NO 616
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 616
uuuaccucuu cauuuugac uug				23

<210> SEQ ID NO 617
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 617
aaagucuuua agaccauguc cca				23

<210> SEQ ID NO 618
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 618
auugccuuuu aaauuugccu cag				23

<210> SEQ ID NO 619
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 619
uauggacaaa gucuuuaaga cca				23

<210> SEQ ID NO 620
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 620
ugccuuuuaa auuugccuca guu				23

<210> SEQ ID NO 621
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 621
aucuuuguuu uccgggauug cau				23

<210> SEQ ID NO 622
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 622
uugccuuuua aauuugccuc agu                                              23

<210> SEQ ID NO 623
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 623
uucacuuuuu guugaaguag aau                                              23

<210> SEQ ID NO 624
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 624
uauuacagau uuuuacacau acu                                              23

<210> SEQ ID NO 625
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 625
uuuguuuucc gggauugcau ugg                                              23

<210> SEQ ID NO 626
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 626
uucuucuagg aggcuuucaa guu                                              23

<210> SEQ ID NO 627
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 627
auuacagauu uuuacacaua cuc                                              23

<210> SEQ ID NO 628
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 628

-continued

```
aagauuuuua cacauacucu gug                                          23

<210> SEQ ID NO 629
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 629
uacagauuuu uacacauacu cug                                          23

<210> SEQ ID NO 630
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 630
uuaagaccau gucccaacug aag                                          23

<210> SEQ ID NO 631
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 631
auggacaaag ucuuuaagac cau                                          23

<210> SEQ ID NO 632
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 632
uuauggacaa agucuuuaag acc                                          23

<210> SEQ ID NO 633
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 633
uaagaccaug ucccaacuga agg                                          23

<210> SEQ ID NO 634
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 634
aaagacaaca aacauuauau u                                            21
```

<210> SEQ ID NO 635
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 635
acaauuaagc uccuucuuuu u                                              21

<210> SEQ ID NO 636
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 636
ugucacuuga acucaacuca a                                              21

<210> SEQ ID NO 637
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 637
ucacaauuaa gcuccuucuu u                                              21

<210> SEQ ID NO 638
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 638
cuugaacuca acucaaaacu u                                              21

<210> SEQ ID NO 639
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 639
cuccauagug aagcaaucua a                                              21

<210> SEQ ID NO 640
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 640
caauuaagcu ccuucuuuu a                                               21

<210> SEQ ID NO 641
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 641
acccagcaac ucucaaguuu u                                            21

<210> SEQ ID NO 642
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 642
gaauauguca cuugaacuca a                                            21

<210> SEQ ID NO 643
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 643
aauuaagcuc cuucuuuuua u                                            21

<210> SEQ ID NO 644
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 644
cauuauauug aauauucuuu u                                            21

<210> SEQ ID NO 645
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 645
acuaacuaac uuaauucaaa a                                            21

<210> SEQ ID NO 646
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 646
uuauuguucc ucuaguuauu u                                            21

<210> SEQ ID NO 647
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 647
cauagugaag caaucuaauu a                                              21

<210> SEQ ID NO 648
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 648
ccauagugaa gcaaucuaau u                                              21

<210> SEQ ID NO 649
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 649
gaucacaaaa cuucaaugaa a                                              21

<210> SEQ ID NO 650
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 650
auggaagguu auacucuaua a                                              21

<210> SEQ ID NO 651
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 651
uccauaguga agcaaucuaa u                                              21

<210> SEQ ID NO 652
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 652
cuauguuaga cgauguaaaa a                                              21

<210> SEQ ID NO 653

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 653
auuaagcucc uucuuuuuau u                                              21

<210> SEQ ID NO 654
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 654
aacuaacuaa cuuaauucaa a                                              21

<210> SEQ ID NO 655
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 655
ggccaaauua augacauauu u                                              21

<210> SEQ ID NO 656
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 656
uuuuauuguu ccucuaguua u                                              21

<210> SEQ ID NO 657
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 657
acauauuuga ucagucuuuu u                                              21

<210> SEQ ID NO 658
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 658
cccagcaacu cucaaguuuu u                                              21

<210> SEQ ID NO 659
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 659
cagguagucc auggacauua a                                              21

<210> SEQ ID NO 660
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 660
acugagaaga acuacauaua a                                              21

<210> SEQ ID NO 661
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 661
gagcaacuaa cuaacuuaau u                                              21

<210> SEQ ID NO 662
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 662
aacaaccuaa augguaaaua u                                              21

<210> SEQ ID NO 663
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 663
ccuagagaag auauacucca u                                              21

<210> SEQ ID NO 664
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 664
caacauauuu gaucagucuu u                                              21

<210> SEQ ID NO 665
<211> LENGTH: 21
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 665
acaacaaaca uuauauugaa u                                              21

<210> SEQ ID NO 666
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 666
acauauaaac uacaagucaa a                                              21

<210> SEQ ID NO 667
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 667
cuaguuauuu ccuccagaau u                                              21

<210> SEQ ID NO 668
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 668
aagagcaacu aacuaacuua a                                              21

<210> SEQ ID NO 669
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 669
uuuauuguuc cucuaguuau u                                              21

<210> SEQ ID NO 670
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 670
cuccuagaag aaaaaauucu a                                              21

<210> SEQ ID NO 671
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 671
aacaaacauu auauugaaua u                                              21

<210> SEQ ID NO 672
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 672
ggaaaucacg aaaccaacua u                                              21

<210> SEQ ID NO 673
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 673
aacauauuug aucagucuuu u                                              21

<210> SEQ ID NO 674
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 674
uggaagguua uacucuauaa a                                              21

<210> SEQ ID NO 675
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 675
ggagaacuac aaauaugguu u                                              21

<210> SEQ ID NO 676
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 676
gaaaacaaag auuugguguu u                                              21

<210> SEQ ID NO 677
<211> LENGTH: 21
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 677
aguguggaga aaacaaccua a                                              21

<210> SEQ ID NO 678
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 678
gucacuugaa cucaacucaa a                                              21

<210> SEQ ID NO 679
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 679
gauggaucac aaaacuucaa u                                              21

<210> SEQ ID NO 680
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 680
acaaacauua uauugaauau u                                              21

<210> SEQ ID NO 681
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 681
uguggagaaa acaaccuaaa u                                              21

<210> SEQ ID NO 682
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 682
aucagucuuu uuaugaucua u                                              21

<210> SEQ ID NO 683
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 683
gacaacaaac auuauauuga a                                              21

<210> SEQ ID NO 684
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 684
caacagcaua gucaaauaaa a                                              21

<210> SEQ ID NO 685
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 685
cugagaagaa cuacauauaa a                                              21

<210> SEQ ID NO 686
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 686
ugcuauguua gacgauguaa a                                              21

<210> SEQ ID NO 687
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 687
aacccacaga aauuucucua u                                              21

<210> SEQ ID NO 688
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 688
cuucaacaaa aagugaaaua u                                              21

<210> SEQ ID NO 689
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 689
ucacuugaac ucaacucaaa a                                              21

<210> SEQ ID NO 690
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 690
cauagucaaa uaaaagaaau a                                              21

<210> SEQ ID NO 691
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 691
caaaaacuca acauauuuga u                                              21

<210> SEQ ID NO 692
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 692
uacuucaaca aaagugaaa u                                               21

<210> SEQ ID NO 693
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 693
gacccagcaa cucucaaguu u                                              21

<210> SEQ ID NO 694
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 694
uugaaugaac ugaggcaaau u                                              21

<210> SEQ ID NO 695
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 695
uauaaacuac aagucaaaaa u                                              21

<210> SEQ ID NO 696
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 696
aaacaagaua auagcaucaa a                                              21

<210> SEQ ID NO 697
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 697
caacuaacua acuuaauuca a                                              21

<210> SEQ ID NO 698
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 698
gcuauguuag acgauguaaa a                                              21

<210> SEQ ID NO 699
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 699
acuugggauc acaaagcaaa a                                              21

<210> SEQ ID NO 700
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 700
uugcuauguu agacgaugua a                                              21

<210> SEQ ID NO 701
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 701
```
aacugagaag aacuacauau a                                              21

<210> SEQ ID NO 702
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 702
gauguaaaaa uuuuagccaa u                                              21

<210> SEQ ID NO 703
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 703
acuccauagu gaagcaaucu a                                              21

<210> SEQ ID NO 704
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 704
uucaacaaaa agugaaauau u                                              21

<210> SEQ ID NO 705
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 705
cuagagaaga uauacuccau a                                              21

<210> SEQ ID NO 706
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 706
caaccuaaau gguaaauaua a                                              21

<210> SEQ ID NO 707
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 707
gaaaucacga aaccaacuau a                    21

<210> SEQ ID NO 708
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 708
ccacagaaau uucucuaucu u                    21

<210> SEQ ID NO 709
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 709
aaaucaagau uugcuauguu a                    21

<210> SEQ ID NO 710
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 710
acauuaauuc aacaucgaau a                    21

<210> SEQ ID NO 711
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 711
ccagagccaa aaucaagauu u                    21

<210> SEQ ID NO 712
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 712
cuacuucaac aaaagugaa a                    21

<210> SEQ ID NO 713
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 713
gacauuaauu caacaucgaa u                    21

<210> SEQ ID NO 714
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 714
ggacauuaau ucaacaucga a                                              21

<210> SEQ ID NO 715
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 715
gcauagucaa auaaaagaaa u                                              21

<210> SEQ ID NO 716
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 716
cucucaaguu uuucaugucu a                                              21

<210> SEQ ID NO 717
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 717
aucgaauaga uggaucacaa a                                              21

<210> SEQ ID NO 718
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 718
acauuauauu gaauauucuu u                                              21

<210> SEQ ID NO 719
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 719
uuaauucaac aucgaauaga u                                              21

```
<210> SEQ ID NO 720
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 720
gauaauagca ucaaagaccu u                                                   21

<210> SEQ ID NO 721
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 721
ugacauauuu caaaaacuca a                                                   21

<210> SEQ ID NO 722
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 722
aaauuaauga cauauuucaa a                                                   21

<210> SEQ ID NO 723
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 723
gaagauauac uccauaguga a                                                   21

<210> SEQ ID NO 724
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 724
aauauuuaga agagcaacua a                                                   21

<210> SEQ ID NO 725
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 725
cgauguaaaa auuuuagcca a                                                   21
```

<210> SEQ ID NO 726
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 726
uucaacaucg aauagaugga u                                            21

<210> SEQ ID NO 727
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 727
guguggagaa aacaaccuaa a                                            21

<210> SEQ ID NO 728
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 728
ucaacauauu ugaucagucu u                                            21

<210> SEQ ID NO 729
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 729
ucagguaguc cauggacauu a                                            21

<210> SEQ ID NO 730
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 730
uuuagaagag caacuaacua a                                            21

<210> SEQ ID NO 731
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 731
uacauauaaa cuacaaguca a                                            21

<210> SEQ ID NO 732

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 732
ggaucacaaa acuucaauga a                                              21

<210> SEQ ID NO 733
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 733
agagcaacua acuaacuuaa u                                              21

<210> SEQ ID NO 734
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 734
accaacagca uagucaaaua a                                              21

<210> SEQ ID NO 735
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 735
aaccaacagc auagucaaau a                                              21

<210> SEQ ID NO 736
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 736
gaacucaacu caaaacuuga a                                              21

<210> SEQ ID NO 737
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 737
uacucuauaa aaucaaccaa a                                              21

<210> SEQ ID NO 738
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 738
cagcauaguc aaauaaaaga a                                          21

<210> SEQ ID NO 739
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 739
gaaauaagaa auguaaaaca u                                          21

<210> SEQ ID NO 740
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 740
cuaacuaacu uaauucaaaa u                                          21

<210> SEQ ID NO 741
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 741
augaacugag gcaaauuuaa a                                          21

<210> SEQ ID NO 742
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 742
ugaacugagg caaauuuaaa a                                          21

<210> SEQ ID NO 743
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 743
aaacaaccua aaugguaaau a                                          21

<210> SEQ ID NO 744
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 744
acaaccuaaa ugguaaauau a                                              21

<210> SEQ ID NO 745
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 745
aacgugggag aacuacaaau a                                              21

<210> SEQ ID NO 746
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 746
aaugaacuga ggcaaauuua a                                              21

<210> SEQ ID NO 747
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 747
guuggaagac uggaaagaca a                                              21

<210> SEQ ID NO 748
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 748
uggcaauguc cccaaugcaa u                                              21

<210> SEQ ID NO 749
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 749
gguaguccau ggacauuaau u                                              21

<210> SEQ ID NO 750
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 750
cauauaaacu acaagucaaa a                                              21

<210> SEQ ID NO 751
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 751
aaucccggaa aacaaagauu u                                              21

<210> SEQ ID NO 752
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 752
cuacuuggga ucacaaagca a                                              21

<210> SEQ ID NO 753
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 753
ugaaugaacu gaggcaaauu u                                              21

<210> SEQ ID NO 754
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 754
agcauaguca aauaaaagaa a                                              21

<210> SEQ ID NO 755
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 755
auuuagaaga gcaacuaacu a                                              21

<210> SEQ ID NO 756
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 756
aggcaaauuu aaaaggcaau a                                              21

<210> SEQ ID NO 757
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 757
cauauuugau cagucuuuuu a                                              21

<210> SEQ ID NO 758
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 758
aaaacaaaga uuuggguguuu u                                             21

<210> SEQ ID NO 759
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 759
caaucccgga aaacaaagau u                                              21

<210> SEQ ID NO 760
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 760
caacaaacau uauauugaau a                                              21

<210> SEQ ID NO 761
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 761
ggaaaacaaa gauuuggugu u                                              21

<210> SEQ ID NO 762
<211> LENGTH: 21
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 762
acaaagauuu ggcuguuuucu a                                              21

<210> SEQ ID NO 763
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 763
gaaugaacug aggcaaauuu a                                               21

<210> SEQ ID NO 764
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 764
ccauggacau uaauucaaca u                                               21

<210> SEQ ID NO 765
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 765
aacucaacuc aaaacuugaa a                                               21

<210> SEQ ID NO 766
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 766
caguugggac auggucuuaa a                                               21

<210> SEQ ID NO 767
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 767
aacauuauau ugaauauucu u                                               21

<210> SEQ ID NO 768
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 768
accagugaaa ucaaagaaga a                                              21

<210> SEQ ID NO 769
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 769
guugggccua gagaagauau a                                              21

<210> SEQ ID NO 770
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 770
cuccagagcc aaaaucaaga u                                              21

<210> SEQ ID NO 771
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 771
ggcaaauuua aaaggcaaua a                                              21

<210> SEQ ID NO 772
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 772
uacuugggau cacaaagcaa a                                              21

<210> SEQ ID NO 773
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 773
gaucagucuu uuuaugaucu a                                              21

<210> SEQ ID NO 774
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 774
gaaagccucc uagaagaaaa a                                              21

<210> SEQ ID NO 775
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 775
agucaaauaa aagaaauaga a                                              21

<210> SEQ ID NO 776
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 776
auacucuaua aaaucaacca a                                              21

<210> SEQ ID NO 777
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 777
gaacugaggc aaauuuaaaa a                                              21

<210> SEQ ID NO 778
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 778
agacccagca acucucaagu u                                              21

<210> SEQ ID NO 779
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 779
auauaaacua caagucaaaa a                                              21

<210> SEQ ID NO 780
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 780
ugaaagccuc cuagaagaaa a                                              21

<210> SEQ ID NO 781
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 781
gggagaacua caaauauggu u                                              21

<210> SEQ ID NO 782
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 782
agauuugcua uguuagacga u                                              21

<210> SEQ ID NO 783
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 783
gaacccacag aaauuucucu a                                              21

<210> SEQ ID NO 784
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 784
acuucaacaa aaagugaaau a                                              21

<210> SEQ ID NO 785
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 785
aguccaugga cauuaauuca a                                              21

<210> SEQ ID NO 786
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 786

-continued aacugaggca aauuuaaaag a                                           21

<210> SEQ ID NO 787
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 787
gggccaaauu aaugacauau u                                           21

<210> SEQ ID NO 788
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 788
auccauccaa cagauucaga a                                           21

<210> SEQ ID NO 789
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 789
aagauuuggu guuucuacu u                                            21

<210> SEQ ID NO 790
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 790
gucucaaaau ggaagguuau a                                           21

<210> SEQ ID NO 791
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 791
acugaggcaa auuuaaaagg a                                           21

<210> SEQ ID NO 792
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 792
gggacauggu cuuaaagacu u                                           21

<210> SEQ ID NO 793
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 793
augguaaaua uaacaaacca a                                           21

<210> SEQ ID NO 794
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 794
gggaaaucac gaaaccaacu a                                           21

<210> SEQ ID NO 795
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 795
ccaacagcau agucaaauaa a                                           21

<210> SEQ ID NO 796
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 796
uuuucuacuu gggaucacaa a                                           21

<210> SEQ ID NO 797
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 797
agaacuacau auaaacuaca a                                           21

<210> SEQ ID NO 798
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 798
agaguaugug uaaaaaucug u                                           21

```
<210> SEQ ID NO 799
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 799
aaaacaagau aauagcauca a                                              21

<210> SEQ ID NO 800
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 800
aguaugugua aaaaucugua a                                              21

<210> SEQ ID NO 801
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 801
agucaaaaau gaagagguaa a                                              21

<210> SEQ ID NO 802
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 802
ggacaugguc uuaaagacuu u                                              21

<210> SEQ ID NO 803
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 803
gaggcaaauu uaaaaggcaa u                                              21

<210> SEQ ID NO 804
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 804
gucuuaaaga cuuuguccau a                                              21
```

```
<210> SEQ ID NO 805
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 805
cugaggcaaa uuuaaaaggc a                                              21

<210> SEQ ID NO 806
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 806 gcaucccgg aaaacaaaga u                                               21

<210> SEQ ID NO 807
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 807
ugaggcaaau uuaaaaggca a                                              21

<210> SEQ ID NO 808
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 808
ucuacuucaa caaaaaguga a                                              21

<210> SEQ ID NO 809
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 809
uauguguaaa aaucuguaau a                                              21

<210> SEQ ID NO 810
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 810
aaugcaaucc cggaaaacaa a                                              21

<210> SEQ ID NO 811
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 811
cuugaaagcc uccuagaaga a                                                   21

<210> SEQ ID NO 812
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 812
guauguguaa aaaucuguaa u                                                   21

<210> SEQ ID NO 813
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 813
cagaguaugu guaaaaaucu u                                                   21

<210> SEQ ID NO 814
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 814
gaguaugugu aaaaaucugu a                                                   21

<210> SEQ ID NO 815
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 815
ucaguuggga cauggucuua a                                                   21

<210> SEQ ID NO 816
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 816
ggucuuaaag acuuugucca u                                                   21

<210> SEQ ID NO 817
<211> LENGTH: 21
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 817
ucuuaaagac uuuguccaua a                                              21

<210> SEQ ID NO 818
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 818
uucaguuggg acauggucuu a                                              21

<210> SEQ ID NO 819
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 819
aauauaaugu uuguugucuu ucc                                            23

<210> SEQ ID NO 820
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 820
aaaaagaagg agcuuaauug uga                                            23

<210> SEQ ID NO 821
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 821
uugaguugag uucaagugac aua                                            23

<210> SEQ ID NO 822
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 822
aaagaaggag cuuaauugug aac                                            23

<210> SEQ ID NO 823
<211> LENGTH: 23
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 823
aaguuuugag uugaguucaa gug                                              23

<210> SEQ ID NO 824
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 824
uuagauugcu ucacuaugga gua                                              23

<210> SEQ ID NO 825
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 825
uaaaaagaag gagcuuaauu gug                                              23

<210> SEQ ID NO 826
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 826
aaaacuugag aguugcuggg ucu                                              23

<210> SEQ ID NO 827
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 827
uugaguucaa gugacauauu cuu                                              23

<210> SEQ ID NO 828
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 828
auaaaaagaa ggagcuuaau ugu                                              23

<210> SEQ ID NO 829
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 829
aaaagaauau ucaauauaau guu                                              23

<210> SEQ ID NO 830
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 830
uuuugaauua aguuaguuag uug                                              23

<210> SEQ ID NO 831
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 831
aaauaacuag aggaacaaua aaa                                              23

<210> SEQ ID NO 832
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 832
uaauuagauu gcuucacuau gga                                              23

<210> SEQ ID NO 833
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 833
aauuagauug cuucacuaug gag                                              23

<210> SEQ ID NO 834
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 834
uuucauugaa guuuugugau cca                                              23

<210> SEQ ID NO 835
<211> LENGTH: 23
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 835
uuauagagua uaaccuucca uuu                                           23

<210> SEQ ID NO 836
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 836
auuagauugc uucacuaugg agu                                           23

<210> SEQ ID NO 837
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 837
uuuuuacauc gucuaacaua gca                                           23

<210> SEQ ID NO 838
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 838
aauaaaaaga aggagcuuaa uug                                           23

<210> SEQ ID NO 839
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 839
uuugaauuaa guuaguuagu ugc                                           23

<210> SEQ ID NO 840
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 840
aaauauguca uuaauuuggc ccu                                           23

<210> SEQ ID NO 841
<211> LENGTH: 23
<212> TYPE: RNA
<213> ORGANISM: Artificial Sequence
<220> FEATURE:
<223> OTHER INFORMATION: Description of Artificial Sequence: Synthetic

```
        oligonucleotide

<400> SEQUENCE: 841
auaacuagag gaacaauaaa aag                                               23

<210> SEQ ID NO 842
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 842
aaaaagacug aucaaauaug uug                                               23

<210> SEQ ID NO 843
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 843
aaaaacuuga gaguugcugg guc                                               23

<210> SEQ ID NO 844
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 844
uuaaugucca uggacuaccu gau                                               23

<210> SEQ ID NO 845
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 845
uuauauguag uucuucucag uuc                                               23

<210> SEQ ID NO 846
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 846
aauuaaguua guuaguugcu cuu                                               23

<210> SEQ ID NO 847
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 847
auauuuacca uuuagguugu uuu                                          23

<210> SEQ ID NO 848
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 848
auggaguaua ucuucucuag gcc                                          23

<210> SEQ ID NO 849
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 849
aaagacugau caaauauguu gag                                          23

<210> SEQ ID NO 850
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 850
auucaauaua auguuguug ucu                                           23

<210> SEQ ID NO 851
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 851
uuugacuugu aguuuauaug uag                                          23

<210> SEQ ID NO 852
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 852
aauucuggag gaaauaacua gag                                          23

<210> SEQ ID NO 853
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 853
uuaaguuagu uaguugcucu ucu                                           23

<210> SEQ ID NO 854
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 854
aauaacuaga ggaacaauaa aaa                                           23

<210> SEQ ID NO 855
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 855
uagaauuuuu ucuucuagga ggc                                           23

<210> SEQ ID NO 856
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 856
auauucaaua uaauguuugu ugu                                           23

<210> SEQ ID NO 857
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 857
auaguugguu ucgugauuuc cca                                           23

<210> SEQ ID NO 858
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 858
aaaagacuga ucaaauaugu uga                                           23

<210> SEQ ID NO 859
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 859
```
uuuauagagu auaaccuucc auu         23

<210> SEQ ID NO 860
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 860
aaaccauauu uguaguucuc cca         23

<210> SEQ ID NO 861
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 861
aaacaccaaa ucuuuguuuu ccg         23

<210> SEQ ID NO 862
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 862
uuagguuguu uucuccacac uca         23

<210> SEQ ID NO 863
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 863
uuugaguuga guucaaguga cau         23

<210> SEQ ID NO 864
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 864
auugaaguuu ugugauccau cua         23

<210> SEQ ID NO 865
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 865

```
aauauucaau auaauguuug uug                                                 23

<210> SEQ ID NO 866
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 866
auuuagguug uuucuccac acu                                                  23

<210> SEQ ID NO 867
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 867
auagaucaua aaaagacuga uca                                                 23

<210> SEQ ID NO 868
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 868
uucaauauaa uguuuguugu cuu                                                 23

<210> SEQ ID NO 869
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 869
uuuuauuuga cuaugcuguu ggu                                                 23

<210> SEQ ID NO 870
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 870
uuuauaugua guucuucuca guu                                                 23

<210> SEQ ID NO 871
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 871
uuuacaucgu cuaacauagc aaa                                                 23
```

<210> SEQ ID NO 872
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 872
auagagaaau uucugugggu ucu                                              23

<210> SEQ ID NO 873
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 873
auauuucacu uuuuguugaa gua                                              23

<210> SEQ ID NO 874
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 874
uuuugaguug aguucaagug aca                                              23

<210> SEQ ID NO 875
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 875
uauuucuuuu auuugacuau gcu                                              23

<210> SEQ ID NO 876
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 876
aucaaauaug uugaguuuuu gaa                                              23

<210> SEQ ID NO 877
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 877
auuucacuuu uuguugaagu aga                                              23

```
<210> SEQ ID NO 878
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 878
aaacuugaga guugcugggu cug                                              23

<210> SEQ ID NO 879
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 879
aauuugccuc aguucauuca aag                                              23

<210> SEQ ID NO 880
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 880
auuuuugacu uguaguuuau aug                                              23

<210> SEQ ID NO 881
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 881
uuugaugcua uuaucuuguu uuu                                              23

<210> SEQ ID NO 882
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 882
uugaauuaag uuaguuaguu gcu                                              23

<210> SEQ ID NO 883
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 883
uuuuacaucg ucuaacauag caa                                              23
```

```
<210> SEQ ID NO 884
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 884
uuuugcuuug ugaucccaag uag                                           23

<210> SEQ ID NO 885
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 885
uuacaucguc uaacauagca aau                                           23

<210> SEQ ID NO 886
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 886
uauauguagu ucuucucagu ucc                                           23

<210> SEQ ID NO 887
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 887
auuggcuaaa auuuuacau cgu                                            23

<210> SEQ ID NO 888
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 888
uagauugcuu cacuauggag uau                                           23

<210> SEQ ID NO 889
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 889
aauauuucac uuuuuguuga agu                                           23

<210> SEQ ID NO 890
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 890
uauggaguau aucuucucua ggc                                             23

<210> SEQ ID NO 891
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 891
uuauauuuac cauuuagguu guu                                             23

<210> SEQ ID NO 892
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 892
uauaguuggu uucgugauuu ccc                                             23

<210> SEQ ID NO 893
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 893
aagauagaga aauuucugug ggu                                             23

<210> SEQ ID NO 894
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 894
uaacauagca aaucuugauu uug                                             23

<210> SEQ ID NO 895
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 895
uauucgaugu ugaauuaaug ucc                                             23

<210> SEQ ID NO 896
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 896
aaaucuugau uuggcucug gag                                              23

<210> SEQ ID NO 897
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 897
uuucacuuuu uguugaagua gaa                                             23

<210> SEQ ID NO 898
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 898
auucgauguu gaauuaaugu cca                                             23

<210> SEQ ID NO 899
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 899
uucgauguug aauuaauguc cau                                             23

<210> SEQ ID NO 900
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 900
auuucuuuua uuugacuaug cug                                             23

<210> SEQ ID NO 901
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 901
uagacaugaa aaacuugaga guu                                             23

<210> SEQ ID NO 902
<211> LENGTH: 23
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 902
uuugugaucc aucuauucga ugu                                             23

<210> SEQ ID NO 903
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 903
aaagaauauu caauauaaug uuu                                             23

<210> SEQ ID NO 904
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 904
aucuauucga uguugaauua aug                                             23

<210> SEQ ID NO 905
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 905
aaggucuuug augcuauuau cuu                                             23

<210> SEQ ID NO 906
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 906
uugaguuuuu gaaauauguc auu                                             23

<210> SEQ ID NO 907
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 907
uuugaaauau gucauuaauu ugg                                             23

<210> SEQ ID NO 908
<211> LENGTH: 23
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 908
uucacuaugg aguauaucuu cuc                                              23

<210> SEQ ID NO 909
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 909
uuaguugcuc uucuaaauau uuc                                              23

<210> SEQ ID NO 910
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 910
uuggcuaaaa uuuuuacauc guc                                              23

<210> SEQ ID NO 911
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 911
auccaucuau ucgauguuga auu                                              23

<210> SEQ ID NO 912
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 912
uuuagguugu uuucuccaca cuc                                              23

<210> SEQ ID NO 913
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 913
aagacugauc aaauauguug agu                                              23

<210> SEQ ID NO 914
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 914
uaauguccau ggacuaccug aua                                          23

<210> SEQ ID NO 915
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 915
uuaguuaguu gcucuucuaa aua                                          23

<210> SEQ ID NO 916
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 916
uugacuugua guuuauaugu agu                                          23

<210> SEQ ID NO 917
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 917
uucauugaag uuuugugauc cau                                          23

<210> SEQ ID NO 918
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 918
auuaaguuag uuaguugcuc uuc                                          23

<210> SEQ ID NO 919
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 919
uuauuugacu augcuguugg uuu                                          23

<210> SEQ ID NO 920
<211> LENGTH: 23
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 920
uauuugacua ugcuguuggu uua                                           23

<210> SEQ ID NO 921
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 921
uucaaguuuu gaguugaguu caa                                           23

<210> SEQ ID NO 922
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 922
uuugguugau uuuauagagu aua                                           23

<210> SEQ ID NO 923
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 923
uucuuuuauu ugacuaugcu guu                                           23

<210> SEQ ID NO 924
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 924
auguuuuaca uuucuuauuu cau                                           23

<210> SEQ ID NO 925
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 925
auuuugaauu aaguuaguua guu                                           23

<210> SEQ ID NO 926
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 926
uuuaaauuug ccucaguuca uuc                                              23

<210> SEQ ID NO 927
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 927
uuuuaaauuu gccucaguuc auu                                              23

<210> SEQ ID NO 928
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 928
uauuuaccau uuagguuguu uuc                                              23

<210> SEQ ID NO 929
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 929
uauauuuacc auuuagguug uuu                                              23

<210> SEQ ID NO 930
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 930
uauuuguagu ucucccacgu uuc                                              23

<210> SEQ ID NO 931
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 931
uuaaauuugc cucaguucau uca                                              23

<210> SEQ ID NO 932
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 932
uugucuuucc agucuuccaa cuc                                        23

<210> SEQ ID NO 933
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 933
auugcauugg ggacauugcc agu                                        23

<210> SEQ ID NO 934
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 934
aauuaauguc cauggacuac cug                                        23

<210> SEQ ID NO 935
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 935
uuuugacuug uaguuuauau gua                                        23

<210> SEQ ID NO 936
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 936
aaaucuuugu uuuccgggau ugc                                        23

<210> SEQ ID NO 937
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 937
uugcuuugug aucccaagua gaa                                        23

<210> SEQ ID NO 938
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 938
```
aaauuugccu caguucauuc aaa 23

<210> SEQ ID NO 939
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 939
uuucuuuuau uugacuaugc ugu 23

<210> SEQ ID NO 940
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 940
uaguuaguug cucuucuaaa uau 23

<210> SEQ ID NO 941
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 941
uauugccuuu uaaauuugcc uca 23

<210> SEQ ID NO 942
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 942
uaaaaagacu gaucaaauau guu 23

<210> SEQ ID NO 943
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 943
aaaacaccaa aucuuuguuu ucc 23

<210> SEQ ID NO 944
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 944

-continued aaucuuuguu uuccgggauu gca                                          23

<210> SEQ ID NO 945
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 945
uauucaauau aauguuuguu guc                                          23

<210> SEQ ID NO 946
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 946
aacaccaaau cuuuguuuuc cgg                                          23

<210> SEQ ID NO 947
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 947
uagaaaacac caaaucuuug uuu                                          23

<210> SEQ ID NO 948
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 948
uaaauuugcc ucaguucauu caa                                          23

<210> SEQ ID NO 949
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 949
auguugaauu aauguccaug gac                                          23

<210> SEQ ID NO 950
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 950
uuucaaguuu ugaguugagu uca                                          23

<210> SEQ ID NO 951
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 951
uuuaagacca ugucccaacu gaa                                          23

<210> SEQ ID NO 952
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 952
aagaauauuc aauauaaugu uug                                          23

<210> SEQ ID NO 953
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 953
uucuucuuug auuucacugg uuu                                          23

<210> SEQ ID NO 954
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 954
uauaucuucu cuaggcccaa cca                                          23

<210> SEQ ID NO 955
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 955
aucuugauuu uggcucugga gau                                          23

<210> SEQ ID NO 956
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 956
uuauugccuu uuaaauuugc cuc                                          23

-continued

```
<210> SEQ ID NO 957
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 957
uuugcuuugu gaucccaagu aga                                              23

<210> SEQ ID NO 958
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 958
uagaucauaa aaagacugau caa                                              23

<210> SEQ ID NO 959
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 959
uuuuucuucu aggaggcuuu caa                                              23

<210> SEQ ID NO 960
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 960
uucuauuucu uuuauuugac uau                                              23

<210> SEQ ID NO 961
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 961
uugguugauu uuauagagua uaa                                              23

<210> SEQ ID NO 962
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 962
uuuuuaaauu ugccucaguu cau                                              23
```

```
<210> SEQ ID NO 963
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 963
aacuugagag uugcugdguc uga                                               23

<210> SEQ ID NO 964
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 964
uuuuugacuu guaguuuaua ugu                                               23

<210> SEQ ID NO 965
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 965
uuuucuucua ggaggcuuuc aag                                               23

<210> SEQ ID NO 966
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 966
aaccauauuu guaguucucc cac                                               23

<210> SEQ ID NO 967
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 967
aucgucuaac auagcaaauc uug                                               23

<210> SEQ ID NO 968
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 968
uagagaaauu ucugugdguu cuu                                               23

<210> SEQ ID NO 969
```

-continued

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 969
uauuucacuu uuuguugaag uag                                              23

<210> SEQ ID NO 970
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 970
uugaauuaau guccauggac uac                                              23

<210> SEQ ID NO 971
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 971
ucuuuuaaau uugccucagu uca                                              23

<210> SEQ ID NO 972
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 972
aauaugucau uaauuuggcc cuu                                              23

<210> SEQ ID NO 973
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 973
uucugaaucu guuggaugga uca                                              23

<210> SEQ ID NO 974
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 974
aaguagaaaa caccaaaucu uug                                              23

<210> SEQ ID NO 975
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 975
uauaaccuuc cauuugaga cuu                                              23

<210> SEQ ID NO 976
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 976
uccuuuuaaa uuugccucag uuc                                             23

<210> SEQ ID NO 977
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 977
aagucuuuaa gaccaugucc caa                                             23

<210> SEQ ID NO 978
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 978
uugguuuguu auauuuacca uuu                                             23

<210> SEQ ID NO 979
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 979
uaguugguuu cgugauuucc caa                                             23

<210> SEQ ID NO 980
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 980
uuuauuugac uaugcuguug guu                                             23

<210> SEQ ID NO 981
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 981
uuugugaucc caaguagaaa aca                                          23

<210> SEQ ID NO 982
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 982
uuguaguuua uauguaguuc uuc                                          23

<210> SEQ ID NO 983
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 983
acagauuuuu acacauacuc ugu                                          23

<210> SEQ ID NO 984
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 984
uugaugcuau uaucuuguuu uuc                                          23

<210> SEQ ID NO 985
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 985
uuacagauuu uuacacauac ucu                                          23

<210> SEQ ID NO 986
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 986
uuuaccucuu cauuuuugac uug                                          23

<210> SEQ ID NO 987
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 987
aaagucuuua agaccauguc cca                                              23

<210> SEQ ID NO 988
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 988
auugccuuuu aaauuugccu cag                                              23

<210> SEQ ID NO 989
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 989
uauggacaaa gucuuuaaga cca                                              23

<210> SEQ ID NO 990
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 990
ugccuuuuaa auuugccuca guu                                              23

<210> SEQ ID NO 991
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 991
aucuuuguuu uccgggauug cau                                              23

<210> SEQ ID NO 992
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 992
uugccuuuua aauuugccuc agu                                              23

<210> SEQ ID NO 993
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 993
uucacuuuuu guugaaguag aau                                              23

<210> SEQ ID NO 994
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 994
uauuacagau uuuuacacau acu                                              23

<210> SEQ ID NO 995
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 995
uuuguuuucc gggauugcau ugg                                              23

<210> SEQ ID NO 996
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 996
uucuucuagg aggcuuucaa guu                                              23

<210> SEQ ID NO 997
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 997
auuacagauu uuuacacaua cuc                                              23

<210> SEQ ID NO 998
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 998
aagauuuuua cacauacucu gug                                              23

<210> SEQ ID NO 999
<211> LENGTH: 23
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 999
uacagauuuu uacacauacu cug                                                23

<210> SEQ ID NO 1000
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1000
uuaagaccau gucccaacug aag                                                23

<210> SEQ ID NO 1001
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1001
auggacaaag ucuuuaagac cau                                                23

<210> SEQ ID NO 1002
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1002
uuauggacaa agucuuuaag acc                                                23

<210> SEQ ID NO 1003
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1003
uaagaccaug ucccaacuga agg                                                23

<210> SEQ ID NO 1004
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1004
ucacaauuaa gcuccuucuu u                                                  21

<210> SEQ ID NO 1005
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1005
uuauuguucc ucuaguuauu u                                              21

<210> SEQ ID NO 1006
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1006
gcuauguuag acgauguaaa a                                              21

<210> SEQ ID NO 1007
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1007
ggacaugguc uuaaagacuu u                                              21

<210> SEQ ID NO 1008
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1008
caaaaacuca acauauuuga u                                              21

<210> SEQ ID NO 1009
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1009
accagugaaa ucaaagaaga a                                              21

<210> SEQ ID NO 1010
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1010
cacaauuaag cuccuucuuu u                                              21

<210> SEQ ID NO 1011
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1011
cuauguuaga cgauguaaaa a                                              21

<210> SEQ ID NO 1012
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1012
ucaacauauu ugaucagucu u                                              21

<210> SEQ ID NO 1013
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1013
aacugagaag aacuacauau a                                              21

<210> SEQ ID NO 1014
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1014
acaauuaagc uccuucuuuu u                                              21

<210> SEQ ID NO 1015
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1015
cuccagagcc aaaaucaaga u                                              21

<210> SEQ ID NO 1016
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1016
cgauguaaaa auuuuagcca a                                              21

<210> SEQ ID NO 1017
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1017
```
gucuuaaaga cuuuguccau a                                          21

<210> SEQ ID NO 1018
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1018
caacauauuu gaucagucuu u                                          21

<210> SEQ ID NO 1019
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1019
acugagaaga acuacauaua a                                          21

<210> SEQ ID NO 1020
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1020
ccagagccaa aaucaagauu u                                          21

<210> SEQ ID NO 1021
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1021
gauguaaaaa uuuuagccaa u                                          21

<210> SEQ ID NO 1022
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1022
ucuuaaagac uuuguccaua a                                          21

<210> SEQ ID NO 1023
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1023
aacauauuug aucagucuuu u                                              21

<210> SEQ ID NO 1024
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1024
cugagaagaa cuacauauaa a                                              21

<210> SEQ ID NO 1025
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1025
aauuaagcuc cuucuuuuua u                                              21

<210> SEQ ID NO 1026
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1026
aaaucaagau uugcuauguu a                                              21

<210> SEQ ID NO 1027
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1027
uucaguuggg acauggucuu a                                              21

<210> SEQ ID NO 1028
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1028
gggccaaauu aaugacauau u                                              21

<210> SEQ ID NO 1029
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1029
acauauuuga ucagucuuuu u                                              21

-continued

<210> SEQ ID NO 1030
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1030
agaacuacau auaaacuaca a                                              21

<210> SEQ ID NO 1031
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1031
auuaagcucc uucuuuuuau u                                              21

<210> SEQ ID NO 1032
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1032
agauuugcua uguuagacga u                                              21

<210> SEQ ID NO 1033
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1033
ucaguuggga cauggucuua a                                              21

<210> SEQ ID NO 1034
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1034
ggccaaauua augacauauu u                                              21

<210> SEQ ID NO 1035
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1035
cauauuugau cagucuuuuu a                                              21

<210> SEQ ID NO 1036
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1036
uacauauaaa cuacaaguca a                                             21

<210> SEQ ID NO 1037
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1037
uuuuauuguu ccucuaguua u                                             21

<210> SEQ ID NO 1038
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1038
uugcuauguu agacgaugua a                                             21

<210> SEQ ID NO 1039
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1039
caguugggac auggucuuaa a                                             21

<210> SEQ ID NO 1040
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1040
aaauuaauga cauauuucaa a                                             21

<210> SEQ ID NO 1041
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1041
gaucagucuu uuuaugaucu a                                             21

```
<210> SEQ ID NO 1042
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1042
acauauaaac uacaagucaa a                                              21

<210> SEQ ID NO 1043
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1043
uuuauuguuc cucuaguuau u                                              21

<210> SEQ ID NO 1044
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1044
ugcuauguua gacgauguaa a                                              21

<210> SEQ ID NO 1045
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1045
gggacauggu cuuaaagacu u                                              21

<210> SEQ ID NO 1046
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1046
ugacauauuu caaaaacuca a                                              21

<210> SEQ ID NO 1047
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1047
aucagucuuu uuaugaucua u                                              21

<210> SEQ ID NO 1048
```

<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1048
cauauaaacu acaagucaaa a        21

<210> SEQ ID NO 1049
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1049
cuugaacuca acucaaaacu u        21

<210> SEQ ID NO 1050
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1050
cuacuucaac aaaaagugaa a        21

<210> SEQ ID NO 1051
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1051
aagagcaacu aacuaacuua a        21

<210> SEQ ID NO 1052
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1052
aaacaagaua auagcaucaa a        21

<210> SEQ ID NO 1053
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1053
gcauagucaa auaaaagaaa u        21

<210> SEQ ID NO 1054
<211> LENGTH: 21

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1054
auauaaacua caagucaaaa a                                             21

<210> SEQ ID NO 1055
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1055
gaacucaacu caaaacuuga a                                             21

<210> SEQ ID NO 1056
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1056
uacuucaaca aaagugaaa u                                              21

<210> SEQ ID NO 1057
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1057
agagcaacua acuaacuuaa u                                             21

<210> SEQ ID NO 1058
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1058
gauaauagca ucaaagaccu u                                             21

<210> SEQ ID NO 1059
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1059
cauagucaaa uaaagaaau a                                              21

<210> SEQ ID NO 1060
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1060
uauaaacuac aagucaaaaa u                                               21

<210> SEQ ID NO 1061
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1061
aacucaacuc aaaacuugaa a                                               21

<210> SEQ ID NO 1062
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1062
acuucaacaa aaagugaaau a                                               21

<210> SEQ ID NO 1063
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1063
gagcaacuaa cuaacuuaau u                                               21

<210> SEQ ID NO 1064
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1064
aaccaacagc auagucaaau a                                               21

<210> SEQ ID NO 1065
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1065
agucaaauaa aagaaauaga a                                               21

<210> SEQ ID NO 1066
<211> LENGTH: 21
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 1066
agucaaaaau gaagagguaa a                                             21

<210> SEQ ID NO 1067
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1067
cuugaaagcc uccuagaaga a                                             21

<210> SEQ ID NO 1068
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1068
cuucaacaaa aagugaaaua u                                             21

<210> SEQ ID NO 1069
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1069
caacuaacua acuuaauuca a                                             21

<210> SEQ ID NO 1070
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1070
accaacagca uagucaaaua a                                             21

<210> SEQ ID NO 1071
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1071
gaacccacag aaauuucucu a                                             21

<210> SEQ ID NO 1072
<211> LENGTH: 21
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 1072
gaauauguca cuugaacuca a                                              21

<210> SEQ ID NO 1073
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1073
ugaaagccuc cuagaagaaa a                                              21

<210> SEQ ID NO 1074
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1074
uucaacaaaa agugaaauau u                                              21

<210> SEQ ID NO 1075
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1075
aacuaacuaa cuuaauucaa a                                              21

<210> SEQ ID NO 1076
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1076
ccaacagcau agucaaauaa a                                              21

<210> SEQ ID NO 1077
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1077
aacccacaga aauuucucua u                                              21

<210> SEQ ID NO 1078
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 1078
ugucacuuga acucaacuca a                                          21

<210> SEQ ID NO 1079
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1079
gaaagccucc uagaagaaaa a                                          21

<210> SEQ ID NO 1080
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1080
aauauuuaga agagcaacua a                                          21

<210> SEQ ID NO 1081
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1081
acuaacuaac uuaauucaaa a                                          21

<210> SEQ ID NO 1082
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1082
caacagcaua gucaaauaaa a                                          21

<210> SEQ ID NO 1083
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1083
ccacagaaau uucucuaucu u                                          21

<210> SEQ ID NO 1084
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 1084
gucacuugaa cucaacucaa a                                              21

<210> SEQ ID NO 1085
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1085
cuccuagaag aaaaaauucu a                                              21

<210> SEQ ID NO 1086
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1086
auuuagaaga gcaacuaacu a                                              21

<210> SEQ ID NO 1087
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1087
cuaacuaacu uaauucaaaa u                                              21

<210> SEQ ID NO 1088
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1088
cagcauaguc aaauaaaaga a                                              21

<210> SEQ ID NO 1089
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1089
gaaauaagaa auguaaaaca u                                              21

<210> SEQ ID NO 1090
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1090
ucacuugaac ucaacucaaa a                                              21

<210> SEQ ID NO 1091
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1091
ucuacuucaa caaaaaguga a                                              21

<210> SEQ ID NO 1092
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1092
uuuagaagag caacuaacua a                                              21

<210> SEQ ID NO 1093
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1093
aaaacaagau aauagcauca a                                              21

<210> SEQ ID NO 1094
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1094
agcauaguca aauaaaagaa a                                              21

<210> SEQ ID NO 1095
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1095
agacccagca acucucaagu u                                              21

<210> SEQ ID NO 1096
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1096
```
aguccaugga cauuaauuca a        21

<210> SEQ ID NO 1097
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1097
gauggaucac aaaacuucaa u        21

<210> SEQ ID NO 1098
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1098
cuagagaaga uauacuccau a        21

<210> SEQ ID NO 1099
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1099
aaagacaaca aacauuauau u        21

<210> SEQ ID NO 1100
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1100
cauuauauug aauauucuuu u        21

<210> SEQ ID NO 1101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1101
gacccagcaa cucucaaguu u        21

<210> SEQ ID NO 1102
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1102
ggaucacaaa acuucaauga a         21

<210> SEQ ID NO 1103
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1103
gaagauauac uccauaguga a         21

<210> SEQ ID NO 1104
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1104
gacaacaaac auuauauuga a         21

<210> SEQ ID NO 1105
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1105
gggaaaucac gaaaccaacu a         21

<210> SEQ ID NO 1106
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1106
acccagcaac ucucaaguuu u         21

<210> SEQ ID NO 1107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1107
ggacauuaau ucaacaucga a         21

<210> SEQ ID NO 1108
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1108
gaucacaaaa cuucaaugaa a         21

<210> SEQ ID NO 1109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1109
acuccauagu gaagcaaucu a                                              21

<210> SEQ ID NO 1110
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1110
acaacaaaca uuauauugaa u                                              21

<210> SEQ ID NO 1111
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1111
ggaaaucacg aaaccaacua u                                              21

<210> SEQ ID NO 1112
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1112
cccagcaacu cucaaguuuu u                                              21

<210> SEQ ID NO 1113
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1113
gacauuaauu caacaucgaa u                                              21

<210> SEQ ID NO 1114
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1114
aacgugggag aacuacaaau a                                              21

<210> SEQ ID NO 1115
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1115
cuccauagug aagcaaucua a                                              21

<210> SEQ ID NO 1116
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1116
caacaaacau uauauugaau a                                              21

<210> SEQ ID NO 1117
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1117
gaaaucacga aaccaacuau a                                              21

<210> SEQ ID NO 1118
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1118
cucucaaguu uuucaugucu a                                              21

<210> SEQ ID NO 1119
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1119
acauuaauuc aacaucgaau a                                              21

<210> SEQ ID NO 1120
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1120
gggagaacua caaauauggu u                                              21

```
<210> SEQ ID NO 1121
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1121
uccauaguga agcaaucuaa u                                              21

<210> SEQ ID NO 1122
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1122
aacaaacauu auauugaaua u                                              21

<210> SEQ ID NO 1123
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1123
uggcaauguc cccaaugcaa u                                              21

<210> SEQ ID NO 1124
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1124
ucagguaguc cauggacauu a                                              21

<210> SEQ ID NO 1125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1125
uuaauucaac aucgaauaga u                                              21

<210> SEQ ID NO 1126
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1126
ggagaacuac aaauaugguu u                                              21

<210> SEQ ID NO 1127
```

<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1127
ccauagugaa gcaaucuaau u            21

<210> SEQ ID NO 1128
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1128
acaaacauua uauugaauau u            21

<210> SEQ ID NO 1129
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1129
aaugcaaucc cggaaaacaa a            21

<210> SEQ ID NO 1130
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1130
cagguagucc auggacauua a            21

<210> SEQ ID NO 1131
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1131
uucaacaucg aauagaugga u            21

<210> SEQ ID NO 1132
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1132
guugggccua gagaagauau a            21

<210> SEQ ID NO 1133
<211> LENGTH: 21

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1133
cauagugaag caaucuaauu a                                              21

<210> SEQ ID NO 1134
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1134
aacauuauau ugaauauucu u                                              21

<210> SEQ ID NO 1135
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1135
gcaaucccgg aaaacaaaga u                                              21

<210> SEQ ID NO 1136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1136
gguaguccau ggacauuaau u                                              21

<210> SEQ ID NO 1137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1137
aucgaauaga uggaucacaa a                                              21

<210> SEQ ID NO 1138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1138
ccuagagaag auauacucca u                                              21

<210> SEQ ID NO 1139
<211> LENGTH: 21
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 1139
guuggaagac uggaaagaca a                                              21

<210> SEQ ID NO 1140
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1140
acauuauauu gaauauucuu u                                              21

<210> SEQ ID NO 1141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1141
caaucccgga aaacaaagau u                                              21

<210> SEQ ID NO 1142
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1142
cuacuuggga ucacaaagca a                                              21

<210> SEQ ID NO 1143
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1143
acaaccuaaa ugguaaauau a                                              21

<210> SEQ ID NO 1144
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1144
auccauccaa cagauucaga a                                              21

<210> SEQ ID NO 1145
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 1145
aacugaggca aauuuaaaag a                                              21

<210> SEQ ID NO 1146
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1146
agaguaugug uaaaaaucug u                                              21

<210> SEQ ID NO 1147
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1147
aaucccggaa aacaaagauu u                                              21

<210> SEQ ID NO 1148
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1148
uacuugggau cacaaagcaa a                                              21

<210> SEQ ID NO 1149
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1149
caaccuaaau gguaaauaua a                                              21

<210> SEQ ID NO 1150
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1150
uugaaugaac ugaggcaaau u                                              21

<210> SEQ ID NO 1151
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1151
acugaggcaa auuuaaaagg a                                              21

<210> SEQ ID NO 1152
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1152
gaguaugugu aaaaaucugu a                                              21

<210> SEQ ID NO 1153
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1153
acuugggauc acaaagcaaa a                                              21

<210> SEQ ID NO 1154
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1154
augguaaaua uaacaaacca a                                              21

<210> SEQ ID NO 1155
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1155
ugaaugaacu gaggcaaauu u                                              21

<210> SEQ ID NO 1156
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1156
cugaggcaaa uuuaaaaggc a                                              21

<210> SEQ ID NO 1157
<211> LENGTH: 21
<212> TYPE: RNA
<213> ORGANISM: Artificial Sequence
<220> FEATURE:
<223> OTHER INFORMATION: Description of Artificial Sequence: Synthetic
```

-continued

```
        oligonucleotide

<400> SEQUENCE: 1157
aguaugugua aaaaucugua a                                        21

<210> SEQ ID NO 1158
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1158
gaaaacaaag auuuggucuu u                                        21

<210> SEQ ID NO 1159
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1159 aguuggaga aaacaaccua a                                         21

<210> SEQ ID NO 1160
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1160
gucucaaaau ggaagguuau a                                        21

<210> SEQ ID NO 1161
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1161
gaaugaacug aggcaaauuu a                                        21

<210> SEQ ID NO 1162
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1162
ugaggcaaau uuaaaaggca a                                        21

<210> SEQ ID NO 1163
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 1163
guauguguaa aaaucuguaa u                                              21

<210> SEQ ID NO 1164
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1164
aaaacaaaga uuugguguuu u                                              21

<210> SEQ ID NO 1165
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1165
guguggagaa aacaaccuaa a                                              21

<210> SEQ ID NO 1166
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1166
auggaagguu auacucuaua a                                              21

<210> SEQ ID NO 1167
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1167
aaugaacuga ggcaaauuua a                                              21

<210> SEQ ID NO 1168
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1168
gaggcaaauu uaaaaggcaa u                                              21

<210> SEQ ID NO 1169
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1169
uauguguaaa aaucuguaau a								21

<210> SEQ ID NO 1170
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1170
acaaagauuu gguguuuucu a								21

<210> SEQ ID NO 1171
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1171
uguggagaaa acaaccuaaa u								21

<210> SEQ ID NO 1172
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1172
uggaagguua uacucuauaa a								21

<210> SEQ ID NO 1173
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1173
augaacugag gcaaauuuaa a								21

<210> SEQ ID NO 1174
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1174
aggcaaauuu aaaaggcaau a								21

<210> SEQ ID NO 1175
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1175
aagauuuggu guuucuacu u                                              21

<210> SEQ ID NO 1176
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1176
aaacaaccua aaugguaaau a                                             21

<210> SEQ ID NO 1177
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1177
auacucuaua aaaucaacca a                                             21

<210> SEQ ID NO 1178
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1178
ugaacugagg caaauuuaaa a                                             21

<210> SEQ ID NO 1179
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1179
ggcaaauuua aaaggcaaua a                                             21

<210> SEQ ID NO 1180
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1180
uuuucuacuu gggaucacaa a                                             21

<210> SEQ ID NO 1181
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1181
aacaaccuaa augguaaaua u                                       21

<210> SEQ ID NO 1182
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1182
uacucuauaa aaucaaccaa a                                       21

<210> SEQ ID NO 1183
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1183
gaacugaggc aaauuuaaaa a                                       21

<210> SEQ ID NO 1184
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1184
cagaguaugu guaaaaaucu u                                       21

<210> SEQ ID NO 1185
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1185
aaagaaggag cuuaauugug aac                                     23

<210> SEQ ID NO 1186
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1186
aaauaacuag aggaacaaua aaa                                     23

<210> SEQ ID NO 1187
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1187
uuuuacaucg ucuaacauag caa                                     23

<210> SEQ ID NO 1188
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1188 aagucuuua agaccauguc cca                                            23

<210> SEQ ID NO 1189
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1189
aucaaauaug uugaguuuuu gaa                                           23

<210> SEQ ID NO 1190
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1190
uucuucuuug auuucacugg uuu                                           23

<210> SEQ ID NO 1191
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1191
aaaagaagga gcuuaauugu gaa                                           23

<210> SEQ ID NO 1192
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1192
uuuuuacauc gucuaacaua gca                                           23

<210> SEQ ID NO 1193
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1193
aagacugauc aaauauguug agu                                           23

<210> SEQ ID NO 1194
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1194
uauauguagu ucuucucagu ucc                                           23

<210> SEQ ID NO 1195
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1195
aaaaagaagg agcuuaauug uga                                           23

<210> SEQ ID NO 1196
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1196
aucuugauuu uggcucugga gau                                           23

<210> SEQ ID NO 1197
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1197
uuggcuaaaa uuuuuacauc guc                                           23

<210> SEQ ID NO 1198
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1198
uauggacaaa gucuuuaaga cca                                           23

<210> SEQ ID NO 1199
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1199
aaagacugau caaauauguu gag                                           23

```
<210> SEQ ID NO 1200
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1200
uuauauguag uucuucucag uuc                                                23

<210> SEQ ID NO 1201
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1201
aaaucuugau uuggcucug gag                                                 23

<210> SEQ ID NO 1202
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1202
auuggcuaaa auuuuacau cgu                                                 23

<210> SEQ ID NO 1203
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1203
uuauggacaa agucuuuaag acc                                                23

<210> SEQ ID NO 1204
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1204
aaaagacuga ucaaauaugu uga                                                23

<210> SEQ ID NO 1205
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1205
uuuauaugua guucuucuca guu                                                23

<210> SEQ ID NO 1206
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1206
auaaaaagaa ggagcuuaau ugu                                              23

<210> SEQ ID NO 1207
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1207
uaacauagca aaucuugauu uug                                              23

<210> SEQ ID NO 1208
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1208
uaagaccaug ucccaacuga agg                                              23

<210> SEQ ID NO 1209
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1209
aauaugucau uaauuuggcc cuu                                              23

<210> SEQ ID NO 1210
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1210
aaaaagacug aucaaauaug uug                                              23

<210> SEQ ID NO 1211
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1211
uuguaguuua uauguaguuc uuc                                              23

<210> SEQ ID NO 1212
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1212
aauaaaaaga aggagcuuaa uug                                              23

<210> SEQ ID NO 1213
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1213
aucgucuaac auagcaaauc uug                                              23

<210> SEQ ID NO 1214
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1214
uuaagaccau gucccaacug aag                                              23

<210> SEQ ID NO 1215
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1215
aaauauguca uuaauuuggc ccu                                              23

<210> SEQ ID NO 1216
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1216 uaaaagacu gaucaaauau guu                                               23

<210> SEQ ID NO 1217
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1217
uugacuugua guuuauaugu agu                                              23

<210> SEQ ID NO 1218
<211> LENGTH: 23
<212> TYPE: RNA
```

<213> ORGANISM: Artificial Sequence
<220> FEATURE:
<223> OTHER INFORMATION: Description of Artificial Sequence: Synthetic
    oligonucleotide

<400> SEQUENCE: 1218
auaacuagag gaacaauaaa aag                                           23

<210> SEQ ID NO 1219
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1219
uuacaucguc uaacauagca aau                                           23

<210> SEQ ID NO 1220
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1220
uuuaagacca ugucccaacu gaa                                           23

<210> SEQ ID NO 1221
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1221
uuugaaauau gucauuaauu ugg                                           23

<210> SEQ ID NO 1222
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1222
uagaucauaa aaagacugau caa                                           23

<210> SEQ ID NO 1223
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1223
uuugacuugu aguuuauaug uag                                           23

<210> SEQ ID NO 1224
<211> LENGTH: 23
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 1224
aauaacuaga ggaacaauaa aaa                                              23

<210> SEQ ID NO 1225
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1225
uuuacaucgu cuaacauagc aaa                                              23

<210> SEQ ID NO 1226
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1226
aagucuuuaa gaccaugucc caa                                              23

<210> SEQ ID NO 1227
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1227
uugaguuuuu gaaauauguc auu                                              23

<210> SEQ ID NO 1228
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1228
auagaucaua aaaagacuga uca                                              23

<210> SEQ ID NO 1229
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1229
uuuugacuug uaguuuauau gua                                              23

<210> SEQ ID NO 1230
<211> LENGTH: 23
<212> TYPE: RNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 1230
aaguuuugag uugaguucaa gug                                              23

<210> SEQ ID NO 1231
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1231
uuucacuuuu uguugaagua gaa                                              23

<210> SEQ ID NO 1232
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1232 uuaaguagu uaguugcucu ucu                                               23

<210> SEQ ID NO 1233
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1233
uuugaugcua uuaucuuguu uuu                                              23

<210> SEQ ID NO 1234
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1234
auuucuuuua uuugacuaug cug                                              23

<210> SEQ ID NO 1235
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1235
uuuuugacuu guaguuuaua ugu                                              23

<210> SEQ ID NO 1236
<211> LENGTH: 23
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 1236
uucaaguuuu gaguugaguu caa								23

<210> SEQ ID NO 1237
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1237
auuucacuuu uuguugaagu aga								23

<210> SEQ ID NO 1238
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1238
auuaaguuag uuaguugcuc uuc								23

<210> SEQ ID NO 1239
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1239
aaggucuuug augcuauuau cuu								23

<210> SEQ ID NO 1240
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1240
uauuucuuuu auuugacuau gcu								23

<210> SEQ ID NO 1241
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1241
auuuuugacu uguaguuuau aug								23

<210> SEQ ID NO 1242
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1242
uuucaaguuu ugaguugagu uca                                              23

<210> SEQ ID NO 1243
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1243
uauuucacuu uuuguugaag uag                                              23

<210> SEQ ID NO 1244
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1244
aauuaaguua guuaguugcu cuu                                              23

<210> SEQ ID NO 1245
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1245
uauuugacua ugcuguuggu uua                                              23

<210> SEQ ID NO 1246
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1246
uucuauuucu uuuauuugac uau                                              23

<210> SEQ ID NO 1247
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1247
uuuaccucuu cauuuugac uug                                               23

<210> SEQ ID NO 1248
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1248
uucuucuagg aggcuuucaa guu                                          23

<210> SEQ ID NO 1249
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1249
auauuucacu uuuguugaa gua                                           23

<210> SEQ ID NO 1250
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1250
uugaauuaag uuaguuaguu gcu                                          23

<210> SEQ ID NO 1251
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1251
uuauuugacu augcuguugg uuu                                          23

<210> SEQ ID NO 1252
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1252
uagagaaauu ucugugqquu cuu                                          23

<210> SEQ ID NO 1253
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1253
uugaguucaa gugacauauu cuu                                          23

<210> SEQ ID NO 1254
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1254
``` uuucuucua ggaggcuuuc aag                                            23

<210> SEQ ID NO 1255
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1255
aauauuucac uuuuuguuga agu                                           23

<210> SEQ ID NO 1256
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1256
uuugaauuaa guuaguuagu ugc                                           23

<210> SEQ ID NO 1257
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1257
uuuauuugac uaugcuguug guu                                           23

<210> SEQ ID NO 1258
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1258
auagagaaau uucgugggu ucu                                            23

<210> SEQ ID NO 1259
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1259
uugaguugag uucaagugac aua                                           23

<210> SEQ ID NO 1260
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1260

```
uuuuucuucu aggaggcuuu caa                                              23

<210> SEQ ID NO 1261
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1261
uuaguugcuc uucuaaauau uuc                                              23

<210> SEQ ID NO 1262
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1262
uuuugaauua aguuaguuag uug                                              23

<210> SEQ ID NO 1263
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1263
uuuuauuuga cuaugcuguu ggu                                              23

<210> SEQ ID NO 1264
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1264
aagauagaga aauuucugug ggu                                              23

<210> SEQ ID NO 1265
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1265
uuugaguuga guucaaguga cau                                              23

<210> SEQ ID NO 1266
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1266
uagaauuuuu ucuucuagga ggc                                              23
```

<210> SEQ ID NO 1267
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1267
uaguuaguug cucuucuaaa uau                                            23

<210> SEQ ID NO 1268
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1268
auuuugaauu aaguuaguua guu                                            23

<210> SEQ ID NO 1269
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1269
uucuuuuauu ugacuaugcu guu                                            23

<210> SEQ ID NO 1270
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1270
auguuuuaca uuucuuauuu cau                                            23

<210> SEQ ID NO 1271
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1271
uuuugaguug aguucaagug aca                                            23

<210> SEQ ID NO 1272
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1272
uucacuuuuu guugaaguag aau                                            23

<210> SEQ ID NO 1273
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1273
uuaguuaguu gcucuucuaa aua                                             23

<210> SEQ ID NO 1274
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1274
uugaugcuau uaucuuguuu uuc                                             23

<210> SEQ ID NO 1275
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1275
uuucuuuuau uugacuaugc ugu                                             23

<210> SEQ ID NO 1276
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1276
aacuugagag uugcuggguc uga                                             23

<210> SEQ ID NO 1277
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1277
uugaauuaau guccauggac uac                                             23

<210> SEQ ID NO 1278
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1278
auugaaguuu ugugauccau cua                                             23

```
<210> SEQ ID NO 1279
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1279
uauggaguau aucuucucua ggc                                             23

<210> SEQ ID NO 1280
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1280
aauauaaugu uuguugucuu ucc                                             23

<210> SEQ ID NO 1281
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1281
aaaagaauau ucaauauaau guu                                             23

<210> SEQ ID NO 1282
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1282
aaacuugaga guugcugggu cug                                             23

<210> SEQ ID NO 1283
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1283
uucauugaag uuuugugauc cau                                             23

<210> SEQ ID NO 1284
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1284
uucacuaugg aguauaucuu cuc                                             23

<210> SEQ ID NO 1285
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1285
uucaauauaa uguuuguugu cuu                                        23

<210> SEQ ID NO 1286
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1286
uaguugguuu cgugauuucc caa                                        23

<210> SEQ ID NO 1287
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1287
aaaacuugag aguugcuggg ucu                                        23

<210> SEQ ID NO 1288
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1288
uucgauguug aauuaauguc cau                                        23

<210> SEQ ID NO 1289
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1289
uuucauugaa guuuugugau cca                                        23

<210> SEQ ID NO 1290
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1290
uagauugcuu cacuauggag uau                                        23

<210> SEQ ID NO 1291
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1291
auucaauaua auguuuguug ucu                                            23

<210> SEQ ID NO 1292
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1292
auaguugguu ucgugauuuc cca                                            23

<210> SEQ ID NO 1293
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1293
aaaaacuuga gaguugcugg guc                                            23

<210> SEQ ID NO 1294
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1294
auucgauguu gaauuaaugu cca                                            23

<210> SEQ ID NO 1295
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1295
uauuuguagu ucucccacgu uuc                                            23

<210> SEQ ID NO 1296
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1296
uuagauugcu ucacuaugga gua                                            23

<210> SEQ ID NO 1297
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1297
uauucaauau aauguuuguu guc                                           23

<210> SEQ ID NO 1298
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1298
uauaguuggu uucgugauuu ccc                                           23

<210> SEQ ID NO 1299
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1299
uagacaugaa aacuugaga guu                                            23

<210> SEQ ID NO 1300
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1300
uauucgaugu ugaauuaaug ucc                                           23

<210> SEQ ID NO 1301
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1301
aaccauauuu guaguucucc cac                                           23

<210> SEQ ID NO 1302
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1302
auuagauugc uucacuaugg agu                                           23

<210> SEQ ID NO 1303
<211> LENGTH: 23
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 1303
auauucaaua uaauguuugu ugu                                    23

<210> SEQ ID NO 1304
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1304
auugcauugg ggacauugcc agu                                    23

<210> SEQ ID NO 1305
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1305
uaauguccau ggacuaccug aua                                    23

<210> SEQ ID NO 1306
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1306
aucuauucga uguugaauua aug                                    23

<210> SEQ ID NO 1307
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1307
aaaccauauu uguaguucuc cca                                    23

<210> SEQ ID NO 1308
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1308
aauuagauug cuucacuaug gag                                    23

<210> SEQ ID NO 1309
<211> LENGTH: 23
<212> TYPE: RNA
<213> ORGANISM: Artificial Sequence
<220> FEATURE:

<223> OTHER INFORMATION: Description of Artificial Sequence: Synthetic
    oligonucleotide

<400> SEQUENCE: 1309
aauauucaau auaauguuug uug                                          23

<210> SEQ ID NO 1310
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1310
uuuguuuucc gggauugcau ugg                                          23

<210> SEQ ID NO 1311
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1311
uuaaugucca uggacuaccu gau                                          23

<210> SEQ ID NO 1312
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1312
auccaucuau ucgauguuga auu                                          23

<210> SEQ ID NO 1313
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1313
uauaucuucu cuaggcccaa cca                                          23

<210> SEQ ID NO 1314
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1314
uaauuagauu gcuucacuau gga                                          23

<210> SEQ ID NO 1315
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1315
aagaauauuc aauauaaugu uug                                    23

<210> SEQ ID NO 1316
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1316
aucuuuguuu uccgggauug cau                                    23

<210> SEQ ID NO 1317
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1317
aauuaauguc cauggacuac cug                                    23

<210> SEQ ID NO 1318
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1318
uuugugaucc aucuauucga ugu                                    23

<210> SEQ ID NO 1319
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1319
auggaguaua ucuucucuag gcc                                    23

<210> SEQ ID NO 1320
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1320
uugucuuucc agucuuccaa cuc                                    23

<210> SEQ ID NO 1321
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1321
aaagaauauu caauauaaug uuu                                              23

<210> SEQ ID NO 1322
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1322
aaucuuuguu uuccgggauu gca                                              23

<210> SEQ ID NO 1323
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1323
uugcuuugug aucccaagua gaa                                              23

<210> SEQ ID NO 1324
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1324
uauauuuacc auuuagguug uuu                                              23

<210> SEQ ID NO 1325
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1325
uucugaaucu guuggaugga uca                                              23

<210> SEQ ID NO 1326
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1326
ucuuuuaaau uugccucagu uca                                              23

<210> SEQ ID NO 1327
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1327
acagauuuuu acacauacuc ugu                                          23

<210> SEQ ID NO 1328
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1328
aaaucuuugu uuccgggau ugc                                           23

<210> SEQ ID NO 1329
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1329
uuugcuuugu gaucccaagu aga                                          23

<210> SEQ ID NO 1330
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1330
uuauauuuac cauuuagguu guu                                          23

<210> SEQ ID NO 1331
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1331
aauuugccuc aguucauuca aag                                          23

<210> SEQ ID NO 1332
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1332
uccuuuuaaa uuugccucag uuc                                          23

<210> SEQ ID NO 1333
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1333
```
uacagauuuu uacacauacu cug				23

<210> SEQ ID NO 1334
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1334
uuuugcuuug ugaucccaag uag				23

<210> SEQ ID NO 1335
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1335
uugguuuguu auauuuacca uuu				23

<210> SEQ ID NO 1336
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1336
aaauuugccu caguucauuc aaa				23

<210> SEQ ID NO 1337
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1337
ugccuuuuaa auuugccuca guu				23

<210> SEQ ID NO 1338
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1338
uuacagauuu uuacacauac ucu				23

<210> SEQ ID NO 1339
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1339

```
aaacaccaaa ucuuuguuuu ccg                                              23

<210> SEQ ID NO 1340
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1340
uuagguuguu uucuccacac uca                                              23

<210> SEQ ID NO 1341
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1341
uauaaccuuc cauuuugaga cuu                                              23

<210> SEQ ID NO 1342
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1342
uaaauuugcc ucaguucauu caa                                              23

<210> SEQ ID NO 1343
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1343
uugccuuuua aauuugccuc agu                                              23

<210> SEQ ID NO 1344
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1344
auuacagauu uuuacacaua cuc                                              23

<210> SEQ ID NO 1345
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1345
aaaacaccaa aucuuuguuu ucc                                              23
```

```
<210> SEQ ID NO 1346
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1346
uuuagguugu uuucuccaca cuc                                                 23

<210> SEQ ID NO 1347
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1347
uuauagagua uaaccuucca uuu                                                 23

<210> SEQ ID NO 1348
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1348
uuaaauuugc cucaguucau uca                                                 23

<210> SEQ ID NO 1349
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1349
auugccuuuu aaauuugccu cag                                                 23

<210> SEQ ID NO 1350
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1350
uauuacagau uuuuacacau acu                                                 23

<210> SEQ ID NO 1351
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1351
uagaaaacac caaucuuug uuu                                                  23
```

<210> SEQ ID NO 1352
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1352
auuuagguug uuucuccac acu                                              23

<210> SEQ ID NO 1353
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1353
uuuauagagu auaaccuucc auu                                             23

<210> SEQ ID NO 1354
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1354
uuuaaauuug ccucaguuca uuc                                             23

<210> SEQ ID NO 1355
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1355
uauugccuuu uaaauuugcc uca                                             23

<210> SEQ ID NO 1356
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1356
aaguagaaaa caccaaaucu uug                                             23

<210> SEQ ID NO 1357
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1357
uauuuaccau uuagguuguu uuc                                             23

```
<210> SEQ ID NO 1358
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1358
uugguugauu uuauagagua uaa                                              23

<210> SEQ ID NO 1359
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1359
uuuuaaauuu gccucaguuc auu                                              23

<210> SEQ ID NO 1360
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1360
uuauugccuu uuaaauuugc cuc                                              23

<210> SEQ ID NO 1361
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1361
uuugugaucc caaguagaaa aca                                              23

<210> SEQ ID NO 1362
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1362
auauuuacca uuuagguugu uuu                                              23

<210> SEQ ID NO 1363
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1363
uuugguugau uuuauagagu aua                                              23

<210> SEQ ID NO 1364
```

<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1364
uuuuuaaauu ugccucaguu cau                                              23

<210> SEQ ID NO 1365
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1365
aagauuuuua cacauacucu gug                                              23

<210> SEQ ID NO 1366
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1366
ucacaauuaa gcuccuucuu u                                                21

<210> SEQ ID NO 1367
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1367
uuauuguucc ucuaguuauu u                                                21

<210> SEQ ID NO 1368
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1368
gcuauguuag acgauguaaa a                                                21

<210> SEQ ID NO 1369
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1369
ggacaugguc uuaaagacuu u                                                21

<210> SEQ ID NO 1370
<211> LENGTH: 21

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1370
caaaaacuca acauauuuga u                                              21

<210> SEQ ID NO 1371
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1371
accagugaaa ucaaagaaga a                                              21

<210> SEQ ID NO 1372
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1372
cacaauuaag cuccuucuuu u                                              21

<210> SEQ ID NO 1373
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1373
cuauguuaga cgauguaaaa a                                              21

<210> SEQ ID NO 1374
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1374
ucaacauauu ugaucagucu u                                              21

<210> SEQ ID NO 1375
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1375
aacugagaag aacuacauau a                                              21

<210> SEQ ID NO 1376
<211> LENGTH: 21
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 1376
acaauuaagc uccuucuuuu u                                             21

<210> SEQ ID NO 1377
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1377
cuccagagcc aaaaucaaga u                                             21

<210> SEQ ID NO 1378
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1378
cgauguaaaa auuuuagcca a                                             21

<210> SEQ ID NO 1379
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1379
gucuuaaaga cuuuguccau a                                             21

<210> SEQ ID NO 1380
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1380
caacauauuu gaucagucuu u                                             21

<210> SEQ ID NO 1381
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1381
acugagaaga acuacauaua a                                             21

<210> SEQ ID NO 1382
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 1382
ccagagccaa aaucaagauu u                                                    21

<210> SEQ ID NO 1383
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1383
gauguaaaaa uuuuagccaa u                                                    21

<210> SEQ ID NO 1384
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1384
ucuuaaagac uuuguccaua a                                                    21

<210> SEQ ID NO 1385
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1385
aacauauuug aucagucuuu u                                                    21

<210> SEQ ID NO 1386
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1386
cugagaagaa cuacauauaa a                                                    21

<210> SEQ ID NO 1387
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1387
aauuaagcuc cuucuuuuua u                                                    21

<210> SEQ ID NO 1388
<211> LENGTH: 21
<212> TYPE: RNA
<213> ORGANISM: Artificial Sequence
<220> FEATURE:
```

<223> OTHER INFORMATION: Description of Artificial Sequence: Synthetic
oligonucleotide

<400> SEQUENCE: 1388
aaaucaagau uugcuauguu a         21

<210> SEQ ID NO 1389
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1389
uucaguuggg acauggucuu a         21

<210> SEQ ID NO 1390
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1390
gggccaaauu aaugacauau u         21

<210> SEQ ID NO 1391
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1391
acauauuuga ucagucuuuu u         21

<210> SEQ ID NO 1392
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1392
agaacuacau auaaacuaca a         21

<210> SEQ ID NO 1393
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1393
auuaagcucc uucuuuuuau u         21

<210> SEQ ID NO 1394
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1394
agauuugcua uguuagacga u                                              21

<210> SEQ ID NO 1395
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1395
ucaguuggga cauggucuua a                                              21

<210> SEQ ID NO 1396
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1396
ggccaaauua augacauauu u                                              21

<210> SEQ ID NO 1397
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1397
cauauuugau cagucuuuuu a                                              21

<210> SEQ ID NO 1398
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1398
uacauauaaa cuacaaguca a                                              21

<210> SEQ ID NO 1399
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1399
uuuuauuguu ccucuaguua u                                              21

<210> SEQ ID NO 1400
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1400
uugcuauguu agacgaugua a                                          21

<210> SEQ ID NO 1401
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1401
caguugggac auggucuuaa a                                          21

<210> SEQ ID NO 1402
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1402
aaauuaauga cauauuucaa a                                          21

<210> SEQ ID NO 1403
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1403
gaucagucuu uuuaugaucu a                                          21

<210> SEQ ID NO 1404
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1404
acauauaaac uacaagcaa a                                           21

<210> SEQ ID NO 1405
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1405
uuuauuguuc cucuaguuau u                                          21

<210> SEQ ID NO 1406
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1406
ugcuauguua gacgauguaa a                 21

<210> SEQ ID NO 1407
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1407
gggacauggu cuuaaagacu u                 21

<210> SEQ ID NO 1408
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1408
ugacauauuu caaaaacuca a                 21

<210> SEQ ID NO 1409
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1409
aucagucuuu uuaugaucua u                 21

<210> SEQ ID NO 1410
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1410
cauauaaacu acaagucaaa a                 21

<210> SEQ ID NO 1411
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1411
cuugaacuca acucaaaacu u                 21

<210> SEQ ID NO 1412
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1412
cuacuucaac aaaaagugaa a                                              21

<210> SEQ ID NO 1413
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1413
aagagcaacu aacuaacuua a                                              21

<210> SEQ ID NO 1414
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1414
aaacaagaua auagcaucaa a                                              21

<210> SEQ ID NO 1415
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1415
gcauagucaa auaaaagaaa u                                              21

<210> SEQ ID NO 1416
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1416
auauaaacua caagucaaaa a                                              21

<210> SEQ ID NO 1417
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1417
gaacucaacu caaaacuuga a                                              21

<210> SEQ ID NO 1418
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1418
uacuucaaca aaaagugaaa u                          21

<210> SEQ ID NO 1419
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1419
agagcaacua acuaacuuaa u                          21

<210> SEQ ID NO 1420
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1420
gauaauagca ucaaagaccu u                          21

<210> SEQ ID NO 1421
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1421
cauagucaaa uaaagaaau a                           21

<210> SEQ ID NO 1422
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1422
uauaaacuac aagucaaaaa u                          21

<210> SEQ ID NO 1423
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1423
aacucaacuc aaaacuugaa a                          21

<210> SEQ ID NO 1424
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1424
acuucaacaa aaagugaaau a                          21

<210> SEQ ID NO 1425
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1425
gagcaacuaa cuaacuuaau u                                            21

<210> SEQ ID NO 1426
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1426
aaccaacagc auagucaaau a                                            21

<210> SEQ ID NO 1427
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1427
agucaaauaa aagaaauaga a                                            21

<210> SEQ ID NO 1428
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1428
agucaaaaau gaagagguaa a                                            21

<210> SEQ ID NO 1429
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1429
cuugaaagcc uccuagaaga a                                            21

<210> SEQ ID NO 1430
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1430
cuucaacaaa aagugaaaua u                                            21

<210> SEQ ID NO 1431
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1431
caacuaacua acuuaauuca a                                              21

<210> SEQ ID NO 1432
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1432
accaacagca uagucaaaua a                                              21

<210> SEQ ID NO 1433
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1433
gaacccacag aaauuucucu a                                              21

<210> SEQ ID NO 1434
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1434
gaauauguca cuugaacuca a                                              21

<210> SEQ ID NO 1435
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1435
ugaaagccuc cuagaagaaa a                                              21

<210> SEQ ID NO 1436
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1436
uucaacaaaa agugaaauau u                                              21

```
<210> SEQ ID NO 1437
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1437
aacuaacuaa cuuaauucaa a                                                   21

<210> SEQ ID NO 1438
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1438
ccaacagcau agucaaauaa a                                                   21

<210> SEQ ID NO 1439
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1439
aacccacaga aauuucucua u                                                   21

<210> SEQ ID NO 1440
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1440
ugucacuuga acucaacuca a                                                   21

<210> SEQ ID NO 1441
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1441
gaaagccucc uagaagaaaa a                                                   21

<210> SEQ ID NO 1442
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1442
aauauuuaga agagcaacua a                                                   21

<210> SEQ ID NO 1443
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1443
acuaacuaac uuaauucaaa a                                              21

<210> SEQ ID NO 1444
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1444
caacagcaua gucaaauaaa a                                              21

<210> SEQ ID NO 1445
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1445
ccacagaaau uucucuaucu u                                              21

<210> SEQ ID NO 1446
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1446
gucacuugaa cucaacucaa a                                              21

<210> SEQ ID NO 1447
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1447
cuccuagaag aaaaaauucu a                                              21

<210> SEQ ID NO 1448
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1448
auuuagaaga gcaacuaacu a                                              21

<210> SEQ ID NO 1449
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1449
cuaacuaacu uaauucaaaa u                                             21

<210> SEQ ID NO 1450
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1450
cagcauaguc aaauaaaaga a                                             21

<210> SEQ ID NO 1451
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1451
gaaauaagaa auguaaaaca u                                             21

<210> SEQ ID NO 1452
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1452
ucacuugaac ucaacucaaa a                                             21

<210> SEQ ID NO 1453
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1453
ucuacuucaa caaaaaguga a                                             21

<210> SEQ ID NO 1454
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1454
uuuagaagag caacuaacua a                                             21

<210> SEQ ID NO 1455
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1455
aaaacaagau aauagcauca a                                              21

<210> SEQ ID NO 1456
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1456
agcauaguca aauaaaagaa a                                              21

<210> SEQ ID NO 1457
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1457
agacccagca acucucaagu u                                              21

<210> SEQ ID NO 1458
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1458
aguccaugga cauuaauuca a                                              21

<210> SEQ ID NO 1459
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1459
gauggaucac aaaacuucaa u                                              21

<210> SEQ ID NO 1460
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1460
cuagagaaga uauacuccau a                                              21

<210> SEQ ID NO 1461
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1461
aaagacaaca aacauuauau u                                              21

<210> SEQ ID NO 1462
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1462
cauuauauug aauauucuuu u                                              21

<210> SEQ ID NO 1463
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1463
gacccagcaa cucucaaguu u                                              21

<210> SEQ ID NO 1464
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1464
ggaucacaaa acuucaauga a                                              21

<210> SEQ ID NO 1465
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1465
gaagauauac uccauaguga a                                              21

<210> SEQ ID NO 1466
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1466
gacaacaaac auuauauuga a                                              21

<210> SEQ ID NO 1467
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1467
gggaaaucac gaaaccaacu a                                              21

<210> SEQ ID NO 1468
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1468
acccagcaac ucucaaguuu u                                              21

<210> SEQ ID NO 1469
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1469
ggacauuaau ucaacaucga a                                              21

<210> SEQ ID NO 1470
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1470
gaucacaaaa cuucaaugaa a                                              21

<210> SEQ ID NO 1471
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1471
acuccauagu gaagcaaucu a                                              21

<210> SEQ ID NO 1472
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1472
acaacaaaca uuauauugaa u                                              21

<210> SEQ ID NO 1473
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 1473
ggaaaucacg aaaccaacua u                                            21

<210> SEQ ID NO 1474
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1474
cccagcaacu cucaaguuuu u                                            21

<210> SEQ ID NO 1475
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1475
gacauuaauu caacaucgaa u                                            21

<210> SEQ ID NO 1476
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1476
aacgugggag aacuacaaau a                                            21

<210> SEQ ID NO 1477
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1477
cuccauagug aagcaaucua a                                            21

<210> SEQ ID NO 1478
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1478
caacaaacau uauauugaau a                                            21

<210> SEQ ID NO 1479
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 1479
gaaaucacga aaccaacuau a                                              21

<210> SEQ ID NO 1480
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1480
cucucaaguu uuucaugucu a                                              21

<210> SEQ ID NO 1481
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1481
acauuaauuc aacaucgaau a                                              21

<210> SEQ ID NO 1482
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1482
gggagaacua caaauauggu u                                              21

<210> SEQ ID NO 1483
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1483
uccauaguga agcaaucuaa u                                              21

<210> SEQ ID NO 1484
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1484
aacaaacauu auauugaaua u                                              21

<210> SEQ ID NO 1485
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1485
uggcaauguc cccaaugcaa u                                              21

<210> SEQ ID NO 1486
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1486
ucagguaguc cauggacauu a                                              21

<210> SEQ ID NO 1487
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1487
uuaauucaac aucgaauaga u                                              21

<210> SEQ ID NO 1488
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1488
ggagaacuac aaauaugguu u                                              21

<210> SEQ ID NO 1489
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1489
ccauagugaa gcaaucuaau u                                              21

<210> SEQ ID NO 1490
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1490
acaaacauua uauugaauau u                                              21

<210> SEQ ID NO 1491
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1491
```
aaugcaauuc cggaaaacaa a                                        21

<210> SEQ ID NO 1492
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1492
cagguagucc auggacauua a                                        21

<210> SEQ ID NO 1493
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1493
uucaacaucg aauagaugga u                                        21

<210> SEQ ID NO 1494
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1494
guugggccua gagaagauau a                                        21

<210> SEQ ID NO 1495
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1495
cauagugaag caaucuaauu a                                        21

<210> SEQ ID NO 1496
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1496
aacauuauau ugaauauucu u                                        21

<210> SEQ ID NO 1497
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1497
gcaaucccgg aaaacaaaga u                                               21

<210> SEQ ID NO 1498
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1498
gguaguccau ggacauuaau u                                               21

<210> SEQ ID NO 1499
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1499
aucgaauaga uggaucacaa a                                               21

<210> SEQ ID NO 1500
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1500
ccuagagaag auauacucca u                                               21

<210> SEQ ID NO 1501
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1501
guuggaagac uggaaagaca a                                               21

<210> SEQ ID NO 1502
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1502
acauuauauu gaauauucuu u                                               21

<210> SEQ ID NO 1503
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1503
caaucccgga aaacaaagau u                                               21

-continued

<210> SEQ ID NO 1504
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1504
cuacuuggga ucacaaagca a                                          21

<210> SEQ ID NO 1505
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1505
acaaccuaaa ugguaaauau a                                          21

<210> SEQ ID NO 1506
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1506
auccauccaa cagauucaga a                                          21

<210> SEQ ID NO 1507
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1507
aacugaggca aauuuaaaag a                                          21

<210> SEQ ID NO 1508
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1508
agaguaugug uaaaaaucug u                                          21

<210> SEQ ID NO 1509
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1509
aaucccggaa aacaaagauu u                                          21

```
<210> SEQ ID NO 1510
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1510
uacuugggau cacaaagcaa a                                              21

<210> SEQ ID NO 1511
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1511
caaccuaaau gguaaauaua a                                              21

<210> SEQ ID NO 1512
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1512
uugaaugaac ugaggcaaau u                                              21

<210> SEQ ID NO 1513
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1513
acugaggcaa auuuaaaagg a                                              21

<210> SEQ ID NO 1514
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1514
gaguaugugu aaaaaucugu a                                              21

<210> SEQ ID NO 1515
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1515
acuugggauc acaaagcaaa a                                              21
```

```
<210> SEQ ID NO 1516
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1516
augguaaaua uaacaaacca a                                              21

<210> SEQ ID NO 1517
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1517
ugaaugaacu gaggcaaauu u                                              21

<210> SEQ ID NO 1518
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1518
cugaggcaaa uuuaaaaggc a                                              21

<210> SEQ ID NO 1519
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1519
aguaugugua aaaaucugua a                                              21

<210> SEQ ID NO 1520
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1520
gaaaacaaag auuuggguguu u                                             21

<210> SEQ ID NO 1521
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1521
aguguggaga aaacaaccua a                                              21

<210> SEQ ID NO 1522
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1522
gucucaaaau ggaagguuau a                                             21

<210> SEQ ID NO 1523
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1523
gaaugaacug aggcaaauuu a                                             21

<210> SEQ ID NO 1524
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1524
ugaggcaaau uuaaaaggca a                                             21

<210> SEQ ID NO 1525
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1525
guauguguaa aaaucuguaa u                                             21

<210> SEQ ID NO 1526
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1526
aaaacaaaga uuugguguuu u                                             21

<210> SEQ ID NO 1527
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1527
guguggagaa aacaaccuaa a                                             21

<210> SEQ ID NO 1528
<211> LENGTH: 21
```

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1528
auggaagguu auacucuaua a                                              21

<210> SEQ ID NO 1529
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1529
aaugaacuga ggcaaauuua a                                              21

<210> SEQ ID NO 1530
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1530
gaggcaaauu uaaaaggcaa u                                              21

<210> SEQ ID NO 1531
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1531
uauguguaaa aaucuguaau a                                              21

<210> SEQ ID NO 1532
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1532
acaaagauuu gguguuuucu a                                              21

<210> SEQ ID NO 1533
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1533
uguggagaaa acaaccuaaa u                                              21

<210> SEQ ID NO 1534
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1534
uggaagguua uacucuauaa a                                                  21

<210> SEQ ID NO 1535
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1535
augaacugag gcaaauuuaa a                                                   21

<210> SEQ ID NO 1536
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1536
aggcaaauuu aaaaggcaau a                                                   21

<210> SEQ ID NO 1537
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1537
aagauuuggu guuucuacu u                                                    21

<210> SEQ ID NO 1538
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1538
aaacaaccua aaugguaaau a                                                   21

<210> SEQ ID NO 1539
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1539
auacucuaua aaaucaacca a                                                   21

<210> SEQ ID NO 1540
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1540
ugaacugagg caaauuuaaa a                                              21

<210> SEQ ID NO 1541
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1541
ggcaaauuua aaaggcaaua a                                              21

<210> SEQ ID NO 1542
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1542
uuuucuacuu gggaucacaa a                                              21

<210> SEQ ID NO 1543
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1543
aacaaccuaa augguaaaua u                                              21

<210> SEQ ID NO 1544
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1544
uacucuauaa aaucaaccaa a                                              21

<210> SEQ ID NO 1545
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1545
gaacugaggc aaauuuaaaa a                                              21

<210> SEQ ID NO 1546
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1546
cagaguaugu guaaaaaucu u                                              21

<210> SEQ ID NO 1547
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1547
aaagaaggag cuuaauugug aac                                            23

<210> SEQ ID NO 1548
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1548
aaauaacuag aggaacaaua aaa                                            23

<210> SEQ ID NO 1549
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1549
uuuuacaucg ucuaacauag caa                                            23

<210> SEQ ID NO 1550
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1550
aaagucuuua agaccauguc cca                                            23

<210> SEQ ID NO 1551
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1551
aucaaauaug uugaguuuuu gaa                                            23

<210> SEQ ID NO 1552
<211> LENGTH: 23
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 1552
uucuucuuug auuucacugg uuu                                        23

<210> SEQ ID NO 1553
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1553
aaaagaagga gcuuaauugu gaa                                        23

<210> SEQ ID NO 1554
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1554
uuuuuacauc gucuaacaua gca                                        23

<210> SEQ ID NO 1555
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1555
aagacugauc aaauauguug agu                                        23

<210> SEQ ID NO 1556
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1556
uauauguagu ucuucucagu ucc                                        23

<210> SEQ ID NO 1557
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1557
aaaaagaagg agcuuaauug uga                                        23

<210> SEQ ID NO 1558
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1558
aucuugauuu uggcucugga gau                                          23

<210> SEQ ID NO 1559
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1559
uuggcuaaaa uuuuuacauc guc                                          23

<210> SEQ ID NO 1560
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1560
uauggacaaa gucuuuaaga cca                                          23

<210> SEQ ID NO 1561
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1561
aaagacugau caaauauguu gag                                          23

<210> SEQ ID NO 1562
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1562
uuauauguag uucuucucag uuc                                          23

<210> SEQ ID NO 1563
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1563
aaaucuugau uuuggcucug gag                                          23

<210> SEQ ID NO 1564
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1564
auuggcuaaa auuuuacau cgu                                               23

<210> SEQ ID NO 1565
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1565
uuauggacaa agucuuuaag acc                                              23

<210> SEQ ID NO 1566
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1566
aaaagacuga ucaaauaugu uga                                              23

<210> SEQ ID NO 1567
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1567
uuuauaugua guucuucuca guu                                              23

<210> SEQ ID NO 1568
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1568
auaaaaagaa ggagcuuaau ugu                                              23

<210> SEQ ID NO 1569
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1569
uaacauagca aaucuugauu uug                                              23

<210> SEQ ID NO 1570
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1570
```
uaagaccaug ucccaacuga agg                                                23

<210> SEQ ID NO 1571
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1571
aauaugucau uaauuuggcc cuu                                                23

<210> SEQ ID NO 1572
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1572
aaaaagacug aucaaauaug uug                                                23

<210> SEQ ID NO 1573
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1573
uuguaguuua uauguaguuc uuc                                                23

<210> SEQ ID NO 1574
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1574
aauaaaaaga aggagcuuaa uug                                                23

<210> SEQ ID NO 1575
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1575
aucgucuaac auagcaaauc uug                                                23

<210> SEQ ID NO 1576
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1576

```
uuaagaccau gucccaacug aag                                              23
```

<210> SEQ ID NO 1577
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1577

```
aaauauguca uuaauuuggc ccu                                              23
```

<210> SEQ ID NO 1578
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1578

```
uaaaaagacu gaucaaauau guu                                              23
```

<210> SEQ ID NO 1579
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1579

```
uugacuugua guuuauaugu agu                                              23
```

<210> SEQ ID NO 1580
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1580

```
auaacuagag gaacaauaaa aag                                              23
```

<210> SEQ ID NO 1581
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1581

```
uuacaucguc uaacauagca aau                                              23
```

<210> SEQ ID NO 1582
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1582

```
uuuaagacca ugucccaacu gaa                                              23
```

<210> SEQ ID NO 1583
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1583
uuugaaauau gcauuaauu ugg                                              23

<210> SEQ ID NO 1584
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1584
uagaucauaa aaagacugau caa                                             23

<210> SEQ ID NO 1585
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1585
uuugacuugu aguuuauaug uag                                             23

<210> SEQ ID NO 1586
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1586
aauaacuaga ggaacaauaa aaa                                             23

<210> SEQ ID NO 1587
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1587
uuuacaucgu cuaacauagc aaa                                             23

<210> SEQ ID NO 1588
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1588
aagucuuuaa gaccaugucc caa                                             23

<210> SEQ ID NO 1589
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1589
uugaguuuuu gaaauauguc auu                                           23

<210> SEQ ID NO 1590
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1590
auagaucaua aaaagacuga uca                                           23

<210> SEQ ID NO 1591
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1591
uuuugacuug uaguuuauau gua                                           23

<210> SEQ ID NO 1592
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1592
aaguuuugag uugaguucaa gug                                           23

<210> SEQ ID NO 1593
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1593
uuucacuuuu uguugaagua gaa                                           23

<210> SEQ ID NO 1594
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1594
uuaaguuagu uaguugcucu ucu                                           23

```
<210> SEQ ID NO 1595
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1595
uuugaugcua uuaucuuguu uuu                                            23

<210> SEQ ID NO 1596
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1596
auuucuuuua uuugacuaug cug                                            23

<210> SEQ ID NO 1597
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1597
uuuuugacuu guaguuuaua ugu                                            23

<210> SEQ ID NO 1598
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1598
uucaaguuuu gaguugaguu caa                                            23

<210> SEQ ID NO 1599
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1599
auuucacuuu uuguugaagu aga                                            23

<210> SEQ ID NO 1600
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1600
auuaaguuag uuaguugcuc uuc                                            23

<210> SEQ ID NO 1601
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1601
aaggucuuug augcuauuau cuu                                             23

<210> SEQ ID NO 1602
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1602
uauuucuuuu auuugacuau gcu                                             23

<210> SEQ ID NO 1603
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1603
auuuuugacu uguaguuuau aug                                             23

<210> SEQ ID NO 1604
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1604
uuucaaguuu ugaguugagu uca                                             23

<210> SEQ ID NO 1605
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1605
uauuucacuu uuuguugaag uag                                             23

<210> SEQ ID NO 1606
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1606
aauuaaguua guuaguugcu cuu                                             23

<210> SEQ ID NO 1607
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1607
uauuugacua ugcuguuggu uua                                              23

<210> SEQ ID NO 1608
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1608
uucuauuucu uuuauuugac uau                                              23

<210> SEQ ID NO 1609
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1609
uuuaccucuu cauuuugac uug                                               23

<210> SEQ ID NO 1610
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1610
uucuucuagg aggcuuucaa guu                                              23

<210> SEQ ID NO 1611
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1611
auauuucacu uuuuguugaa gua                                              23

<210> SEQ ID NO 1612
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1612
uugaauuaag uuaguuaguu gcu                                              23

<210> SEQ ID NO 1613
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1613
uuauuugacu augcuguugg uuu                                          23

<210> SEQ ID NO 1614
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1614
uagagaaauu ucguggguu cuu                                           23

<210> SEQ ID NO 1615
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1615
uugaguucaa gugacauauu cuu                                          23

<210> SEQ ID NO 1616
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1616
uuuucuucua ggaggcuuuc aag                                          23

<210> SEQ ID NO 1617
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1617
aauauuucac uuuuuguuga agu                                          23

<210> SEQ ID NO 1618
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1618
uuugaauuaa guuaguuagu ugc                                          23

<210> SEQ ID NO 1619
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1619
uuuauuugac uaugcuguug guu                                          23

<210> SEQ ID NO 1620
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1620
auagagaaau uucgugggu ucu                                           23

<210> SEQ ID NO 1621
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1621
uugaguugag uucaagugac aua                                          23

<210> SEQ ID NO 1622
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1622
uuuuucuucu aggaggcuuu caa                                          23

<210> SEQ ID NO 1623
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1623
uuaguugcuc uucuaaauau uuc                                          23

<210> SEQ ID NO 1624
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1624
uuuugaauua aguuaguuag uug                                          23

<210> SEQ ID NO 1625
<211> LENGTH: 23
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1625
uuuuauuuga cuaugcuguu ggu                                             23

<210> SEQ ID NO 1626
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1626
aagauagaga aauuucugug ggu                                             23

<210> SEQ ID NO 1627
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1627
uuugaguuga guucaaguga cau                                             23

<210> SEQ ID NO 1628
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1628
uagaauuuuu ucuucuagga ggc                                             23

<210> SEQ ID NO 1629
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1629
uaguuaguug cucuucuaaa uau                                             23

<210> SEQ ID NO 1630
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1630
auuuugaauu aaguuaguua guu                                             23

<210> SEQ ID NO 1631
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1631
uucuuuuauu ugacuaugcu guu          23

<210> SEQ ID NO 1632
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1632
auguuuuaca uuucuuauuu cau          23

<210> SEQ ID NO 1633
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1633
uuuugaguug aguucaagug aca          23

<210> SEQ ID NO 1634
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1634
uucacuuuuu guugaaguag aau          23

<210> SEQ ID NO 1635
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1635
uuaguuaguu gcucuucaa aua           23

<210> SEQ ID NO 1636
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1636
uugaugcuau uaucuuguuu uuc          23

<210> SEQ ID NO 1637
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1637
uuucuuuuau uugacuaugc ugu				23

<210> SEQ ID NO 1638
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1638
aacuugagag uugcuggguc uga				23

<210> SEQ ID NO 1639
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1639
uugaauuaau guccauggac uac				23

<210> SEQ ID NO 1640
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1640
auugaaguuu ugugauccau cua				23

<210> SEQ ID NO 1641
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1641
uauggaguau aucuucucua ggc				23

<210> SEQ ID NO 1642
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1642
aauauaaugu uuguugucuu ucc				23

<210> SEQ ID NO 1643
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1643
aaaagaauau ucaauauaau guu                                              23

<210> SEQ ID NO 1644
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1644
aaacuugaga guugcugggu cug                                              23

<210> SEQ ID NO 1645
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1645
uucauugaag uuuugugauc cau                                              23

<210> SEQ ID NO 1646
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1646
uucacuaugg aguauaucuu cuc                                              23

<210> SEQ ID NO 1647
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1647
uucaauauaa uguuuguugu cuu                                              23

<210> SEQ ID NO 1648
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1648
uaguugguuu cgugauuucc caa                                              23

<210> SEQ ID NO 1649
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1649
```

```
aaaacuugag aguugcuggg ucu                                              23

<210> SEQ ID NO 1650
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1650
uucgauguug aauuaauguc cau                                              23

<210> SEQ ID NO 1651
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1651
uuucauugaa guuugugau cca                                               23

<210> SEQ ID NO 1652
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1652
uagauugcuu cacuauggag uau                                              23

<210> SEQ ID NO 1653
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1653
auucaauaua auguuuguug ucu                                              23

<210> SEQ ID NO 1654
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1654
auaguugguu ucgugauuuc cca                                              23

<210> SEQ ID NO 1655
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1655
```
aaaaacuuga gaguugcugg guc                                                  23

<210> SEQ ID NO 1656
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1656
auucgauguu gaauuaaugu cca                                                  23

<210> SEQ ID NO 1657
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1657
uauuuguagu ucucccacgu uuc                                                  23

<210> SEQ ID NO 1658
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1658
uuagauugcu ucacuaugga gua                                                  23

<210> SEQ ID NO 1659
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1659
uauucaauau aauguuuguu guc                                                  23

<210> SEQ ID NO 1660
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1660
uauaguuggu uucgugauuu ccc                                                  23

<210> SEQ ID NO 1661
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1661
uagacaugaa aaacuugaga guu                                                  23

<210> SEQ ID NO 1662
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1662
uauucgaugu ugaauuaaug ucc                                            23

<210> SEQ ID NO 1663
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1663
aaccauauuu guaguucucc cac                                            23

<210> SEQ ID NO 1664
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1664
auuagauugc uucacuaugg agu                                            23

<210> SEQ ID NO 1665
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1665
auauucaaua uaauguuugu ugu                                            23

<210> SEQ ID NO 1666
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1666
auugcauugg ggacauugcc agu                                            23

<210> SEQ ID NO 1667
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1667
uaauguccau ggacuaccug aua                                            23

-continued

<210> SEQ ID NO 1668
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1668
aucuauucga uguugaauua aug                                            23

<210> SEQ ID NO 1669
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1669
aaaccauauu uguaguucuc cca                                            23

<210> SEQ ID NO 1670
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1670
aauuagauug cuucacuaug gag                                            23

<210> SEQ ID NO 1671
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1671
aauauucaau auaauguuug uug                                            23

<210> SEQ ID NO 1672
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1672
uuuguuuucc gggauugcau ugg                                            23

<210> SEQ ID NO 1673
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1673
uuaaugucca uggacuaccu gau                                            23

```
<210> SEQ ID NO 1674
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1674
auccaucuau ucgauguuga auu                                              23

<210> SEQ ID NO 1675
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1675
uauaucuucu cuaggcccaa cca                                              23

<210> SEQ ID NO 1676
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1676
uaauuagauu gcuucacuau gga                                              23

<210> SEQ ID NO 1677
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1677
aagaauauuc aauauaaugu uug                                              23

<210> SEQ ID NO 1678
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1678
aucuuuguuu uccgggauug cau                                              23

<210> SEQ ID NO 1679
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1679
aauuaauguc cauggacuac cug                                              23

<210> SEQ ID NO 1680
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1680
uuugugaucc aucuauucga ugu                                            23

<210> SEQ ID NO 1681
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1681
auggaguaua ucuucucuag gcc                                            23

<210> SEQ ID NO 1682
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1682 uugcuuucc agucuuccaa cuc                                             23

<210> SEQ ID NO 1683
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1683
aaagaauauu caauauaaug uuu                                            23

<210> SEQ ID NO 1684
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1684
aaucuuuguu uuccgggauu gca                                            23

<210> SEQ ID NO 1685
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1685 uugcuugug aucccaagua gaa                                             23

<210> SEQ ID NO 1686
<211> LENGTH: 23
```

-continued

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1686
uauauuuacc auuuagguug uuu                                              23

<210> SEQ ID NO 1687
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1687
uucugaaucu guuggaugga uca                                              23

<210> SEQ ID NO 1688
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1688
ucuuuuaaau uugccucagu uca                                              23

<210> SEQ ID NO 1689
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1689
acagauuuuu acacauacuc ugu                                              23

<210> SEQ ID NO 1690
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1690
aaaucuuugu uuccgggau ugc                                               23

<210> SEQ ID NO 1691
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1691
uuugcuuugu gaucccaagu aga                                              23

<210> SEQ ID NO 1692
<211> LENGTH: 23
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1692
uuauauuuac cauuuagguu guu                                        23

<210> SEQ ID NO 1693
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1693
aauuugccuc aguucauuca aag                                        23

<210> SEQ ID NO 1694
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1694
uccuuuuaaa uuugccucag uuc                                        23

<210> SEQ ID NO 1695
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1695
uacagauuuu uacacauacu cug                                        23

<210> SEQ ID NO 1696
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1696
uuuugcuuug ugaucccaag uag                                        23

<210> SEQ ID NO 1697
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1697
uugguuuguu auauuuacca uuu                                        23

<210> SEQ ID NO 1698
<211> LENGTH: 23
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 1698
aaauuugccu caguucauuc aaa                                              23

<210> SEQ ID NO 1699
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1699
ugccuuuuaa auuugccuca guu                                              23

<210> SEQ ID NO 1700
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1700
uuacagauuu uuacacauac ucu                                              23

<210> SEQ ID NO 1701
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1701
aaacaccaaa ucuuuguuuu ccg                                              23

<210> SEQ ID NO 1702
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1702
uuagguuguu uucuccacac uca                                              23

<210> SEQ ID NO 1703
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1703
uauaaccuuc cauuuugaga cuu                                              23

<210> SEQ ID NO 1704
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1704
uaaauuugcc ucaguucauu caa                                              23

<210> SEQ ID NO 1705
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1705
uugccuuuua aauuugccuc agu                                              23

<210> SEQ ID NO 1706
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1706
auuacagauu uuuacacaua cuc                                              23

<210> SEQ ID NO 1707
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1707
aaaacaccaa aucuuuguuu ucc                                              23

<210> SEQ ID NO 1708
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1708
uuuagguugu uuucuccaca cuc                                              23

<210> SEQ ID NO 1709
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1709
uuauagagua uaaccuucca uuu                                              23

<210> SEQ ID NO 1710
<211> LENGTH: 23
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 1710
uuaaauuugc cucaguucau uca                                              23

<210> SEQ ID NO 1711
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1711
auugccuuuu aaauuugccu cag                                              23

<210> SEQ ID NO 1712
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1712
uauuacagau uuuuacacau acu                                              23

<210> SEQ ID NO 1713
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1713
uagaaaacac caaaucuuug uuu                                              23

<210> SEQ ID NO 1714
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1714
auuuagguug uuuucuccac acu                                              23

<210> SEQ ID NO 1715
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1715
uuuauagagu auaaccuucc auu                                              23

<210> SEQ ID NO 1716
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1716
uuuaaauuug ccucaguuca uuc                                               23

<210> SEQ ID NO 1717
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1717
uauugccuuu uaaauuugcc uca                                               23

<210> SEQ ID NO 1718
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1718
aaguagaaaa caccaaaucu uug                                               23

<210> SEQ ID NO 1719
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1719
uauuuaccau uuagguuguu uuc                                               23

<210> SEQ ID NO 1720
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1720
uugguugauu uuauagagua uaa                                               23

<210> SEQ ID NO 1721
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1721
uuuuaaauuu gccucaguuc auu                                               23

<210> SEQ ID NO 1722
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1722
uuauugccuu uuaaauuugc cuc                                               23

<210> SEQ ID NO 1723
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1723
uuugugaucc caaguagaaa aca                                               23

<210> SEQ ID NO 1724
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1724
auauuuacca uuuagguugu uuu                                               23

<210> SEQ ID NO 1725
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1725
uuugguugau uuuauagagu aua                                               23

<210> SEQ ID NO 1726
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1726
uuuuuaaauu ugccucaguu cau                                               23

<210> SEQ ID NO 1727
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1727
aagauuuuua cacauacucu gug                                               23

<210> SEQ ID NO 1728
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1728
cacuuacgcu gaguacuucg a				21

<210> SEQ ID NO 1729
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1729
ucgaaguacu cagcguaagu gau			23

ANGIOPOIETIN-LIKE 3 (ANGPTL3) IRNA COMPOSITIONS AND METHODS OF USE THEREOF

RELATED APPLICATIONS

This application is a continuation of U.S. patent application Ser. No. 16/411,261, filed on May 14, 2019, which is a continuation of U.S. patent application Ser. No. 15/683,999, filed on Aug. 23, 2017, now U.S. Pat. No. 10,337,010, issued on Jul. 2, 2019, which is a continuation of U.S. patent application Ser. No. 15/068,912, now U.S. Pat. No. 9,771,591, issued on Sep. 26, 2017, which is a continuation of U.S. patent application Ser. No. 14/132,999, now U.S. Pat. No. 9,322,018, issued on Apr. 26, 2016, which is a 35 U.S.C. 111(a) continuation application, which claims priority to PCT/US2012/043378, filed on Jun. 20, 2012, U.S. Provisional Application No. 61/499,620, filed on Jun. 21, 2011, and to U.S. Provisional Application No. 61/638,288, filed on Apr. 25, 2012. The entire contents of each of the foregoing applications are hereby incorporated herein by reference.

SEQUENCE LISTING

The instant application contains a Sequence Listing which has been submitted in ASCII format via EFS-Web and is hereby incorporated by reference in its entirety. Said ASCII copy, created on Nov. 4, 2020, is named Seq_Listing_121301_00308.txt and is 444,473 bytes in size.

BACKGROUND OF THE INVENTION

Angiopoietin-like 3 (ANGPTL3) is a member of the angiopoietin-like family of secreted factors that regulates lipid metabolism and that is predominantly expressed in the liver (Koishi, R. et al., (2002) *Nat. Genet.* 30(2):151-157). ANGPTL3 dually inhibits the catalytic activities of lipoprotein lipase (LPL), which catalyzes the hydrolysis of triglycerides, and of endothelial lipase (EL), which hydrolyzes high density lipoprotein (HDL) phospholipids. In hypolipidemic, yet obese, KK/Snk mice, a reduction in ANGPTL3 expression has a protective effect against hyperlipidemia and artherosclerosis by promoting the clearance of triglycerides (Ando et al., (2003) *J. Lipid Res.*, 44:1216-1223). Human ANGPTL3 plasma concentrations positively correlate with plasma HDL cholesterol and HDL phospholipid levels (Shimamura et al., (2007) *Arterioscler. Thromb. Vasc. Biol.*, 27:366-372).

Disorders of lipid metabolism can lead to elevated levels of serum lipids, such as triglycerides and/or cholesterol. Elevated serum lipids are strongly associated with high blood pressure, cardiovascular disease, diabetes and other pathologic conditions. Hypertriglyceridemia is an example of a lipid metabolism disorder that is characterized by high blood levels of triglycerides. It has been associated with atherosclerosis, even in the absence of high cholesterol levels (hypercholesterolemia). When triglyceride concentrations are excessive (i.e., greater than 1000 mg/dl or 12 mmol/1), hypertriglyceridemia can also lead to pancreatitis. Hyperlipidemia is another example of a lipid metabolism disorder that is characterized by elevated levels of any one or all lipids and/or lipoproteins in the blood. Current treatments for disorders of lipid metabolism, including dieting, exercise and treatment with statins and other drugs, are not always effective. Accordingly, there is a need in the art for alternative treatments for subjects having disorders of lipid metabolism.

SUMMARY OF THE INVENTION

The present invention provides iRNA compositions which effect the RNA-induced silencing complex (RISC)-mediated cleavage of RNA transcripts of an ANGPL3 gene. The ANGPL3 gene may be within a cell, e.g., a cell within a subject, such as a human. The present invention also provides methods of using the iRNA compositions of the invention for inhibiting the expression of an ANGPL3 gene and/or for treating a subject who would benefit from inhibiting or reducing the expression of an ANGPL3 gene, e.g., a subject suffering or prone to suffering from a disorder of lipid metabolism, such as a subject suffering or prone to suffering from hyperlipidemia or hypertriglyceridemia.

Accordingly, in one aspect, the present invention provides double-stranded ribonucleic acids (dsRNAs) for inhibiting expression of ANGPTL3. The dsRNAs comprise a sense strand and an antisense strand, wherein the sense strand comprises at least 15 contiguous nucleotides differing by no more than 3 nucleotides from the nucleotide sequence of SEQ ID NO:1 and the antisense strand comprises at least 15 contiguous nucleotides differing by no more than 3 nucleotides from the nucleotide sequence of SEQ ID NO:5.

In another aspect, the present invention provides double-stranded ribonucleic acids (dsRNAs) for inhibiting expression of ANGPTL3. The dsRNAs comprise a sense strand and an antisense strand, the antisense strand comprising a region of complementarity which comprises at least 15 contiguous nucleotides differing by no more than 3 nucleotides from any one of the antisense sequences listed in Tables 2, 3, 7, 8, 9 and 10.

In one embodiment, the sense and antisense strands comprise sequences selected from the group consisting of AD-53063.1, AD-53001.1, AD-53015.1, AD-52986.1, AD-52981.1, AD-52953.1, AD-53024.1, AD-53033.1, AD-53030.1, AD-53080.1, AD-53073.1, AD-53132.1, AD-52983.1, AD-52954.1, AD-52961.1, AD-52994.1, AD-52970.1, AD-53075.1, AD-53147.1, AD-53077.1 of Tables 7 and 8.

In certain embodiments of the invention, the dsRNAs comprise at least one modified nucleotide. In one embodiment, at least one of the modified nucleotides is selected from the group consisting of a 2'-O-methyl modified nucleotide, a nucleotide comprising a 5'-phosphorothioate group, and a terminal nucleotide linked to a cholesteryl derivative or a dodecanoic acid bisdecylamide group. In another embodiment, the modified nucleotide is selected from the group consisting of a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, and a non-natural base comprising nucleotide.

The region of complementarity of the dsRNAs may be at least 17 nucleotides in length, between 19 and 21 nucleotides in length, or 19 nucleotides in length.

In one embodiment, each strand of a dsRNA is no more than 30 nucleotides in length.

At least one strand of a dsRNA may comprise a 3' overhang of at least 1 nucleotide or at least 2 nucleotides.

In certain embodiments, a dsRNA further comprises a ligand. In one embodiment, the ligand is conjugated to the 3' end of the sense strand of the dsRNA.

In some embodiments, the ligand is one or more N-acetyl-galactosamine (GalNAc) derivatives attached through a bivalent or trivalent branched linker. In particular embodiments, the ligand is

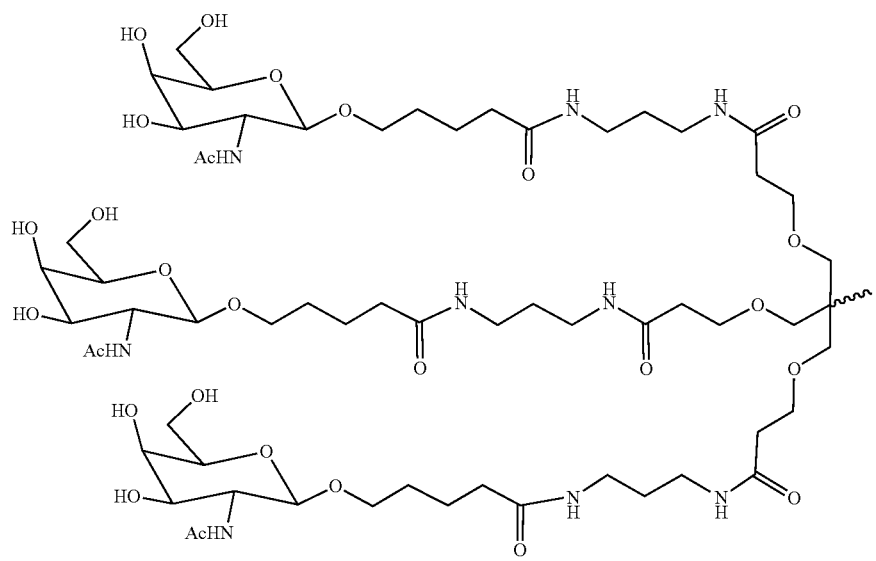

In some embodiments, the RNAi agent is conjugated to the ligand as shown in the following schematic

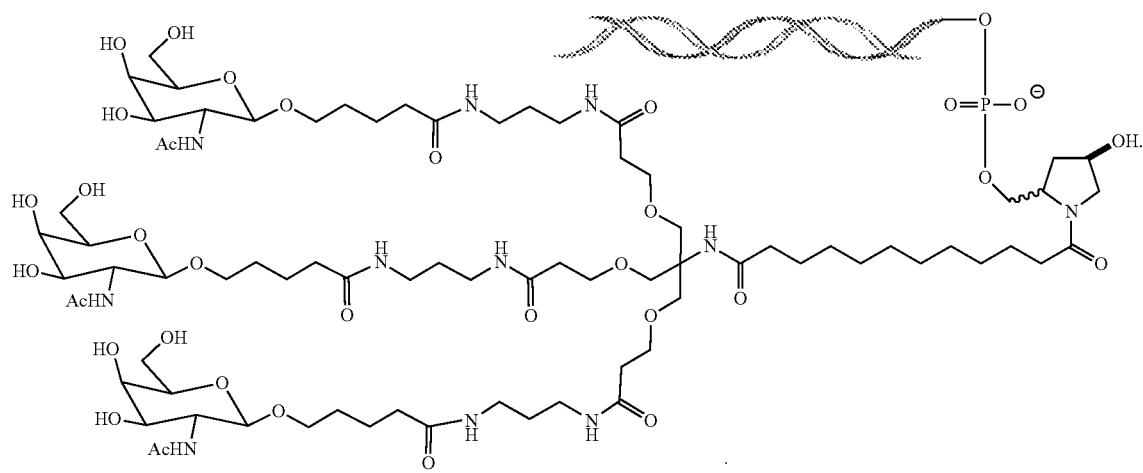 [SMILES: COP(=O)([O-])OCC1C[C@@H](O)CN1C(=O)CCCCCCCCCCC(=O)NC(COCCC(=O)NCCCNC(=O)CCCCOC1OC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O]

In some embodiments, the RNAi agent further includes at least one phosphorothioate or methylphosphonate internucleotide linkage. In some embodiments, the phosphorothioate or methylphosphonate internucleotide linkage is at the 3'-terminal of one strand. In some embodiments, the strand is the antisense strand. In other embodiments, the strand is the sense strand.

In one embodiment, the region of complementarity of a dsRNA consists of one of the antisense sequences of Tables 2, 3, 7, 8, 9 and 10.

In another embodiment, a dsRNA comprises a sense strand consisting of a sense strand sequence selected from the sequences of Tables 2, 3, 7, 8, 9 and 10, and an antisense strand consisting of an antisense sequence selected from the sequences of Tables 2, 3, 7, 8, 9 and 10.

In another aspect, the present invention provides a cell, e.g., a hepatocyte, containing a dsRNA of the invention.

In yet another aspect, the present invention provides a vector encoding at least one strand of a dsRNA, wherein the dsRNA comprises a region of complementarity to at least a part of an mRNA encoding ANGPTL3, wherein the dsRNA is 30 base pairs or less in length, and wherein the dsRNA targets the mRNA for cleavage. The region of complementarity may be least 15 nucleotides in length or 19 to 21 nucleotides in length.

In a further aspect, the present invention provides a cell comprising a vector encoding at least one strand of a dsRNA, wherein the dsRNA comprises a region of complementarity to at least a part of an mRNA encoding ANGPTL3, wherein the dsRNA is 30 base pairs or less in length, and wherein the dsRNA targets the mRNA for cleavage.

In one aspect, the present invention provides a pharmaceutical composition for inhibiting expression of an ANGPTL3 gene comprising a dsRNA or vector of the invention.

In one embodiment, the pharmaceutical composition comprises a lipid formulation, such as a MC3, SNALP or XTC formulation.

In another aspect, the present invention provides methods of inhibiting ANGPTL3 expression in a cell. The methods include contacting the cell with a dsRNA or a vector of the invention, and maintaining the cell produced for a time sufficient to obtain degradation of the mRNA transcript of an ANGPTL3 gene, thereby inhibiting expression of the ANGPTL3 gene in the cell.

The cell may be within a subject, such as a human subject, for example a human subject suffering from a disorder of lipid metabolism, e.g., hyperlipidemia or hypertriglyceridemia.

In one embodiment of the methods of the invention, ANGPTL3 expression is inhibited by at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%.

In another aspect, the present invention provides methods of treating a subject having a disorder that would benefit from reduction in ANGPTL3 expression, e.g., a disorder of lipid metabolism, such as hyperlipidemia or hypertriglyceridemia. The methods include administering to the subject a therapeutically effective amount of a dsRNA or a vector of the invention, thereby treating the subject.

The disorder may be disorder of lipid metabolism, such as hyperlipidemia or hypertriglyceridemia In one embodiment, the administration of the dsRNA to the subject causes a decrease in the level of a serum lipid, triglycerides, cholesterol and/or free fatty acids; and/or a decrease in ANGPTL3 protein accumulation. In one embodiment, administration of the dsRNA to the subject causes a decrease in the level of LDL-C, HDL-C, VLDL-C, IDL-C and/or total cholesterol.

In one embodiment, the dsRNA is administered at a dose of about 0.01 mg/kg to about 10 mg/kg, e.g., about 0.05 mg/kg to about 5 mg/kg, about 0.05 mg/kg to about 10 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 1 mg/kg to about 5 mg/kg, about 1 mg/kg to about 10 mg/kg, about 1.5 mg/kg to about 5 mg/kg, about 1.5 mg/kg to about 10 mg/kg, about 2 mg/kg to about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg. Values and ranges intermediate to the recited values are also intended to be part of this invention.

For example, the dsRNA may be administered at a dose of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8. 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8. 6.9, 7, 7.1, 7.2, 7.3, 7.4, 7.5, 7.6, 7.7, 7.8. 7.9, 8, 8.1, 8.2, 8.3, 8.4, 8.5, 8.6, 8.7, 8.8. 8.9, 9, 9.1, 9.2, 9.3, 9.4, 9.5, 9.6, 9.7, 9.8. 9.9, or about 10 mg/kg. Values and ranges intermediate to the recited values are also intended to be part of this invention.

In another embodiment, the dsRNA is administered at a dose of about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. Values and ranges intermediate to the recited values are also intended to be part of this invention.

For example, subjects can be administered a therapeutic amount of iRNA, such as about 0.5, 0.6, 0.7. 0.8, 0.9, 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8. 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8. 6.9, 7, 7.1, 7.2, 7.3, 7.4, 7.5, 7.6, 7.7, 7.8. 7.9, 8, 8.1, 8.2, 8.3, 8.4, 8.5, 8.6, 8.7, 8.8. 8.9, 9, 9.1, 9.2, 9.3, 9.4, 9.5, 9.6, 9.7, 9.8. 9.9, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

In another aspect, the present invention provides methods of inhibiting the expression of ANGPTL3 in a subject. The methods include administering to the subject a therapeutically effective amount of a dsRNA or a vector of the invention, thereby inhibiting the expression of ANGPTL3 in the subject.

In yet another aspect, the invention provides kits for performing the methods of the invention. In one aspect, the invention provides a kit for performing a method of inhibiting expression of ANGPTL3 gene in a cell by contacting a cell with a double stranded RNAi agent in an amount effective to inhibit expression of the ANGPTL3 in the cell. The kit comprises an RNAi agent and instructions for use and, optionally, means for administering the RNAi agent to a subject.

DETAILED DESCRIPTION OF THE INVENTION

Figure 1:
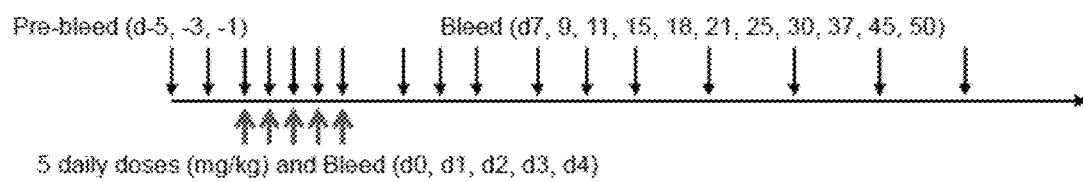
FIG. 1 is a schematic of the experimental procedure used for in vivo tests described in Example 2.

The present invention provides iRNA compositions, which effect the RNA-induced silencing complex (RISC)-mediated cleavage of RNA transcripts of an ANGPTL3gene. The ANGPTL3 gene may be within a cell, e.g., a cell within a subject, such as a human. The present invention also provides methods of using the iRNA compositions of the invention for inhibiting the expression of an ANGPTL3gene and/or for treating a subject having a disorder that would benefit from inhibiting or reducing the expression of an ANGPTL3gene, e.g., a disorder of lipid metabolism, such as hyperlipidemia or hypertriglyceridemia.

The iRNAs of the invention include an RNA strand (the antisense strand) having a region which is about 30 nucleotides or less in length, e.g., 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length, which region is substantially complementary to at least part of an mRNA transcript of an ANGPTL3 gene. The use of these iRNAs enables the targeted degradation of mRNAs of an ANGPTL3 gene in mammals. Very low dosages of ANGPTL3 iRNAs, in particular, can specifically and efficiently mediate RNA interference (RNAi), resulting in significant inhibition of expression of an ANGPTL3 gene. Using cell-based assays, the present inventors have demonstrated that iRNAs targeting ANGPTL3 can mediate RNAi, resulting in significant inhibition of expression of an ANGPTL3 gene. Thus, methods and compositions including these iRNAs are useful for treating a subject who would benefit by a reduction in the levels and/or activity of an ANGPTL3 protein, such as a subject having a disorder of lipid metabolism, such as hyperlipidemia or hypertriglyceridemia.

The following detailed description discloses how to make and use compositions containing iRNAs to inhibit the expression of an ANGPTL3 gene, as well as compositions and methods for treating subjects having diseases and disorders that would benefit from inhibition and/or reduction of the expression of this gene.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to". The term "or" is used herein to mean, and is used interchangeably with, the term "and/or," unless context clearly indicates otherwise.

The term "ANGPTL3" refers to an angiopoietin like protein 3 having an amino acid sequence from any vertebrate or mammalian source, including, but not limited to, human, bovine, chicken, rodent, mouse, rat, porcine, ovine, primate, monkey, and guinea pig, unless specified otherwise. The term also refers to fragments and variants of native ANGPTL3 that maintain at least one in vivo or in vitro activity of a native ANGPTL3. The term encompasses full-length unprocessed precursor forms of ANGPTL3 as well as mature forms resulting from post-translational cleavage of the signal peptide and forms resulting from proteolytic processing of the fibrinogen-like domain. The sequence of a human ANGPTL3 mRNA transcript can be found at, for example, GenBank Accession No. GI:

41327750 (NM_014495.2; SEQ ID NO:1). The predicted sequence of rhesus ANGPTL3 mRNA can be found at, for example, GenBank Accession No. GI: 297278846 (XM_001086114.2; SEQ ID NO:2). The sequence of mouse ANGPTL3 mRNA can be found at, for example, GenBank Accession No. GI: 142388354 (NM 013913.3; SEQ ID NO:3). The sequence of rat ANGPTL3 mRNA can be found at, for example, GenBank Accession No. GI: 68163568 (NM_001025065.1; SEQ ID NO:4).

The term "ANGPTL3" as used herein also refers to a particular polypeptide expressed in a cell by naturally occurring DNA sequence variations of the ANGPTL3 gene, such as a single nucleotide polymorphism in the ANGPTL3 gene. Numerous SNPs within the ANGPTL3 gene have been identified and may be found at, for example, NCBI dbSNP (see, e.g., www.ncbi.nlm.nih.gov/snp). Non-limiting examples of SNPs within the ANGPTL3 gene may be found at, NCBI dbSNP Accession Nos. rs193064039; rs192778191; rs192764027; rs192528948; rs191931953; rs191293319; rs191171206; rs191145608; rs191086880; rs191012841; or rs190255403.

As used herein, "target sequence" refers to a contiguous portion of the nucleotide sequence of an mRNA molecule formed during the transcription of an ANGPTL3 gene, including mRNA that is a product of RNA processing of a primary transcription product. In one embodiment, the target portion of the sequence will be at least long enough to serve as a substrate for iRNA-directed cleavage at or near that portion of the nucleotide sequence of an mRNA molecule formed during the transcription of an ANGPTL3gene.

The target sequence may be from about 9-36 nucleotides in length, e.g., about 15-30 nucleotides in length. For example, the target sequence can be from about 15-30 nucleotides, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

As used herein, the term "strand comprising a sequence" refers to an oligonucleotide comprising a chain of nucleotides that is described by the sequence referred to using the standard nucleotide nomenclature.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

The terms "iRNA", "RNAi agent," "iRNA agent,", "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of ANGPTL3 in a cell, e.g., a cell within a subject, such as a mammalian subject.

In one embodiment, an RNAi agent of the invention includes a single stranded RNA that interacts with a target RNA sequence, e.g., an ANGPTL3 target mRNA sequence, to direct the cleavage of the target RNA. Without wishing to be bound by theory, long double stranded RNA introduced into cells is broken down into siRNA by a Type III endonuclease known as Dicer (Sharp et al., Genes Dev. 2001, 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleave the target to induce silencing (Elbashir, et al., (2001) Genes Dev. 15:188). Thus, in one aspect the invention relates to a single stranded RNA (siRNA) generated within a cell and which promotes the formation of a RISC complex to effect silencing of the target gene, i.e., an ANGPTL3 gene. Accordingly, the term "siRNA" is also used herein to refer to an RNAi as described above.

In another aspect, the RNAi agent is a single-stranded antisense RNA molecule. An antisense RNA molecule is complementary to a sequence within the target mRNA. Antisense RNA can inhibit translation in a stoichiometric manner by base pairing to the mRNA and physically obstructing the translation machinery, see Dias, N. et al., (2002) Mol. Cancer Ther. 1:347-355. The single-stranded antisense RNA molecule may be about 13 to about 30 nucleotides in length and have a sequence that is complimentary to a target sequence. For example, the single-stranded antisense RNA molecule may comprise a sequence that is at least about 13, 14, 15, 16, 17, 18, 19, 20, or more contiguous nucleotides from one of the antisense sequences in Tables 2, 3, 7, 8, 9 and 10.

In another embodiment, an "iRNA" for use in the compositions and methods of the invention is a double-stranded RNA and is referred to herein as a "double stranded RNAi agent," "double-stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., an ANGPTL3 gene. In some embodiments of the invention, a double-stranded RNA (dsRNA) triggers the degradation of a target RNA, e.g., an mRNA, through a post-transcriptional gene-silencing mechanism referred to herein as RNA interference or RNAi.

The duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at least 2, at least 3, at least 4, at least 5, at least 6, at least 7, at least 8, at least 9, at least 10, at least 20, at least 23 or more unpaired nucleotides.

Where the two substantially complementary strands of a dsRNA are comprised by separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

In one embodiment, the antisense strand of a dsRNA has a 1-10 nucleotide, e.g., a 1, 2, 3, 4, 5, 6, 7, 8, 9, or 10 nucleotide, overhang at the 3'-end and/or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end and/or the 5'-end. In another embodiment, one or more of the nucleotides in the overhang is replaced with a nucleoside thiophosphate.

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt. Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double-stranded over its entire length.

The term "antisense strand" or "guide strand" refers to the strand of an iRNA, e.g., a dsRNA, which includes a region that is substantially complementary to a target sequence, e.g., an ANGPTL3 mRNA. As used herein, the term "region of complementarity" refers to the region on the antisense strand that is substantially complementary to a sequence, for example a target sequence, e.g., an ANGPTL3 nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the iRNA.

The term "sense strand" or "passenger strand" as used herein, refers to the strand of an iRNA that includes a region that is substantially complementary to a region of the antisense strand as that term is defined herein.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding ANGPTL3). For example, a polynucleotide is complementary to at least a part of an ANGPTL3mRNA if the sequence is substantially complementary to a non-interrupted portion of an mRNA encoding ANGPTL3.

In general, the majority of nucleotides of each strand are ribonucleotides, but as described in detail herein, each or both strands can also include one or more non-ribonucleotides, e.g., a deoxyribonucleotide and/or a modified nucleotide. In addition, an "iRNA" may include ribonucleotides with chemical modifications. Such modifications may include all types of modifications disclosed herein or known in the art. Any such modifications, as used in an iRNA molecule, are encompassed by "iRNA" for the purposes of this specification and claims.

The term "inhibiting," as used herein, is used interchangeably with "reducing," "silencing," "downregulating," "suppressing" and other similar terms, and includes any level of inhibition.

The phrase "inhibiting expression of an ANGPTL3," as used herein, includes inhibition of expression of any ANGPTL3 gene (such as, e.g., a mouse ANGPTL3 gene, a rat ANGPTL3 gene, a monkey ANGPTL3 gene, or a human ANGPTL3 gene) as well as variants or mutants of an ANGPTL3 gene that encode an ANGPTL3 protein.

"Inhibiting expression of an ANGPTL3 gene" includes any level of inhibition of an ANGPTL3 gene, e.g., at least partial suppression of the expression of an ANGPTL3 gene, such as an inhibition by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%.

The expression of an ANGPTL3 gene may be assessed based on the level of any variable associated with ANGPTL3 gene expression, e.g., ANGPTL3 mRNA level or ANGPTL3 protein level. The expression of an ANGPTL3 may also be assessed indirectly based on the levels of a serum lipid, a triglyceride, cholesterol (including LDL-C, HDL-C, VLDL-C, IDL-C and total cholesterol), or free fatty acids. Inhibition may be assessed by a decrease in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In one embodiment, at least partial suppression of the expression of an ANGPTL3 gene, is assessed by a reduction of the amount of ANGPTL3 mRNA which can be isolated from or detected in a first cell or group of cells in which an ANGPTL3 gene is transcribed and which has or have been treated such that the expression of an ANGPTL3 gene is inhibited, as compared to a second cell or group of cells substantially identical to the first cell or group of cells but which has or have not been so treated (control cells). The degree of inhibition may be expressed in terms of:

$$\frac{(\text{mRNA in control cells}) - (\text{mRNA in treated cells})}{(\text{mRNA in control cells})} \cdot 100\%$$

The phrase "contacting a cell with an RNAi agent," such as a dsRNA, as used herein, includes contacting a cell by any possible means. Contacting a cell with an RNAi agent includes contacting a cell in vitro with the iRNA or contacting a cell in vivo with the iRNA. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, e.g., the bloodstream or the subcutaneous space, such that the agent will subsequently reach the tissue where the cell to be contacted is located. For example, the RNAi agent may contain and/or be coupled to a ligand, e.g., GalNAc3, that directs the RNAi agent to a site of interest, e.g., the liver. Combinations of in vitro and in vivo methods of contacting are also possible. For example, a cell may also be contacted in vitro with an RNAi agent and subsequently transplanted into a subject.

In one embodiment, contacting a cell with an iRNA includes "introducing" or "delivering the iRNA into the cell" by facilitating or effecting uptake or absorption into the cell. Absorption or uptake of an iRNA can occur through unaided diffusive or active cellular processes, or by auxiliary agents or devices. Introducing an iRNA into a cell may be in vitro and/or in vivo. For example, for in vivo introduction, iRNA can be injected into a tissue site or administered systemically. In vivo delivery can also be done by a beta-glucan delivery system, such as those described in U.S. Pat. Nos. 5,032,401 and 5,607,677, and U.S. Publication No. 2005/0281781, the entire contents of which are hereby incorporated herein by reference. In vitro introduction into a cell includes methods known in the art such as electroporation and lipofection. Further approaches are described herein below and/or are known in the art.

The term "SNALP" refers to a stable nucleic acid-lipid particle. A SNALP is a vesicle of lipids coating a reduced aqueous interior comprising a nucleic acid such as an iRNA or a plasmid from which an iRNA is transcribed. SNALPs are described, e.g., in U.S. Patent Application Publication Nos. 20060240093, 20070135372, and in International Application No. WO 2009082817, the entire contents of which are hereby incorporated herein by reference. Examples of "SNALP" formulations are described below.

As used herein, a "subject" is an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). In an embodiment, the subject is a human, such as a human being treated or assessed for a disease, disorder or condition that would benefit from reduction in ANGPTL3 expression; a human at risk for a disease, disorder or condition that would benefit from reduction in ANGPTL3 expression; a human having a disease, disorder or condition that would benefit from reduction in ANGPTL3 expression; and/or human being treated for a disease, disorder or condition that would benefit from reduction in ANGPTL3 expression as described herein. As used herein, the terms "treating" or "treatment" refer to a beneficial or desired result including, such as lowering levels of triglycerides in a subject. The terms "treating" or "treatment" also include, but are not limited to, alleviation or amelioration of one or more symptoms of a disorder of lipid metabolism, such as, e.g., a decrease in the size of eruptive xanthomas. "Treatment" can also mean prolonging survival as compared to expected survival in the absence of treatment.

By "lower" in the context of a disease marker or symptom is meant a statistically significant decrease in such level. The decrease can be, for example, at least 10%, at least 20%, at least 30%, at least 40% or more, and is preferably down to a level accepted as within the range of normal for an individual without such disorder. As used herein, "prevention" or "preventing," when used in reference to a disease, disorder or condition thereof, that would benefit from a reduction in expression of an ANGPTL3 gene, refers to a reduction in the likelihood that a subject will develop a symptom associated with such disease, disorder, or condition, e.g., high triglyceride levels or eruptive xanthoma. The likelihood of developing a high tryglyceride levels or eruptive xanthoma is reduced, for example, when an individual having one or more risk factors for a high tryglyceride levels or eruptive xanthoma either fails to develop high tryglyceride levels or eruptive xanthoma or develops high tryglyceride levels or eruptive xanthoma with less severity relative to a population having the same risk factors and not receiving treatment as described herein. The failure to develop a disease, disorder or condition, or the reduction in the development of a symptom associated with such a disease, disorder or condition i (e.g., by at least about 10% on a clinically accepted scale for that disease or disorder), or the exhibition of delayed symptoms delayed (e.g., by days, weeks, months or years) is considered effective prevention.

As used herein, the term "serum lipid" refers to any major lipid present in the blood. Serum lipids may be present in the blood either in free form or as a part of a protein complex, e.g., a lipoprotein complex. Non-limiting examples of serum lipids may include triglycerides and cholesterol, such as total cholesterol (TG), low density lipoprotein cholesterol (LDL-C), high-density lipoprotein cholesterol (HDL-C), very low density lipoprotein cholesterol (VLDL-C) and intermediate-density lipoprotein cholesterol (IDL-C).

As used herein, a "disorder of lipid metabolism" refers to any disorder associated with or caused by a disturbance in lipid metabolism. For example, this term includes any disorder, disease or condition that can lead to hyperlipidemia, or condition characterized by abnormal elevation of levels of any or all lipids and/or lipoproteins in the blood. This term refers to an inherited disorder, such as familial hypertriglyceridemia, or an acquired disorder, such as a disorder acquired as a result of a diet or intake of certain drugs. Exemplary disorders of lipid metabolism include, but are not limited to, atherosclerosis, dyslipidemia, hypertriglyceridemia (including drug-induced hypertriglyceridemia, diuretic-induced hypertriglyceridemia, alcohol-induced hypertriglyceridemia, β-adrenergic blocking agent-induced hypertriglyceridemia, estrogen-induced hypertriglyceridemia, glucocorticoid-induced hypertriglyceridemia, retinoid-induced hypertriglyceridemia, cimetidine-induced hypertriglyceridemia, and familial hypertriglyceridemia), acute pancreatitis associated with hypertriglyceridemia, chylomicron syndrom, familial chylomicronemia, Apo-E deficiency or resistance, LPL deficiency or hypoactivity, hyperlipidemia (including familial combined hyperlipidemia), hypercholesterolemia, gout associated with hypercholesterolemia, xanthomatosis (subcutaneous cholesterol deposits).

Cardiovascular diseases associated with disorders of lipid metabolism are also considered "disorders of lipid metabolism", as defined herein. These diseases may include coronary artery disease (also called ischemic heart disease), inflammation associated with coronary artery disease, restenosis, peripheral vascular diseases, and stroke.

Disorders related to body weight are also considered "disorders of lipid metabolism", as defined herein. Such disorders may include obesity, metabolic syndrome including independent components of metabolic syndrome (e.g., central obesity, FBG/pre-diabetes/diabetes, hypercholesterolemia, hypertriglyceridemia, and hypertension), hypothyroidism, uremia, and other conditions associated with weight gain (including rapid weight gain), weight loss, maintenance of weight loss, or risk of weight regain following weight loss.

Blood sugar disorders are further considered "disorders of lipid metabolism", as defined herein. Such disorders may include diabetes, hypertension, and polycystic ovarian syndrome related to insulin resistance. Other exemplary disorders of lipid metabolism may also include renal transplantation, nephrotic syndrome, Cushing's syndrome, acromegaly, systemic lupus erythematosus, dysglobulinemia, lipodystrophy, glycogenosis type I, and Addison's disease.

"Therapeutically effective amount," as used herein, is intended to include the amount of an RNAi agent that, when administered to a subject having a disorder of lipid metabolism, is sufficient to effect treatment of the disease (e.g., by diminishing, ameliorating or maintaining the existing disease or one or more symptoms of disease). The "therapeutically effective amount" may vary depending on the RNAi agent, how the agent is administered, the disease and its severity and the history, age, weight, family history, genetic makeup, the types of preceding or concomitant treatments, if any, and other individual characteristics of the subject to be treated.

"Prophylactically effective amount," as used herein, is intended to include the amount of an iRNA that, when administered to a subject having a disorder of lipid metabolism, is sufficient to prevent or ameliorate the disease or one or more symptoms of the disease. Ameliorating the disease includes slowing the course of the disease or reducing the severity of later-developing disease. The "prophylactically effective amount" may vary depending on the iRNA, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylactically effective amount" also includes an amount of an RNAi agent that produces some desired local or systemic effect at a reasonable benefit/risk ratio applicable to any treatment.

iRNA employed in the methods of the present invention may be administered in a sufficient amount to produce a reasonable benefit/risk ratio applicable to such treatment.

The phrase "pharmaceutically acceptable" is employed herein to refer to those compounds, materials, compositions, and/or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In some embodiments, a "sample derived from a subject" refers to blood or plasma drawn from the subject.

II. iRNAs of the Invention

Described herein are iRNAs which inhibit the expression of an ANGPTL3 gene. In one embodiment, the iRNA agent includes double-stranded ribonucleic acid (dsRNA) molecules for inhibiting the expression of an ANGPTL3 gene in a cell, such as a cell within a subject, e.g., a mammal, such as a human having a disorder of lipid metabolism, e.g., familial hyperlipidemia. The dsRNA includes an antisense strand having a region of complementarity which is complementary to at least a part of an mRNA formed in the expression of an ANGPTL3 gene, The region of complementarity is about 30 nucleotides or less in length (e.g., about 30, 29, 28, 27, 26, 25, 24, 23, 22, 21, 20, 19, or 18 nucleotides or less in length). Upon contact with a cell expressing the ANGPTL3 gene, the iRNA inhibits the expression of the ANGPTL3 gene (e.g., a human, a primate, a non-primate, or a bird ANGPTL3 gene) by at least about 10% as assayed by, for example, a PCR or branched DNA (bDNA)-based method, or by a protein-based method, such as by immunofluorescence analysis, using, for example, Western Blotting or flowcytometric techniques.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of an ANGPTL3gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is between 15 and 30 base pairs in length, e.g., between, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

Similarly, the region of complementarity to the target sequence is between 15 and 30 nucleotides in length, e.g., between 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

In some embodiments, the dsRNA is between about 15 and about 20 nucleotides in length, or between about 25 and about 30 nucleotides in length. In general, the dsRNA is long enough to serve as a substrate for the Dicer enzyme. For example, it is well known in the art that dsRNAs longer than about 21-23 nucleotides can serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 9 to 36 base pairs, e.g., about 10-36, 11-36, 12-36, 13-36, 14-36, 15-36, 9-35, 10-35, 11-35, 12-35, 13-35, 14-35, 15-35, 9-34, 10-34, 11-34, 12-34, 13-34, 14-34, 15-34, 9-33, 10-33, 11-33, 12-33, 13-33, 14-33, 15-33, 9-32, 10-32, 11-32, 12-32, 13-32, 14-32, 15-32, 9-31, 10-31, 11-31, 12-31, 13-32, 14-31, 15-31, 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs. Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, an iRNA agent useful to target ANGPTL3 expression is not generated in the target cell by cleavage of a larger dsRNA.

A dsRNA as described herein can further include one or more single-stranded nucleotide overhangs e.g., 1, 2, 3, or 4 nucleotides. dsRNAs having at least one nucleotide overhang can have unexpectedly superior inhibitory properties relative to their blunt-ended counterparts. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

A dsRNA can be synthesized by standard methods known in the art as further discussed below, e.g., by use of an automated DNA synthesizer, such as are commercially available from, for example, Biosearch, Applied Biosystems, Inc.

iRNA compounds of the invention may be prepared using a two-step procedure. First, the individual strands of the double-stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Single-stranded oligonucleotides of the invention can be prepared using solution-phase or solid-phase organic synthesis or both.

In one aspect, a dsRNA of the invention includes at least two nucleotide sequences, a sense sequence and an antisense sequence. The sense strand is selected from the group of sequences provided in Tables 2, 3, 7, 8, 9 and 10, and the corresponding antisense strand of the sense strand is selected from the group of sequences of Tables 2, 3, 7, 8, 9 and 10. In this aspect, one of the two sequences is complementary to the other of the two sequences, with one of the sequences being substantially complementary to a sequence of an mRNA generated in the expression of an ANGPTL3gene. As such, in this aspect, a dsRNA will include two oligonucleotides, where one oligonucleotide is described as the sense strand in Tables 2, 3, 7, 8, 9 and 10, and the second oligonucleotide is described as the corresponding antisense strand of the sense strand in Tables 2, 3, 7, 8, 9 and 10. In one embodiment, the substantially complementary sequences of the dsRNA are contained on separate oligonucleotides. In another embodiment, the substantially complementary sequences of the dsRNA are contained on a single oligonucleotide.

The skilled person is well aware that dsRNAs having a duplex structure of between about 20 and 23 base pairs, e.g., 21, base pairs have been hailed as particularly effective in inducing RNA interference (Elbashir et al., (2001) *EMBO J.*, 20:6877-6888). However, others have found that shorter or longer RNA duplex structures can also be effective (Chu and Rana (2007) *RNA* 14:1714-1719; Kim et al. (2005) *Nat Biotech* 23:222-226). In the embodiments described above, by virtue of the nature of the oligonucleotide sequences provided in Tables 2, 3, 7, 8, 9 and 10, dsRNAs described herein can include at least one strand of a length of minimally 21 nucleotides. It can be reasonably expected that shorter duplexes having one of the sequences of Tables 2, 3, 7, 8, 9 and 10 minus only a few nucleotides on one or both ends can be similarly effective as compared to the dsRNAs described above. Hence, dsRNAs having a sequence of at least 15, 16, 17, 18, 19, 20, or more contiguous nucleotides derived from one of the sequences of Tables 2, 3, 7, 8, 9 and 10, and differing in their ability to inhibit the expression of an ANGPTL3gene by not more than about 5, 10, 15, 20, 25, or 30% inhibition from a dsRNA comprising the full sequence, are contemplated to be within the scope of the present invention.

In addition, the RNAs provided in Tables 2, 3, 7, 8, 9 and 10 identify a site(s) in an ANGPTL3 transcript that is susceptible to RISC-mediated cleavage. As such, the present invention further features iRNAs that target within one of these sites. As used herein, an iRNA is said to target within a particular site of an RNA transcript if the iRNA promotes cleavage of the transcript anywhere within that particular site. Such an iRNA will generally include at least about 15 contiguous nucleotides from one of the sequences provided in Tables 2, 3, 7, 8, 9 and 10 coupled to additional nucleotide sequences taken from the region contiguous to the selected sequence in an ANGPTL3gene.

While a target sequence is generally about 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an iRNA agent, mediate the best inhibition of target gene expression. Thus, while the sequences identified, for example, in Tables 2, 3, 7, 8, 9 and 10 represent effective target sequences, it is contemplated that further optimization of inhibition efficiency can be achieved by progressively "walking the window" one nucleotide upstream or downstream of the given sequences to identify sequences with equal or better inhibition characteristics.

Further, it is contemplated that for any sequence identified, e.g., in Tables 2, 3, 7, 8, 9 and 10, further optimization could be achieved by systematically either adding or removing nucleotides to generate longer or shorter sequences and testing those sequences generated by walking a window of 5 the longer or shorter size up or down the target RNA from that point. Again, coupling this approach to generating new candidate targets with testing for effectiveness of iRNAs based on those target sequences in an inhibition assay as known in the art and/or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes) as an expression inhibitor.

An iRNA as described herein can contain one or more mismatches to the target sequence. In one embodiment, an iRNA as described herein contains no more than 3 mismatches. If the antisense strand of the iRNA contains mismatches to a target sequence, it is preferable that the area of mismatch is not located in the center of the region of complementarity. If the antisense strand of the iRNA contains mismatches to the target sequence, it is preferable that the mismatch be restricted to be within the last 5 nucleotides from either the 5'- or 3'-end of the region of complementarity. For example, for a 23 nucleotide iRNA agent the strand which is complementary to a region of an ANGPTL3 gene, generally does not contain any mismatch within the central 13 nucleotides. The methods described herein or methods known in the art can be used to determine whether an iRNA containing a mismatch to a target sequence is effective in inhibiting the expression of an ANGPTL3 gene. Consideration of the efficacy of iRNAs with mismatches in inhibiting expression of an ANGPTL3 gene is important, especially if the particular region of complementarity in an ANGPTL3 gene is known to have polymorphic sequence variation within the population.

III. Modified iRNAs of the Invention

In one embodiment, the RNA of an iRNA of the invention, e.g., a dsRNA, is chemically modified to enhance stability or other beneficial characteristics. The nucleic acids featured in the invention can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in iRNAs, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., *Science,* 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—N($CH_3$)—N($CH_3$)—$CH_2$—, and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O—, S—, or N-alkyl; O—, S—, or N-alkenyl; O—, S— or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$).$_n$O$CH_3$, O($CH_2$)$_n$$NH_2$, O($CH_2$)$_n$$CH_3$, O($CH_2$)$_n$O$NH_2$, and O($CH_2$).$_n$ON[($CH_2$)$_n$$CH_3$)]$_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, S$CH_3$, OCN, Cl, Br, CN, $CF_3$, O$CF_3$, SO$CH_3$, $SO_2$$CH_3$, O$NO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2$$CH_2$O$CH_3$, also known as 2'-O-(2-methoxyethyl) or 2'-MOE) (Martin et al., *Helv. Chim. Acta,* 1995, 78:486-504) i.e., an alkoxy-alkoxy group. Another exemplary modification is 2'-dimethylaminooxyethoxy, i.e., a O($CH_2$)$_2$ON($CH_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_3$)$_2$.

Other modifications include 2'-methoxy (2'-O$CH_3$), 2'-aminopropoxy (2'-O$CH_2$$CH_2$$CH_2$$NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., (1991) *Angewandte Chemie, International Edition,* 30:613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-

447; Mook, O R. et al., (2007) *Mol Canc Ther* 6(3):833-843; Grunweller, A. et al., (2003) *Nucleic Acids Research* 31(12): 3185-3193).

Representative U.S. Patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

IV. iRNAs Conjugated to Ligands

Another modification of the RNA of an iRNA of the invention involves chemically linking to the RNA one or more ligands, moieties or conjugates that enhance the activity, cellular distribution or cellular uptake of the iRNA. Such moieties include but are not limited to lipid moieties such as a cholesterol moiety (Letsinger et al., (1989) *Proc. Natl. Acid. Sci. USA,* 86: 6553-6556), cholic acid (Manoharan et al., (1994) *Biorg. Med. Chem. Let.,* 4:1053-1060), a thioether, e.g., beryl-S-tritylthiol (Manoharan et al., (1992) *Ann. N.Y. Acad. Sci.,* 660:306-309; Manoharan et al., (1993) *Biorg. Med. Chem. Let.,* 3:2765-2770), a thiocholesterol (Oberhauser et al., (1992) *Nucl. Acids Res.,* 20:533-538), an aliphatic chain, e.g., dodecandiol or undecyl residues (Saison-Behmoaras et al., (1991) *EMBO J,* 10:1111-1118; Kabanov et al., (1990) *FEBS Lett.,* 259:327-330; Svinarchuk et al., (1993) *Biochimie,* 75:49-54), a phospholipid, e.g., di-hexadecyl-rac-glycerol or triethyl-ammonium 1,2-di-O-hexadecyl-rac-glycero-3-phosphonate (Manoharan et al., (1995) *Tetrahedron Lett.,* 36:3651-3654; Shea et al., (1990) *Nucl. Acids Res.,* 18:3777-3783), a polyamine or a polyethylene glycol chain (Manoharan et al., (1995) *Nucleosides & Nucleotides,* 14:969-973), or adamantane acetic acid (Manoharan et al., (1995) *Tetrahedron Lett.,* 36:3651-3654), a palmityl moiety (Mishra et al., (1995) *Biochim. Biophys. Acta,* 1264:229-237), or an octadecylamine or hexylaminocarbonyloxycholesterol moiety (Crooke et al., (1996) *J. Pharmacol. Exp. Ther.,* 277:923-937).

In one embodiment, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylglucosamine, N-acetylgalactosamine or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated oligonucleotides of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

In the ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conujugates

In one embodiment, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

B. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 13). An RFGF analogue (e.g., amino acid sequence AALLPVL-LAAP (SEQ ID NO: 10) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 11) and the *Drosophila* Antennapedia protein (RQIKIWFQNRRMKWKK (SEQ ID NO: 12) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to a dsRNA agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glyciosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, a α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

C. Carbohydrate Conjugates

In some embodiments of the compositions and methods of the invention, an iRNA oligonucleotide further comprises a carbohydrate. The carbohydrate conjugated iRNA are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In one embodiment, a carbohydrate conjugate for use in the compositions and methods of the invention is a monosaccharide. In one embodiment, the monosaccharide is an N-acetylgalactosamine, such as

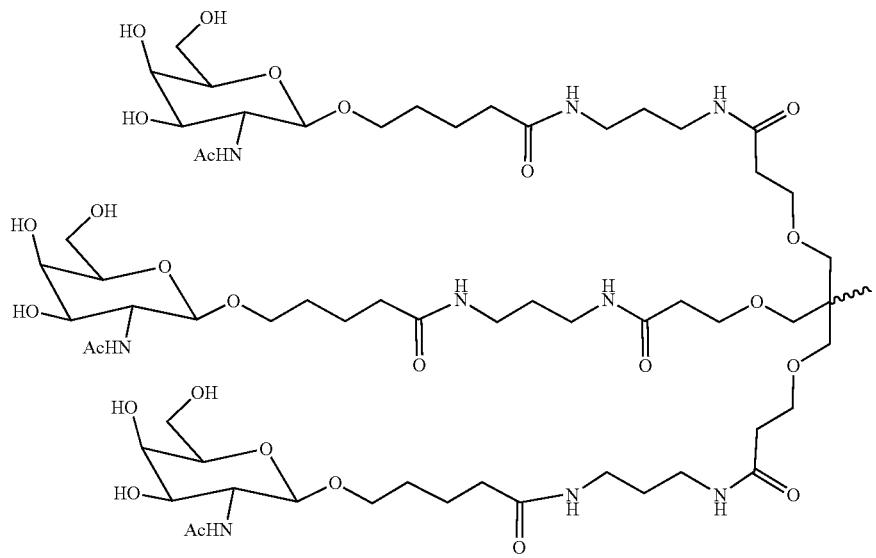

Formula II

In another embodiment, a carbohydrate conjugate for use in the compositions and methods of the invention is selected from the group consisting of:

Formula II
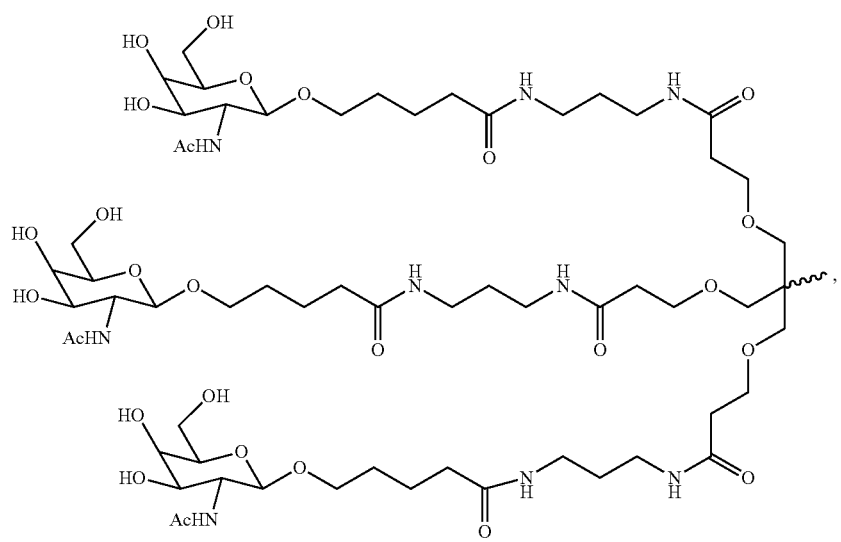
Formula III
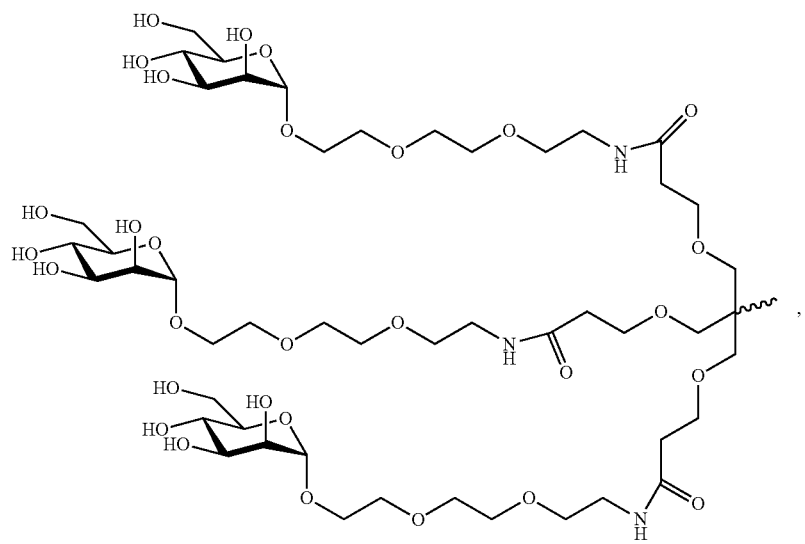
Formula IV
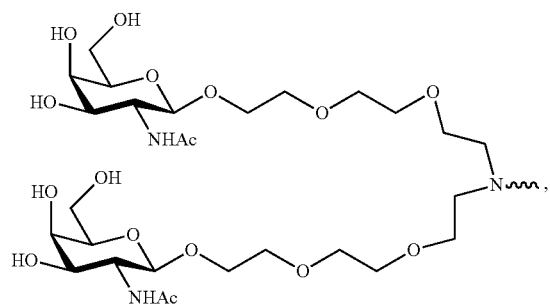
Formula V
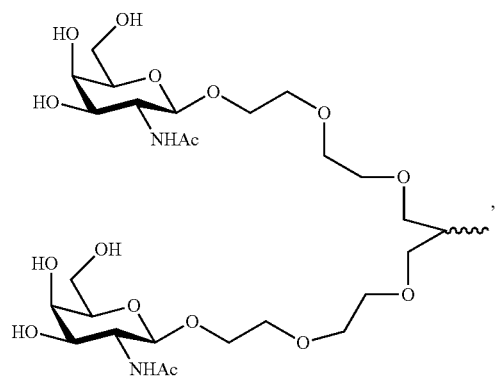

Formula VI
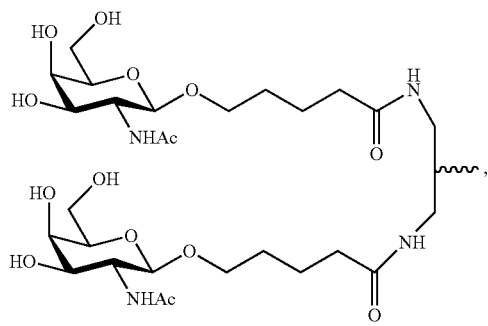
Formula VII
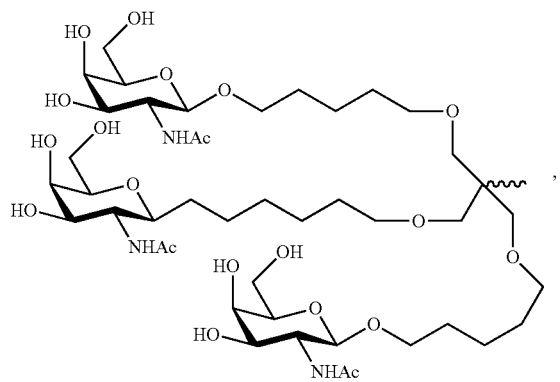
Formula VIII
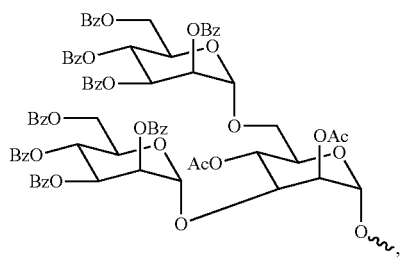
Formula IX
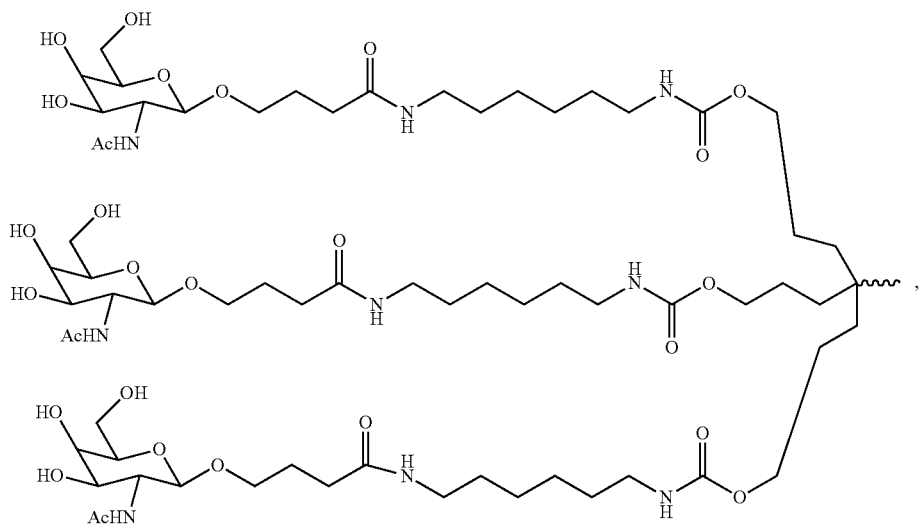

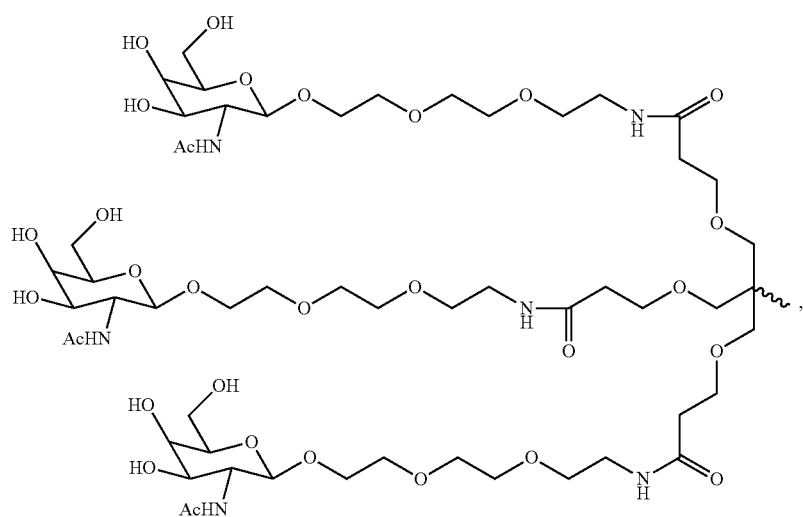
Formula X
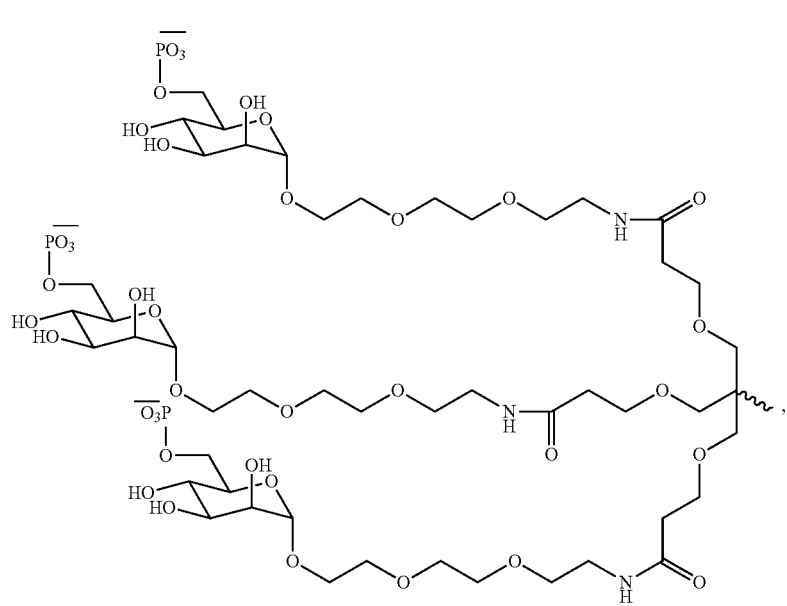
Formula XI

Formula XII
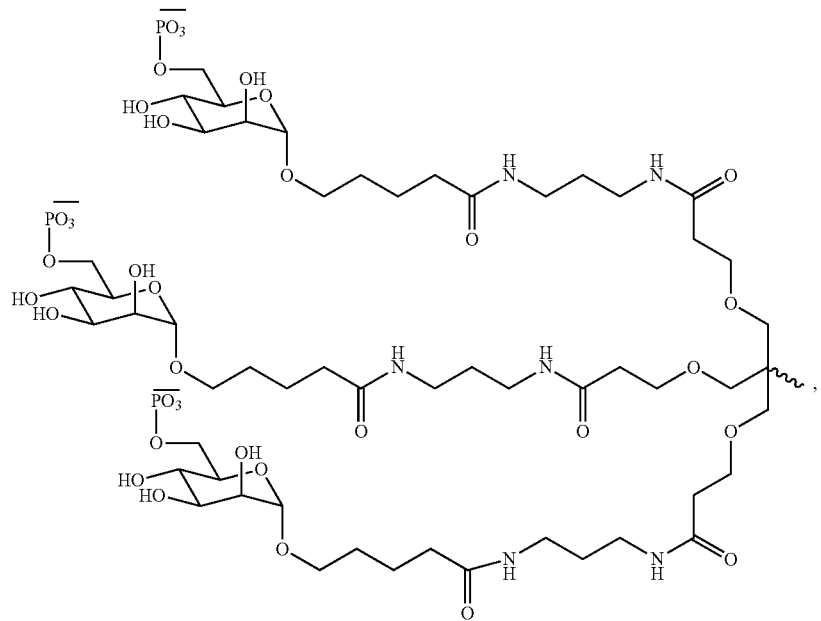
Formula XIII
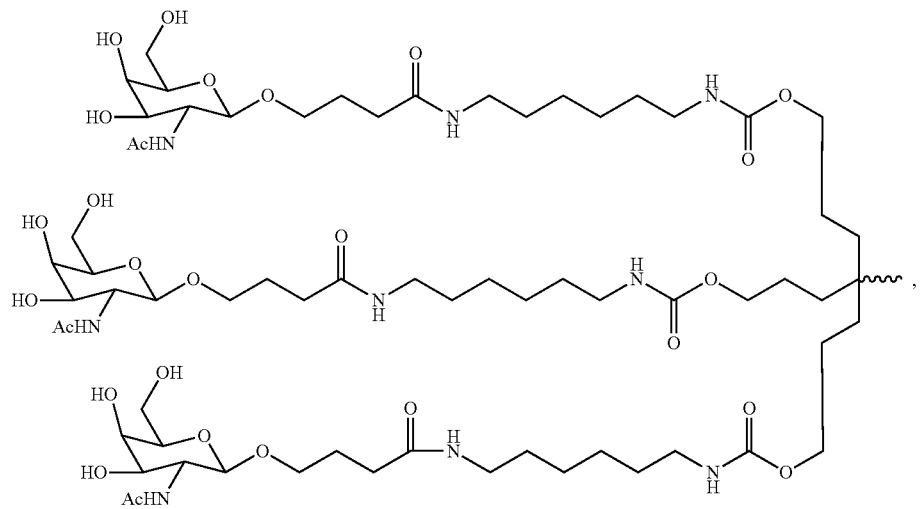
Formula XIV
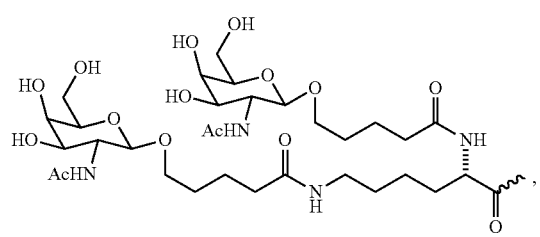
Formula XV
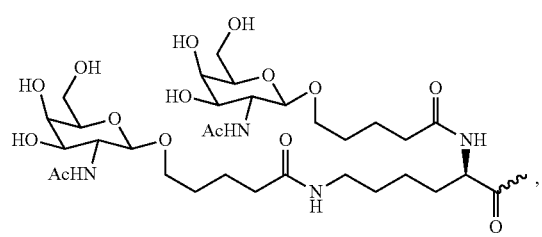
Formula XVI
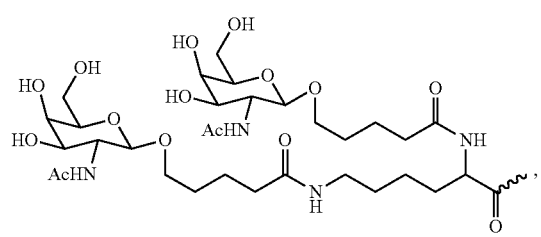
Formula XVII
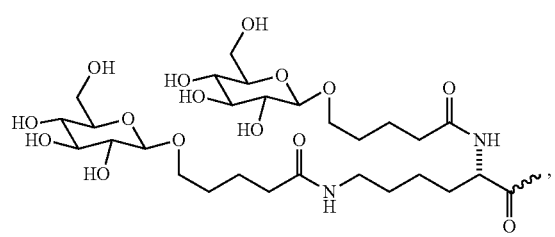

-continued

Formula XVIII

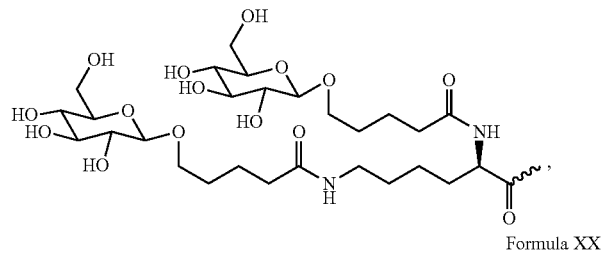

Formula XIX

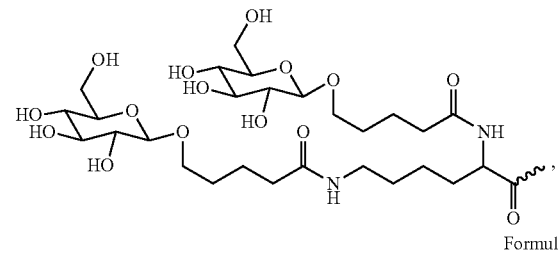

Formula XX

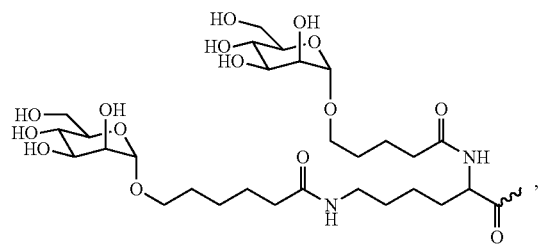

Formula XXI

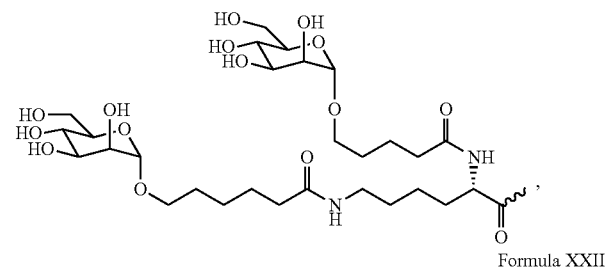

Formula XXII

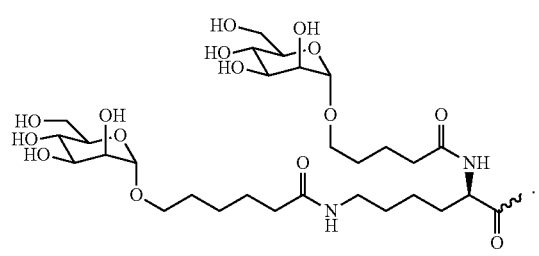

Another representative carbohydrate conjugate for use in the embodiments described herein includes, but is not limited to,

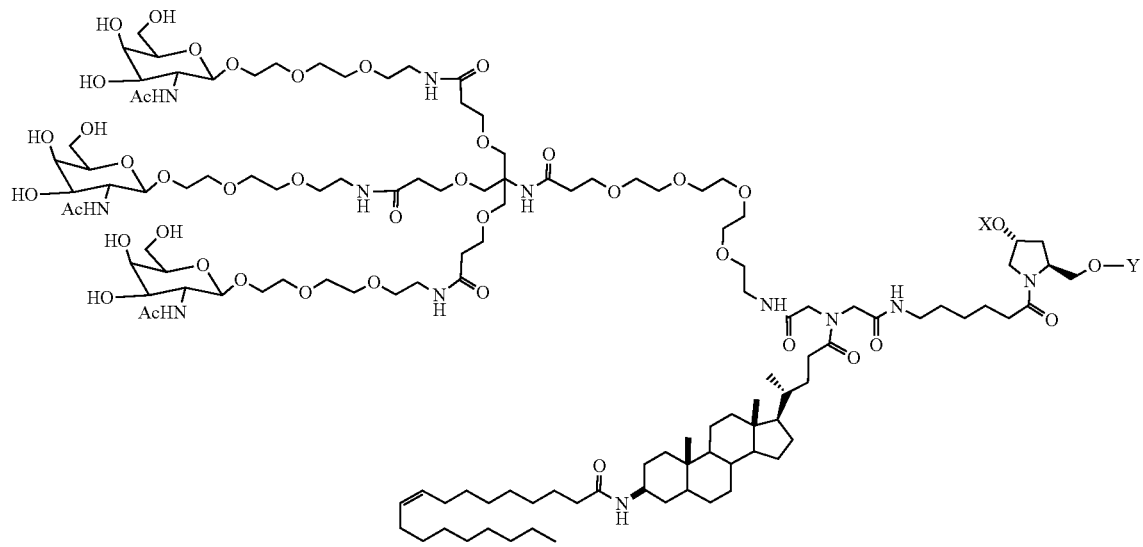

(Formula XXIII), when one of X or Y is an oligonucleotide, the other is a hydrogen.

In some embodiments, the carbohydrate conjugate further comprises one or more additional ligands as described above, such as, but not limited to, a PK modulator and/or a cell permeation peptide.

D. Linkers

In some embodiments, the conjugate or ligand described herein can be attached to an iRNA oligonucleotide with various linkers that can be cleavable or non cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, SO$_2$, SO$_2$NH or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), SO$_2$, N(R8), C(O), substituted or unsubstituted aryl, substituted or unsubstituted heteroaryl, substituted or unsubstituted heterocyclic; where R8 is hydrogen, acyl, aliphatic or substituted aliphatic. In one embodiment, the linker is between about 1-24 atoms, 2-24, 3-24, 4-24, 5-24, 6-24, 6-18, 7-18, 8-18 atoms, 7-17, 8-17, 6-16, 7-17, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

i. Redox Cleavable Linking Groups

In one embodiment, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In Another Embodiment, a Cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

iii. Acid Cleavable Linking Groups

In another embodiment, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Linking Groups

In another embodiment, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

v. Peptide-Based Cleaving Groups

In yet another embodiment, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

In one embodiment, an iRNA of the invention is conjugated to a carbohydrate through a linker. Non-limiting examples of iRNA carbohydrate conjugates with linkers of the compositions and methods of the invention include, but are not limited to, (Formula XXIV)

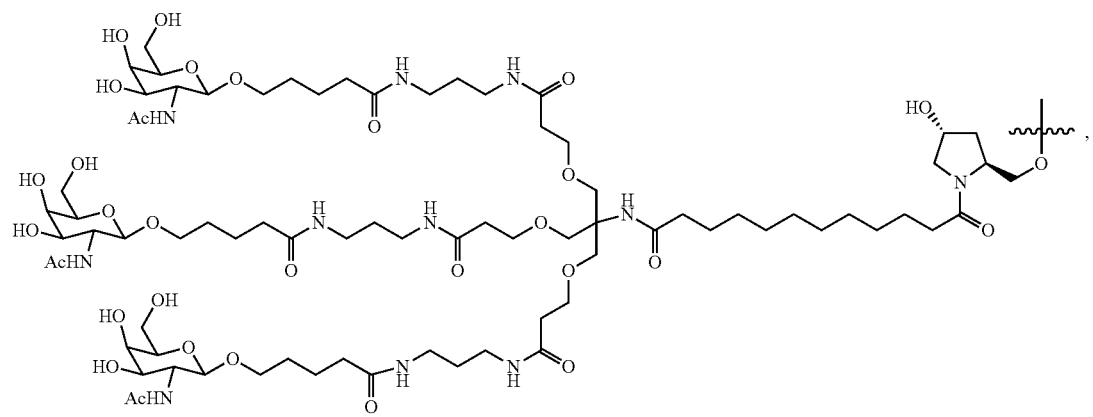

(Formula XXV)
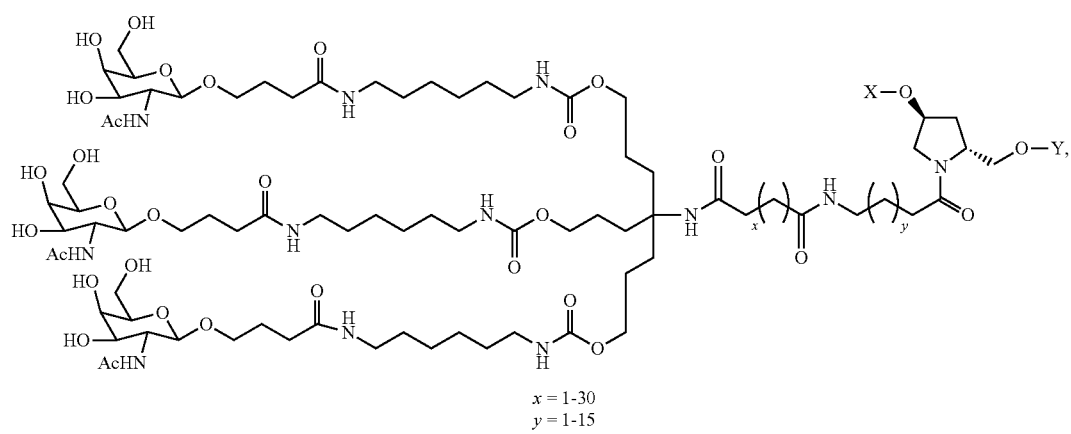
x = 1-30
y = 1-15
(Formula XXVI)
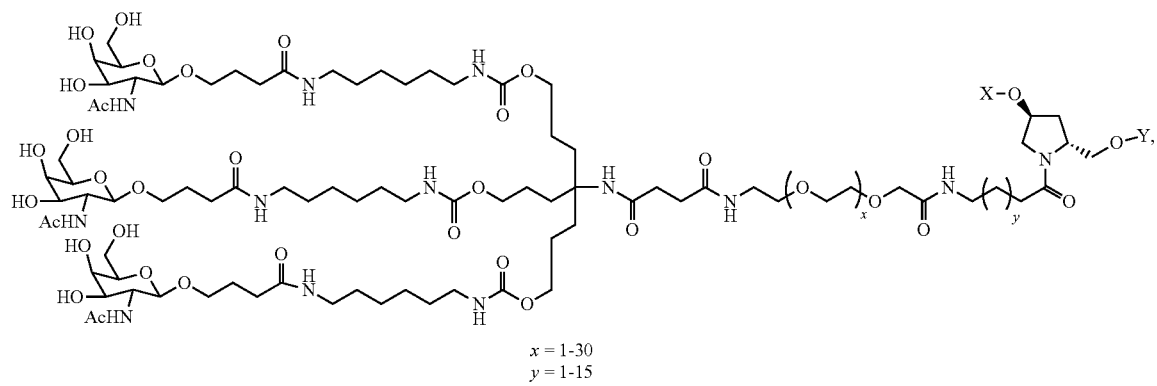
x = 1-30
y = 1-15
(Formula XXVII)
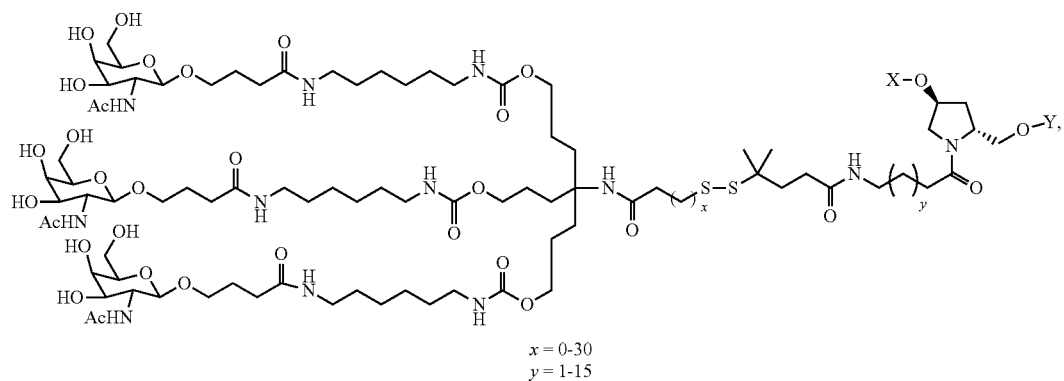
x = 0-30
y = 1-15
(Formula XXVIII)
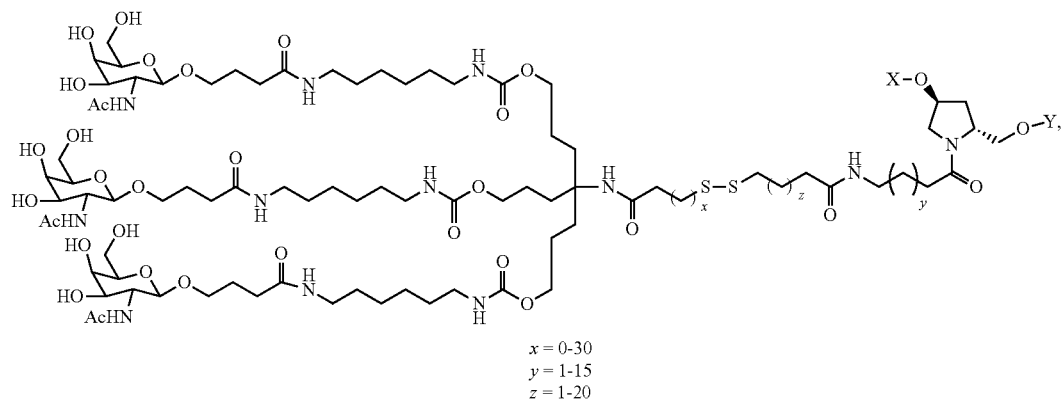
x = 0-30
y = 1-15
z = 1-20

(Formula XXIX)

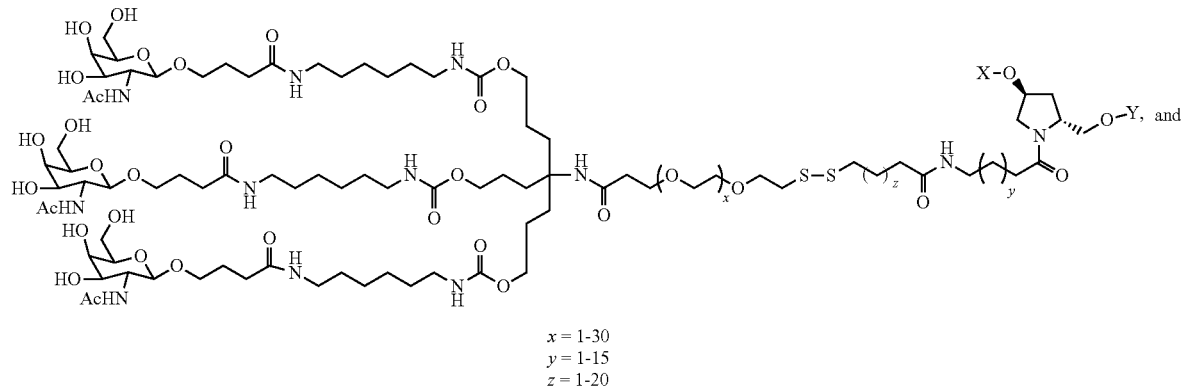

x = 1-30
y = 1-15
z = 1-20

(Formula XXX)

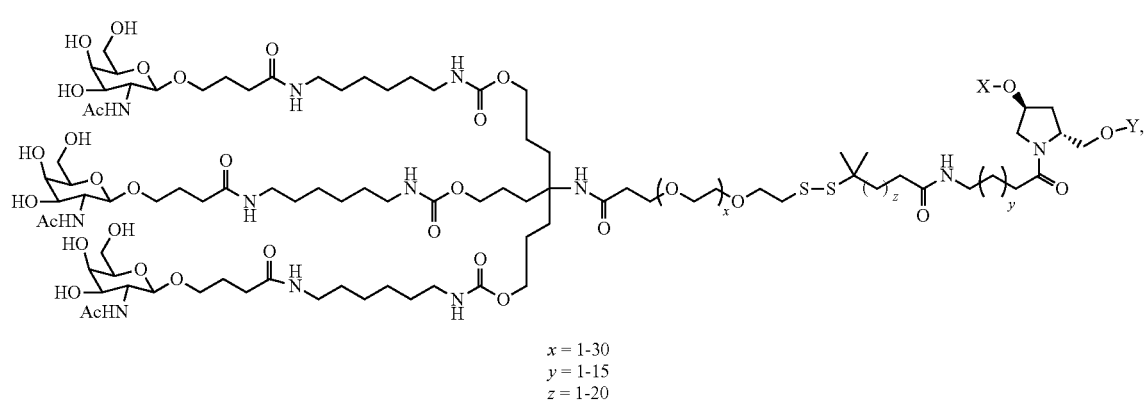

x = 1-30
y = 1-15
z = 1-20 when one of X or Y is an oligonucleotide, the other is a hydrogen.

In certain embodiments of the compositions and methods of the invention, a ligand is one or more GalNAc (N-acetyl-galactosamine) derivatives attached through a bivalent or trivalent branched linker.

In one embodiment, a dsRNA of the invention is conjugated to a bivalent or trivalent branched linker selected from the group of structures shown in any of formula (XXXI)-(XXXIV):

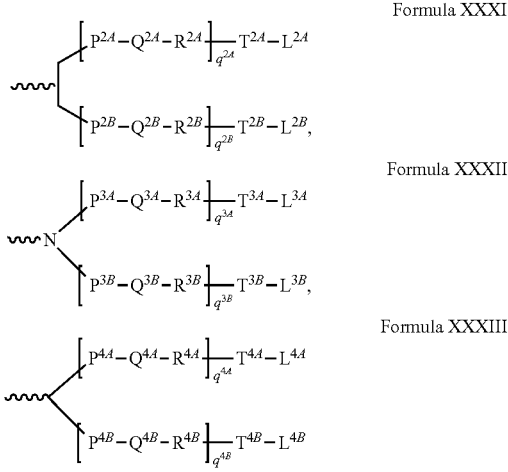

Formula XXXI

Formula XXXII

Formula XXXIII

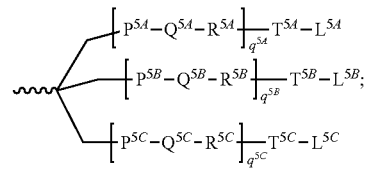

Formula XXXIV wherein:

q2A, q2B, q3A, q3B, q4A, q4B, q5A, q5B and q5C represent independently for each occurrence 0-20 and wherein the repeating unit can be the same or different; $p^{2A}$, $p^{2B}$, $p^{3A}$, $p^{3B}$, $p^{4A}$, $p^{4B}$, $p^{5A}$, $p^{5B}$, $p^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), $CH_2$, $CH_2NH$ or $CH_2O$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')=C(R"), C≡C or C(O); $R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, —C(O)—CH($R^a$)—NH—, CO, CH=N—O,

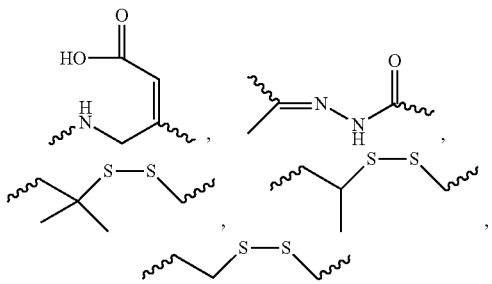

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain. Trivalent conjugating GalNAc derivatives are particularly useful for use with RNAi agents for inhibiting the expression of a target gene, such as those of formula (XXXV):

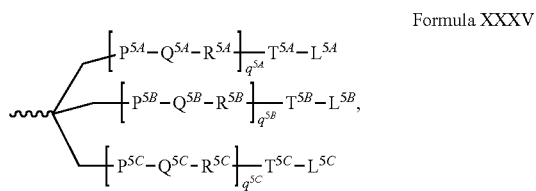

Formula XXXV wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II_VII, XI, X, and XIII Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNAs, which contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, and/or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., Biochem. Biophys. Res. Comm., 2007, 365(1):54-61; Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-S-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

IV. Delivery of an iRNA of the Invention

The delivery of an iRNA of the invention to a cell e.g., a cell within a subject, such as a human subject (e.g., a subject in need thereof, such as a subject having a disorder of lipid metabolism) can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S. and Julian R L., (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. The non-specific effects of an iRNA can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the iRNA molecule to be administered. Several studies have shown successful knockdown of gene products when an iRNA is administered locally. For example, intraocular delivery of a VEGF dsRNA by intravitreal injection in cynomolgus monkeys (Tolentino, M J. et al., (2004) *Retina* 24:132-138) and subretinal injections in mice (Reich, S J. et al. (2003) *Mol. Vis.* 9:210-216) were both shown to prevent neovascularization in an experimental model of age-related macular degeneration. In addition, direct intratumoral injection of a dsRNA in mice reduces tumor volume (Pille, J. et al. (2005) *Mol. Ther.* 11:267-274) and can prolong survival of tumor-bearing mice (Kim, W J. et al., (2006) *Mol. Ther.* 14:343-350; Li, S. et al., (2007) *Mol. Ther.* 15:515-523). RNA interference has also shown success with local delivery to the CNS by direct injection (Dorn, G. et al., (2004) *Nucleic Acids* 32:e49; Tan, P H. et al. (2005) *Gene Ther.* 12:59-66; Makimura, H. et al. (2002) *BMC Neurosci.* 3:18; Shishkina, G T., et al. (2004) *Neuroscience* 129:521-528; Thakker, E R., et al. (2004) *Proc. Natl. Acad. Sci. U.S.A.* 101:17270-17275; Akaneya, Y., et al. (2005) *J. Neurophysiol.* 93:594-602) and to the lungs by intranasal administration (Howard, K A. et al., (2006) *Mol. Ther.* 14:476-484; Zhang, X. et al., (2004) *J. Biol. Chem.* 279:10677-10684; Bitko, V. et al., (2005) *Nat. Med.* 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J. et al., (2004) *Nature* 432:173-178). Conjugation of an iRNA to an aptamer has been shown to inhibit tumor growth and mediate tumor regression in a mouse model of prostate cancer (McNamara, J O. et al., (2006) *Nat. Biotechnol.* 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim SH. et al., (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al. (2003) *J Mol. Biol* 327:761-766; Verma, U N. et al., (2003) *Clin. Cancer Res.* 9:1291-1300; Arnold, A S et al., (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N. et al., (2003), supra), Oligofectamine, "solid nucleic acid lipid particles" (Zimmermann, T S. et al., (2006) *Nature* 441:111-114), cardiolipin (Chien, P Y. et al., (2005) *Cancer Gene Ther.* 12:321-328; Pal, A. et al., (2005) *Intl Oncol.* 26:1087-1091), polyethyleneimine (Bonnet M E. et al., (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A. et al., (2007) *Biochem. Soc. Trans.* 35:61-67; Yoo, H. et al., (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

A. Vector Encoded iRNAs of the Invention iRNA targeting the ANGPTL3 gene can be expressed from transcription units inserted into DNA or RNA vectors (see, e.g., Couture, A, et al., *TIG.* (1996), 12:5-10; Skillern, A., et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., (1995) *Proc. Natl. Acad. Sci. USA* 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

iRNA expression plasmids can be transfected into target cells as a complex with cationic lipid carriers (e.g., Oligofectamine) or non-cationic lipid-based carriers (e.g., Transit-TKO™). Multiple lipid transfections for iRNA-mediated knockdowns targeting different regions of a target RNA over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are further described below.

Vectors useful for the delivery of an iRNA will include regulatory elements (promoter, enhancer, etc.) sufficient for expression of the iRNA in the desired target cell or tissue. The regulatory elements can be chosen to provide either constitutive or regulated/inducible expression.

Expression of the iRNA can be precisely regulated, for example, by using an inducible regulatory sequence that is sensitive to certain physiological regulators, e.g., circulating glucose levels, or hormones (Docherty et al., 1994, FASEB J. 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the iRNA transgene.

Viral vectors that contain nucleic acid sequences encoding an iRNA can be used. For example, a retroviral vector can be used (see Miller et al., (1993) *Meth. Enzymol.* 217:581-599). These retroviral vectors contain the components necessary for the correct packaging of the viral genome and integration into the host cell DNA. The nucleic acid sequences encoding an iRNA are cloned into one or more vectors, which facilitate delivery of the nucleic acid into a patient. More detail about retroviral vectors can be found, for example, in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., (1994) *J. Clin. Invest.* 93:644-651; Kiem et al., (1994) *Blood* 83:1467-1473; Salmons and Gunzberg, (1993) *Human Gene Therapy* 4:129-141; and Grossman and Wilson, (1993) *Curr. Opin. in Genetics and Devel.* 3:110-114. Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of iRNAs of the invention. Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, (1993) *Current Opinion in Genetics and Development* 3:499-503 present a review of adenovirus-based gene therapy. Bout et al., (1994) *Human Gene Therapy* 5:3-10 demonstrated the use of adenovirus vectors to transfer genes to the respiratory epithelia of rhesus monkeys. Other instances of the use of adenoviruses in gene therapy can be found in Rosenfeld et al., (1991) *Science* 252:431-434; Rosenfeld et al., (1992) *Cell* 68:143-155; Mastrangeli et al., (1993) *J. Clin. Invest.* 91:225-234; PCT Publication WO94/12649; and Wang et al., (1995) *Gene Therapy* 2:775-783. A suitable AV vector for expressing an iRNA featured in the invention, a method for constructing the recombinant AV vector, and a method for delivering the vector into target cells, are described in Xia H et al. (2002), *Nat. Biotech.* 20: 1006-1010.

Adeno-associated virus (AAV) vectors may also be used to delivery an iRNA of the invention (Walsh et al., (1993) *Proc. Soc. Exp. Biol. Med.* 204:289-300; U.S. Pat. No. 5,436,146). In one embodiment, the iRNA can be expressed as two separate, complementary single-stranded RNA molecules from a recombinant AAV vector having, for example, either the U6 or H1 RNA promoters, or the cytomegalovirus (CMV) promoter. Suitable AAV vectors for expressing the dsRNA featured in the invention, methods for constructing the recombinant AV vector, and methods for delivering the vectors into target cells are described in Samulski R et. al. (1987), *J. Virol.* 61: 3096-3101; Fisher K J et al. (1996), *J. Virol,* 70: 520-532; Samulski R et al. (1989), *J. Virol.* 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

Another viral vector suitable for delivery of an iRNA of the invention is a pox virus such as a vaccinia virus, for example an attenuated vaccinia such as Modified Virus Ankara (MVA) or NYVAC, an avipox such as fowl pox or canary pox.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes; see, e.g., Rabinowitz J E et al. (2002), *J Virol* 76:791-801, the entire disclosure of which is herein incorporated by reference.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

V. Pharmaceutical Compositions of the Invention

The present invention also includes pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for treating a disease or disorder associated with the expression or activity of an ANGPTL3 gene, e.g., a disorder of lipid metabolism, such as hypertriglyceridemia.

Such pharmaceutical compositions are formulated based on the mode of delivery. One example is compositions that are formulated for systemic administration via parenteral delivery, e.g., by intravenous (IV) or for subcutaneous delivery. Another example is compositions that are formulated for direct delivery into the liver, e.g., by infusion into the liver, such as by continuous pump infusion.

The pharmaceutical compositions of the invention may be administered in dosages sufficient to inhibit expression of a ANGPTL3 gene. In general, a suitable dose of an iRNA of the invention will be in the range of about 0.001 to about 200.0 milligrams per kilogram body weight of the recipient per day, generally in the range of about 1 to 50 mg per kilogram body weight per day. For example, the dsRNA can be administered at about 0.01 mg/kg, about 0.05 mg/kg, about 0.5 mg/kg, about 1 mg/kg, about 1.5 mg/kg, about 2 mg/kg, about 3 mg/kg, about 10 mg/kg, about 20 mg/kg, about 30 mg/kg, about 40 mg/kg, or about 50 mg/kg per single dose.

For example, the dsRNA may be administered at a dose of about 0.1, 0.2, 0.3, 0.4, 0.5, 0.6, 0.7. 0.8, 0.9, 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8. 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8. 6.9, 7, 7.1, 7.2, 7.3, 7.4, 7.5, 7.6, 7.7, 7.8. 7.9, 8, 8.1, 8.2, 8.3, 8.4, 8.5, 8.6, 8.7, 8.8. 8.9, 9, 9.1, 9.2, 9.3, 9.4, 9.5, 9.6, 9.7, 9.8. 9.9, or about 10 mg/kg. Values and ranges intermediate to the recited values are also intended to be part of this invention.

In another embodiment, the dsRNA is administered at a dose of about 0.1 to about 50 mg/kg, about 0.25 to about 50 mg/kg, about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.1 to about 20 mg/kg, about 0.25 to about 20 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. Values and ranges intermediate to the recited values are also intended to be part of this invention.

For example, the dsRNA may be administered at a dose of about 0.01, 0.02, 0.03, 0.04, 0.05, 0.06, 0.07, 0.08, 0.09, 0.1, 0.2, 0.3, 0.4, 0.5, 0.6, 0.7. 0.8, 0.9, 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8. 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8. 6.9, 7, 7.1, 7.2, 7.3, 7.4, 7.5, 7.6, 7.7, 7.8. 7.9, 8, 8.1, 8.2, 8.3, 8.4, 8.5, 8.6, 8.7, 8.8. 8.9, 9, 9.1, 9.2, 9.3, 9.4, 9.5, 9.6, 9.7, 9.8. 9.9, or about 10 mg/kg. Values and ranges intermediate to the recited values are also intended to be part of this invention.

In another embodiment, the dsRNA is administered at a dose of about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. Values and ranges intermediate to the recited values are also intended to be part of this invention.

For example, subjects can be administered a therapeutic amount of iRNA, such as about 0.5, 0.6, 0.7. 0.8, 0.9, 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8. 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8. 6.9, 7, 7.1, 7.2, 7.3, 7.4, 7.5, 7.6, 7.7, 7.8. 7.9, 8, 8.1, 8.2, 8.3, 8.4, 8.5, 8.6, 8.7, 8.8. 8.9, 9, 9.1, 9.2, 9.3, 9.4, 9.5, 9.6, 9.7, 9.8. 9.9, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

The pharmaceutical composition can be administered once daily, or the iRNA can be administered as two, three, or more sub-doses at appropriate intervals throughout the day or even using continuous infusion or delivery through a controlled release formulation. In that case, the iRNA contained in each sub-dose must be correspondingly smaller in order to achieve the total daily dosage. The dosage unit can also be compounded for delivery over several days, e.g., using a conventional sustained release formulation which provides sustained release of the iRNA over a several day period. Sustained release formulations are well known in the art and are particularly useful for delivery of agents at a particular site, such as could be used with the agents of the present invention. In this embodiment, the dosage unit contains a corresponding multiple of the daily dose.

The effect of a single dose on ANGPTL3 levels can be long lasting, such that subsequent doses are administered at not more than 3, 4, or 5 day intervals, or at not more than 1, 2, 3, or 4 week intervals.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using an appropriate animal model, as described elsewhere herein.

Advances in mouse genetics have generated a number of mouse models for the study of various human diseases, such as disorders of lipid metabolism that would benefit from reduction in the expression of ANGPTL3. Such models can be used for in vivo testing of iRNA, as well as for determining a therapeutically effective dose. Suitable mouse models are known in the art and include, for example, an obese (ob/ob) mouse containing a mutation in the obese (ob) gene (Wiegman et al., (2003) *Diabetes,* 52:1081-1089); a mouse containing homozygous knock-out of an LDL receptor (LDLR −/− mouse; Ishibashi et al., (1993) *J Clin Invest* 92(2):883-893); diet-induced artherosclerosis mouse model (Ishida et al., (1991) *J. Lipid. Res.,* 32:559-568); and heterozygous lipoprotein lipase knockout mouse model (Weistock et al., (1995) J. Clin. Invest. 96(6):2555-2568).

The pharmaceutical compositions of the present invention can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The iRNA can be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention can be encapsulated within liposomes or can form complexes thereto, in particular to cationic liposomes. Alternatively, iRNAs can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan- 2-one, an acylcarnitine, an acylcholine, or a $C_{1-20}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference.

A. IRNA Formulations Comprising Membranous Molecular Assemblies

An iRNA for use in the compositions and methods of the invention can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the iRNA composition. The lipophilic material isolates the aqueous interior from an aqueous exterior, which typically does not include the iRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the iRNA are delivered into the cell where the iRNA can specifically bind to a target RNA and can mediate RNAi. In some cases the liposomes are also specifically targeted, e.g., to direct the iRNA to particular cell types.

A liposome containing a RNAi agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The RNAi agent preparation is then added to the micelles that include the lipid component. The cationic groups on the lipid interact with the RNAi agent and condense around the RNAi agent to form a liposome. After condensation, the detergent is removed, e.g., by dialysis, to yield a liposomal preparation of RNAi agent.

If necessary a carrier compound that assists in condensation can be added during the condensation reaction, e.g., by controlled addition. For example, the carrier compound can be a polymer other than a nucleic acid (e.g., spermine or spermidine). pH can also adjusted to favor condensation.

Methods for producing stable polynucleotide delivery vehicles, which incorporate a polynucleotide/cationic lipid complex as structural components of the delivery vehicle, are further described in, e.g., WO 96/37194, the entire contents of which are incorporated herein by reference. Liposome formation can also include one or more aspects of exemplary methods described in Felgner, P. L. et al., (1987) *Proc. Natl. Acad. Sci. USA* 8:7413-7417; U.S. Pat. Nos. 4,897,355; 5,171,678; Bangham et al., (1965) *M Mol. Biol.* 23:238; Olson et al., (1979) *Biochim. Biophys. Acta* 557:9; Szoka et al., (1978) *Proc. Natl. Acad. Sci.* 75: 4194; Mayhew et al., (1984) *Biochim. Biophys. Acta* 775:169; Kim et al., (1983) *Biochim. Biophys. Acta* 728:339; and Fukunaga et al., (1984) *Endocrinol.* 115:757. Commonly used techniques for preparing lipid aggregates of appropriate size for use as delivery vehicles include sonication and freeze-thaw plus extrusion (see, e.g., Mayer et al., (1986) *Biochim. Biophys. Acta* 858:161. Microfluidization can be used when consistently small (50 to 200 nm) and relatively uniform aggregates are desired (Mayhew et al., (1984) *Biochim. Biophys. Acta* 775:169. These methods are readily adapted to packaging RNAi agent preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al. (1987) *Biochem. Biophys. Res. Commun.,* 147:980-985).

Liposomes, which are pH-sensitive or negatively charged, entrap nucleic acids rather than complex with them. Since both the nucleic acid and the lipid are similarly charged, repulsion rather than complex formation occurs. Nevertheless, some nucleic acid is entrapped within the aqueous interior of these liposomes. pH sensitive liposomes have been used to deliver nucleic acids encoding the thymidine kinase gene to cell monolayers in culture. Expression of the exogenous gene was detected in the target cells (Zhou et al. (1992) *Journal of Controlled Release,* 19:269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. Nos. 5,283,185; 5,171,678; WO 94/00569; WO 93/24640; WO 91/16024; Felgner, (1994) *J. Biol. Chem.* 269:2550; Nabel, (1993) *Proc. Natl. Acad. Sci.* 90:11307; Nabel, (1992) *Human Gene Ther.* 3:649; Gershon, (1993) *Biochem.* 32:7143; and Strauss, (1992) *EMBO J* 11:417.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al., (1994) *S.T.P.Pharma. Sci.,* 4(6):466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., (1987) *FEBS Letters,* 223:42; Wu et al., (1993) *Cancer Research,* 53:3765).

Various liposomes comprising one or more glycolipids are known in the art. Papahadjopoulos et al. (Ann. N.Y. Acad. Sci., (1987), 507:64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, (1988), 85, :6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver RNAi agents to macrophages.

Further advantages of liposomes include: liposomes obtained from natural phospholipids are biocompatible and biodegradable; liposomes can incorporate a wide range of water and lipid soluble drugs; liposomes can protect encapsulated RNAi agents in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of RNAi agent (see, e.g., Felgner, P. L. et al., (1987) *Proc. Natl. Acad. Sci. USA* 8:7413-7417, and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., (1991) *Biochim. Biophys. Res. Commun.* 179:280). Lipopolylysine, made by conjugating polylysine to DOPE, has been reported to be effective for transfection in the presence of serum (Zhou, X. et al., (1991) *Biochim. Biophys. Acta* 1065:8). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer RNAi agent into the skin. In some implementations, liposomes are used for delivering RNAi agent to epidermal cells and also to enhance the penetration of RNAi agent into dermal tissues, e.g., into skin. For example, the liposomes can be applied topically. Topical delivery of drugs formulated as liposomes to the skin has been documented (see, e.g., Weiner et al., (1992) *Journal of Drug Targeting,* vol. 2, 405-410 and du Plessis et al., (1992) *Antiviral Research,* 18:259-265; Mannino, R. J. and Fould-Fogerite, S., (1998) *Biotechniques* 6:682-690; Itani, T. et al., (1987) *Gene* 56:267-276; Nicolau, C. et al. (1987) *Meth. Enzymol.* 149: 157-176; Straubinger, R. M. and Papahadjopoulos, D. (1983) *Meth. Enzymol.* 101:512-527; Wang, C. Y. and Huang, L., (1987) *Proc. Natl. Acad. Sci. USA* 84:7851-7855).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with RNAi agent are useful for treating a dermatological disorder.

Liposomes that include iRNA can be made highly deformable. Such deformability can enable the liposomes to penetrate through pore that are smaller than the average radius of the liposome. For example, transferosomes are a type of deformable liposomes. Transferosomes can be made by adding surface edge activators, usually surfactants, to a standard liposomal composition. Transfersomes that include RNAi agent can be delivered, for example, subcutaneously by infection in order to deliver RNAi agent to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present invention are described in U.S. provisional application Ser. No. 61/018, 616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

The iRNA for use in the methods of the invention can also be provided as micellar formulations. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to C22 alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

B. Nucleic Acid Lipid Particles iRNAs, e.g., dsRNAs of in the invention may be fully encapsulated in the lipid formulation, e.g., to form a SPLP, pSPLP, SNALP, or other nucleic acid-lipid particle. As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection and accumulate at distal sites (e.g., sites physically separated from the administration site). SPLPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; U.S. Publication No. 2010/0324120 and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the invention.

The cationic lipid can be, for example, N,N-dioleyl-N,N-dimethylammonium chloride (DODAC), N,N-distearyl-N,N-dimethylammonium bromide (DDAB), N-(I-(2,3-dioleoyloxy)propyl)-N,N,N-trimethylammonium chloride (DOTAP), N-(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethyl amino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1), or a mixture thereof. The cationic lipid can comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-siRNA particle includes 40% 2, 2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/Lipid Ratio.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles can be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98.4HCl (MW 1487) (see U.S. patent application Ser. No. 12/056,230, filed Mar. 26, 2008, which is incorporated herein by reference), Cholesterol (Sigma-Aldrich), and PEG-Ceramide C16 (Avanti Polar Lipids) can be used to prepare lipid-dsRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous dsRNA (e.g., in sodium acetate pH 5) such that the final ethanol concentration is about 35-45% and the final sodium acetate concentration is about 100-300 mM. LipiddsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

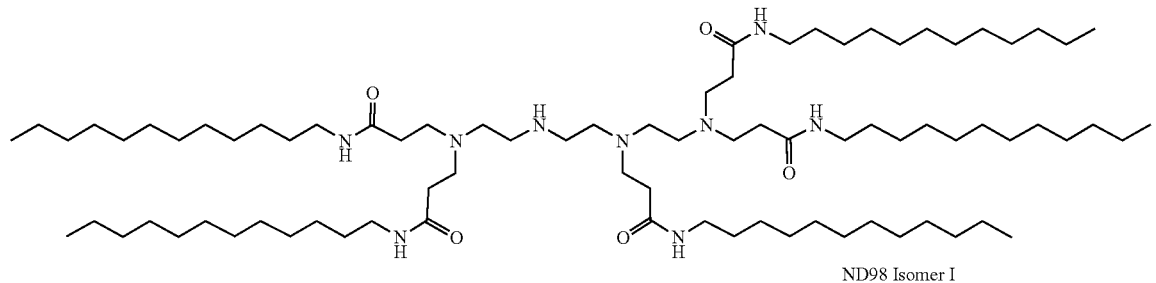

ND98 Isomer I

LNP01 formulations are described, e.g., in International Application Publication No. WO 2008/042973, which is hereby incorporated by reference.

Additional exemplary lipid-dsRNA formulations are described in the table below.

|  | Ionizable/Cationic Lipid | cationic lipid/non-cationic lipid/cholesterol/PEG-lipid conjugate Lipid:siRNA ratio |
|---|---|---|
| SNALP-1 | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA ~7:1 |
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA ~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |

| | Ionizable/Cationic Lipid | cationic lipid/non-cationic lipid/cholesterol/PEG-lipid conjugate Lipid:siRNA ratio |
|---|---|---|
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |
| LNP21 | C12-200 | C12-200/DSPC/Chol/PEG-DSG 50/10/38.5/1.5 Lipid:siRNA: 7:1 |
| LNP22 | XTC | XTC/DSPC/Chol/PEG-DSG 50/10/38.5/1.5 Lipid:siRNA: 10:1 |

DSPC: distearoylphosphatidylcholine
DPPC: dipalmitoylphosphatidylcholine
PEG-DMG: PEG-didimyristoyl glycerol (C14-PEG, or PEG-C14) (PEG with avg mol wt of 2000)
PEG-DSG: PEG-distyryl glycerol (C18-PEG, or PEG-C18) (PEG with avg mol wt of 2000)
PEG-cDMA: PEG-carbamoyl-1,2-dimyristyloxypropylamine (PEG with avg mol wt of 2000)
SNALP (1,2-Dilinolenyloxy-N,N-dimethylaminopropane (DLinDMA)) comprising formulations are described in International Publication No. WO2009/127060, filed Apr. 15, 2009, which is hereby incorporated by reference.
XTC comprising formulations are described, e.g., in U.S. Provisional Ser. No. 61/148,366, filed Jan. 29, 2009; U.S. Provisional Ser. No. 61/156,851, filed Mar. 2, 2009; U.S. Provisional Ser. No. filed Jun. 10, 2009; U.S. Provisional Ser. No. 61/228,373, filed Jul. 24, 2009; U.S. Provisional Ser. No. 61/239,686, filed Sep. 3, 2009, and International Application No. PCT/US2010/022614, filed Jan. 29, 2010, which are hereby incorporated by reference.
MC3 comprising formulations are described, e.g., in U.S. Publication No. 2010/0324120, filed Jun. 10, 2010, the entire contents of which are hereby incorporated by reference.
ALNY-100 comprising formulations are described, e.g., International patent application number PCT/US09/63933, filed on Nov. 10, 2009, which is hereby incorporated by reference.
C12-200 comprising formulations are described in U.S. Provisional Ser. No. 61/175,770, filed May 5, 2009 and International Application No. PCT/US10/33777, filed May 5, 2010, which are hereby incorporated by reference.

Synthesis of Ionizable/Cationic Lipids

Any of the compounds, e.g., cationic lipids and the like, used in the nucleic acid-lipid particles of the invention can be prepared by known organic synthesis techniques, including the methods described in more detail in the Examples. All substituents are as defined below unless indicated otherwise.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(=O)alkyl, —C(=O)alkenyl, and —C(=O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms can be optionally oxidized, and the nitrogen heteroatom can be optionally quaternized, including bicyclic rings in which any of the above heterocycles are fused to a benzene ring. The heterocycle can be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" means that, when substituted, at least one hydrogen atom is replaced with a substituent. In the case of an oxo substituent (=O) two hydrogen atoms are replaced. In this regard, substituents include oxo, halogen, heterocycle, —CN, —ORx, —NRxRy, —NRxC(=O)Ry, —NRxSO2Ry, —C(=O)Rx, —C(=O)ORx, —C(=O)NRxRy, —SOnRx and —SOnNRxRy, wherein n is 0, 1 or 2, Rx and Ry are the same or different and independently hydrogen, alkyl or heterocycle, and each of said alkyl and heterocycle substituents can be further substituted with one or more of oxo, halogen, —OH, —CN, alkyl, —ORx, heterocycle, —NRxRy, —NRxC(=O)Ry, —NRxSO2Ry, —C(=O)Rx, —C(=O)ORx, —C(=O)NRxRy, —SOnRx and —SOnNRxRy.

"Halogen" means fluoro, chloro, bromo and iodo.

In some embodiments, the methods of the invention can require the use of protecting groups. Protecting group methodology is well known to those skilled in the art (see, for example, Protective Groups in Organic Synthesis, Green, T. W. et al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

Synthesis of Formula A

In some embodiments, nucleic acid-lipid particles of the invention are formulated using a cationic lipid of formula A:

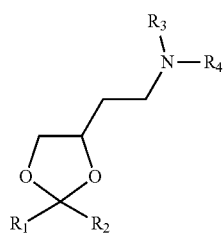

where R1 and R2 are independently alkyl, alkenyl or alkynyl, each can be optionally substituted, and R3 and R4 are independently lower alkyl or R3 and R4 can be taken together to form an optionally substituted heterocyclic ring. In some embodiments, the cationic lipid is XTC (2,2-Dilinoleyl-4-dimethylaminoethyl[1,3]-dioxolane). In general, the lipid of formula A above can be made by the following Reaction Schemes 1 or 2, wherein all substituents are as defined above unless indicated otherwise.

Scheme 1

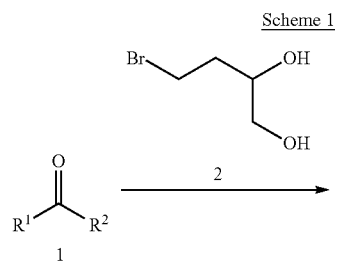

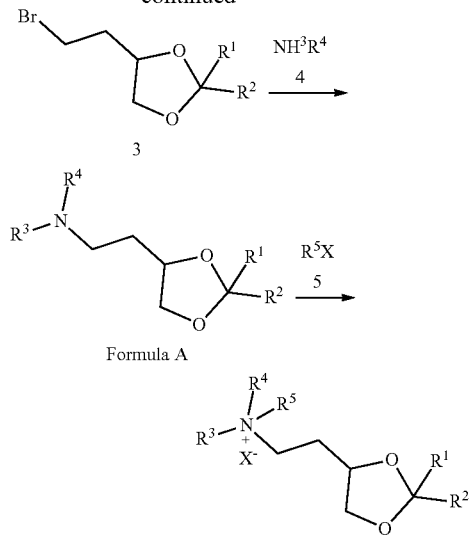

Lipid A, where R1 and R2 are independently alkyl, alkenyl or alkynyl, each can be optionally substituted, and R3 and R4 are independently lower alkyl or R3 and R4 can be taken together to form an optionally substituted heterocyclic ring, can be prepared according to Scheme 1. Ketone 1 and bromide 2 can be purchased or prepared according to methods known to those of ordinary skill in the art. Reaction of 1 and 2 yields ketal 3. Treatment of ketal 3 with amine 4 yields lipids of formula A. The lipids of formula A can be converted to the corresponding ammonium salt with an organic salt of formula 5, where X is anion counter ion selected from halogen, hydroxide, phosphate, sulfate, or the like.

Scheme 2

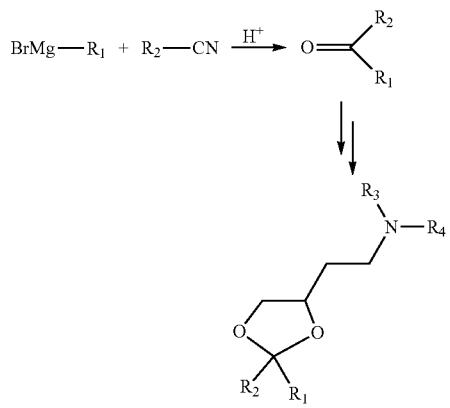

Alternatively, the ketone 1 starting material can be prepared according to Scheme 2. Grignard reagent 6 and cyanide 7 can be purchased or prepared according to methods known to those of ordinary skill in the art. Reaction of 6 and 7 yields ketone 1. Conversion of ketone 1 to the corresponding lipids of formula A is as described in Scheme 1.

Synthesis of MC3

Preparation of DLin-M-C3-DMA (i.e., (6Z,9Z,28Z,31Z)-heptatriaconta-6,9,28,31-tetraen-19-yl 4-(dimethylamino)butanoate) was as follows. A solution of (6Z,9Z,28Z,31Z)- heptatriaconta-6,9,28,31-tetraen-19-ol (0.53 g), 4-N,N-dimethylaminobutyric acid hydrochloride (0.51 g), 4-N,N-dimethylaminopyridine (0.61 g) and 1-ethyl-3-(3-dimethylaminopropyl)carbodiimide hydrochloride (0.53 g) in dichloromethane (5 mL) was stirred at room temperature overnight. The solution was washed with dilute hydrochloric acid followed by dilute aqueous sodium bicarbonate. The organic fractions were dried over anhydrous magnesium sulphate, filtered and the solvent removed on a rotovap. The residue was passed down a silica gel column (20 g) using a 1-5% methanol/dichloromethane elution gradient. Fractions containing the purified product were combined and the solvent removed, yielding a colorless oil (0.54 g).

Synthesis of ALNY-100

Synthesis of ketal 519 [ALNY-100] was performed using the following scheme 3:

evaporated to give crude material which was purified by silica gel column chromatography to get 516 as sticky mass. Yield: 11 g (89%). $^1$H-NMR (CDCl$_3$, 400 MHz): δ=7.36-7.27 (m, 5H), 5.69 (s, 2H), 5.12 (s, 2H), 4.96 (br., 1H) 2.74 (s, 3H), 2.60 (m, 2H), 2.30-2.25 (m, 2H). LC-MS [M+H] −232.3 (96.94%).

Synthesis of 517A and 517B

The cyclopentene 516 (5 g, 0.02164 mol) was dissolved in a solution of 220 mL acetone and water (10:1) in a single neck 500 mL RBF and to it was added N-methyl morpholine-N-oxide (7.6 g, 0.06492 mol) followed by 4.2 mL of 7.6% solution of OsO$_4$ (0.275 g, 0.00108 mol) in tert-butanol at room temperature. After completion of the reaction (~3 h), the mixture was quenched with addition of solid Na$_2$SO$_3$ and resulting mixture was stirred for 1.5 h at room temperature. Reaction mixture was diluted with DCM (300

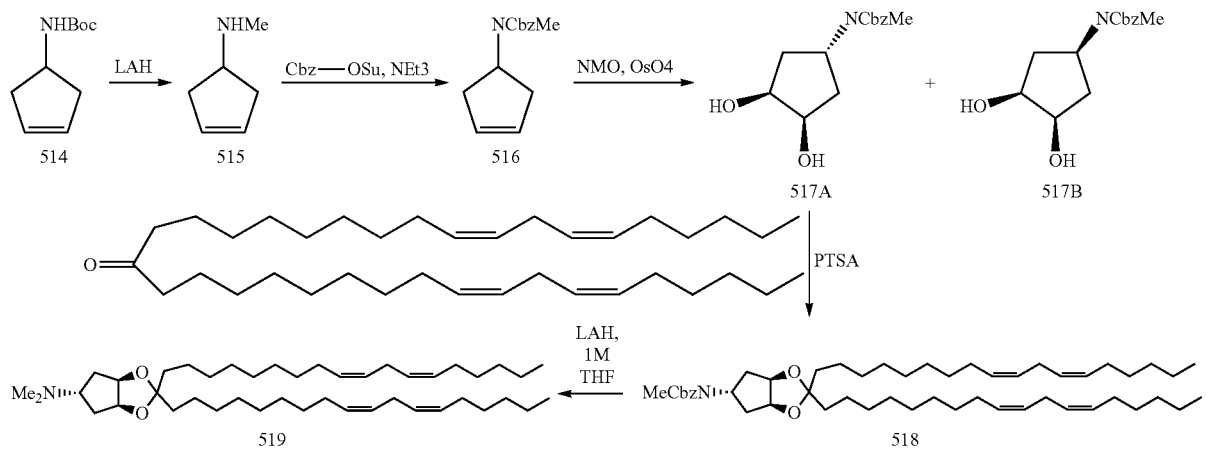

Synthesis of 515

To a stirred suspension of LiAlH$_4$ (3.74 g, 0.09852 mol) in 200 ml anhydrous THF in a two neck RBF (1 L), was added a solution of 514 (10 g, 0.04926 mol) in 70 mL of THF slowly at 0° C. under nitrogen atmosphere. After complete addition, reaction mixture was warmed to room temperature and then heated to reflux for 4 h. Progress of the reaction was monitored by TLC. After completion of reaction (by TLC) the mixture was cooled to 0° C. and quenched with careful addition of saturated Na$_2$SO$_4$ solution. Reaction mixture was stirred for 4 h at room temperature and filtered off. Residue was washed well with THF. The filtrate and washings were mixed and diluted with 400 mL dioxane and 26 mL conc. HCl and stirred for 20 minutes at room temperature. The volatilities were stripped off under vacuum to furnish the hydrochloride salt of 515 as a white solid. Yield: 7.12 g $^1$H-NMR (DMSO, 400 MHz): δ=9.34 (broad, 2H), 5.68 (s, 2H), 3.74 (m, 1H), 2.66-2.60 (m, 2H), 2.50-2.45 (m, 5H).

Synthesis of 516

To a stirred solution of compound 515 in 100 mL dry DCM in a 250 mL two neck RBF, was added NEt$_3$ (37.2 mL, 0.2669 mol) and cooled to 0° C. under nitrogen atmosphere. After a slow addition of N-(benzyloxy-carbonyloxy)-succinimide (20 g, 0.08007 mol) in 50 mL dry DCM, reaction mixture was allowed to warm to room temperature. After completion of the reaction (2-3 h by TLC) mixture was washed successively with 1N HCl solution (1×100 mL) and saturated NaHCO$_3$ solution (1×50 mL). The organic layer was then dried over anhyd. Na$_2$SO$_4$ and the solvent was mL) and washed with water (2×100 mL) followed by saturated NaHCO$_3$ (1×50 mL) solution, water (1×30 mL) and finally with brine (lx 50 mL). Organic phase was dried over an.Na$_2$SO$_4$ and solvent was removed in vacuum. Silica gel column chromatographic purification of the crude material was afforded a mixture of diastereomers, which were separated by prep HPLC. Yield: ~6 g crude 517A—Peak-1 (white solid), 5.13 g (96%). 1H-NMR (DMSO, 400 MHz): δ=7.39-7.31 (m, 5H), 5.04 (s, 2H), 4.78-4.73 (m, 1H), 4.48-4.47 (d, 2H), 3.94-3.93 (m, 2H), 2.71 (s, 3H), 1.72-1.67 (m, 4H). LC-MS—[M+H]−266.3, [M+NH4+]−283.5 present, HPLC-97.86%. Stereochemistry confirmed by X-ray.

Synthesis of 518

Using a procedure analogous to that described for the synthesis of compound 505, compound 518 (1.2 g, 41%) was obtained as a colorless oil. 1H-NMR (CDCl$_3$, 400 MHz): δ=7.35-7.33 (m, 4H), 7.30-7.27 (m, 1H), 5.37-5.27 (m, 8H), 5.12 (s, 2H), 4.75 (m, 1H), 4.58-4.57 (m, 2H), 2.78-2.74 (m, 7H), 2.06-2.00 (m, 8H), 1.96-1.91 (m, 2H), 1.62 (m, 4H), 1.48 (m, 2H), 1.37-1.25 (br m, 36H), 0.87 (m, 6H). HPLC-98.65%.

General Procedure for the Synthesis of Compound 519

A solution of compound 518 (1 eq) in hexane (15 mL) was added in a drop-wise fashion to an ice-cold solution of LAH in THF (1 M, 2 eq). After complete addition, the mixture was heated at 40° C. over 0.5 h then cooled again on an ice bath. The mixture was carefully hydrolyzed with saturated aqueous Na$_2$SO$_4$ then filtered through celite and reduced to an oil. Column chromatography provided the pure 519 (1.3 g, 68%) which was obtained as a colorless oil. $^{13}$C NMR δ=130.2, 130.1 (×2), 127.9 (×3), 112.3, 79.3, 64.4, 44.7, 38.3, 35.4, 31.5, 29.9 (×2), 29.7, 29.6 (×2), 29.5 (×3), 29.3 (×2), 27.2 (×3), 25.6, 24.5, 23.3, 226, 14.1; Electrospray MS (+ve): Molecular weight for $C_{44}H_{80}NO_2$ (M+H)+ Calc. 654.6, Found 654.6.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total dsRNA concentration in the formulation, as well as the entrapped fraction, is estimated using a dye exclusion assay. A sample of the formulated dsRNA can be incubated with an RNA-binding dye, such as Ribogreen (Molecular Probes) in the presence or absence of a formulation disrupting surfactant, e.g., 0.5% Triton-X100. The total dsRNA in the formulation can be determined by the signal from the sample containing the surfactant, relative to a standard curve. The entrapped fraction is determined by subtracting the "free" dsRNA content (as measured by the signal in the absence of surfactant) from the total dsRNA content. Percent entrapped dsRNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the invention are administered in conjunction with one or more penetration enhancer surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention can be delivered orally, in granular form including sprayed dried particles, or complexed to form micro or nanoparticles. DsRNA complexing agents include poly-amino acids; polyimines; polyacrylates; poly-alkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension can also contain stabilizers.

C. Additional Formulations i. Emulsions

The compositions of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present invention, the compositions of iRNAs and nucleic acids are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., Pharmaceutical Research, 1994, 11, 1385; Ho et al., J. Pharm. Sci., 1996, 85, 138-143). Often microemulsions can form spontaneously when their components are brought together at ambient temperature. This can be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention can also contain additional components and additives such as sorbitan monostearate (Grill 3), Labrasol, and penetration enhancers to improve the properties of the formulation and to enhance the absorption of the iRNAs and nucleic acids of the present invention. Penetration enhancers used in the microemulsions of the present invention can be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

iii. Microparticles an RNAi agent of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating agents, as used in connection with the present invention, can be defined as compounds that remove metallic ions from solution by forming complexes therewith, with the result that absorption of iRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of iRNAs at the cellular level can also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen; Carlsbad, Calif.), Lipofectamine 2000™ (Invitrogen; Carlsbad, Calif.), 293Fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPass$^a$ D1 Transfection Reagent (New England Biolabs; Ipswich, Mass., USA), LyoVec™/LipoGen™ (Invitrogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents can be utilized to enhance the penetration of the administered nucleic acids, including glycols such as ethylene glycol and propylene glycol, pyrrols such as 2-pyrrol, azones, and terpenes such as limonene and menthone.

v. Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

vi. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions can contain substances which increase the viscosity of the suspension including, for example, sodium carboxymethylcellulose, sorbitol and/or dextran. The suspension can also contain stabilizers.

In some embodiments, pharmaceutical compositions featured in the invention include (a) one or more iRNA compounds and (b) one or more agents which function by a non-RNAi mechanism and which are useful in treating a disorder of lipid metabolism. Examples of such agents include, but are not limited to an anti-inflammatory agent, anti-steatosis agent, anti-viral, and/or anti-fibrosis agent. In addition, other substances commonly used to protect the liver, such as silymarin, can also be used in conjunction with the iRNAs described herein. Other agents useful for treating liver diseases include telbivudine, entecavir, and protease inhibitors such as telaprevir and other disclosed, for example, in Tung et al., U.S. Application Publication Nos. 2005/0148548, 2004/0167116, and 2003/0144217; and in Hale et al., U.S. Application Publication No. 2004/0127488.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the $ED_{50}$ with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the iRNAs featured in the invention can be administered in combination with other known agents effective in treatment of pathological processes mediated by ANGPTL3 expression. In any event, the administering physician can adjust the amount and timing of iRNA administration on the basis of results observed using standard measures of efficacy known in the art or described herein.

VI. Methods of the Invention

The present invention also provides methods of using an iRNA of the invention and/or a composition containing an iRNA of the invention to reduce and/or inhibit ANGPTL3 expression in a cell. The methods include contacting the cell with a dsRNA of the invention and maintaining the cell for a time sufficient to obtain degradation of the mRNA transcript of an ANGPTL3 gene, thereby inhibiting expression of the ANGPTL3 gene in the cell. Reduction in gene expression can be assessed by any methods known in the art. For example, a reduction in the expression of ANGPTL3 may be determined by determining the mRNA expression level of ANGPTL3 using methods routine to one of ordinary skill in the art, e.g., Northern blotting, qRT-PCR; by determining the protein level of ANGPTL3 using methods routine to one of ordinary skill in the art, such as Western blotting, immunological techniques. A reduction in the expression of ANGPTL3 may also be assessed indirectly by measuring a decrease in biological activity of ANGPTL3, e.g., a decrease in the level of serum lipid, triglycerides, cholesterol and/or free fatty acids.

In the methods of the invention the cell may be contacted in vitro or in vivo, i.e., the cell may be within a subject.

A cell suitable for treatment using the methods of the invention may be any cell that expresses an ANGPTL3gene. A cell suitable for use in the methods of the invention may be a mammalian cell, e.g., a primate cell (such as a human cell or a non-human primate cell, e.g., a monkey cell or a chimpanzee cell), a non-primate cell (such as a cow cell, a pig cell, a camel cell, a llama cell, a horse cell, a goat cell, a rabbit cell, a sheep cell, a hamster, a guinea pig cell, a cat cell, a dog cell, a rat cell, a mouse cell, a lion cell, a tiger cell, a bear cell, or a buffalo cell), a bird cell (e.g., a duck cell or a goose cell), or a whale cell. In one embodiment, the cell is a human cell, e.g., a human liver cell.

ANGPTL3 expression is inhibited in the cell by at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100%.

The in vivo methods of the invention may include administering to a subject a composition containing an iRNA, where the iRNA includes a nucleotide sequence that is complementary to at least a part of an RNA transcript of the ANGPTL3 gene of the mammal to be treated. When the organism to be treated is a mammal such as a human, the composition can be administered by any means known in the art including, but not limited to oral, intraperitoneal, or parenteral routes, including intracranial (e.g., intraventricular, intraparenchymal and intrathecal), intravenous, intramuscular, subcutaneous, transdermal, airway (aerosol), nasal, rectal, and topical (including buccal and sublingual) administration. In certain embodiments, the compositions are administered by intravenous infusion or injection. In certain embodiments, the compositions are administered by subcutaneous injection.

In some embodiments, the administration is via a depot injection. A depot injection may release the iRNA in a consistent way over a prolonged time period. Thus, a depot injection may reduce the frequency of dosing needed to obtain a desired effect, e.g., a desired inhibition of ANGPTL3, or a therapeutic or prophylactic effect. A depot injection may also provide more consistent serum concentrations. Depot injections may include subcutaneous injections or intramuscular injections. In preferred embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intravenous, subcutaneous, arterial, or epidural infusions. In preferred embodiments, the infusion pump is a subcutaneous infusion pump. In other embodiments, the pump is a surgically implanted pump that delivers the iRNA to the liver.

The mode of administration may be chosen based upon whether local or systemic treatment is desired and based upon the area to be treated. The route and site of administration may be chosen to enhance targeting.

In one aspect, the present invention also provides methods for inhibiting the expression of an ANGPTL3 gene in a mammal. The methods include administering to the mammal a composition comprising a dsRNA that targets an ANGPTL3 gene in a cell of the mammal and maintaining the mammal for a time sufficient to obtain degradation of the mRNA transcript of the ANGPTL3 gene, thereby inhibiting expression of the ANGPTL3 gene in the cell. Reduction in gene expression can be assessed by any methods known it the art and by methods, e.g. qRT-PCR, described herein. Reduction in protein production can be assessed by any methods known it the art and by methods, e.g. ELISA, described herein. In one embodiment, a puncture liver biopsy sample serves as the tissue material for monitoring the reduction in ANGPTL3 gene and/or protein expression.

The present invention further provides methods of treatment of a subject in need thereof. The treatment methods of the invention include administering an iRNA of the invention to a subject, e.g., a subject that would benefit from a reduction and/or inhibition of ANGPTL3 expression, in a therapeutically effective amount of an iRNA targeting an ANGPTL3 gene or a pharmaceutical composition comprising an iRNA targeting an ANGPTL3 gene.

An iRNA of the invention may be administered as a "free iRNA." A free iRNA is administered in the absence of a pharmaceutical composition. The naked iRNA may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the iRNA can be adjusted such that it is suitable for administering to a subject.

Alternatively, an iRNA of the invention may be administered as a pharmaceutical composition, such as a dsRNA liposomal formulation.

Subjects that would benefit from a reduction and/or inhibition of ANGPTL3 gene expression are those having a disorder of lipid metabolism, e.g., an inherited disorder of lipid metabolism or an acquired disorder of lipid metabolism. In one embodiment, a subject having disorder of lipid metabolism has hyperlipidemia. In another embodiment, a subject having a disorder of lipid metabolism has hypertriglyceridemia. Treatment of a subject that would benefit from a reduction and/or inhibition of ANGPTL3 gene expression includes therapeutic treatment (e.g., a subject is having eruptive xanthomas) and prophylactic treatment (e.g., the subject is not having eruptive xanthomas or a subject may be at risk of developing eruptive xanthomas).

The invention further provides methods for the use of an iRNA or a pharmaceutical composition thereof, e.g., for treating a subject that would benefit from reduction and/or inhibition of ANGPTL3 expression, e.g., a subject having a disorder of lipid metabolism, in combination with other pharmaceuticals and/or other therapeutic methods, e.g., with known pharmaceuticals and/or known therapeutic methods, such as, for example, those which are currently employed for treating these disorders. For example, in certain embodiments, an iRNA targeting ANGPTL3 is administered in combination with, e.g., an agent useful in treating a disorder of lipid metabolism as described elsewhere herein. For example, additional agents suitable for treating a subject that would benefit from reducton in ANGPTL3 expression, e.g., a subject having a disorder of lipid metabolism, may include agents that lower one or more serum lipids. Non-limiting examples of such agents may include cholesterol synthesis inhibitors, such as HMG-CoA reductase inhibitors, e.g., statins. Statins may include atorvastatin (Lipitor), fluvastatin (Lescol), lovastatin (Mevacor), lovastatin extended-release (Altoprev), pitavastatin (Livalo), pravastatin (Pravachol), rosuvastatin (Crestor), and simvastatin (Zocor). Other agents useful in treating a disorder of lipid metabolism may include bile sequestering agents, such as cholestyramine and other resins; VLDL secretion inhibitors, such as niacin; lipophilic antioxidants, such as Probucol; acyl-CoA cholesterol acyl transferase inhibitors; farnesoid X receptor antagonists; sterol regulatory binding protein cleavage activating protein (SCAP) activators; microsomal triglyceride transfer protein (MTP) inhibitors; ApoE-related peptide; and therapeutic antibodies against ANGPTL3. The additional therapeutic agents may also include agents that raise high density lipoprotein (HDL), such as cholesteryl ester transfer protein (CETP) inhibitors. Furthermore, the additional therapeutic agents may also include dietary supplements, e.g., fish oil. The iRNA and additional therapeutic agents may be administered at the same time and/or in the same combination, e.g., parenterally, or the additional therapeutic agent can be administered as part of a separate composition or at separate times and/or by another method known in the art or described herein.

In one embodiment, the method includes administering a composition featured herein such that expression of the target ANGPTL3 gene is decreased, such as for about 1, 2, 3, 4, 5, 6, 7, 8, 12, 16, 18, 24 hours, 28, 32, or about 36 hours. In one embodiment, expression of the target ANGPTL3 gene is decreased for an extended duration, e.g., at least about two, three, four days or more, e.g., about one week, two weeks, three weeks, or four weeks or longer.

Preferably, the iRNAs useful for the methods and compositions featured herein specifically target RNAs (primary or processed) of the target ANGPTL3gene. Compositions and methods for inhibiting the expression of these genes using iRNAs can be prepared and performed as described herein.

Administration of the dsRNA according to the methods of the invention may result in a reduction of the severity, signs, symptoms, and/or markers of such diseases or disorders in a patient with a disorder of lipid metabolism. By "reduction" in this context is meant a statistically significant decrease in such level. The reduction can be, for example, at least about 5%, 10%, 15%, 20%, 25%, 30%, 35%, 40%, 45%, 50%, 55%, 60%, 65%, 70%, 75%, 80%, 85%, 90%, 95%, or about 100%.

Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of a disorder of lipid metabolism may be assessed, for example, by periodic monitoring of one or more serum lipid levels. Comparisons of the later readings with the initial readings provide a physician an indication of whether the treatment is effective. It is well within the ability of one skilled in the art to monitor efficacy of treatment or prevention by measuring any one of such parameters, or any combination of parameters. In connection with the administration of an iRNA targeting ANGPTL3 or pharmaceutical composition thereof, "effective against" a disorder of lipid metabolism indicates that administration in a clinically appropriate manner results in a beneficial effect for at least a statistically significant fraction of patients, such as a improvement of symptoms, a cure, a reduction in disease, extension of life, improvement in quality of life, or other effect generally recognized as positive by medical doctors familiar with treating disorder of lipid metabolisms and the related causes.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given iRNA drug or formulation of that drug can also be judged using an experimental animal model for the given disease as known in the art. When using an experimental animal model, efficacy of treatment is evidenced when a statistically significant reduction in a marker or symptom is observed.

Alternatively, the efficacy can be measured by a reduction in the severity of disease as determined by one skilled in the art of diagnosis based on a clinically accepted disease severity grading scale, as but one example the Child-Pugh score (sometimes the Child-Turcotte-Pugh score). Any positive change resulting in e.g., lessening of severity of disease measured using the appropriate scale, represents adequate treatment using an iRNA or iRNA formulation as described herein.

Subjects can be administered a therapeutic amount of dsRNA, such as about 0.01 mg/kg to about 5 mg/kg, about 0.01 mg/kg to about 10 mg/kg, about 0.05 mg/kg to about 5 mg/kg, about 0.05 mg/kg to about 10 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 1 mg/kg to about 5 mg/kg, about 1 mg/kg to about 10 mg/kg, about 1.5 mg/kg to about 5 mg/kg, about 1.5 mg/kg to about 10 mg/kg, about 2 mg/kg to about about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg. Values and ranges intermediate to the recited values are also intended to be part of this invention.

For example, the dsRNA may be administered at a dose of about 0.1, 0.2, 0.3, 0.4, 0.5, 0.6, 0.7. 0.8, 0.9, 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8. 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8. 6.9, 7, 7.1, 7.2, 7.3, 7.4, 7.5, 7.6, 7.7, 7.8. 7.9, 8, 8.1, 8.2, 8.3, 8.4, 8.5, 8.6, 8.7, 8.8. 8.9, 9, 9.1, 9.2, 9.3, 9.4, 9.5, 9.6, 9.7, 9.8. 9.9, or about 10 mg/kg. Values and ranges intermediate to the recited values are also intended to be part of this invention.

In other embodiments, for example, when a composition of the invention comprises a dsRNA as described herein and an N-acetylgalactosamine, subjects can be administered a therapeutic amount of dsRNA, such as a dose of about 0.1 to about 50 mg/kg, about 0.25 to about 50 mg/kg, about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.1 to about 20 mg/kg, about 0.25 to about 20 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. Values and ranges intermediate to the recited values are also intended to be part of this invention.

For example, subjects can be administered a therapeutic amount of dsRNA, such as about 0.1, 0.2, 0.3, 0.4, 0.5, 0.6, 0.7. 0.8, 0.9, 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8. 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8. 6.9, 7, 7.1, 7.2, 7.3, 7.4, 7.5, 7.6, 7.7, 7.8. 7.9, 8, 8.1, 8.2, 8.3, 8.4, 8.5, 8.6, 8.7, 8.8. 8.9, 9, 9.1, 9.2, 9.3, 9.4, 9.5, 9.6, 9.7, 9.8. 9.9, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or about 50 mg/kg. Values and ranges intermediate to the recited values are also intended to be part of this invention.

The iRNA can be administered by intravenous infusion over a period of time, such as over a 5, 6, 7, 8, 9, 10, 11, 12, 13, 14, 15, 16, 17, 18, 19, 20, 21, 22, 23, 24, or about a 25 minute period. The administration may be repeated, for example, on a regular basis, such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Administration of the iRNA can reduce ANGPTL3 levels, e.g., in a cell, tissue, blood, urine or other compartment of the patient by at least about 5%, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 39, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or at least about 99% or more.

Before administration of a full dose of the iRNA, patients can be administered a smaller dose, such as a 5% infusion reaction, and monitored for adverse effects, such as an allergic reaction. In another example, the patient can be monitored for unwanted immunostimulatory effects, such as increased cytokine (e.g., TNF-alpha or INF-alpha) levels.

Alternatively, the iRNA can be administered subcutaneously, i.e., by subcutaneous injection. One or more injections may be used to deliver the desired daily dose of iRNA to a subject. The injections may be repeated over a period of time, such as over 2, 3, 4, 5, 6, 7, 8, 9, 10 or 15 days. The administration may be repeated, for example, on a regular basis, such as biweekly (i.e., every two weeks) for one month, two months, three months, four months or longer. After an initial treatment regimen, the treatments can be administered on a less frequent basis. In some embodiments, a single dose of iRNA is followed by monthly dosing. In some embodiments, the dosing may comprise a loading phase of multiple doses on consequitive days.

Unless otherwise defined, all technical and scientific terms used herein have the same meaning as commonly understood by one of ordinary skill in the art to which this invention belongs. Although methods and materials similar or equivalent to those described herein can be used in the practice or testing of the iRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1. IRNA Synthesis

Source of Reagents

Where the source of a reagent is not specifically given herein, such reagent can be obtained from any supplier of reagents for molecular biology at a quality/purity standard for application in molecular biology.

Transcripts siRNA design was carried out to identify siRNAs targeting the human ANGPTL3 transcript annotated in the NCBI Gene database (http://www.ncbi.nlm.nih.gov/gene/) and a cynomolgus monkey (*Macaca fascicularis*; henceforth "cyno") ANGPTL3 transcript produced via sequencing of cDNA prepared from liver RNA. Sequencing of cyno ANGPTL3 mRNA was done in-house, and the mRNA sequence is shown in SEQ ID NO:9. Design used the following transcripts from the NCBI collection: Human—NM_014495.2 (SEQ ID NO:1); Mouse—NM_013913.3 (SEQ ID NO:2). All siRNA duplexes were designed that shared 100% identity with the listed human and cyno transcripts. A subset of siRNA duplexes, described below, also shared 100% identity with the mouse (*Mus musculus*) ANGPTL3 transcript found in NCBI Gene database.

siRNA Design, Specificity, and Efficacy Prediction

The predicted specificity of all possible 19mers was predicted from each sequence. Candidate 19mers were then selected that lacked repeats longer than 7 nucleotides. These 977 candidate human/cyno siRNAs, and a subset of 38 that also matched mouse ("human/cyno/mouse candidate siRNAs") were then used in a comprehensive search against the human transcriptome (defined as the set of NM_ and XM_ records within the human NCBI Refseq set) using an exhaustive "brute-force" algorithm implemented in the python script 'BruteForce.py'. The script next parsed the transcript-oligo alignments to generate a score based on the position and number of mismatches between the siRNA and any potential 'off-target' transcript. The off-target score is weighted to emphasize differences in the 'seed' region of siRNAs, in positions 2-9 from the 5' end of the molecule. Each oligo-transcript pair from the brute-force search was given a mismatch score by summing the individual mismatch scores; mismatches in the position 2-9 were counted as 2.8, mismatches in the cleavage site positions 10-11 were counted as 1.2, and mismatches in region 12-19 counted as 1.0. An additional off-target prediction was carried out by comparing the frequency of heptamers and octomers derived from 3 distinct, seed-derived hexamers of each oligo. The hexamers from positions 2-7 relative to the 5' start were used to create 2 heptamers and one octomer. 'Heptamer1' was created by adding a 3' A to the hexamer; 'heptamer2' was created by adding a 5' A to the hexamer; octomer was created by adding an A to both 5' and 3' ends of the hexamer. The frequency of octomers and heptamers in the human 3'UTRome (defined as the subsequence of the transcriptome from NCBI's Refseq database where the end of the coding region, the 'CDS', is clearly defined) was pre-calculated. The octomer frequency was normalized to the heptamer frequency using the median value from the range of octomer frequencies. A 'mirSeedScore' was then calculated by calculating the sum of ((3×normalized octomer count)+(2× heptamer2 count)+(1×heptamer1 count)).

Both siRNAs strands were assigned to a category of specificity according to the calculated scores: a score above 3 qualifies as highly specific, equal to 3 as specific and between 2.2 and 2.8 as moderately specific. Sorting was carried out by the specificity of the antisense strand. Duplexes were then selected from the human/cyno set with antisense oligos lacking miRNA seed matches, scores of 3 or better, less than 65% overall GC content, no GC at the first position, 4 or more Us or As in the seed region, and GC at the nineteenth position. Duplexes from the human/cyno/ mouse set with antisense oligos having scores of 2 or better, less than 65% overall GC content, and no GC at the first position were also selected.

siRNA Sequence Selection

A total of 47 sense and 47 antisense derived siRNA oligos from the human/cyno set were synthesized and formed into duplexes. A total of 15 sense and 15 antisense derived siRNAs from the human/cyno/mouse set were synthesized and formed into duplexes.

Synthesis of ANGPTL3 Sequences

ANGPTL3 sequences were synthesized on a MerMade 192 synthesizer at either a 1 or 0.2 µmol scale. Single strands were synthesized with 2'O-methyl modifications for transfection based in vitro screening. For use in free uptake screening assays, 3' GalNAc conjugates were made with 2'F and 2'-O-methyl chemical modifications. In these designs, GalNAc moiety was placed at the 3'end of the sense strand.

The antisense sequence was 23 nucleotides in length and also contained 2'F and 2'Omethyl chemical modifications with two phosphorothioate linkages at the 3' end.

On one set of 21mer single strands and duplexes, 'endolight' chemistry was applied as detailed below.

All pyrimidines (cytosine and uridine) in the sense strand were modified with 2'-O-Methyl nucleotides (2' O-Methyl C and 2'-O-Methyl U)

In the antisense strand, pyrimidines adjacent (towards 5' position) to ribo A nucleoside were replaced with their corresponding 2'-O-Methyl nucleosides A two base dTsdT extension at the 3' end of both sense and anti sense sequences was introduced For GalNAc conjugated 21mer sense and complementary 23mer antisense sequences, 2'F and 2'OMethyl modified single strands were synthesized. The synthesis was performed on a GalNAc modified CPG support for the sense strand and CPG modified with universal support for the antisense sequence at a 1 µmol scale. The sequence motif named TOFFEE was applied, in which the sense strand contained a three-nucleotide 2'F-modified motif at positions 9, 10 and 11 and in the antisense, a 2'OMethyl-modified motif was included at positions 11, 12 and 13.

Synthesis, Cleavage and Deprotection

The synthesis of ANGPTL3 sequences used solid supported oligonucleotide synthesis using phosphoramidite chemistry. For 21 mer endolight sequences, a deoxy thymidine CPG was used as the solid support while for the GalNAc conjugates, GalNAc solid support for the sense strand and a universal CPG for the antisesense strand were used.

The synthesis of the above sequences was performed at either a 1 or 0.2 µm scale in 96 well plates. The amidite solutions were prepared at 0.1M concentration and ethyl thio tetrazole (0.6M in Acetonitrile) was used as the activator.

The synthesized sequences were cleaved and deprotected in 96 well plates, using methylamine in the first step and fluoride reagent in the second step. For GalNAc and 2'F nucleoside containing sequences, deprotection conditions were modified. Sequences after cleavage and deprotection were precipitated using an acetone:ethanol (80:20) mix and the pellets were re-suspended in 0.2M sodium acetate buffer. Samples from each sequence were analyzed by LC-MS to confirm the identity, UV for quantification and a selected set of samples by IEX chromatography to determine purity.

Purification, Desalting and Annealing

ANGPTL3 sequences were precipitated and purified on an AKTA Purifier system using a Sephadex column. The ANGPTL3 was run at ambient temperature. Sample injection and collection was performed in 96 well plates with 1.8 mL deep wells. A single peak corresponding to the full length sequence was collected in the eluent. The desalted ANGPTL3 sequences were analyzed for concentration (by UV measurement at $A_{260}$) and purity (by ion exchange HPLC). The complementary single strands were then combined in a 1:1 stoichiometric ratio to form siRNA duplexes.

Example 2. In Vitro Screening

Cell Culture and Transfections

Hep3B cells (ATCC, Manassas, Va.) were grown to near confluence at 37° C. in an atmosphere of 5% $CO_2$ in RPMI (ATCC) supplemented with 10% FBS, streptomycin, and glutamine (ATCC) before being released from the plate by trypsinization. Transfection was carried out by adding 14.8 µl of Opti-MEM plus 0.2 µl of Lipofectamine RNAiMax per well (Invitrogen, Carlsbad Calif. cat #13778-150) to 5 µl of siRNA duplexes per well into a 96-well plate and incubated at room temperature for 15 minutes. 80 µl of complete growth media without antibiotic containing ~$2\times10^4$ Hep3B cells were then added to the siRNA mixture. Cells were incubated for either 24 or 120 hours prior to RNA purification. Single dose experiments were performed at 10 nM and 0.1 nM final duplex concentration and dose response experiments were done at 10, 1, 0.5, 0.1, 0.05, 0.01, 0.005, 0.001, 0.0005, 0.0001, 0.00005 and 0.00001 nM final duplex concentration unless otherwise stated.

Free Uptake Transfection

5 µl of each GalNac conjugated siRNA in PBS was combined with $4\times10^4$ freshly thawed cryopreserved Cynomolgus monkey hepatocytes resuspended in 95 µl of In Vitro Gro CP media (In Vitro Technologies—Celsis, Baltimore, Md.) in each well of a 96 well plate. The mixture was incubated for about 24 hrs at 37° C. in an atmosphere of 5% $CO_2$. siRNAs were tested at final concentrations of 500 nM, 100 nM and 10 nM for efficacy free uptake assays. For dose response screens, final siRNA concentrations were 500 nM, 100 nM, 20 nM, 4 nM, 0.8 nM, 0.16 nM, 0.032 nM and 0.0064 nM.

Total RNA Isolation Using DYNABEADS mRNA Isolation Kit (Invitrogen, Part #: 610-12)

Cells were harvested and lysed in 150 µl of Lysis/Binding Buffer then mixed for 5 minute at 850 rpm using an Eppendorf Thermomixer (the mixing speed was the same throughout the process). Ten microliters of magnetic beads and 80 µl of Lysis/Binding Buffer mixture were added to a round bottom plate and mixed for 1 minute. Magnetic beads were captured using magnetic stand and the supernatant was removed without disturbing the beads. After removing supernatant, the lysed cells were added to the remaining beads and mixed for 5 minutes. After removing supernatant, magnetic beads were washed 2 times with 150 µl Wash Buffer A and mixed for 1 minute. Beads were captured again and supernatant removed. Beads were then washed with 150 µl of Wash Buffer B, captured, and the supernatant was removed. Beads were next washed with 150 µl Elution Buffer, captured, and the supernatant was removed. Beads were allowed to dry for 2 minutes. After drying, 50 µl of Elution Buffer was added and mixed for 5 minutes at 70° C. Beads were captured on magnet for 5 minutes. 40 µl of supernatant was removed and added to another 96 well plate.

cDNA Synthesis Using ABI High Capacity cDNA Reverse Transcription Kit (Applied Biosystems, Foster City, Calif., Cat #4368813)

A master mix of 2 µl 10× Buffer, 0.8 µl 25×dNTPs, 2 µl Random primers, 1 µl Reverse Transcriptase, 1 µl RNase inhibitor and 3.2 µl of $H_2O$ per reaction were added into 10 µl total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.

Real Time PCR

2 µl of cDNA was added to a master mix containing 0.5 µl GAPDH TaqMan Probe (Applied Biosystems Cat #4326317E), 0.5 µl ANGPTL TaqMan probe (Applied Biosystems cat #Hs00205581_m1) and 5 µl Lightcycler 480 probe master mix (Roche Cat #04887301001) per well in a 384 well 50 plates (Roche cat #04887301001). Real time PCR was done in an ABI 7900HT Real Time PCR system (Applied Biosystems) using the ΔΔCt(RQ) assay. Each duplex was tested in two independent transfections, and each transfection was assayed in duplicate, unless otherwise noted in the summary tables.

To calculate relative fold change, real time data was analyzed using the ΔΔCt method and normalized to assays performed with cells transfected with 10 nM AD-1955, or mock transfected cells. $IC_{50}s$ were calculated using a 4 parameter fit model using XLFit and normalized to cells transfected with AD-1955 or naïve cells over the same dose range, or to its own lowest dose. AD-1955 sequence, used as a negative control, targets luciferase and has the following sequence: sense: cuuAcGcuGAGuAcuucGAdTsdT (SEQ ID NO: 14); antisense: UCGAAGuACUcAGCGuAAGdTsdT (SEQ ID NO: 15).

Viability Screens

Cell viability was measured on days 3 and 6 in HeLa and Hep3B cells following transfection with 10, 1, 0.5, 0.1, 0.05 nM siRNA. Cells were plated at a density of 10,000 cells per well in 96 well plates. Each siRNA was assayed in triplicate and the data averaged. siRNAs targeting PLK1 and AD-19200 were included as positive controls for loss of viability, and AD-1955 and mock transfected cells as negative controls. PLK1 and AD-19200 result in a dose dependent loss of viability. To measure viability, 20 μl of CellTiter Blue (Promega) was added to each well of the 96 well plates after 3 or 6 days and incubated at 37° C. for 2 hours. Plates were then read in a Spectrophotometer (Molecular Devices) at 560Ex/590Em. Viability was expressed as the average value of light units from three replicate transfections+/− standard deviation. Relative viability was assessed by first averaging the three replicate transfections and then normalizing Mock transfected cells. Data is expressed as % viabile cells.

TABLE 1

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
| --- | --- |
| A | adenosine |
| C | cytidine |
| G | guanosine |
| T | thymidine |
| U | uridine |
| N | any nucleotide (G, A, C, T or U) |
| a | 2'-O-methyladenosine |
| c | 2'-O-methylcytidine |
| g | 2'-O-methylguanosine |
| u | 2'-O-methyluridine |
| dT | 2'-deoxythymidine |
| s | phosphorothioate linkage |

TABLE 2

Unmodified sense and antisense strand sequences of ANGPTL3 dsRNAs

| Duplex ID | Sense Name | Sense Sequence (SEQ ID NOS 16-77, respectively, in order of appearance) | Position in NM_014495.2 | Antisense Name | Antisense Sequence (SEQ ID NOS 78-139, respectively, in order of appearance) | Position in NM_014495.2 |
| --- | --- | --- | --- | --- | --- | --- |
| AD-45939.1 | A-96225.1 | UAUUUGAUCAGUCUUUUUA | 281-299 | A-96226.1 | UAAAAAGACUGAUCAAAUA | 281-299 |
| AD-45858.1 | A-96149.1 | GAGCAACUAACUAACUUAA | 478-496 | A-96150.1 | UUAAGUUAGUUAGUUGCUC | 478-496 |
| AD-45869.1 | A-96137.1 | GGCCAAAUUAAUGACAUAU | 247-265 | A-96138.1 | AUAUGUCAUUAAUUUGGCC | 247-265 |
| AD-45884.1 | A-96189.1 | CGAAUUGAGUUGGAAGACU | 1045-1063 | A-96190.1 | AGUCUUCCAACUCAAUUCG | 1045-1063 |
| AD-45892.1 | A-96129.1 | CCUCCUUCAGUUGGGACAU | 198-216 | A-96130.1 | AUGUCCCAACUGAAGGAGG | 198-216 |
| AD-45899.1 | A-96147.1 | CACUUGAACUCAACUCAAA | 401-419 | A-96148.1 | UUUGAGUUGAGUUCAAGUG | 401-419 |
| AD-45915.1 | A-96231.1 | GUCCAUGGACAUUAAUUCA | 890-908 | A-96232.1 | UGAAUUAAUGUCCAUGGAC | 890-908 |
| AD-45924.1 | A-96219.1 | AAUCAAGAUUUGCUAUGUU | 152-170 | A-96220.1 | AACAUAGCAAAUCUUGAUU | 152-170 |
| AD-45860.1 | A-96181.1 | CUAGAGAAGAUAUACUCCA | 1000-1018 | A-96182.1 | UGGAGUAUAUCUUCUCUAG | 1000-1018 |
| AD-45870.1 | A-96153.1 | CUAACUAACUUAAUUCAAA | 484-502 | A-96154.1 | UUUGAAUUAAGUUAGUUAG | 484-502 |
| AD-45870.2 | A-96153.2 | CUAACUAACUUAAUUCAAA | 484-502 | A-96154.2 | UUUGAAUUAAGUUAGUUAG | 484-502 |
| AD-45877.1 | A-96171.1 | CAUUAAUUCAACAUCGAAU | 899-917 | A-96172.1 | AUUCGAUGUUGAAUUAAUG | 899-917 |
| AD-45885.1 | A-96205.1 | CAAAAUGUUGAUCCAUCCA | 1392-1410 | A-96206.1 | UGGAUGGAUCAACAUUUUG | 1392-1410 |
| AD-45893.1 | A-96145.1 | CAUAUAAACUACAAGUCAA | 359-377 | A-96146.1 | UUGACUUGUAGUUUAUAUG | 359-377 |
| AD-45900.1 | A-96163.1 | GACCCAGCAACUCUCAAGU | 839-857 | A-96164.1 | ACUUGAGAGUUGCUGGGUC | 839-857 |
| AD-45925.1 | A-96235.1 | GGUUGGGCCUAGAGAAGAU | 992-1010 | A-96236.1 | AUCUUCUCUAGGCCCAACC | 992-1010 |
| AD-45861.1 | A-96197.1 | GUGUGGAGAAAACAACCUA | 1272-1290 | A-96198.1 | UAGGUUGUUUUCUCCACAC | 1272-1290 |
| AD-45871.1 | A-96169.1 | GACAUUAAUUCAACAUCGA | 897-915 | A-96170.1 | UCGAUGUUGAAUUAAUGUC | 897-915 |
| AD-45878.1 | A-96187.1 | CAUAGUGAAGCAAUCUAAU | 1017-1035 | A-96188.1 | AUUAGAUUGCUUCACUAUG | 1017-1035 |
| AD-45886.1 | A-96127.1 | CUAUGUUAGACGAUGUAAA | 164-182 | A-96128.1 | UUUACAUCGUCUAACAUAG | 164-182 |

TABLE 2-continued

Unmodified sense and antisense strand sequences of ANGPTL3 dsRNAs

| Duplex ID | Sense Name | Sense Sequence (SEQ ID NOS 16-77, respectively, in order of appearance) | Position in NM_014495.2 | Antisense Name | Antisense Sequence (SEQ ID NOS 78-139, respectively, in order of appearance) | Position in NM_014495.2 |
|---|---|---|---|---|---|---|
| AD-45894.1 | A-96161.1 | CACAGAAAUUUCUCUAUCU | 684-702 | A-96162.1 | AGAUAGAGAAAUUUCUGUG | 684-702 |
| AD-45901.1 | A-96179.1 | GUUGGGCCUAGAGAAGAUA | 993-1011 | A-96180.1 | UAUCUUCUCUAGGCCCAAC | 993-1011 |
| AD-45909.1 | A-96213.1 | GCCAAAAUCAAGAUUUGCU | 147-165 | A-96214.1 | AGCAAAUCUUGAUUUUGGC | 147-165 |
| AD-45934.1 | A-96223.1 | ACAUAUUUGAUCAGUCUUU | 278-296 | A-96224.1 | AAAGACUGAUCAAAUAUGU | 278-296 |
| AD-45934.2 | A-96223.2 | ACAUAUUUGAUCAGUCUUU | 278-296 | A-96224.2 | AAAGACUGAUCAAAUAUGU | 278-296 |
| AD-45863.1 | A-96135.1 | CUUAAAGACUUUGUCCAUA | 220-238 | A-96136.1 | UAUGGACAAAGUCUUUAAG | 220-238 |
| AD-45872.1 | A-96185.1 | CCAUAGUGAAGCAAUCUAA | 1016-1034 | A-96186.1 | UUAGAUUGCUUCACUAUGG | 1016-1034 |
| AD-45879.1 | A-96203.1 | CAACCAAAAUGUUGAUCCA | 1388-1406 | A-96204.1 | UGGAUCAACAUUUUGGUUG | 1388-1406 |
| AD-45887.1 | A-96143.1 | CUACAUAUAAACUACAAGU | 356-374 | A-96144.1 | ACUUGUAGUUUAUAUGUAG | 356-374 |
| AD-45895.1 | A-96177.1 | GGGAGGCUUGAUGGAGAAU | 970-988 | A-96178.1 | AUUCUCCAUCAAGCCUCCC | 970-988 |
| AD-45902.1 | A-96195.1 | GGUGUUUUCUACUUGGGAU | 1188-1206 | A-96196.1 | AUCCCAAGUAGAAAACACC | 1188-1206 |
| AD-45910.1 | A-96229.1 | AAGAGCACCAAGAACUACU | 711-729 | A-96230.1 | AGUAGUUCUUGGUGCUCUU | 711-729 |
| AD-45935.1 | A-96239.1 | UGGAGAAAACAACCUAAAU | 1275-1293 | A-96240.1 | AUUUAGGUUGUUUUCUCCA | 1275-1293 |
| AD-45864.1 | A-96151.1 | GCAACUAACUAACUUAAUU | 480-498 | A-96152.1 | AAUUAAGUUAGUUAGUUGC | 480-498 |
| AD-45873.1 | A-96201.1 | CAACCUAAAUGGUAAAUAU | 1284-1302 | A-96202.1 | AUAUUUACCAUUUAGGUUG | 1284-1302 |
| AD-45880.1 | A-96125.1 | GCUAUGUUAGACGAUGUAA | 163-181 | A-96126.1 | UUACAUCGUCUAACAUAGC | 163-181 |
| AD-45888.1 | A-96159.1 | CCCACAGAAAUUUCUCUAU | 682-700 | A-96160.1 | AUAGAGAAAUUUCUGUGGG | 682-700 |
| AD-45896.1 | A-96193.1 | GAUUUGGUGUUUUCUACUU | 1183-1201 | A-96194.1 | AAGUAGAAAACACCAAAUC | 1183-1201 |
| AD-45903.1 | A-96211.1 | CAGAGCCAAAAUCAAGAUU | 143-161 | A-96212.1 | AAUCUUGAUUUUGGCUCUG | 143-161 |
| AD-45919.1 | A-96217.1 | AAAUCAAGAUUUGCUAUGU | 151-169 | A-96218.1 | ACAUAGCAAAUCUUGAUUU | 151-169 |
| AD-45865.1 | A-96167.1 | CAUGGACAUUAAUUCAACA | 893-911 | A-96168.1 | UGUUGAAUUAAUGUCCAUG | 893-911 |
| AD-45874.1 | A-96123.1 | GAUUUGCUAUGUUAGACGA | 158-176 | A-96124.1 | UCGUCUAACAUAGCAAAUC | 158-176 |
| AD-45881.1 | A-96141.1 | GAACUACAUAUAAACUACA | 353-371 | A-96142.1 | UGUAGUUUAUAUGUAGUUC | 353-371 |
| AD-45889.1 | A-96175.1 | CGAAUAGAUGGAUCACAAA | 913-931 | A-96176.1 | UUUGUGAUCCAUCUAUUCG | 913-931 |
| AD-45897.1 | A-96209.1 | CUUGUUAAACUCUAAACU | 1817-1835 | A-96210.1 | AGUUUAGAGUUUUAACAAG | 1817-1835 |
| AD-45904.1 | A-96227.1 | AUUUGAUCAGUCUUUUUAU | 282-300 | A-96228.1 | AUAAAAGACUGAUCAAAU | 282-300 |
| AD-45920.1 | A-96233.1 | UCCAUGGACAUUAAUUCAA | 891-909 | A-96234.1 | UUGAAUUAAUGUCCAUGGA | 891-909 |
| AD-45856.1 | A-96117.1 | CACAAUUAAGCUCCUUCUU | 57-75 | A-96118.1 | AAGAAGGAGCUUAAUUGUG | 57-75 |
| AD-45929.1 | A-96221.1 | CAACAUAUUUGAUCAGUCU | 276-294 | A-96222.1 | AGACUGAUCAAAUAUGUUG | 276-294 |
| AD-45866.1 | A-96183.1 | CUCCAUAGUGAAGCAAUCU | 1014-1032 | A-96184.1 | AGAUUGCUUCACUAUGGAG | 1014-1032 |
| AD-45875.1 | A-96139.1 | GCCAAAUUAAUGACAUAUU | 248-266 | A-96140.1 | AAUAUGUCAUUAAUUUGGC | 248-266 |
| AD-45882.1 | A-96157.1 | CAACAGCAUAGUCAAAUAA | 622-640 | A-96158.1 | UUAUUUGACUAUGCUGUUG | 622-640 |
| AD-45890.1 | A-96191.1 | GGAAAUCACGAAACCAACU | 1105-1123 | A-96192.1 | AGUUGGUUUCGUGAUUUCC | 1105-1123 |
| AD-45898.1 | A-96131.1 | CAGUUGGGACAUGGUCUUA | 205-223 | A-96132.1 | UAAGACCAUGUCCCAACUG | 205-223 |
| AD-45857.1 | A-96133.1 | GACAUGGUCUUUAAGACUU | 212-230 | A-96134.1 | AAGUCUUAAGACCAUGUC | 212-230 |
| AD-45930.1 | A-96237.1 | UGUGGAGAAAACAACCUAA | 1273-1291 | A-96238.1 | UUAGGUUGUUUUCUCCACA | 1273-1291 |
| AD-45867.1 | A-96199.1 | GUGGAGAAAACAACCUAAA | 1274-1292 | A-96200.1 | UUUAGGUUGUUUUCUCCAC | 1274-1292 |

TABLE 2-continued

Unmodified sense and antisense strand sequences of ANGPTL3 dsRNAs

| Duplex ID | Sense Name | Sense Sequence (SEQ ID NOS 16-77, respectively, in order of appearance) | Position in NM_014495.2 | Antisense Name | Antisense Sequence (SEQ ID NOS 78-139, respectively, in order of appearance) | Position in NM_014495.2 |
|---|---|---|---|---|---|---|
| AD-45876.1 | A-96155.1 | CCAACAGCAUAGUCAAAUA | 621-639 | A-96156.1 | UAUUUGACUAUGCUGUUGG | 621-639 |
| AD-45883.1 | A-96173.1 | CAACAUCGAAUAGAUGGAU | 907-925 | A-96174.1 | AUCCAUCUAUUCGAUGUUG | 907-925 |
| AD-45891.1 | A-96207.1 | GCAAAUUUAAAAGGCAAUA | 1441-1459 | A-96208.1 | UAUUGCCUUUUAAAUUUGC | 1441-1459 |
| AD-45914.1 | A-96215.1 | CAAAAUCAAGAUUUGCUAU | 149-167 | A-96216.1 | AUAGCAAAUCUUGAUUUUG | 149-167 |
| AD-15838.1 | A-26242.1 | AGAGCCAAAAUCAAGAUUU | 144-162 | A-26243.2 | AAAUCUUGAUUUUGGCUCU | 144-162 |

TABLE 3

Modified sense and antisense strand sequences of ANGPTL3 dsRNAs

| Duplex ID | Sense OligoName | Sense Sequence (SEQ ID NOS 140-201, respectively, in order of appearance) | Antisense OligoName | Antisense Sequence (SEQ ID NOS 202-263, respectively, in order of appearance) |
|---|---|---|---|---|
| AD-45939.1 | A-96225.1 | uAuuuGAucAGucuuuuuAdTsdT | A-96226.1 | uAAAAGACUGAUcAAAuAdTsdT |
| AD-45858.1 | A-96149.1 | GAGcAAcuAAcuAAcuuAAdTsdT | A-96150.1 | UuAAGUuAGUuAGUUGCUCdTsdT |
| AD-45869.1 | A-96137.1 | GGccAAAuuAAuGAcAuAudTsdT | A-96138.1 | AuAUGUcAUuAAUUUGCCdTsdT |
| AD-45884.1 | A-96189.1 | cGAAuuGAGuuGGAAGAcudTsdT | A-96190.1 | AGUCUUCcAACUcAAUUCGdTsdT |
| AD-45892.1 | A-96129.1 | ccuccuucAGuuGGGAcAudTsdT | A-96130.1 | AUGUCCcAACUGAAGGAGGdTsdT |
| AD-45899.1 | A-96147.1 | cAcuuGAAcucAAcucAAAdTsdT | A-96148.1 | UUUGAGUUGAGUUCAAGUGdTsdT |
| AD-45915.1 | A-96231.1 | GuccAuGGAcAuuAAuucAdTsdT | A-96232.1 | UGAAUuAAUGUCcAUGGACdTsdT |
| AD-45924.1 | A-96219.1 | AAucAAGAuuuGcuAuGuudTsdT | A-96220.1 | AAcAuAGcAAAUCUUGAUUdTsdT |
| AD-45860.1 | A-96181.1 | cuAGAGAAGAuAuAcuccAdTsdT | A-96182.1 | UGGAGuAuAUCUUCUCuAGdTsdT |
| AD-45870.1 | A-96153.1 | cuAAcuAAcuuAAuucAAAdTsdT | A-96154.1 | UUUGAAUuAAGUuAGUuAGdTsdT |
| AD-45870.2 | A-96153.2 | cuAAcuAAcuuAAuucAAAdTsdT | A-96154.2 | UUUGAAUuAAGUuAGUuAGdTsdT |
| AD-45877.1 | A-96171.1 | cAuuAAuucAAcAucGAAudTsdT | A-96172.1 | AUUCGAUGUUGAAUuAAUGdTsdT |
| AD-45885.1 | A-96205.1 | cAAAAuGuuGAuccAuccAdTsdT | A-96206.1 | UGGAUGGAUcAAcAUUUUGdTsdT |
| AD-45893.1 | A-96145.1 | cAuAuAAAcuAcAAGucAAdTsdT | A-96146.1 | UUGACUUGuAGUUuAuAUGdTsdT |
| AD-45900.1 | A-96163.1 | GAcccAGcAAcucucAAGudTsdT | A-96164.1 | ACUUGAGAGUUGCUGGGUCdTsdT |
| AD-45925.1 | A-96235.1 | GGuuGGGccuAGAGAAGAudTsdT | A-96236.1 | AUCUUCUCuAGGCCcAACCdTsdT |
| AD-45861.1 | A-96197.1 | GuGuGGAGAAAAcAAccuAdTsdT | A-96198.1 | uAGGUuGUUUUCUCcAcACdTsdT |
| AD-45871.1 | A-96169.1 | GAcAuuAAuucAAcAucGAdTsdT | A-96170.1 | UCGAUGUUGAAUuAAUGUCdTsdT |
| AD-45878.1 | A-96187.1 | cAuAGuGAAGcAAucuAAudTsdT | A-96188.1 | AUuAGAUUGCUUcACuAUGdTsdT |
| AD-45886.1 | A-96127.1 | cuAuGuuAGAcGAuGuAAAdTsdT | A-96128.1 | UUuAcAUCGUCuAAcAuAGdTsdT |
| AD-45894.1 | A-96161.1 | cAcAGAAAuuucucuAucudTsdT | A-96162.1 | AGAuAGAGAAAUUUCUGUGdTsdT |
| AD-45901.1 | A-96179.1 | GuuGGGccuAGAGAAGAuAdTsdT | A-96180.1 | uAUCUUCUCuAGGCCcAACCdTsdT |
| AD-45909.1 | A-96213.1 | GccAAAAucAAGAuuuGcudTsdT | A-96214.1 | AGcAAAUCUUGAUUUUGGCdTsdT |
| AD-45934.1 | A-96223.1 | AcAuAuuuGAucAGucuuudTsdT | A-96224.1 | AAAGACUGAUcAAAuAUGUdTsdT |
| AD-45934.2 | A-96223.2 | AcAuAuuuGAucAGucuuudTsdT | A-96224.2 | AAAGACUGAUcAAAuAUGUdTsdT |

TABLE 3 -continued

Modified sense and antisense strand sequences of ANGPTL3 dsRNAs

| Duplex ID | Sense OligoName | Sense Sequence (SEQ ID NOS 140-201, respectively, in order of appearance) | Antisense OligoName | Antisense Sequence (SEQ ID NOS 202-263, respectively, in order of appearance) |
|---|---|---|---|---|
| AD-45863.1 | A-96135.1 | cuuAAAGAcuuuGuccAuAdTsdT | A-96136.1 | uAUGGAcAAAGUCUUuAAGdTsdT |
| AD-45872.1 | A-96185.1 | ccAuAGuGAAGcAAucuAAdTsdT | A-96186.1 | UuAGAUUGCUUcACuAUGGdTsdT |
| AD-45879.1 | A-96203.1 | cAAccAAAAuGuuGAuccAdTsdT | A-96204.1 | UGGAUcAAcAUUUUGGUUGdTsdT |
| AD-45887.1 | A-96143.1 | cuAcAuAuAAAcuAcAAGudTsdT | A-96144.1 | ACUUGuAGUUuAuAUGuAGdTsdT |
| AD-45895.1 | A-96177.1 | GGGAGGcuuGAuGGAGAAudTsdT | A-96178.1 | AUUCUCcAUcAAGCCUCCCdTsdT |
| AD-45902.1 | A-96195.1 | GGuGuuuucuAcuuGGGAudTsdT | A-96196.1 | AUCCcAAGuAGAAAAcACCdTsdT |
| AD-45910.1 | A-96229.1 | AAGAGcAccAAGAAcuAcudTsdT | A-96230.1 | AGuAGUUCUUGGUGCUCUUdTsdT |
| AD-45935.1 | A-96239.1 | uGGAGAAAAcAAccuAAAudTsdT | A-96240.1 | AUUuAGGUUGUUUUCUCcAdTsdT |
| AD-45864.1 | A-96151.1 | GcAAcuAAcuAAcuuAAuudTsdT | A-96152.1 | AAUuAAGUuAGUuAGUUGCdTsdT |
| AD-45873.1 | A-96201.1 | cAAccAAAuGGuAAAAuAdTsdT | A-96202.1 | AuAUUuACcAUUuAGGUUGdTsdT |
| AD-45880.1 | A-96125.1 | GcuAuGuuAGAcGAuGuAAdTsdT | A-96126.1 | UuAcAUCGUCuAAcAuAGCdTsdT |
| AD-45888.1 | A-96159.1 | cccAcAGAAAuuucucuAudTsdT | A-96160.1 | AuAGAGAAAUUUCUGUGGGdTsdT |
| AD-45896.1 | A-96193.1 | GAuuuGGuGuuuucuAcuudTsdT | A-96194.1 | AAGuAGAAAAcACCAAAUCdTsdT |
| AD-45903.1 | A-96211.1 | cAGAGccAAAAucAAGAAudTsdT | A-96212.1 | AAUCUUGAUUUUGGCUCUGdTsdT |
| AD-45919.1 | A-96217.1 | AAAucAAGAuuuGcuAuGudTsdT | A-96218.1 | AcAuAGcAAAUCUUGAUUUdTsdT |
| AD-45865.1 | A-96167.1 | cAuGGAcAuuAAuucAAcAdTsdT | A-96168.1 | UGUUGAAUuAAUGUCcAUGdTsdT |
| AD-45874.1 | A-96123.1 | GAuuuGcuAuGuuAGAcGAdTsdT | A-96124.1 | UCGUCuAAcAuAGcAAAUCdTsdT |
| AD-45881.1 | A-96141.1 | GAAcuAcAuAuAAAcuAcAdTsdT | A-96142.1 | UGuAGUUuAuAUGuAGUUCdTsdT |
| AD-45889.1 | A-96175.1 | cGAAuAGAuGGAucAcAAAdTsdT | A-96176.1 | UUUGUGAUCcAUCuAUUCGdTsdT |
| AD-45897.1 | A-96209.1 | cuuGuuAAAAcucuAAAcudTsdT | A-96210.1 | AGUUuAGAGUUUuAAcAAGdTsdT |
| AD-45904.1 | A-96227.1 | AuuuGAucAGucuuuuuAudTsdT | A-96228.1 | AuAAAAAGACUGAUcAAAUdTsdT |
| AD-45920.1 | A-96233.1 | uccAuGGAcAuuAAuucAAdTsdT | A-96234.1 | UUGAAUuAAUGUCcAUGGAdTsdT |
| AD-45856.1 | A-96117.1 | cAcAAuuAAGcuccuucuudTsdT | A-96118.1 | AAGAAGGAGCUuAAUUGUGdTsdT |
| AD-45929.1 | A-96221.1 | cAAcAuAuuuGAucAGucudTsdT | A-96222.1 | AGACUGAUcAAAuAUGUUGdTsdT |
| AD-45866.1 | A-96183.1 | cuccAuAGuGAAGcAAucudTsdT | A-96184.1 | AGAUUGCUUcACuAUGGAGdTsdT |
| AD-45875.1 | A-96139.1 | GccAAAuuAAuGAcAuAuudTsdT | A-96140.1 | AAuAUGUcAUuAAUUUGGCdTsdT |
| AD-45882.1 | A-96157.1 | cAAcAGcAuAGucAAAuAAdTsdT | A-96158.1 | UuAUUUGACuAUGCUGUUGdTsdT |
| AD-45890.1 | A-96191.1 | GGAAAucAcGAAAccAAcudTsdT | A-96192.1 | AGUUGGUUUCGUGAUUUCCdTsdT |
| AD-45898.1 | A-96131.1 | cAGuuGGGAcAuGGucuudTsdT | A-96132.1 | uAAGACcAUGUCCcAACUGdTsdT |
| AD-45857.1 | A-96133.1 | GAcAuGGucuuAAAGAcuudTsdT | A-96134.1 | AAGUCUUuAAGACcAUGUCdTsdT |
| AD-45930.1 | A-96237.1 | uGuGGAGAAAAcAAccuAAdTsdT | A-96238.1 | UuAGGUUGUUUUCUCcAcAdTsdT |
| AD-45867.1 | A-96199.1 | GuGGAGAAAAcAAccuAAAdTsdT | A-96200.1 | UUuAGGUUGUUUUCUCcACdTsdT |
| AD-45876.1 | A-96155.1 | ccAAcAGcAuAGucAAAuAdTsdT | A-96156.1 | uAUUUGACuAUGCUGUUGGdTsdT |
| AD-45883.1 | A-96173.1 | cAAcAucGAAuAGAuGGAudTsdT | A-96174.1 | AUCcAUCuAUUCGAUGUUGdTsdT |
| AD-45891.1 | A-96207.1 | GcAAAuuuAAAAGGcAAuAdTsdT | A-96208.1 | uAUUGCCUUUuAAAUUUGCdTsdT |

TABLE 3 -continued

Modified sense and antisense strand sequences of ANGPTL3 dsRNAs

| Duplex ID | Sense OligoName | Sense Sequence (SEQ ID NOS 140-201, respectively, in order of appearance) | Antisense OligoName | Antisense Sequence (SEQ ID NOS 202-263, respectively, in order of appearance) |
|---|---|---|---|---|
| AD-45914.1 | A-96215.1 | cAAAAucAAGAuuuGcuAudTsdT | A-96216.1 | AuAGcAAAUCUUGAUUUUGdTsdT |
| AD-15838.1 | A-26242.1 | AGAGccAAAAucAAGAuuudTsdT | A-26243.2 | AAAUCUuGAUUUuGGCUCUdTsdT |

Lowercase nucleotides (a, u, g, c) are 2'-O-methyl nucleotides; s is aphosphothioate linkage.

TABLE 4

Results of single dose screen using ANGPTL3 dsRNA sequences
The experiments were conducted using modified oligonucleotide duplexes listed in Table 3. The sequence of AD-15838.2 is identical to the sequence of AD-15838.1. Delivery of siRNA duplexes was done using LNPs.
Human Hep3B

| Duplex | 10 nM | 0.1 nM | STDEV, 10 nM | STDEV, 0.1 nM |
|---|---|---|---|---|
| AD-15838.2 | 0.09 | 0.66 | 0.008 | 0.030 |
| AD-45856.1 | 0.32 | 0.91 | 0.026 | 0.032 |
| AD-45857.1 | 2.46 | 1.07 | 0.140 | 0.044 |
| AD-45858.1 | 0.10 | 0.74 | 0.010 | 0.070 |
| AD-45860.1 | 0.02 | 0.47 | 0.002 | 0.097 |
| AD-45861.1 | 0.03 | 0.68 | 0.004 | 0.062 |
| AD-45863.1 | 1.42 | 0.95 | 0.145 | 0.126 |
| AD-45864.1 | 0.02 | 0.17 | 0.002 | 0.045 |
| AD-45865.1 | 0.32 | 0.93 | 0.022 | 0.062 |
| AD-45866.1 | 0.10 | 0.92 | 0.010 | 0.041 |
| AD-45867.1 | 0.04 | 0.61 | 0.000 | 0.048 |
| AD-45869.1 | 0.45 | 1.08 | 0.028 | 0.081 |
| AD-45870.1 | 0.01 | 0.10 | 0.003 | 0.010 |
| AD-45871.1 | 0.05 | 0.57 | 0.006 | 0.071 |
| AD-45872.1 | 0.07 | 0.71 | 0.007 | 0.034 |
| AD-45873.1 | 0.02 | 0.23 | 0.001 | 0.011 |
| AD-45874.1 | 0.08 | 0.75 | 0.013 | 0.049 |
| AD-45875.1 | 0.13 | 0.82 | 0.017 | 0.040 |
| AD-45876.1 | 0.03 | 0.54 | 0.000 | 0.013 |
| AD-45877.1 | 0.06 | 0.47 | 0.002 | 0.025 |
| AD-45878.1 | 0.02 | 0.44 | 0.002 | 0.031 |
| AD-45879.1 | 0.03 | 0.35 | 0.003 | 0.023 |
| AD-45880.1 | 0.49 | 1.00 | 0.039 | 0.088 |
| AD-45881.1 | 0.20 | 0.90 | 0.019 | 0.095 |
| AD-45882.1 | 0.20 | 0.95 | 0.012 | 0.086 |
| AD-45883.1 | 0.16 | 0.98 | 0.011 | 0.058 |
| AD-45884.1 | 0.09 | 0.94 | 0.003 | 0.044 |
| AD-45885.1 | 0.22 | 0.91 | 0.020 | 0.145 |
| AD-45886.1 | 0.04 | 0.40 | 0.008 | 0.080 |
| AD-45887.1 | 0.03 | 0.35 | 0.002 | 0.057 |
| AD-45888.1 | 0.05 | 0.80 | 0.006 | 0.042 |
| AD-45889.1 | 0.31 | 0.91 | 0.013 | 0.052 |
| AD-45890.1 | 0.06 | 0.90 | 0.001 | 0.047 |
| AD-45891.1 | 0.06 | 0.82 | 0.007 | 0.034 |
| AD-45892.1 | 1.01 | 1.09 | 0.033 | 0.211 |
| AD-45893.1 | 0.04 | 0.58 | 0.002 | 0.046 |
| AD-45894.1 | 0.04 | 0.59 | 0.003 | 0.024 |
| AD-45895.1 | 0.84 | 1.00 | 0.047 | 0.047 |
| AD-45896.1 | 0.84 | 0.98 | 0.032 | 0.095 |
| AD-45897.1 | 0.36 | 0.61 | 0.032 | 0.053 |
| AD-45898.1 | 0.98 | 1.09 | 0.021 | 0.117 |
| AD-45899.1 | 0.04 | 0.59 | 0.005 | 0.095 |
| AD-45900.1 | 0.06 | 0.80 | 0.005 | 0.091 |
| AD-45901.1 | 0.33 | 0.94 | 0.025 | 0.096 |
| AD-45902.1 | 0.24 | 1.03 | 0.010 | 0.079 |
| AD-45903.1 | 0.74 | 1.02 | 0.003 | 0.092 |
| AD-45904.1 | 0.39 | 0.87 | 0.010 | 0.010 |
| AD-45909.1 | 0.04 | 0.73 | 0.008 | 0.013 |
| AD-45910.1 | 1.08 | 1.01 | 0.037 | 0.089 |
| AD-45914.1 | 0.52 | 0.99 | 0.018 | 0.071 |
| AD-45915.1 | 0.06 | 0.48 | 0.004 | 0.046 |
| AD-45919.1 | 0.67 | 0.98 | 0.048 | 0.064 |
| AD-45920.1 | 0.61 | 1.00 | 0.031 | 0.038 |
| AD-45924.1 | 0.09 | 0.67 | 0.005 | 0.012 |
| AD-45925.1 | 0.13 | 0.90 | 0.008 | 0.100 |
| AD-45929.1 | 0.02 | 0.42 | 0.001 | 0.083 |
| AD-45930.1 | 0.05 | 0.63 | 0.005 | 0.052 |
| AD-45934.1 | 0.04 | 0.41 | 0.001 | 0.062 |
| AD-45935.1 | 0.08 | 0.76 | 0.006 | 0.058 |
| AD-45939.1 | 0.23 | 0.82 | 0.030 | 0.028 |
| AD-1955.1 | 0.93 | 0.93 | 0.068 | 0.073 |
| AD-1955.1 | 0.94 | 1.01 | 0.028 | 0.113 |
| AD-1955.1 | 1.00 | 1.02 | 0.032 | 0.065 |
| AD-1955.1 | 1.15 | 1.06 | 0.053 | 0.019 |

TABLE 5

Dose response screen results for ANGPTL3 dsRNA sequences
The experiments were conducted using modified oligonucleotide duplexes listed in Table 3. The sequence of AD-15838.2 is identical to the sequence of AD-15838.1.
Hep3B $IC_{50}$

| | 24 hrs | | | 120 hrs | | |
|---|---|---|---|---|---|---|
| Duplex | $IC_{50}$ I (nM) | $IC_{50}$ II (nM) | $IC_{50}$ weighted (nM) | $IC_{50}$ I (nM) | $IC_{50}$ II (nM) | $IC_{50}$ weighted (nM) |
| AD-15838.2 | 0.027 | 0.006 | 0.017 | 0.657 | 0.937 | 0.800 |
| AD-45860.1 | 0.006 | 0.002 | 0.004 | 0.045 | 0.032 | 0.039 |
| AD-45864.1 | 0.002 | 0.001 | 0.002 | 0.046 | 0.042 | 0.044 |
| AD-45870.1 | 0.002 | 0.001 | 0.001 | 0.011 | 0.008 | 0.010 |
| AD-45873.1 | 0.005 | 0.004 | 0.005 | 0.037 | 0.025 | 0.031 |
| AD-45876.1 | 0.032 | 0.006 | 0.019 | 0.269 | 0.045 | 0.156 |
| AD-45877.1 | 0.018 | 0.012 | 0.015 | 1.660 | 0.538 | 1.091 |
| AD-45878.1 | 0.023 | 0.015 | 0.019 | 0.252 | 0.131 | 0.190 |
| AD-45879.1 | 0.002 | 0.003 | 0.003 | 0.023 | 0.029 | 0.026 |
| AD-45886.1 | 0.004 | 0.004 | 0.004 | 0.030 | 0.018 | 0.025 |
| AD-45887.1 | 0.010 | 0.009 | 0.010 | 0.058 | 0.059 | 0.059 |
| AD-45915.1 | 0.016 | 0.015 | 0.015 | 0.110 | 0.056 | 0.083 |
| AD-45929.1 | 0.023 | 0.008 | 0.016 | 0.227 | 0.025 | 0.124 |
| AD-45934.1 | 0.006 | 0.006 | 0.006 | 0.110 | 0.045 | 0.077 |

TABLE 6

Results of cell viability screens using modified ANGPTL3 dsRNA sequences
The experiments were conducted using modified oligonucleotide duplexes listed
in Table 3. The sequence of AD-15838.2 is identical to the sequence of AD-
15838.1. Viability data is expressed as % viable relative to mock treated cells.

| Target | Duplex | Ave 10 nM | Ave 1 nM | Ave 500 pM | Ave 100 pM | Ave 50 pM | SD 10 nM | SD 1 nM | SD 500 pM | SD 100 pM | SD 50 pM |
|---|---|---|---|---|---|---|---|---|---|---|---|
| HeLa day 3 | | | | | | | | | | | |
| ANGPTL3 | AD-15838.2 | 37.34 | 58.67 | 70.92 | 89.86 | 94.98 | 9.45 | 12.28 | 15.06 | 22.37 | 18.23 |
| ANGPTL3 | AD-15838.2 | 29.13 | 48.99 | 63.18 | 79.21 | 94.47 | 1.62 | 5.56 | 4.34 | 11.15 | 11.31 |
| ANGPTL3 | AD-45860.1 | 67.10 | 75.49 | 77.93 | 86.57 | 90.51 | 6.99 | 12.93 | 6.39 | 6.97 | 3.57 |
| ANGPTL3 | AD-45864.1 | 99.13 | 96.95 | 86.77 | 89.20 | 84.36 | 7.90 | 7.22 | 12.60 | 4.85 | 6.87 |
| ANGPTL3 | AD-45870.1 | 82.36 | 97.02 | 95.33 | 95.67 | 92.27 | 8.07 | 5.12 | 7.97 | 7.05 | 10.29 |
| ANGPTL3 | AD-45873.1 | 67.96 | 90.01 | 90.60 | 94.20 | 103.63 | 11.26 | 22.61 | 15.92 | 22.92 | 16.97 |
| ANGPTL3 | AD-45876.1 | 64.00 | 76.71 | 80.21 | 81.71 | 91.23 | 6.60 | 13.94 | 10.15 | 10.81 | 13.89 |
| ANGPTL3 | AD-45877.1 | 79.55 | 77.33 | 79.98 | 91.96 | 93.46 | 1.66 | 9.80 | 8.73 | 16.63 | 11.41 |
| ANGPTL3 | AD-45878.1 | 81.95 | 78.22 | 78.74 | 87.93 | 85.03 | 15.37 | 22.72 | 22.59 | 30.84 | 40.04 |
| ANGPTL3 | AD-45878.1 | 66.83 | 70.71 | 82.14 | 82.80 | 83.14 | 17.48 | 6.49 | 6.86 | 19.92 | 21.15 |
| ANGPTL3 | AD-45879.1 | 37.56 | 45.55 | 59.28 | 76.35 | 78.38 | 3.50 | 7.96 | 19.73 | 34.33 | 33.99 |
| ANGPTL3 | AD-45886.1 | 72.75 | 57.90 | 64.51 | 81.92 | 82.89 | 14.73 | 12.64 | 11.78 | 25.60 | 23.14 |
| ANGPTL3 | AD-45887.1 | 38.01 | 53.91 | 59.31 | 76.44 | 85.73 | 0.58 | 10.81 | 6.27 | 11.12 | 10.92 |
| ANGPTL3 | AD-45915.1 | 48.06 | 52.17 | 67.90 | 95.45 | 100.77 | 8.13 | 15.15 | 29.11 | 32.49 | 38.79 |
| ANGPTL3 | AD-45929.1 | 29.27 | 44.58 | 52.87 | 76.45 | 88.03 | 4.17 | 9.67 | 14.49 | 31.74 | 28.82 |
| ANGPTL3 | AD-45934.1 | 68.20 | 64.11 | 76.92 | 79.57 | 92.11 | 15.79 | 11.25 | 19.99 | 26.08 | 26.30 |
| (+) control | AD-19200 | 41.09 | 85.94 | 95.13 | 101.29 | 96.60 | 9.99 | 25.31 | 24.56 | 32.26 | 26.35 |
| (+) control | AD-19200 | 23.99 | 72.76 | 86.51 | 108.10 | 111.13 | 5.35 | 34.52 | 29.24 | 35.99 | 31.88 |
| (−) control | AD-1955 | 89.65 | 99.87 | 94.59 | 104.04 | 105.10 | 4.57 | 5.94 | 4.19 | 5.78 | 7.46 |
| (−) control | AD-1955 | 104.74 | 99.78 | 105.79 | 109.19 | 108.08 | 10.94 | 7.74 | 11.12 | 7.91 | 10.30 |
| (−) control | mock | 100.00 | | | | | 6.92 | | | | |
| (−) control | mock | 100.00 | | | | | 9.85 | | | | |
| (+) control | PLK | 10.66 | 26.65 | 46.16 | 92.42 | 98.78 | 1.70 | 8.65 | 13.47 | 22.99 | 23.48 |
| (+) control | PLK | 10.74 | 11.41 | 17.33 | 61.02 | 86.59 | 3.39 | 2.61 | 1.49 | 27.42 | 37.31 |
| HeLa day 6 | | | | | | | | | | | |
| ANGPTL3 | AD-15838.2 | 47.94 | 80.97 | 90.44 | 94.37 | 96.10 | 29.05 | 25.12 | 13.62 | 8.88 | 4.72 |
| ANGPTL3 | AD-15838.2 | 40.32 | 83.80 | 89.88 | 95.94 | 98.27 | 22.47 | 16.51 | 10.03 | 3.83 | 4.19 |
| ANGPTL3 | AD-45860.1 | 57.38 | 84.84 | 88.90 | 96.74 | 94.03 | 24.55 | 17.35 | 9.67 | 3.17 | 6.58 |
| ANGPTL3 | AD-45864.1 | 98.65 | 100.87 | 101.13 | 96.86 | 98.24 | 4.35 | 1.91 | 2.22 | 3.41 | 1.80 |
| ANGPTL3 | AD-45870.1 | 92.69 | 98.71 | 98.49 | 100.07 | 99.28 | 3.94 | 2.67 | 2.36 | 1.19 | 2.65 |
| ANGPTL3 | AD-45873.1 | 91.78 | 97.38 | 98.81 | 97.57 | 96.22 | 12.47 | 6.26 | 4.08 | 6.22 | 8.64 |
| ANGPTL3 | AD-45876.1 | 63.54 | 85.68 | 92.13 | 96.48 | 95.97 | 14.74 | 16.50 | 10.03 | 5.81 | 7.51 |
| ANGPTL3 | AD-45877.1 | 94.17 | 93.21 | 96.39 | 96.70 | 96.98 | 7.12 | 8.00 | 4.58 | 3.05 | 6.15 |
| ANGPTL3 | AD-45878.1 | 66.46 | 85.75 | 89.73 | 94.60 | 96.59 | 8.20 | 7.41 | 5.27 | 3.21 | 3.91 |
| ANGPTL3 | AD-45878.1 | 70.80 | 89.30 | 92.54 | 96.60 | 95.09 | 5.18 | 2.13 | 1.61 | 0.50 | 4.15 |
| ANGPTL3 | AD-45879.1 | 8.29 | 48.25 | 73.54 | 87.47 | 92.19 | 4.66 | 20.05 | 16.04 | 9.06 | 7.90 |
| ANGPTL3 | AD-45886.1 | 23.69 | 60.65 | 78.49 | 93.41 | 94.15 | 8.19 | 13.90 | 7.15 | 3.35 | 4.06 |
| ANGPTL3 | AD-45887.1 | 7.24 | 26.03 | 57.68 | 95.99 | 98.80 | 3.07 | 13.10 | 14.94 | 1.40 | 2.54 |
| ANGPTL3 | AD-45915.1 | 10.38 | 58.38 | 85.69 | 97.24 | 99.76 | 6.83 | 15.66 | 8.39 | 1.33 | 4.15 |
| ANGPTL3 | AD-45929.1 | 11.73 | 36.67 | 51.90 | 76.71 | 85.08 | 4.80 | 14.19 | 15.34 | 12.37 | 10.60 |
| ANGPTL3 | AD-45934.1 | 73.57 | 88.48 | 92.94 | 91.50 | 95.97 | 5.36 | 2.96 | 5.50 | 5.44 | 4.39 |
| (+) control | AD-19200 | 63.58 | 90.14 | 95.44 | 94.65 | 93.28 | 34.11 | 14.32 | 8.78 | 10.90 | 12.13 |
| (+) control | AD-19200 | 16.05 | 78.65 | 85.78 | 93.09 | 96.22 | 9.77 | 15.57 | 19.50 | 13.34 | 10.96 |
| (−) control | AD-1955 | 93.52 | 97.36 | 97.90 | 99.65 | 100.07 | 5.02 | 1.78 | 0.84 | 0.58 | 1.14 |
| (−) control | AD-1955 | 75.39 | 93.61 | 97.79 | 99.60 | 100.96 | 8.37 | 2.50 | 2.27 | 2.68 | 3.16 |
| (−) control | mock | 100.00 | | | | | 1.32 | | | | |
| (−) control | mock | 100.00 | | | | | 3.35 | | | | |
| (+) control | PLK | 3.68 | 55.22 | 63.00 | 89.39 | 95.33 | 1.42 | 30.96 | 33.97 | 15.85 | 8.54 |
| (+) control | PLK | 2.69 | 3.74 | 9.74 | 67.07 | 82.96 | 0.15 | 0.96 | 3.60 | 22.70 | 19.34 |
| Hep3B day 3 | | | | | | | | | | | |
| ANGPTL3 | AD-15838.2 | 35.33 | 61.00 | 68.79 | 82.74 | 90.41 | 2.41 | 6.21 | 4.21 | 2.61 | 7.07 |
| ANGPTL3 | AD-15838.2 | 35.34 | 61.04 | 72.14 | 89.71 | 106.88 | 1.49 | 2.61 | 7.37 | 6.48 | 7.13 |
| ANGPTL3 | AD-45860.1 | 17.79 | 39.25 | 60.57 | 94.28 | 99.85 | 1.07 | 3.51 | 3.57 | 13.09 | 16.41 |
| ANGPTL3 | AD-45864.1 | 80.35 | 88.19 | 87.01 | 89.39 | 92.09 | 6.93 | 6.98 | 9.42 | 7.41 | 17.05 |
| ANGPTL3 | AD-45870.1 | 75.00 | 93.30 | 96.64 | 106.29 | 99.08 | 7.10 | 12.24 | 4.01 | 5.95 | 9.64 |
| ANGPTL3 | AD-45873.1 | 42.68 | 78.45 | 82.26 | 97.11 | 96.58 | 5.17 | 5.04 | 8.31 | 12.11 | 11.33 |
| ANGPTL3 | AD-45876.1 | 31.37 | 55.00 | 70.69 | 93.49 | 91.00 | 4.39 | 6.09 | 5.47 | 15.11 | 6.38 |
| ANGPTL3 | AD-45877.1 | 74.45 | 94.60 | 96.70 | 103.77 | 106.75 | 3.27 | 2.44 | 3.45 | 6.10 | 7.40 |
| ANGPTL3 | AD-45878.1 | 50.22 | 69.65 | 80.49 | 92.77 | 97.37 | 2.51 | 14.94 | 10.44 | 8.21 | 5.30 |
| ANGPTL3 | AD-45878.1 | 44.85 | 65.39 | 75.67 | 92.83 | 109.67 | 10.10 | 7.76 | 8.56 | 7.78 | 4.97 |
| ANGPTL3 | AD-45879.1 | 23.73 | 60.81 | 84.59 | 95.72 | 108.68 | 6.43 | 21.36 | 19.62 | 13.69 | 5.95 |
| ANGPTL3 | AD-45886.1 | 27.19 | 55.35 | 64.97 | 100.18 | 102.09 | 0.97 | 6.65 | 11.46 | 6.91 | 4.08 |
| ANGPTL3 | AD-45887.1 | 41.70 | 97.18 | 101.91 | 111.27 | 105.18 | 9.26 | 6.81 | 7.36 | 1.72 | 2.23 |
| ANGPTL3 | AD-45915.1 | 45.10 | 66.31 | 82.22 | 97.97 | 103.30 | 6.91 | 11.84 | 14.79 | 6.54 | 2.48 |
| ANGPTL3 | AD-45929.1 | 48.58 | 79.14 | 89.96 | 95.00 | 101.37 | 10.40 | 10.29 | 10.52 | 18.24 | 10.53 |
| ANGPTL3 | AD-45934.1 | 80.15 | 102.93 | 112.82 | 114.16 | 113.98 | 5.28 | 0.62 | 4.19 | 0.75 | 3.99 |
| (+) control | AD-19200 | 14.79 | 55.23 | 72.90 | 89.64 | 94.30 | 2.17 | 5.42 | 7.19 | 10.28 | 16.39 |
| (+) control | AD-19200 | 22.76 | 92.02 | 101.56 | 106.68 | 113.09 | 6.61 | 18.99 | 7.41 | 9.83 | 10.64 |

TABLE 6-continued

Results of cell viability screens using modified ANGPTL3 dsRNA sequences
The experiments were conducted using modified oligonucleotide duplexes listed
in Table 3. The sequence of AD-15838.2 is identical to the sequence of AD-
15838.1. Viability data is expressed as % viable relative to mock treated cells.

| Target | Duplex | Ave 10 nM | Ave 1 nM | Ave 500 pM | Ave 100 pM | Ave 50 pM | SD 10 nM | SD 1 nM | SD 500 pM | SD 100 pM | SD 50 pM |
|---|---|---|---|---|---|---|---|---|---|---|---|
| (−) control | AD-1955 | 77.77 | 81.25 | 82.23 | 88.21 | 95.02 | 2.83 | 5.40 | 5.08 | 5.42 | 6.63 |
| (−) control | AD-1955 | 80.42 | 86.70 | 90.23 | 93.46 | 97.04 | 10.53 | 5.70 | 8.14 | 3.27 | 3.45 |
| (−) control | mock | 100.00 | | | | | 5.77 | | | | |
| (−) control | mock | 100.00 | | | | | 9.79 | | | | |
| (+) control | PLK | 10.91 | 12.89 | 14.31 | 23.87 | 50.93 | 0.17 | 0.87 | 1.64 | 1.13 | 7.80 |
| (+) control | PLK | 13.19 | 16.12 | 22.89 | 55.03 | 94.35 | 0.78 | 0.88 | 8.36 | 18.88 | 9.85 |
| | | | | Hep3B day 6 | | | | | | | |
| ANGPTL3 | AD-15838.2 | 78.88 | 89.58 | 93.08 | 91.10 | 100.66 | 11.60 | 9.15 | 12.04 | 10.51 | 5.87 |
| ANGPTL3 | AD-15838.2 | 81.17 | 85.91 | 87.27 | 103.95 | 103.59 | 7.75 | 3.29 | 8.07 | 7.93 | 9.82 |
| ANGPTL3 | AD-45860.1 | 84.11 | 87.77 | 93.22 | 99.15 | 96.75 | 14.22 | 13.36 | 20.98 | 13.15 | 17.62 |
| ANGPTL3 | AD-45864.1 | 99.27 | 111.82 | 106.28 | 99.15 | 97.55 | 7.77 | 16.31 | 14.24 | 15.40 | 9.18 |
| ANGPTL3 | AD-45870.1 | 95.49 | 109.60 | 104.16 | 104.65 | 106.76 | 11.92 | 12.98 | 9.25 | 10.29 | 19.12 |
| ANGPTL3 | AD-45873.1 | 71.45 | 90.62 | 93.44 | 102.07 | 107.72 | 4.71 | 4.40 | 15.02 | 11.96 | 10.16 |
| ANGPTL3 | AD-45876.1 | 76.92 | 82.09 | 89.44 | 95.27 | 105.41 | 9.39 | 13.55 | 7.93 | 9.77 | 10.42 |
| ANGPTL3 | AD-45877.1 | 82.98 | 98.05 | 95.07 | 103.55 | 104.14 | 11.22 | 13.45 | 1.27 | 8.88 | 6.49 |
| ANGPTL3 | AD-45878.1 | 75.14 | 82.48 | 89.68 | 92.71 | 95.72 | 8.65 | 10.07 | 10.77 | 12.44 | 15.04 |
| ANGPTL3 | AD-45878.1 | 65.90 | 77.37 | 78.33 | 84.54 | 99.49 | 10.21 | 13.22 | 9.95 | 11.65 | 11.17 |
| ANGPTL3 | AD-45879.1 | 86.42 | 89.45 | 101.50 | 97.30 | 100.66 | 10.59 | 10.12 | 19.77 | 13.19 | 9.54 |
| ANGPTL3 | AD-45886.1 | 91.15 | 79.31 | 80.76 | 86.52 | 94.04 | 12.89 | 11.88 | 5.38 | 4.92 | 6.80 |
| ANGPTL3 | AD-45887.1 | 91.67 | 103.38 | 107.88 | 100.05 | 102.05 | 10.80 | 14.84 | 19.18 | 13.72 | 18.00 |
| ANGPTL3 | AD-45915.1 | 81.97 | 85.91 | 91.81 | 94.95 | 102.13 | 18.49 | 19.30 | 7.19 | 12.72 | 16.64 |
| ANGPTL3 | AD-45929.1 | 61.92 | 79.39 | 87.28 | 88.09 | 96.00 | 6.80 | 10.76 | 5.80 | 10.68 | 16.66 |
| ANGPTL3 | AD-45934.1 | 85.84 | 89.66 | 97.67 | 99.91 | 102.54 | 12.39 | 14.25 | 4.74 | 9.51 | 4.28 |
| (+) control | AD-19200 | 50.48 | 65.62 | 79.67 | 98.61 | 96.87 | 4.60 | 4.64 | 7.20 | 5.08 | 7.37 |
| (+) control | AD-19200 | 52.01 | 75.89 | 92.59 | 101.47 | 99.66 | 4.35 | 20.87 | 13.57 | 6.50 | 11.76 |
| (−) control | AD-1955 | 91.77 | 95.87 | 93.06 | 95.10 | 97.52 | 8.87 | 3.46 | 1.46 | 2.00 | 3.84 |
| (−) control | AD-1955 | 93.65 | 94.41 | 89.42 | 100.59 | 103.91 | 9.91 | 14.90 | 6.80 | 11.99 | 10.31 |
| (−) control | mock | 100.00 | | | | | 5.10 | | | | |
| (−) control | mock | 100.00 | | | | | 7.35 | | | | |
| (+) control | PLK | 36.43 | 37.75 | 40.19 | 55.25 | 64.59 | 3.44 | 2.75 | 3.65 | 5.33 | 5.02 |
| (+) control | PLK | 38.70 | 43.68 | 50.32 | 75.17 | 89.62 | 3.40 | 3.85 | 8.10 | 10.54 | 10.69 |

TABLE 7

Unmodified sense and antisense strand sequences of ANGPTL3 GalNac-conjugated dsRNAs

| Duplex ID | Sense Name | Sense Sequence (SEQ ID NOS 264-448, respectively, in order of appearance) | Position in NM_014495.2 | Antisense Name | Antisense Sequence (SEQ ID NOS 449-633, respectively, in order of appearance) | Position in NM_014495.2 |
|---|---|---|---|---|---|---|
| AD-53063.1 | A-108558.1 | AAAGACAACAAACAUUAUAUUx | 1066-1086 | A-108559.1 | AAUAUAAUGUUUGUUGUCUUUCC | 1064-1086 |
| AD-52965.1 | A-108310.1 | ACAAUUAAGCUCCUUCUUUUUx | 58-78 | A-108311.1 | AAAAAGAAGGAGCUUAAUUGUGA | 56-78 |
| AD-53030.1 | A-108410.1 | UGUCACUUGAACUCAACUCAAx | 398-418 | A-108411.1 | UUGAGUUGAGUUCAAGUGACAUA | 396-418 |
| AD-52953.1 | A-108306.1 | UCACAAUUAAGCUCCUUCUUUx | 56-76 | A-108307.1 | AAAGAAGGAGCUUAAUUGUGAAC | 54-76 |
| AD-53001.1 | A-108416.1 | CUUGAACUCAACUCAAAACUUx | 403-423 | A-108417.1 | AAGUUUUGAGUUGAGUUCAAGUG | 401-423 |
| AD-53080.1 | A-108548.1 | CUCCAUAGUGAAGCAAUCUAAx | 1014-1034 | A-108549.1 | UUAGAUUGCUUCACUAUGGAGUA | 1012-1034 |
| AD-52971.1 | A-108312.1 | CAAUUAAGCUCCUUCUUUUUAx | 59-79 | A-108313.1 | UAAAAAGAAGGAGCUUAAUUGUG | 57-79 |
| AD-53071.1 | A-108498.1 | ACCCAGCAACUCUCAAGUUUUx | 840-860 | A-108499.1 | AAAACUUGAGAGUUGCUGGGUCU | 838-860 |
| AD-53024.1 | A-108408.1 | GAAUAUGUCACUUGAACUCAAx | 393-413 | A-108409.1 | UUGAGUUCAAGUGACAUAUUCUU | 391-413 |
| AD-52977.1 | A-108314.1 | AAUUAAGCUCCUUCUUUUUAUx | 60-80 | A-108315.1 | AUAAAAAGAAGGAGCUUAAUUGU | 58-80 |
| AD-53064.1 | A-108574.1 | CAUUAUAUUGAAUAUUCUUUUx | 1078-1098 | A-108575.1 | AAAAGAAUAUUCAAUAUAAUGUU | 1076-1098 |
| AD-53033.1 | A-108458.1 | ACUAACUAACUUAAUUCAAAx | 483-503 | A-108459.1 | UUUUGAAUUAAGUUAGUUAGUUG | 481-503 |
| AD-52954.1 | A-108322.1 | UUAUUGUUCCUCUAGUUAUUx | 77-97 | A-108323.1 | AAAUAACUAGAGGAACAAUAAAA | 75-97 |
| AD-53098.1 | A-108554.1 | CAUAGUGAAGCAAUCUAAUUAx | 1017-1037 | A-108555.1 | UAAUUAGAUUGCUUCACUAUGGA | 1015-1037 |

TABLE 7-continued

Unmodified sense and antisense strand sequences of ANGPTL3 GalNac-conjugated dsRNAs

| Duplex ID | Sense Name | Sense Sequence (SEQ ID NOS 264-448, respectively, in order of appearance) | Position in NM_014495.2 | Antisense Name | Antisense Sequence (SEQ ID NOS 449-633, respectively, in order of appearance) | Position in NM_014495.2 |
|---|---|---|---|---|---|---|
| AD-53092.1 | A-108552.1 | CCAUAGUGAAGCAAUCUAAUUx | 1016-1036 | A-108553.1 | AAUUAGAUUGCUUCACUAUGGAG | 1014-1036 |
| AD-53073.1 | A-108530.1 | GAUCACAAAACUUCAAUGAAAx | 923-943 | A-108531.1 | UUUCAUUGAAGUUUUGUGAUCCA | 921-943 |
| AD-53132.1 | A-108628.1 | AUGGAAGGUUAUACUCUAUAAx | 1364-1384 | A-108629.1 | UUAUAGAGUAUAACCUUCCAUUU | 1362-1384 |
| AD-53086.1 | A-108550.1 | UCCAUAGUGAAGCAAUCUAAUx | 1015-1035 | A-108551.1 | AUUAGAUUGCUUCACUAUGGAGU | 1013-1035 |
| AD-52961.1 | A-108340.1 | CUAUGUUAGACGAUGUAAAAAx | 164-184 | A-108341.1 | UUUUUACAUCGUCUAACAUAGCA | 162-184 |
| AD-52983.1 | A-108316.1 | AUUAAGCUCCUUCUUUUUAUUx | 61-81 | A-108317.1 | AAUAAAAAGAAGGAGCUUAAUUG | 59-81 |
| AD-53027.1 | A-108456.1 | AACUAACUAACUUAAUUCAAAx | 482-502 | A-108457.1 | UUUGAAUUAAGUUAGUUAGUUGC | 480-502 |
| AD-52986.1 | A-108364.1 | GGCCAAAUUAAUGACAUAUUUx | 247-267 | A-108365.1 | AAAUAUGUCAUUAAUUUGGCCCU | 245-267 |
| AD-52989.1 | A-108318.1 | UUUUAUUGUUCCUCUAGUUAUx | 75-95 | A-108319.1 | AUAACUAGAGGAACAAUAAAAAG | 73-95 |
| AD-52981.1 | A-108378.1 | ACAUAUUUGAUCAGUCUUUUUx | 278-298 | A-108379.1 | AAAAAGACUGAUCAAAUAUGUUG | 276-298 |
| AD-53077.1 | A-108500.1 | CCCAGCAACUCUCAAGUUUUUx | 841-861 | A-108501.1 | AAAAACUUGAGAGUUGCUGGGUC | 839-861 |
| AD-53095.1 | A-108506.1 | CAGGUAGUCCAUGGACAUUAAx | 884-904 | A-108507.1 | UUAAUGUCCAUGGACUACCUGAU | 882-904 |
| AD-52970.1 | A-108390.1 | ACUGAGAAGAACUACAUAUAAx | 345-365 | A-108391.1 | UUAUAUGUAGUUCUUCUCAGUUC | 343-365 |
| AD-53015.1 | A-108452.1 | GAGCAACUAACUAACUUAAUUx | 478-498 | A-108453.1 | AAUUAAGUUAGUUAGUUGCUCUU | 476-498 |
| AD-53147.1 | A-108618.1 | AACAACCUAAAUGGUAAAUAUx | 1282-1302 | A-108619.1 | AUAUUUACCAUUUAGGUUGUUUU | 1280-1302 |
| AD-53103.1 | A-108540.1 | CCUAGAGAAGAUAUACUCCAUx | 999-1019 | A-108541.1 | AUGGAGUAUAUCUUCUCUAGGCC | 997-1019 |
| AD-52969.1 | A-108374.1 | CAACAUAUUUGAUCAGUCUUUx | 276-296 | A-108375.1 | AAAGACUGAUCAAAUAUGUUGAG | 274-296 |
| AD-53075.1 | A-108562.1 | ACAACAAACAUUAUAUUGAAUx | 1070-1090 | A-108563.1 | AUUCAAUAUAAUGUUUGUUGUCU | 1068-1090 |
| AD-52994.1 | A-108398.1 | ACAUAUAAACUACAAGUCAAAx | 358-378 | A-108399.1 | UUUGACUUGUAGUUUAUAUGUAG | 356-378 |
| AD-52960.1 | A-108324.1 | CUAGUUAUUCCUCCAGAAUUx | 88-108 | A-108325.1 | AAUUCUGGAGGAAAUAACUAGAG | 86-108 |
| AD-53003.1 | A-108448.1 | AAGAGCAACUAACUAACUUAAx | 476-496 | A-108449.1 | UUAAGUUAGUUAGUUGCUCUUCU | 474-496 |
| AD-52995.1 | A-108320.1 | UUUUAUUGUUCCUCUAGUUAUUx | 76-96 | A-108321.1 | AAUAACUAGAGGAACAAUAAAAA | 74-96 |
| AD-53037.1 | A-108428.1 | CUCCUAGAAGAAAAAAUUCUAx | 430-450 | A-108429.1 | UAGAAUUUUUCUUCUAGGAGGC | 428-450 |
| AD-53087.1 | A-108566.1 | AACAAACAUUAUAUUGAAUAUx | 1072-1092 | A-108567.1 | AUAUUCAAUAUAAUGUUUGUUGU | 1070-1092 |
| AD-53076.1 | A-108578.1 | GGAAAUCACGAAACCAACUAUx | 1105-1125 | A-108579.1 | AUAGUUGGUUUCGUGAUUUCCCA | 1103-1125 |
| AD-52975.1 | A-108376.1 | AACAUAUUUGAUCAGUCUUUUx | 277-297 | A-108377.1 | AAAAGACUGAUCAAAUAUGUUGA | 275-297 |
| AD-53138.1 | A-108630.1 | UGGAAGGUUAUACUCUAUAAAx | 1365-1385 | A-108631.1 | UUUAUAGAGUAUAACCUUCCAUU | 1363-1385 |
| AD-53091.1 | A-108536.1 | GGAGAACUACAAAUAUGGUUUx | 948-968 | A-108537.1 | AAACCAUAUUUGUAGUUCUCCCA | 946-968 |
| AD-53124.1 | A-108594.1 | GAAAACAAAGAUUUGGUGUUUx | 1174-1194 | A-108595.1 | AAACACCAAAUCUUUGUUUUCCG | 1172-1194 |
| AD-53125.1 | A-108610.1 | AGUGUGGAGAAAACAACCUAAx | 1271-1291 | A-108611.1 | UUAGGUUGUUUUCUCCACACUCA | 1269-1291 |
| AD-53036.1 | A-108412.1 | GUCACUUGAACUCAACUCAAAx | 399-419 | A-108413.1 | UUUGAGUUGAGUUCAAGUGACAU | 397-419 |
| AD-53061.1 | A-108526.1 | GAUGGAUCACAAAACUUCAAUx | 919-939 | A-108527.1 | AUUGAAGUUUUGUGAUCCAUCUA | 917-939 |
| AD-53093.1 | A-108568.1 | ACAAACAUUAUAUUGAAUAUUx | 1073-1093 | A-108569.1 | AAUAUUCAAUAUAAUGUUUGUUG | 1071-1093 |
| AD-53137.1 | A-108614.1 | UGUGGAGAAAACAACCUAAAUx | 1273-1293 | A-108615.1 | AUUUAGGUUGUUUUCUCCACACU | 1271-1293 |
| AD-52999.1 | A-108384.1 | AUCAGUCUUUUUAUGAUCUAUx | 287-307 | A-108385.1 | AUAGAUCAUAAAAAGACUGAUCA | 285-307 |
| AD-53069.1 | A-108560.1 | GACAACAAACAUUAUAUUGAAx | 1069-1089 | A-108561.1 | UUCAAUAUAAUGUUUGUUGUCUU | 1067-1089 |

TABLE 7-continued

Unmodified sense and antisense strand sequences of ANGPTL3 GalNac-conjugated dsRNAs

| Duplex ID | Sense Name | Sense Sequence (SEQ ID NOS 264-448, respectively, in order of appearance) | Position in NM_014495.2 | Antisense Name | Antisense Sequence (SEQ ID NOS 449-633, respectively, in order of appearance) | Position in NM_014495.2 |
|---|---|---|---|---|---|---|
| AD-53034.1 | A-108474.1 | CAACAGCAUAGUCAAAUAAAAx | 622-642 | A-108475.1 | UUUUAUUGACUAUGCUGUUGGU | 620-642 |
| AD-52976.1 | A-108392.1 | CUGAGAAGAACUACAUAUAAAx | 346-366 | A-108393.1 | UUUAUAUGUAGUUCUUCUCAGUU | 344-366 |
| AD-52996.1 | A-108336.1 | UGCUAUGUUAGACGAUGUAAAx | 162-182 | A-108337.1 | UUUACAUCGUCUAACAUAGCAAA | 160-182 |
| AD-53029.1 | A-108488.1 | AACCCACAGAAAUUUCUCUAUx | 680-700 | A-108489.1 | AUAGAGAAAUUUCUGUGGGUUCU | 678-700 |
| AD-53020.1 | A-108438.1 | CUUCAACAAAAGUGAAAUAUx | 451-471 | A-108439.1 | AUAUUUCACUUUUUGUUGAAGUA | 449-471 |
| AD-53042.1 | A-108414.1 | UCACUUGAACUCAACUCAAAx | 400-420 | A-108415.1 | UUUUGAGUUGAGUUCAAGUGACA | 398-420 |
| AD-53011.1 | A-108482.1 | CAUAGUCAAAUAAAAGAAAUAx | 628-648 | A-108483.1 | UAUUUCUUUUAUUUGACUAUGCU | 626-648 |
| AD-52957.1 | A-108370.1 | CAAAAACUCAACAUAUUUGAUx | 268-288 | A-108371.1 | AUCAAAUAUGUUGAGUUUUUGAA | 266-288 |
| AD-53008.1 | A-108434.1 | UACUUCAACAAAAGUGAAAUx | 449-469 | A-108435.1 | AUUUCACUUUUUGUUGAAGUAGA | 447-469 |
| AD-53065.1 | A-108496.1 | GACCCAGCAACUCUCAAGUUUx | 839-859 | A-108497.1 | AAACUUGAGAGUUGCUGGGUCUG | 837-859 |
| AD-53115.1 | A-108638.1 | UUGAAUGAACUGAGGCAAAUx | 1427-1447 | A-108639.1 | AAUUUGCCUCAGUUCAUUCAAAG | 1425-1447 |
| AD-53012.1 | A-108404.1 | UAUAAACUACAAGUCAAAAAUx | 361-381 | A-108405.1 | AUUUUUGACUUGUAGUUUAUAUG | 359-381 |
| AD-53004.1 | A-108464.1 | AAACAAGAUAAUAGCAUCAAAx | 559-579 | A-108465.1 | UUUGAUGCUAUUAUCUUGUUUUU | 557-579 |
| AD-53021.1 | A-108454.1 | CAACUAACUAACUUAAUUCAAx | 481-501 | A-108455.1 | UUGAAUUAAGUUAGUUAGUUGCU | 479-501 |
| AD-52955.1 | A-108338.1 | GCUAUGUUAGACGAUGUAAAAx | 163-183 | A-108339.1 | UUUUACAUCGUCUAACAUAGCAA | 161-183 |
| AD-53119.1 | A-108608.1 | ACUUGGGAUCACAAAGCAAAx | 1198-1218 | A-108609.1 | UUUUGCUUUGUGAUCCCAAGUAG | 1196-1218 |
| AD-52990.1 | A-108334.1 | UUGCUAUGUUAGACGAUGUAAx | 161-181 | A-108335.1 | UUACAUCGUCUAACAUAGCAAAU | 159-181 |
| AD-52964.1 | A-108388.1 | AACUGAGAAGAACUACAUAUAx | 344-364 | A-108389.1 | UAUAUGUAGUUCUUCUCAGUUCC | 342-364 |
| AD-52973.1 | A-108344.1 | GAUGUAAAAUUUUAGCCAAUx | 175-195 | A-108345.1 | AUUGGCUAAAAUUUUUACAUCGU | 173-195 |
| AD-53074.1 | A-108546.1 | ACUCCAUAGUGAAGCAAUCUAx | 1013-1033 | A-108547.1 | UAGAUUGCUUCACUAUGGAGUAU | 1011-1033 |
| AD-53026.1 | A-108440.1 | UUCAACAAAAGUGAAAUAUUx | 452-472 | A-108441.1 | AAUAUUUCACUUUUUGUUGAAGU | 450-472 |
| AD-53062.1 | A-108542.1 | CUAGAGAAGAUAUACUCCAUAx | 1000-1020 | A-108543.1 | UAUGGAGUAUAUCUUCUCUAGGC | 998-1020 |
| AD-53114.1 | A-108622.1 | CAACCUAAAUGGUAAAUAUAAx | 1284-1304 | A-108623.1 | UUAUAUUUACCAUUUAGGUUGUU | 1282-1304 |
| AD-53082.1 | A-108580.1 | GAAAUCACGAAACCAACUAUAx | 1106-1126 | A-108581.1 | UAUAGUUGGUUUCGUGAUUUCCC | 1104-1126 |
| AD-53035.1 | A-108490.1 | CCACAGAAAUUUCUCUAUCUUx | 683-703 | A-108491.1 | AAGAUAGAGAAAUUUCUGUGGGU | 681-703 |
| AD-52978.1 | A-108330.1 | AAAUCAAGAUUUGCUAUGUUAx | 151-171 | A-108331.1 | UAACAUAGCAAAUCUUGAUUUUG | 149-171 |
| AD-53084.1 | A-108518.1 | ACAUUAAUUCAACAUCGAAUAx | 898-918 | A-108519.1 | UAUUCGAUGUUGAAUUAAUGUCC | 896-918 |
| AD-52972.1 | A-108328.1 | CCAGAGCCAAAAUCAAGAUUUx | 142-162 | A-108329.1 | AAAUCUUGAUUUUGGCUCUGGAG | 140-162 |
| AD-53002.1 | A-108432.1 | CUACUUCAACAAAAGUGAAAx | 448-468 | A-108433.1 | UUUCACUUUUUGUUGAAGUAGAA | 446-468 |
| AD-53078.1 | A-108516.1 | GACAUUAAUUCAACAUCGAAUx | 897-917 | A-108517.1 | AUUCGAUGUUGAAUUAAUGUCCA | 895-917 |
| AD-53072.1 | A-108514.1 | GGACAUUAAUUCAACAUCGAAx | 896-916 | A-108515.1 | UUCGAUGUUGAAUUAAUGUCCAU | 894-916 |
| AD-53005.1 | A-108480.1 | GCAUAGUCAAAUAAAAGAAAUx | 627-647 | A-108481.1 | AUUUCUUUUAUUUGACUAUGCUG | 625-647 |
| AD-53083.1 | A-108502.1 | CUCUCAAGUUUUUCAUGUCUAx | 849-869 | A-108503.1 | UAGACAUGAAAAACUUGAGAGUU | 847-869 |
| AD-53102.1 | A-108524.1 | AUCGAAUAGAUGGAUCACAAAx | 911-931 | A-108525.1 | UUUGUGAUCCAUCUAUUCGAUGU | 909-931 |
| AD-53105.1 | A-108572.1 | ACAUUAUAUUGAAUAUUCUUUx | 1077-1097 | A-108573.1 | AAAGAAUAUUCAAUAUAAUGUUU | 1075-1097 |
| AD-53090.1 | A-108520.1 | UUAAUUCAACAUCGAAUAGAUx | 901-921 | A-108521.1 | AUCUAUUCGAUGUUGAAUUAAUG | 899-921 |
| AD-53010.1 | A-108466.1 | GAUAAUAGCAUCAAAGACCUUx | 565-585 | A-108467.1 | AAGGUCUUUGAUGCUAUUAUCUU | 563-585 |

TABLE 7-continued

Unmodified sense and antisense strand sequences of ANGPTL3 GalNac-conjugated dsRNAs

| Duplex ID | Sense Name | Sense Sequence (SEQ ID NOS 264-448, respectively, in order of appearance) | Position in NM_014495.2 | Antisense Name | Antisense Sequence (SEQ ID NOS 449-633, respectively, in order of appearance) | Position in NM_014495.2 |
|---|---|---|---|---|---|---|
| AD-52998.1 | A-108368.1 | UGACAUAUUUCAAAAACUCAAx | 258-278 | A-108369.1 | UUGAGUUUUUGAAAUAUGUCAUU | 256-278 |
| AD-52992.1 | A-108366.1 | AAAUUAAUGACAUAUUUCAAAx | 251-271 | A-108367.1 | UUUGAAAUAUGUCAUUAAUUUGG | 249-271 |
| AD-53068.1 | A-108544.1 | GAAGAUAUACUCCAUAGUGAAx | 1005-1025 | A-108545.1 | UUCACUAUGGAGUAUAUCUUCUC | 1003-1025 |
| AD-53032.1 | A-108442.1 | AAUAUUUAGAAGAGCAACUAAx | 467-487 | A-108443.1 | UUAGUUGCUCUUCUAAAUAUUUC | 465-487 |
| AD-52967.1 | A-108342.1 | CGAUGUAAAAAUUUUAGCCAAx | 174-194 | A-108343.1 | UUGGCUAAAAUUUUUACAUCGUC | 172-194 |
| AD-53096.1 | A-108522.1 | UUCAACAUCGAAUAGAUGGAUx | 905-925 | A-108523.1 | AUCCAUCUAUUCGAUGUUGAAUU | 903-925 |
| AD-53131.1 | A-108612.1 | GUGUGGAGAAAACAACCUAAAx | 1272-1292 | A-108613.1 | UUUAGGUUGUUUUCUCCACACUC | 1270-1292 |
| AD-52963.1 | A-108372.1 | UCAACAUAUUUGAUCAGUCUUx | 275-295 | A-108373.1 | AAGACUGAUCAAAUAUGUUGAGU | 273-295 |
| AD-53089.1 | A-108504.1 | UCAGGUAGUCCAUGGACAUUAx | 883-903 | A-108505.1 | UAAUGUCCAUGGACUACCUGAUA | 881-903 |
| AD-53044.1 | A-108446.1 | UUUAGAAGAGCAACUAACUAAx | 471-491 | A-108447.1 | UUAGUUAGUUGCUCUUCUAAAUA | 469-491 |
| AD-52988.1 | A-108396.1 | UACAUAUAAACUACAAGUCAAx | 357-377 | A-108397.1 | UUGACUUGUAGUUUAUAUGUAGU | 355-377 |
| AD-53067.1 | A-108528.1 | GGAUCACAAAACUUCAAUGAAx | 922-942 | A-108529.1 | UUCAUUGAAGUUUUGUGAUCCAU | 920-942 |
| AD-53009.1 | A-108450.1 | AGAGCAACUAACUAACUUAAUx | 477-497 | A-108451.1 | AUUAAGUUAGUUAGUUGCUCUUC | 475-497 |
| AD-53022.1 | A-108470.1 | ACCAACAGCAUAGUCAAAUAAx | 620-640 | A-108471.1 | UUAUUUGACUAUGCUGUUGGUUU | 618-640 |
| AD-53016.1 | A-108468.1 | AACCAACAGCAUAGUCAAAUAx | 619-639 | A-108469.1 | UAUUUGACUAUGCUGUUGGUUUA | 617-639 |
| AD-53007.1 | A-108418.1 | GAACUCAACUCAAAACUUGAAx | 406-426 | A-108419.1 | UUCAAGUUUUGAGUUGAGUUCAA | 404-426 |
| AD-53148.1 | A-108634.1 | UACUCUAUAAAAUCAACCAAAx | 1375-1395 | A-108635.1 | UUUGGUUGAUUUUAUAGAGUAUA | 1373-1395 |
| AD-53040.1 | A-108476.1 | CAGCAUAGUCAAAUAAAGAAx | 625-645 | A-108477.1 | UUCUUUUAUUUGACUAUGCUGUU | 623-645 |
| AD-53041.1 | A-108492.1 | GAAAUAAGAAAUGUAAAACAUx | 748-768 | A-108493.1 | AUGUUUUACAUUUCUUAUUUCAU | 746-768 |
| AD-53039.1 | A-108460.1 | CUAACUAACUUAAUUCAAAAUx | 484-504 | A-108461.1 | AUUUUGAAUUAAGUUAGUUAGUU | 482-504 |
| AD-53139.1 | A-108646.1 | AUGAACUGAGGCAAAUUUAAAx | 1431-1451 | A-108647.1 | UUUAAAUUUGCCUCAGUUCAUUC | 1429-1451 |
| AD-53144.1 | A-108648.1 | UGAACUGAGGCAAAUUUAAAAx | 1432-1452 | A-108649.1 | UUUUAAAUUUGCCUCAGUUCAUU | 1430-1452 |
| AD-53142.1 | A-108616.1 | AAACAACCUAAAUGGUAAAUAx | 1281-1301 | A-108617.1 | UAUUUACCAUUUAGGUUGUUUUC | 1279-1301 |
| AD-53108.1 | A-108620.1 | ACAACCUAAAUGGUAAAUAUAx | 1283-1303 | A-108621.1 | UAUAUUUACCAUUUAGGUUGUUU | 1281-1303 |
| AD-53079.1 | A-108532.1 | AACGUGGGAGAACUACAAUAx | 942-962 | A-108533.1 | UAUUGUAGUUCUCCCACGUUC | 940-962 |
| AD-53133.1 | A-108644.1 | AAUGAACUGAGGCAAAUUUAAx | 1430-1450 | A-108645.1 | UUAAAUUUGCCUCAGUUCAUUCA | 1428-1450 |
| AD-53104.1 | A-108556.1 | GUUGGAAGACUGGAAAGACAAx | 1053-1073 | A-108557.1 | UUGUCUUUCCAGUCUUCCAACUC | 1051-1073 |
| AD-53088.1 | A-108582.1 | UGGCAAUGUCCCCAAUGCAUx | 1149-1169 | A-108583.1 | AUGCAUUGGGGACAUUGCCAGU | 1147-1169 |
| AD-53101.1 | A-108508.1 | GGUAGUCCAUGGACAUUAAUUx | 886-906 | A-108509.1 | AAUUAAUGUCCAUGGACUACCUG | 884-906 |
| AD-53000.1 | A-108400.1 | CAUAUAAACUACAAGUCAAAx | 359-379 | A-108401.1 | UUUUGACUUGUAGUUUAUAUGUA | 357-379 |
| AD-53112.1 | A-108590.1 | AAUCCCGGAAAACAAAGAUUUx | 1167-1187 | A-108591.1 | AAAUCUUUGUUUUCCGGGAUUGC | 1165-1187 |
| AD-53107.1 | A-108604.1 | CUACUUGGGAUCACAAAGCAAx | 1196-1216 | A-108605.1 | UUGCUUUGUGAUCCCAAGUAGAA | 1194-1216 |
| AD-53121.1 | A-108640.1 | UGAAUGAACUGAGGCAAAUUUx | 1428-1448 | A-108641.1 | AAAUUUGCCUCAGUUCAUUCAA | 1426-1448 |
| AD-53046.1 | A-108478.1 | AGCAUAGUCAAAUAAAGAAx | 626-646 | A-108479.1 | UUUCUUUUAUUUGACUAUGCUGU | 624-646 |
| AD-53038.1 | A-108444.1 | AUUUAGAAGAGCAACUAACUAx | 470-490 | A-108445.1 | UAGUUAGUUGCUCUUCUAAAUAU | 468-490 |
| AD-53140.1 | A-108662.1 | AGGCAAAUUUAAAAGGCAAUAx | 1439-1459 | A-108663.1 | UAUUGCCUUUUAAAUUUGCCUCA | 1437-1459 |

TABLE 7-continued

Unmodified sense and antisense strand sequences of ANGPTL3 GalNac-conjugated dsRNAs

| Duplex ID | Sense Name | Sense Sequence (SEQ ID NOS 264-448, respectively, in order of appearance) | Position in NM_014495.2 | Antisense Name | Antisense Sequence (SEQ ID NOS 449-633, respectively, in order of appearance) | Position in NM_014495.2 |
|---|---|---|---|---|---|---|
| AD-52987.1 | A-108380.1 | CAUAUUUGAUCAGUCUUUUUAx | 279-299 | A-108381.1 | UAAAAAGACUGAUCAAAUAUGUU | 277-299 |
| AD-53130.1 | A-108596.1 | AAAACAAAGAUUUGGUGUUUUx | 1175-1195 | A-108597.1 | AAAACACCAAAUCUUUGUUUUCC | 1173-1195 |
| AD-53106.1 | A-108588.1 | CAAUCCCGGAAAACAAAGAUUx | 1166-1186 | A-108589.1 | AAUCUUUGUUUUCCGGGAUUGCA | 1164-1186 |
| AD-53081.1 | A-108564.1 | CAACAAACAUUAUAUUGAAUAx | 1071-1091 | A-108565.1 | UAUUCAAUAUAAUGUUUGUUGUC | 1069-1091 |
| AD-53118.1 | A-108592.1 | GGAAAACAAAGAUUUGGUGUUx | 1173-1193 | A-108593.1 | AACACCAAAUCUUUGUUUUCCGG | 1171-1193 |
| AD-53136.1 | A-108598.1 | ACAAAGAUUUGGUGUUUUCUAx | 1178-1198 | A-108599.1 | UAGAAAACACCAAAUCUUUGUUU | 1176-1198 |
| AD-53127.1 | A-108642.1 | GAAUGAACUGAGGCAAAUUUAx | 1429-1449 | A-108643.1 | UAAAUUUGCCUCAGUUCAUUCAA | 1427-1449 |
| AD-53066.1 | A-108512.1 | CCAUGGACAUUAAUUCAACAUx | 892-912 | A-108513.1 | AUGUUGAAUUAAUGUCCAUGGAC | 890-912 |
| AD-53013.1 | A-108420.1 | AACUCAACUCAAAACUUGAAAx | 407-427 | A-108421.1 | UUUCAAGUUUUGAGUUGAGUUCA | 405-427 |
| AD-52991.1 | A-108350.1 | CAGUUGGGACAUGGUCUUAAAx | 205-225 | A-108351.1 | UUUAAGACCAUGUCCCAACUGAA | 203-225 |
| AD-53099.1 | A-108570.1 | AACAUUAUAUUGAAUAUUCUUx | 1076-1096 | A-108571.1 | AAGAAUAUUCAAUAUAAUGUUUG | 1074-1096 |
| AD-52958.1 | A-108386.1 | ACCAGUGAAAUCAAAGAAGAAx | 316-336 | A-108387.1 | UUCUUCUUUGAUUUCACUGGUUU | 314-336 |
| AD-53097.1 | A-108538.1 | GUUGGGCCUAGAGAAGAUAUAx | 993-1013 | A-108539.1 | UAUAUCUUCUCUAGGCCCAACCA | 991-1013 |
| AD-52966.1 | A-108326.1 | CUCCAGAGCCAAAAUCAAGAUx | 140-160 | A-108327.1 | AUCUUGAUUUUGGCUCUGGAGAU | 138-160 |
| AD-53145.1 | A-108664.1 | GGCAAAUUUAAAAGGCAAUAAx | 1440-1460 | A-108665.1 | UUAUUGCCUUUUAAAUUUGCCUC | 1438-1460 |
| AD-53113.1 | A-108606.1 | UACUUGGGAUCACAAAGCAAAx | 1197-1217 | A-108607.1 | UUUGCUUUGUGAUCCCAAGUAGA | 1195-1217 |
| AD-52993.1 | A-108382.1 | GAUCAGUCUUUUUAUGAUCUAx | 286-306 | A-108383.1 | UAGAUCAUAAAAAGACUGAUCAA | 284-306 |
| AD-53031.1 | A-108426.1 | GAAAGCCUCCUAGAAGAAAAAx | 424-444 | A-108427.1 | UUUUUCUUCUAGGAGGCUUUCAA | 422-444 |
| AD-53017.1 | A-108484.1 | AGUCAAAUAAAAGAAAUAGAAx | 631-651 | A-108485.1 | UUCUAUUUCUUUUAUUUGACUAU | 629-651 |
| AD-53143.1 | A-108632.1 | AUACUCUAUAAAAUCAACCAAx | 1374-1394 | A-108633.1 | UUGGUUGAUUUUAUAGAGUAUAA | 1372-1394 |
| AD-53149.1 | A-108650.1 | GAACUGAGGCAAAUUUAAAAAx | 1433-1453 | A-108651.1 | UUUUUAAAUUUGCCUCAGUUCAU | 1431-1453_G21A |
| AD-53059.1 | A-108494.1 | AGACCCAGCAACUCUCAAGUUx | 838-858 | A-108495.1 | AACUUGAGAGUUGCUGGGUCUGA | 836-858 |
| AD-53006.1 | A-108402.1 | AUAUAAACUACAAGUCAAAAAx | 360-380 | A-108403.1 | UUUUUGACUUGUAGUUUAUAUGU | 358-380 |
| AD-53025.1 | A-108424.1 | UGAAAGCCUCCUAGAAGAAAAx | 423-443 | A-108425.1 | UUUUCUUCUAGGAGGCUUUCAAG | 421-443 |
| AD-53085.1 | A-108534.1 | GGGAGAACUACAAAUAUGGUUx | 947-967 | A-108535.1 | AACCAUAUUUGUAGUUCUCCCAC | 945-967 |
| AD-52984.1 | A-108332.1 | AGAUUUGCUAUGUUAGACGAUx | 157-177 | A-108333.1 | AUCGUCUAACAUAGCAAAUCUUG | 155-177 |
| AD-53023.1 | A-108486.1 | GAACCCACAGAAAUUUCUCUAx | 679-699 | A-108487.1 | UAGAGAAAUUUCUGUGGGUUCUU | 677-699 |
| AD-53014.1 | A-108436.1 | ACUUCAACAAAAAGUGAAAUAx | 450-470 | A-108437.1 | UAUUUCACUUUUUGUUGAAGUAG | 448-470 |
| AD-53060.1 | A-108510.1 | AGUCCAUGGACAUUAAUUCAAx | 889-909 | A-108511.1 | UUGAAUUAAUGUCCAUGGACUAC | 887-909 |
| AD-53110.1 | A-108652.1 | AACUGAGGCAAAUUUAAAAGAx | 1434-1454 | A-108653.1 | UCUUUUAAAUUUGCCUCAGUUCA | 1432-1454_G21A |
| AD-52980.1 | A-108362.1 | GGGCCAAAUUAAUGACAUAUUx | 246-266 | A-108363.1 | AAUAUGUCAUUAAUUUGGCCCUU | 244-266 |
| AD-53109.1 | A-108636.1 | AUCCAUCCAACAGAUUCAGAAx | 1402-1422 | A-108637.1 | UUCUGAAUCUGUUGGAUGGAUCA | 1400-1422 |
| AD-53141.1 | A-108600.1 | AAGAUUUGGUGUUUUCUACUUx | 1181-1201 | A-108601.1 | AAGUAGAAAACACCAAAUCUUUG | 1179-1201 |
| AD-53126.1 | A-108626.1 | GUCUCAAAUGGAAGGUUAUAx | 1356-1376 | A-108627.1 | UAUAACCUUCCAUUUGAGACUU | 1354-1376 |
| AD-53116.1 | A-108654.1 | ACUGAGGCAAAUUUAAAAGGAx | 1435-1455 | A-108655.1 | UCCUUUUAAAUUUGCCUCAGUUC | 1433-1455_C21A |

TABLE 7-continued

Unmodified sense and antisense strand sequences of ANGPTL3 GalNac-conjugated dsRNAs

| Duplex ID | Sense Name | Sense Sequence (SEQ ID NOS 264-448, respectively, in order of appearance) | Position in NM_014495.2 | Antisense Name | Antisense Sequence (SEQ ID NOS 449-633, respectively, in order of appearance) | Position in NM_014495.2 |
|---|---|---|---|---|---|---|
| AD-52997.1 | A-108352.1 | GGGACAUGGUCUUAAAGACUUUx | 210-230 | A-108353.1 | AAGUCUUUAAGACCAUGUCCCAA | 208-230 |
| AD-53120.1 | A-108624.1 | AUGGUAAAUAUAACAAACCAAx | 1292-1312 | A-108625.1 | UUGGUUUGUUAUAUUUACCAUUU | 1290-1312 |
| AD-53070.1 | A-108576.1 | GGGAAAUCACGAAACCAACUAx | 1104-1124 | A-108577.1 | UAGUUGGUUUCGUGAUUUCCCAA | 1102-1124 |
| AD-53028.1 | A-108472.1 | CCAACAGCAUAGUCAAAUAAAx | 621-641 | A-108473.1 | UUUAUUUGACUAUGCUGUUGGUU | 619-641 |
| AD-53146.1 | A-108602.1 | UUUUCUACUUGGGAUCACAAAx | 1192-1212 | A-108603.1 | UUUGUGAUCCCAAGUAGAAAACA | 1190-1212 |
| AD-52982.1 | A-108394.1 | AGAACUACAUAUAAACUACAAx | 352-372 | A-108395.1 | UUGUAGUUUAUAUGUAGUUCUUC | 350-372 |
| AD-53111.1 | A-108668.1 | AGAGUAUGUGUAAAAAUCUGUx | 1915-1935 | A-108669.1 | ACAGAUUUUUACACAUACUCUGU | 1913-1935 |
| AD-53045.1 | A-108462.1 | AAAACAAGAUAAUAGCAUCAAx | 558-578 | A-108463.1 | UUGAUGCUAUUAUCUUGUUUUUC | 556-578 |
| AD-53123.1 | A-108672.1 | AGUAUGUGUAAAAAUCUGUAAx | 1917-1937 | A-108673.1 | UUACAGAUUUUUACACAUACUCU | 1915-1937 |
| AD-53018.1 | A-108406.1 | AGUCAAAAAUGAAGAGGUAAAx | 372-392 | A-108407.1 | UUUACCUCUUCAUUUUUGACUUG | 370-392 |
| AD-52956.1 | A-108354.1 | GGACAUGGUCUUAAAGACUUUx | 211-231 | A-108355.1 | AAAGUCUUUAAGACCAUGUCCCA | 209-231 |
| AD-53134.1 | A-108660.1 | GAGGCAAAUUUAAAAGGCAAUx | 1438-1458 | A-108661.1 | AUUGCCUUUUAAAUUUGCCUCAG | 1436-1458 |
| AD-52968.1 | A-108358.1 | GUCUUAAAGACUUUGUCCAUAx | 218-238 | A-108359.1 | UAUGGACAAAGUCUUUAAGACCA | 216-238 |
| AD-53122.1 | A-108656.1 | CUGAGGCAAAUUUAAAAGGCAx | 1436-1456 | A-108657.1 | UGCCUUUUAAAUUUGCCUCAGUU | 1434-1456 |
| AD-53100.1 | A-108586.1 | GCAAUCCCGGAAAACAAAGAUx | 1165-1185 | A-108587.1 | AUCUUUGUUUUCCGGGAUUGCAU | 1163-1185 |
| AD-53128.1 | A-108658.1 | UGAGGCAAAUUUAAAAGGCAAx | 1437-1457 | A-108659.1 | UUGCCUUUUAAAUUUGCCUCAGU | 1435-1457 |
| AD-53043.1 | A-108430.1 | UCUACUUCAACAAAAAGUGAAx | 447-467 | A-108431.1 | UUCACUUUUUGUUGAAGUAGAAU | 445-467 |
| AD-53135.1 | A-108676.1 | UAUGUGUAAAAAUCUGUAAUAx | 1919-1939 | A-108677.1 | UAUUACAGAUUUUUACACAUACU | 1917-1939 |
| AD-53094.1 | A-108584.1 | AAUGCAAUCCCGGAAAACAAAx | 1162-1182 | A-108585.1 | UUUGUUUUCCGGGAUUGCAUUGG | 1160-1182 |
| AD-53019.1 | A-108422.1 | CUUGAAAGCCUCCUAGAAGAAx | 421-441 | A-108423.1 | UUCUUCUAGGAGGCUUUCAAGUU | 419-441 |
| AD-53129.1 | A-108674.1 | GUAUGUGUAAAAAUCUGUAAUx | 1918-1938 | A-108675.1 | AUUACAGAUUUUUACACAUACUC | 1916-1938 |
| AD-53150.1 | A-108666.1 | CAGAGUAUGUGUAAAAAUCUUx | 1914-1934 | A-108667.1 | AAGAUUUUUACACAUACUCUGUG | 1912-1934_G21U |
| AD-53117.1 | A-108670.1 | GAGUAUGUGUAAAAAUCUGUAx | 1916-1936 | A-108671.1 | UACAGAUUUUUACACAUACUCUG | 1914-1936 |
| AD-52985.1 | A-108348.1 | UCAGUUGGGACAUGGUCUUAAx | 204-224 | A-108349.1 | UUAAGACCAUGUCCCAACUGAAG | 202-224 |
| AD-52962.1 | A-108356.1 | GGUCUUAAAGACUUUGUCCAUx | 217-237 | A-108357.1 | AUGGACAAAGUCUUUAAGACCAU | 215-237 |
| AD-52974.1 | A-108360.1 | UCUUAAAGACUUUGUCCAUAAx | 219-239 | A-108361.1 | UUAUGGACAAAGUCUUUAAGACC | 217-239 |
| AD-52979.1 | A-108346.1 | UUCAGUUGGGACAUGGUCUUAx | 203-223 | A-108347.1 | UAAGACCAUGUCCCAACUGAAGG | 201-223 |

The symbol "x" indicates that the sequence contains aGalNAc conjugate.

TABLE 8

Modified sense and antisense strand sequences of ANGPTL3 GalNac-conjugated dsRNAs

| Duplex ID | Sense OligoName | Sense Sequence (SEQ ID NOS 634-818, respectively, in order of appearance) | Antisense OligoName | Antisense Sequence (SEQ ID NOS 819-1003, respectively, in order of appearance) |
|---|---|---|---|---|
| AD-53063.1 | A-108558.1 | AfaAfgAfcAfaCfAfAfaCfaUfuUfaUfaAfuUfL96 | A-108559.1 | aAfuAfuAfaUfgUfuugUfuGfuCfuUfusCfsc |
| AD-52965.1 | A-108310.1 | AfcAfaUfuAfaGfCfUfcCfuUfcUfuUfuAfL96 | A-108311.1 | aAfaAfaGfaAfgGfagcUfuAfaUfuGfusGfsa |

TABLE 8 -continued

Modified sense and antisense strand sequences of ANGPTL3 GalNac-conjugated dsRNAs

| Duplex ID | Sense Sequence<br>Sense (SEQ ID NOS 634-818, respectively,<br>OligoName in order of appearance) | Antisense Sequence<br>Antisense (SEQ ID NOS 819-1003, respectively,<br>OligoName in order of appearance) |
|---|---|---|
| AD-53030.1 | A-108410.1UfgUfcAfcUfuGfAfAfcUfcAfaCfuCfaAfL96 | A-108411.1uUfgAfgUfuGfaGfuucAfaGfuGfaCfasUfsa |
| AD-52953.1 | A-108306.1UfcAfcAfaUfuAfAfGfcUfcCfuUfcUfuUfL96 | A-108307.1aAfaGfaAfgGfaGfcuuAfaUfuGfuGfasAfsc |
| AD-53001.1 | A-108416.1CfuUfgAfaCfuCfAfAfcUfcAfaAfaCfuUfL96 | A-108417.1aAfgUfuUfuGfaGfuugAfgUfuCfaAfgsUfsg |
| AD-53080.1 | A-108548.1CfuCfcAfuAfgUfGfAfaGfcAfaUfcUfaAfL96 | A-108549.1uUfaGfaUfuGfcUfucaCfuAfuGfgAfgsUfsa |
| AD-52971.1 | A-108312.1CfaAfuUfaAfgCfUfCfcUfuCfuUfuUfuAfL96 | A-108313.1uAfaAfaAfgAfaGfgagCfuUfaAfuUfgsUfsg |
| AD-53071.1 | A-108498.1AfcCfcAfgCfaAfCfUfcUfcAfaGfuUfuUfL96 | A-108499.1aAfaAfcUfuGfaGfaguUfgCfuGfgGfusCfsu |
| AD-53024.1 | A-108408.1GfaAfuAfuGfuCfAfCfuUfgAfaCfuCfaAfL96 | A-108409.1uUfgAfgUfuCfaAfgugAfcAfuAfuUfcsUfsu |
| AD-52977.1 | A-108314.1AfaUfuAfaGfcUfCfCfuUfcUfuUfuUfaUfL96 | A-108315.1aUfaAfaAfaGfaAfggaGfcUfuAfaUfusGfsu |
| AD-53064.1 | A-108574.1CfaUfuAfuAfuUfGfAfaUfaUfcUfuUfuUfL96 | A-108575.1aAfaAfgAfaUfaUfucaAfuAfuAfaUfgsUfsu |
| AD-53033.1 | A-108458.1AfcUfaAfcUfaAfCfUfuAfaUfcUfaAfaAfL96 | A-108459.1uUfuUfgAfaUfuAfaguUfaGfuUfaGfusUfsg |
| AD-52954.1 | A-108322.1UfuAfuUfgUfuCfCfUfuCfuGfuUfaUfuUfL96 | A-108323.1aAfaUfaAfcUfaGfaggAfaCfaAfuAfasAfsa |
| AD-53098.1 | A-108554.1CfaUfaGfuGfaAfGfCfaAfuCfuAfaUfuAfL96 | A-108555.1uAfaUfuAfgAfuUfgcUffcAfcUfaUfgsGfsa |
| AD-53092.1 | A-108552.1CfcAfuAfgUfgAfAfGfcAfaUfcUfaAfuUfL96 | A-108553.1aAfuUfaGfaUfuGfcuuCfaCfuAfuGfgsAfsg |
| AD-53073.1 | A-108530.1GfaUfcAfcAfaAfAfCfuUfcAfaUfgAfaAfL96 | A-108531.1uUfuCfaUfuGfaAfguuUfuGfuGfaUfcsCfsa |
| AD-53132.1 | A-108628.1AfuGfgAfaGfgUfUfAfuAfcUfcUfaUfaAfL96 | A-108629.1uUfaUfaGfaGfuUfauaCfcUfcUfcAfusUfsu |
| AD-53086.1 | A-108550.1UfcCfaUfaGfuGfAfAfgCfaAfuCfuAfaAfL96 | A-108551.1aUfuAfgAfuUfgCfuucAfcUfaUfgGfasGfsu |
| AD-52961.1 | A-108340.1CfuAfuGfuUfaGfAfCfgAfuGfuAfaAfaAfL96 | A-108341.1uUfuUfuAfcAfuCfgucUfaAfcAfuAfgsCfsa |
| AD-52983.1 | A-108316.1AfuUfaAfgCfuCfCfUfuCfuUfuUfaUfuUfL96 | A-108317.1aAfuAfaAfaAfgAfaggAfgCfuUfaAfusUfsg |
| AD-53027.1 | A-108456.1AfaCfuAfaCfuAfAfCfuUfaAfuUfcAfaAfL96 | A-108457.1uUfuGfaAfuUfaAfguuAfgUfuAfgUfusGfsc |
| AD-52986.1 | A-108364.1GfgCfcAfaAfuUfAfAfuGfaCfaUfaUfuUfL96 | A-108365.1aAfaUfaUfgUfcAfuuaAfuUfuGfgCfcsCfsu |
| AD-52989.1 | A-108318.1UfuUfuAfuUfgUfUfCfcUfcUfaGfuUfuUfL96 | A-108319.1aUfaAfcUfaGfaGfgaaCfaAfuAfaAfasAfsg |
| AD-52981.1 | A-108378.1AfcAfuAfuUfuGfAfAfUfcAfgUfcUfuUfuUfL96 | A-108379.1aAfaAfgAfcUfgAfaucAfaAfuAfuGfusUfsg |
| AD-53077.1 | A-108500.1CfcCfaGfcAfaCfUfCfuCfaAfgUfuUfuUfL96 | A-108501.1aAfaAfcUfuGfaGfagUfGfcUfgGfgsGfsc |
| AD-53095.1 | A-108506.1CfaGfgUfaGfuCfCfAfuGfgAfcAfuUfaAfL96 | A-108507.1uUfaAfuGfuCfcAfuggAfcUfaCfcUfgsAfsu |
| AD-52970.1 | A-108390.1AfcUfgAfgAfaGfAfAfcUfaCfaUfaAfaAfL96 | A-108391.1uUfaUfaUfgUfaGfuucUfuCfuCfaGfusUfsc |

TABLE 8 -continued

Modified sense and antisense strand sequences of ANGPTL3 GalNac-conjugated dsRNAs

| Duplex ID | Sense Sequence<br>Sense (SEQ ID NOS 634-818, respectively,<br>OligoName in order of appearance) | Antisense Sequence<br>Antisense (SEQ ID NOS 819-1003, respectively,<br>OligoName in order of appearance) |
| --- | --- | --- |
| AD-53015.1 | A-108452.1GfaGfcAfaCfuAfAfCfuAfaCfuUfaAfuUfUfL96 | A-108453.1aAfuUfaAfgUfuAfguuAfgUfuGfcUfcsUfsu |
| AD-53147.1 | A-108618.1AfaCfaAfcCfuAfAfAfuGfgUfaAfaUfaUfgL96 | A-108619.1aUfaUfuUfaCfcAfuuuAfgGfuUfgUfusUfsu |
| AD-53103.1 | A-108540.1CfcUfaGfaGfaAfGfAfuAfuAfcUfcCfaUffL96 | A-108541.1aUfgGfaGfuAfuAfucuUfcUfcUfaGfsCfsc |
| AD-52969.1 | A-108374.1CfaAfcAfuAfuUfUfGfaUfcAfgUfcUfuUfL96 | A-108375.1aAfaGfaCfuGfaUfcaaAfuAfuGfuUfgsAfsg |
| AD-53075.1 | A-108562.1AfcAfaCfaAfaCfAfUfuAfuAfuUfgAfaUfL96 | A-108563.1aUfuCfaAfuAfuAfaugUfuUfgUfuGfusCfsu |
| AD-52994.1 | A-108398.1AfcAfuAfuAfaAfCfUfaCfaAfgUfcAfaAfL96 | A-108399.1uUfuGfaCfuUfgUfaguUfuAfuAfuGfusAfsg |
| AD-52960.1 | A-108324.1CfuAfgUfuAfuUfUfCfcUfcCfaGfaAfuUfL96 | A-108325.1aAfuUfcUfgGfaGfgaaAfuAfaCfuAfgsAfsg |
| AD-53003.1 | A-108448.1AfaGfaGfcAfaCfUfAfaCfuAfaCfuUfaAfL96 | A-108449.1uUfaAfgUfuAfgUfuagUfuGfcUfcUfusCfsu |
| AD-52995.1 | A-108320.1UfuUfaUfuGfuUfCfCfuCfuaAfgUfuAfuAfUfL96 | A-108321.1aAfuAfaCfuAfgAfggaAfcAfaUfaAfasAfsa |
| AD-53037.1 | A-108428.1CfuCfcUfaGfaAfGfAfaAfaAfuCfuAfuUfL96 | A-108429.1uAfgAfaUfUfuUfucuUfcUfaGfgAfgsGfsc |
| AD-53087.1 | A-108566.1AfaCfaAfaCfaUfUfAfuAfuUfgAfaUfaAfL96 | A-108567.1aUfaUfuCfaAfuAfuaaUfgUfuUfgUfusGfsu |
| AD-53076.1 | A-108578.1GfgAfaAfuCfaCfGfAfaAfcCfaAfcUfaAfL96 | A-108579.1aUfaGfuUfgGfuUfucgUfgAfuUfuCfcsCfsa |
| AD-52975.1 | A-108376.1AfaCfaUfaUfuUfGfAfuCfaGfuCfuUfuUfL96 | A-108377.1aAfaAfgAfcUfgAfucaAfaUfaUfgUfusGfsa |
| AD-53138.1 | A-108630.1UfgGfaAfgGfuUfAfUfaCfuCfuAfuAfaAfL96 | A-108631.1uUfuAfuAfgAfgUfauaAfcCfuUfcCfasUfsu |
| AD-53091.1 | A-108536.1GfgAfgAfaCfuAfCfAfaAfuAfuGfgUfuUfL96 | A-108537.1aAfaCfcAfuAfuUfuguAfgUfuCfuCfcsCfsa |
| AD-53124.1 | A-108594.1GfaAfaAfcAfaAfGfAfuUfuGfgUfgUfuUfL96 | A-108595.1aAfaCfaCfcAfaAfucuUfuGfuUfuUfcsCfsg |
| AD-53125.1 | A-108610.1AfgUfgUfgGfaGfAfAfaAfcAfaCfcUfaAfL96 | A-108611.1uUfaGfgUfuGfuUfuucUfcCfaCfaCfusCfsa |
| AD-53036.1 | A-108412.1GfuCfaCfuUfgAfAfCfuCfaAfcUfcAfaAfL96 | A-108413.1uUfuGfaGfuUfgAfguuCfaAfgUfgAfcsAfsu |
| AD-53061.1 | A-108526.1GfaUfgGfaUfcAfCfAfaAfaCfuUfcAfaUfL96 | A-108527.1aUfuGfaAfgUfuUfuguGfaUfcCfaUfcsUfsa |
| AD-53093.1 | A-108568.1AfcAfaAfcAfuUfAfUfaUfuGfaAfuAfuUfL96 | A-108569.1aAfuAfuUfcAfaUfauaAfuGfuUfuGfusUfsg |
| AD-53137.1 | A-108614.1UfgUfgGfaGfaAfAfAfcAfaCfcUfaAfAfL96 | A-108615.1aUfuUfaGfgUfuGfuuuUfcUfcCfaCfasCfsu |
| AD-52999.1 | A-108384.1AfuCfaGfuCfuUfUfUfuAfuGfaUfcUfaAfL96 | A-108385.1aUfaGfaUfcAfuAfaaaAfgAfcUfgAfusCfsa |
| AD-53069.1 | A-108560.1GfaCfaAfcAfaAfCfAfuUfaUfaUfuGfaAfL96 | A-108561.1uUfcAfaUfaUfaAfuguUfuGfuUfgUfcsUfsu |
| AD-53034.1 | A-108474.1CfaAfcAfgCfaUfAfGfuCfaAfaUfaAfaAfL96 | A-108475.1uUfuUfaUfuUfgAfcuaUfgCfuGfuUfgsGfsu |

TABLE 8 -continued

Modified sense and antisense strand sequences of ANGPTL3 GalNac-conjugated dsRNAs

| Duplex ID | Sense Sequence<br>Sense (SEQ ID NOS 634-818, respectively,<br>OligoName in order of appearance) | Antisense Sequence<br>Antisense (SEQ ID NOS 819-1003, respectively,<br>OligoName in order of appearance) |
|---|---|---|
| AD-52976.1 | A-108392.1CfuGfaGfaAfgAfAfCfuAfcAfuAfaAfaAfL96 | A-108393.1uUfuAfuAfuGfuAfguuCfuCfUfcUfcAfgsUfsu |
| AD-52996.1 | A-108336.1UfgCfuAfuGfuUfAfGfaCfgAfuGfuAfaAfL96 | A-108337.1uUfuAfcAfuCfgUfcuaAfcAfuAfgCfasAfsa |
| AD-53029.1 | A-108488.1AfaCfcCfaCfaGfAfAfaUfuUfcUfcUfaUfL96 | A-108489.1aUfaGfaGfaAfaUfuucUfgUfgGfgUfusCfsu |
| AD-53020.1 | A-108438.1CfuUfcAfaCfaAfAfAfaGfuGfaAfaUfaUfL96 | A-108439.1aUfaUfuUfcAfcUfuuuUfgUfuGfaAfgsUfsa |
| AD-53042.1 | A-108414.1UfcAfcUfuGfaAfCfUfcAfaCfuCfaAfaAfL96 | A-108415.1uUfuUfgAfgUfuGfaguUfcAfaGfuGfasCfsa |
| AD-53011.1 | A-108482.1CfaUfaGfuCfaAfAfUfaAfaAfgAfaAfuAfL96 | A-108483.1uAfuUfuCfUfuUfauuUfgAfcUfaUfgsCfsu |
| AD-52957.1 | A-108370.1CfaAfaAfaCfuCfAfAfcAfuAfuUfgUfaUfL96 | A-108371.1aUfcAfaAfuAfuGfuugAfgUfuUfuUfgsAfsa |
| AD-53008.1 | A-108434.1UfaCfuUfcAfaCfAfAfaAfaGfuGfaAfaUfL96 | A-108435.1aUfuUfcAfcUfuUfuugUfuGfaAfgUfasGfsa |
| AD-53065.1 | A-108496.1GfaCfcCfaGfcAfAfCfuCfuCfaAfgUfuUfL96 | A-108497.1aAfaCfuUfgAfgAfguuGfcUfgGfgUfcsUfsg |
| AD-53115.1 | A-108638.1UfuGfaAfuGfaAfCfUfgAfgGfcAfaAfuUfL96 | A-108639.1aAfuUfuGfcCfuCfaguUfcAfuUfcAfasAfsg |
| AD-53012.1 | A-108404.1UfaUfaAfaCfuAfCfAfaGfuCfaAfaAfUfL96 | A-108405.1aUfuUfuUfgAfcUfuguAfgUfuUfaUfasUfsg |
| AD-53004.1 | A-108464.1AfaAfcAfaGfaUfAfAfuAfgCfaUfcAfaAfL96 | A-108465.1uUfuGfaUfgCfuAfuuAfcUfuGfuUfusUfsu |
| AD-53021.1 | A-108454.1CfaAfcUfaAfcUfAfAfcUfaAfuUfcAfaAfL96 | A-108455.1uUfgAfaUfuAfaGfuuAfgUfuAfgUfgsCfsu |
| AD-52955.1 | A-108338.1GfcUfaUfgUfAfGfAfcGfaUfgUfaAfaAfL96 | A-108339.1uUfuUfaCfaUfcGfucuAfcAfuAfgCfsAfsa |
| AD-53119.1 | A-108608.1AfcUfuGfgGfaUfCfAfcAfaAfgCfaAfaAfL96 | A-108609.1uUfuUfgCfuUfuGfugaUfcCfcAfaGfusAfsg |
| AD-52990.1 | A-108334.1UfuGfcUfaUfgUfUfAfgAfcGfaUfgUfaAfL96 | A-108335.1uUfaCfaUfcGfuCfuaaCfaUfaGfcAfasAfsu |
| AD-52964.1 | A-108388.1AfaCfuGfaGfaAfGfAfaCfuAfcAfuAfuUfL96 | A-108389.1uUfuAfuGfuAfgUfucuUfcUfcAfgUfusCfsc |
| AD-52973.1 | A-108344.1GfaUfgUfaAfaAfAfUfuUfaAfgCfcAfaUfL96 | A-108345.1aUfuGfgCfuUfaAfauuUfuUfaCfaUfcsGfsu |
| AD-53074.1 | A-108546.1AfcUfcCfaUfaGfUfGfaAfgCfaAfuCfuAfL96 | A-108547.1uUfgAfuUfgCfuUfcacUfaUfgGfaGfusAfsu |
| AD-53026.1 | A-108440.1UfuCfaAfcAfaAfAfAfgUfgAfaAfuAfuUfL96 | A-108441.1aAfuAfuUfuCfaCfuuuUfgUfuGfaAfasGfsu |
| AD-53062.1 | A-108542.1CfuAfgAfgAfaGfAfUfaUfaCfuCfcAfuAfL96 | A-108543.1uAfuGfgAfgUfaUfaucUfcUfuCfuAfgsGfsc |
| AD-53114.1 | A-108622.1CfaAfcCfuAfaAfUfGfgUfaAfaUfaUfaAfL96 | A-108623.1uUfaUfaUfuUfaCfcauUfaGfgUfuGfgsUfsu |
| AD-53082.1 | A-108580.1GfaAfaUfcAfcGfAfAfaCfcAfaCfuAfuAfL96 | A-108581.1uAfuAfgUfuGfgUfuucGfuGfaUfuUfcsCfsc |
| AD-53035.1 | A-108490.1CfcAfcAfgAfaAfUfUfuCfuCfuAfcUfuUfL96 | A-108491.1aAfgAfuAfgAfgAfaauUfcUfgUfgGfgsUfsu |

TABLE 8 -continued

Modified sense and antisense strand sequences of ANGPTL3 GalNac-conjugated dsRNAs

| Duplex ID | Sense Sequence (SEQ ID NOS 634-818, respectively, OligoName in order of appearance) | Antisense Sequence (SEQ ID NOS 819-1003, respectively, OligoName in order of appearance) |
|---|---|---|
| AD-52978.1 | A-108330.1AfaAfuCfaAfgAfUfUfuGfcUfaUfgUfuAfL96 | A-108331.1uAfaCfaUfaGfcAfaauCfuUfgAfuUfusUfsg |
| AD-53084.1 | A-108518.1AfcAfuUfaAfuUfCfAfaCfaUfcGfaAfuAfL96 | A-108519.1uAfuUfcGfaUfgUfugaAfuUfaAfuGfusCfsc |
| AD-52972.1 | A-108328.1CfcAfgAfgCfcAfAfaUfcAfaGfaUfuUfL96 | A-108329.1aAfaUfcUfuGfaUfuuuGfgCfuCfuGfgsAfsg |
| AD-53002.1 | A-108432.1CfuAfcUfuCfaAfCfAfaAfaAfgUfgAfaAfL96 | A-108433.1uUfuCfaCfuUfuUfuguUfgAfaGfuAfgsAfsa |
| AD-53078.1 | A-108516.1GfaCfaUfuAfaUfUfCfaAfcAfuCfgAfaUfL96 | A-108517.1aUfuCfgAfuGfuUfgaaUfuAfaUfgUfcsCfsa |
| AD-53072.1 | A-108514.1GfgAfcAfuUfaAfUfUfcAfaCfaUfcGfaAfL96 | A-108515.1uUfcGfaUfgUfuGfaauUfaAfuGfuCfcsAfsu |
| AD-53005.1 | A-108480.1GfcAfuAfgUfcAfAfAfuAfaAfaGfaAfaUfL96 | A-108481.1aUfuUfcUfuUfuAfuuuGfaCfuAfuGfcsUfsg |
| AD-53083.1 | A-108502.1CfuCfuCfaAfgUfUfUfuUfcAfuGfuCfuAfL96 | A-108503.1uAfgAfcAfuGfaAfaaaCfuUfgAfgAfgsUfsu |
| AD-53102.1 | A-108524.1AfuCfgAfaUfaGfAfUfgGfaUfcAfcAfaAfL96 | A-108525.1uUfuGfuGfaUfcCfaucUfaUfuCfgAfusGfsu |
| AD-53105.1 | A-108572.1AfcAfuUfaUfaUfUfGfaAfuAfuUfcUfuUfL96 | A-108573.1aAfaGfaAfuAfuUfcaaUfaUfaAfuGfusUfsu |
| AD-53090.1 | A-108520.1UfuAfaUfuCfaAfCfAfuCfgAfaUfaGfaUfL96 | A-108521.1aUfcUfaUfuCfgAfuguUfgAfaUfuAfasUfsg |
| AD-53010.1 | A-108466.1GfaUfaAfuAfgCfAfUfcAfaAfgAfcCfuUfL96 | A-108467.1aAfgGfuCfuUfuGfaugCfuAfuUfaUfcsUfsu |
| AD-52998.1 | A-108368.1UfgAfcAfuAfuUfUfCfaAfaAfaCfuCfaUfL96 | A-108369.1uUfgAfgUfuUfuUfgaaAfuAfuGfuCfasUfsu |
| AD-52992.1 | A-108366.1AfaAfuAfaUfgAfCfaUfaUfuUfcAfaAfL96 | A-108367.1uUfuGfaAfaUfaUfgucAfuUfaAfuUfusGfsg |
| AD-53068.1 | A-108544.1GfaAfgAfuAfuAfCfUfcCfaUfaGfuGfaAfL96 | A-108545.1uUfcAfcUfaUfgGfaguAfuAfuCfuUfcsCfsc |
| AD-53032.1 | A-108442.1AfaUfaUfuUfaGfAfAfgAfgCfaAfcUfaAfL96 | A-108443.1uUfaGfuUfgCfuCfuucUfaAfaUfaUfusUfsc |
| AD-52967.1 | A-108342.1CfgAfuGfuAfaAfAfAfuUfuUfaGfcCfaAfL96 | A-108343.1uUfgGfcUfaAfaAfuuuUfuAfcAfuCfgsUfsc |
| AD-53096.1 | A-108522.1UfuCfaAfcAfuCfGfAfaUfaGfaUfgGfaUfL96 | A-108523.1aUfcCfaUfcUfaUfucgAfuGfuUfgAfasUfsu |
| AD-53131.1 | A-108612.1GfuGfuGfgAfgAfAfaCfaAfcCfuAfaAfL96 | A-108613.1uUfuAfgGfuUfgUfuuuCfuCfcAfcAfcsUfsc |
| AD-52963.1 | A-108372.1UfcAfaCfaUfaUfUfUfgAfuCfaGfuCfuUfL96 | A-108373.1aAfgAfcUfgAfuCfaaaUfaUfgUfuGfasGfsu |
| AD-53089.1 | A-108504.1UfcAfgGfuAfgUfCfCfaUfgGfaCfaUfuUfL96 | A-108505.1uAfaUfgUfcCfaUfggaCfuAfcCfuGfasUfsa |
| AD-53044.1 | A-108446.1UfuUfaGfaAfgAfGfCfaAfcUfaAfcUfaAfL96 | A-108447.1uUfaGfuUfaGfuUfgcuCfuUfcUfaAfasUfsa |
| AD-52988.1 | A-108396.1UfaCfaUfaUfaAfAfCfuAfcAfaGfuCfaAfL96 | A-108397.1uUfgAfcUfuGfuAfguuUfaUfaUfgUfasGfsu |
| AD-53067.1 | A-108528.1GfgAfuCfaCfaAfAfAfcUfcAfaUfgAfaUfL96 | A-108529.1uUfcAfuUfgAfaGfuuuUfgUfgAfuCfcsAfsu |
| AD-53009.1 | A-108450.1AfgAfgCfaAfcUfAfAfcUfaAfcUfaAfuUfL96 | A-108451.1aUfuAfaGfuUfaGfuuaGfuUfgCfuCfusUfsc |

TABLE 8 -continued

Modified sense and antisense strand sequences of ANGPTL3 GalNac-conjugated dsRNAs

| Duplex ID | Sense Sequence<br>Sense (SEQ ID NOS 634-818, respectively,<br>OligoName in order of appearance) | Antisense Sequence<br>Antisense (SEQ ID NOS 819-1003, respectively,<br>OligoName in order of appearance) |
|---|---|---|
| AD-53022.1 | A-108470.1AfcCfaAfcAfgCfAfUfaGfuCfaAfaUfaAfL96 | A-108471.1uUfaUfuUfgAfcUfaugCfuGfuUfgGfusUfsu |
| AD-53016.1 | A-108468.1AfaCfcAfaCfaGfCfAfuAfgUfCfaAfaUfAfL96 | A-108469.1uAfuUfuGfaCfuAfugcUfgUfuGfgUfusUfsa |
| AD-53007.1 | A-108418.1GfaAfcUfcAfaCfUfCfaAfaAfcUfuGfaAfL96 | A-108419.1uUfcAfaGfuUfuUfgagUfuGfaGfuUfcsAfsa |
| AD-53148.1 | A-108634.1UfaCfuCfuAfuAfAfaAfcAfaCfcAfaAfL96 | A-108635.1uUfuGfgUfuGfaUfuuuAfuAfgAfgUfasUfsa |
| AD-53040.1 | A-108476.1CfaGfcAfuAfgUfCfAfaAfuAfaAfaGfaAfL96 | A-108477.1uUfcUfuUfuAfuUfugaCfuAfuGfcUfgsUfsu |
| AD-53041.1 | A-108492.1GfaAfaUfaAfgAfAfAfuGfuAfaAfaCfaUfL96 | A-108493.1aUfgUfuUfuAfcAfuuuCfuAfuUfuUfcsAfsu |
| AD-53039.1 | A-108460.1CfuAfaCfuAfaCfUfUfaAfuUfcAfaAfaUfL96 | A-108461.1aUfuUfuGfaAfuUfaagUfuAfgUfuAfgsUfsu |
| AD-53139.1 | A-108646.1AfuGfaAfcUfgAfGfGfcAfaAfuUfuAfaAfL96 | A-108647.1uUfuAfaAfuUfuGfccuCfaGfuUfcAfusUfsc |
| AD-53144.1 | A-108648.1UfgAfaCfuGfaGfGfCfaAfaUfuAfaAfaAfL96 | A-108649.1uUfuUfaAfaUfuUfgccUfcAfgUfuCfasUfsu |
| AD-53142.1 | A-108616.1AfaAfcAfaCfcUfAfAfaUfgGfuAfaAfuAfL96 | A-108617.1uAfuUfuAfcCfaUfuuaGfuUfgUfuUfusUfsc |
| AD-53108.1 | A-108620.1AfcAfaCfcUfaAfAfUfgGfuAfaAfuAfuAfL96 | A-108621.1uAfuAfuUfuAfcCfauuUfaGfgUfuGfusUfsu |
| AD-53079.1 | A-108532.1AfaCfgUfgGfaGfAfGfaCfuAfcAfaAfuAfL96 | A-108533.1uAfuUfuGfuAfgUfucuCfcCfaCfgUfusUfsc |
| AD-53133.1 | A-108644.1AfaUfgAfaCfuGfAfGfgCfaAfaUfuAfaAfL96 | A-108645.1uUfaAfaUfuUfgCfcucAfgUfuCfaUfusCfsa |
| AD-53104.1 | A-108556.1GfuUfgGfaAfgAfCfUfgGfaAfaGfaCfaAfL96 | A-108557.1uUfgUfcUfuUfcCfaguCfuUfcCfaAfcsUfsc |
| AD-53088.1 | A-108582.1UfgGfcAfaUfgUfCfCfcCfaAfuGfcAfaUfL96 | A-108583.1aUfuGfcAfuUfgGfggaCfaUfuGfcCfasGfsu |
| AD-53101.1 | A-108508.1GfgUfaGfuCfcAfUfGfgAfcAfuUfaAfuUfL96 | A-108509.1aAfuUfaAfuGfuCfcauGfgAfcUfaCfcsUfsg |
| AD-53000.1 | A-108400.1CfaUfaUfaAfaCfUfAfcAfaGfuCfaAfaAfL96 | A-108401.1uUfuUfgAfcUfuGfuagUfuUfaUfaUfgsUfsa |
| AD-53112.1 | A-108590.1AfaUfcCfcGfgAfAfAfaCfaAfaGfaUfuUfL96 | A-108591.1aAfaUfcUfuUfgUfuuuCfcGfgGfaUfusGfsc |
| AD-53107.1 | A-108604.1CfuAfcUfuGfgGfAfUfcAfcAfaAfgCfaAfL96 | A-108605.1uUfgCfuUfuGfuGfaucCfcAfaGfuAfgsAfsa |
| AD-53121.1 | A-108640.1UfgAfaUfgAfaCfUfGfaGfgCfaAfaUfuUfL96 | A-108641.1aAfaUfuUfgCfcUfcagUfuCfaUfuCfasAfsa |
| AD-53046.1 | A-108478.1AfgCfaUfaGfuCfAfAfaUfaAfaAfgAfaAfL96 | A-108479.1uUfuCfuUfuUfaUfuugAfcUfaUfgCfusGfsu |
| AD-53038.1 | A-108444.1AfuUfuAfgAfaGfAfGfcAfaCfuAfaCfuAfL96 | A-108445.1uAfgUfuAfgUfuGfcucUfuCfuAfaAfusAfsu |
| AD-53140.1 | A-108662.1AfgGfcAfaAfuUfUfAfaAfaGfcAfaUfuAfL96 | A-108663.1uAfuUfgCfcUfuUfuaaAfuUfuGfcCfusCfsa |
| AD-52987.1 | A-108380.1CfaUfaUfuUfgAfUfCfaGfuCfuUfuUfuAfL96 | A-108381.1uAfaAfaAfgAfcUfgauCfaAfaUfaUfgsUfsu |

TABLE 8 -continued

Modified sense and antisense strand sequences of ANGPTL3 GalNac-conjugated dsRNAs

| Duplex ID | Sense Sequence Sense (SEQ ID NOS 634-818, respectively, OligoName in order of appearance) | Antisense Sequence Antisense (SEQ ID NOS 819-1003, respectively, OligoName in order of appearance) |
|---|---|---|
| AD-53130.1 | A-108596.1AfaAfaCfaAfaGfAfUfuUfgGfuGfuUfuUfuL96 | A-108597.1aAfaAfcAfcCfaAfaucUfuUfgUfuUfusCfsc |
| AD-53106.1 | A-108588.1CfaAfuCfcCfgGfAfAfaAfcAfaAfgAfuUfuL96 | A-108589.1aAfuCfuUfuGfuUfuucCfgGfgAfuUfgsCfsa |
| AD-53081.1 | A-108564.1CfaAfcAfaAfcAfUfUfaUfaUfuGfaAfuAfL96 | A-108565.1uAfuUfcAfaUfaUfaauGfuUfuGfuUfgsUfsc |
| AD-53118.1 | A-108592.1GfgAfaAfaCfaAfAfGfaUfuUfgGfuGfuUfL96 | A-108593.1aAfcAfcCfaAfaUfcuuUfgUfuUfuCfcsGfsg |
| AD-53136.1 | A-108598.1AfcAfaAfgAfuUfUfGfgUfgUfuUfuCfuAfL96 | A-108599.1uAfgAfaAfaCfaCfcaaAfuCfuUfuGfusUfsu |
| AD-53127.1 | A-108642.1GfaAfuGfaAfcUfGfAfgGfcAfaAfuUfuAfL96 | A-108643.1uAfaAfuUfuGfcCfucaGfuUfcAfuUfcsAfsa |
| AD-53066.1 | A-108512.1CfcAfuGfgAfcAfUfUfaAfuUfcAfaCfaUfL96 | A-108513.1aUfgUfuGfaAfuUfaauGfuCfcAfuGfgsAfsc |
| AD-53013.1 | A-108420.1AfaCfuCfaAfcUfCfAfaAfaCfuUfgAfaAfL96 | A-108421.1uUfuCfaAfgUfuUfugaGfuUfgAfgUfusCfsa |
| AD-52991.1 | A-108350.1CfaGfuUfgGfgAfCfAfuGfgUfcUfuAfaAfL96 | A-108351.1uUfuAfaGfaCfcAfuguCfcCfaAfcUfgsAfsa |
| AD-53099.1 | A-108570.1AfaCfaUfuAfuAfUfUfgAfaUfaUfcUfuAfL96 | A-108571.1aAfgAfuAfuUfcAfaauAfuAfaUfgUfusUfsg |
| AD-52958.1 | A-108386.1AfcCfaGfuGfaAfAfUfcAfaAfgAfaGfaAfL96 | A-108387.1uUfcUfuCfuUfuGfauuUfcAfcUfgGfusUfsu |
| AD-53097.1 | A-108538.1GfuUfgGfgCfuUfAfGfgaGfaAfgAfuAfuAfL96 | A-108539.1uAfuAfuCfuUfcUfcuaGfcCfcAfaCfcsCfsa |
| AD-52966.1 | A-108326.1CfuCfcAfgAfgCfCfAfaAfaUfcAfaGfaAfL96 | A-108327.1aUfcUfuGfaUfuUfuggCfuCfuGfgAfgsAfsu |
| AD-53145.1 | A-108664.1GfgCfaAfaUfuUfAfAfaAfgGfcAfuAfaAfL96 | A-108665.1uUfaUfgCfcUfuuuAfaUfuUfgCfcsUfsc |
| AD-53113.1 | A-108606.1UfaCfuUfgGfgAfUfCfaCfaAfaGfcAfaAfL96 | A-108607.1uUfuGfcUfuUfgUfgauCfcCfaAfgUfasGfsa |
| AD-52993.1 | A-108382.1GfaUfcAfgUfcUfUfUfuUfaUfgAfuCfuAfL96 | A-108383.1uAfgAfuCfaUfaAfaaaGfaCfuGfaUfcsAfsa |
| AD-53031.1 | A-108426.1GfaAfaGfcCfuCfCfUfaGfaAfgAfaAfaAfL96 | A-108427.1uUfuUfuCfuUfcUfaggAfgGfcUfuUfcsAfsa |
| AD-53017.1 | A-108484.1AfgUfcAfaAfuAfAfAfaGfaAfaUfaGfaAfL96 | A-108485.1uUfcUfaUfuUfcUfuuuAfuUfuGfaCfusAfsu |
| AD-53143.1 | A-108632.1AfuAfcUfcUfaUfAfAfaAfuCfaAfcCfaAfL96 | A-108633.1uUfgGfuUfgAfuUfuuaUfaGfaGfuAfusAfsa |
| AD-53149.1 | A-108650.1GfaAfcUfgAfgGfCfAfaAfuUfuAfaAfaAfL96 | A-108651.1uUfuUfuAfaAfuUfugcCfuCfaGfuUfcsAfsu |
| AD-53059.1 | A-108494.1AfgAfcCfcAfgCfAfAfcUfcUfcAfaGfuUfL96 | A-108495.1aAfcUfuGfaGfaGfuugCfuGfgGfuCfusGfsa |
| AD-53006.1 | A-108402.1AfuAfuAfaAfcUfAfCfaAfgUfcAfaAfaAfL96 | A-108403.1uUfuUfuGfaCfuUfguaGfuUfuAfuAfusGfsu |
| AD-53025.1 | A-108424.1UfgAfaAfgCfcUfCfCfuAfgAfaGfaAfaAfL96 | A-108425.1uUfuUfcUfuCfuAfggaGfgCfuUfuCfasAfsg |
| AD-53085.1 | A-108534.1GfgGfaGfaAfcUfAfCfaAfaUfaUfgGfuUfL96 | A-108535.1aAfcCfaUfaUfuUfguaGfuUfcUfcCfcsAfsc |
| AD-52984.1 | A-108332.1AfgAfuUfuGfcUfAfUfgUfuAfgAfcGfaUfL96 | A-108333.1aUfcGfuCfuAfaCfauaGfcAfaAfuCfusUfsg |

TABLE 8 -continued

Modified sense and antisense strand sequences of ANGPTL3 GalNac-conjugated dsRNAs

| Duplex ID | Sense Sequence<br>Sense (SEQ ID NOS 634-818, respectively,<br>OligoName in order of appearance) | Antisense Sequence<br>Antisense (SEQ ID NOS 819-1003, respectively,<br>OligoName in order of appearance) |
|---|---|---|
| AD-53023.1 | A-108486.1GfaAfcCfcAfcAfGfAfaAfuUfuCfuCfuAfL96 | A-108487.1uAfgAfgAfaAfuUfucuGfuGfgGfuUfcsUfsu |
| AD-53014.1 | A-108436.1AfcUfuCfaAfcAfAfaAfgUfgAfaAfuAfL96 | A-108437.1uAfuUfuCfaCfuUfuuuGfuUfgAfaGfusAfsg |
| AD-53060.1 | A-108510.1AfgUfcCfaUfgGfAfcAfuAfaUfcCfaAfL96 | A-108511.1uUfgAfaUfuAfaUfgucCfaUfgGfaCfusAfsc |
| AD-53110.1 | A-108652.1AfaCfuGfaGfgCfAfAfaUfuAfaAfgAfL96 | A-108653.1uCfuUfuUfaAfaUfuugCfcUfcAfgUfusCfsa |
| AD-52980.1 | A-108362.1GfgGfcCfaAfaUfUfAfaUfgAfcAfuAfuUfL96 | A-108363.1aAfuAfuGfuCfaUfuaaUfuUfgGfcCfcsUfsu |
| AD-53109.1 | A-108636.1AfuCfcAfuCfcAfAfCfaGfaUfcAfGfaAfL96 | A-108637.1uUfcUfgAfaUfcUfguuGfaUfgGfaUfusCfsa |
| AD-53141.1 | A-108600.1AfaGfaUfuUfgGfUfGfuUfuUfcUfaCfuUfL96 | A-108601.1aAfgUfaGfaAfaAfcacCfaAfaUfcUfusUfsg |
| AD-53126.1 | A-108626.1GfuCfuCfaAfaAfUfGfgAfaGfgUfuAfuAfL96 | A-108627.1uAfuAfaCfcUfuCfcauUfuUfgAfgAfcsUfsu |
| AD-53116.1 | A-108654.1AfcUfgAfgGfcAfAfAfuUfuAfaAfaGfaAfL96 | A-108655.1uCfcUfuUfuAfaAfuuuGfcCfuCfaGfusUfsc |
| AD-52997.1 | A-108352.1GfgGfaCfaUfgGfUfCfuUfaAfaGfaCfuUfL96 | A-108353.1aAfgUfcUfuUfaAfgacCfaUfgUfcCfcsAfsa |
| AD-53120.1 | A-108624.1AfuGfgUfaAfaUfAfUfaAfcAfaAfcCfaAfL96 | A-108625.1uUfgGfuUfuGfuUfauaUfuUfaCfcAfusUfsu |
| AD-53070.1 | A-108576.1GfgGfaAfaUfcAfCfGfaAfaCfcAfaCfuAfL96 | A-108577.1uAfgUfuGfgUfuUfcguGfaUfuUfcCfcsAfsa |
| AD-53028.1 | A-108472.1CfcAfaCfaGfcAfUfAfgUfcAfaAfuAfaAfL96 | A-108473.1uUfuAfuUfuGfaCfuauGfcUfgUfuGfgsUfsu |
| AD-53146.1 | A-108602.1UfuUfuCfuAfcUfUfGfgGfaUfcAfcAfaAfL96 | A-108603.1uUfuGfuGfaUfcCfcaaGfuAfgAfaAfasCfsa |
| AD-52982.1 | A-108394.1AfgAfaCfuAfcAfUfAfuAfaAfcUfaCfaAfL96 | A-108395.1uUfgUfaGfuUfuAfuauGfuAfgUfuCfusUfsc |
| AD-53111.1 | A-108668.1AfgAfgUfaUfgUfGfUfaAfaAfaUfcUfgUfL96 | A-108669.1aCfaGfaUfuUfuUfacaCfaUfaCfuCfusGfsu |
| AD-53045.1 | A-108462.1AfaAfaCfaAfgAfUfAfaUfaGfcAfuCfaAfL96 | A-108463.1uUfgAfuGfcUfaUfuauCfuUfgUfuUfusUfsc |
| AD-53123.1 | A-108672.1AfgUfaUfgUfgUfAfAfaAfaUfcUfgUfaAfL96 | A-108673.1uUfaCfaGfaUfuUfuuaCfaCfaUfaCfusCfsu |
| AD-53018.1 | A-108406.1AfgUfcAfaAfaAfUfGfaAfgAfgGfuAfaAfL96 | A-108407.1uUfuAfcCfuCfuUfcauUfuUfuGfaCfusUfsg |
| AD-52956.1 | A-108354.1GfgAfcAfuGfgUfCfUfuAfaAfgAfcUfuUfL96 | A-108355.1aAfaGfuCfuUfuAfagaCfcAfuGfuCfcsCfsa |
| AD-53134.1 | A-108660.1GfaGfgCfaAfaUfUfUfaAfaAfgGfcAfaAfL96 | A-108661.1aUfuGfcCfuUfuUfaaaUfuUfgCfcUfcsAfsg |
| AD-52968.1 | A-108358.1GfuCfuUfaAfaGfAfCfuUfuGfuCfcAfuAfL96 | A-108359.1uAfuGfgAfcAfaAfgucUfuUfaAfgAfcsCfsa |
| AD-53122.1 | A-108656.1CfuGfaGfgCfaAfAfUfuAfaAfaGfcAfL96 | A-108657.1uGfcCfuUfuUfaAfauuUfgCfcUfcAfgsUfsu |
| AD-53100.1 | A-108586.1GfcAfaUfcCfcGfGffAfaAfaCfaAfaGfaUfL96 | A-108587.1aUfcUfuUfgUfuUfuccGfgGfaUfuGfcsAfsu |

TABLE 8 -continued

Modified sense and antisense strand sequences of ANGPTL3 GalNac-conjugated dsRNAs

| Duplex ID | Sense OligoName | Sense Sequence (SEQ ID NOS 634-818, respectively, in order of appearance) | Antisense OligoName | Antisense Sequence (SEQ ID NOS 819-1003, respectively, in order of appearance) |
|---|---|---|---|---|
| AD-53128.1 | A-108658.1 | UfgAfgGfcAfaAfUfUfuAfaAfaGfgCfaAfL96 | A-108659.1 | uUfgCfcUfuUfuAfaauUfuGfcCfuCfasGfsu |
| AD-53043.1 | A-108430.1 | UfcUfaCfuUfcAfAfCfaAfaAfaGfuGfaAfL96 | A-108431.1 | uUfcAfcUfuUfuUfguuGfaAfgUfaGfasAfsu |
| AD-53135.1 | A-108676.1 | UfaUfgUfgUfaAfAfAfaUfcUfgUfaAfuAfL96 | A-108677.1 | uAfuUfaCfaGfaUfuuuUfaCfaCfaUfasCfsu |
| AD-53094.1 | A-108584.1 | AfaUfgCfaAfuCfCfCfgGfaAfaAfcAfaAfL96 | A-108585.1 | uUfuGfuUfuUfcCfgggAfuUfgCfaUfusGfsg |
| AD-53019.1 | A-108422.1 | CfuUfgAfaAfgCfCfUfcCfuAfgAfaGfaAfL96 | A-108423.1 | uUfcUfuCfuAfgGfaggCfuUfuCfaAfgsUfsu |
| AD-53129.1 | A-108674.1 | GfuAfuGfuGfuAfAfAfaAfuCfuGfuAfaUfL96 | A-108675.1 | aUfuAfcAfgAfuUfuuuAfcAfcAfuAfcsUfsc |
| AD-53150.1 | A-108666.1 | CfaGfaGfuAfuGfUfGfuAfaAfaAfuCfuUfL96 | A-108667.1 | aAfgAfuUfuUfuAfcacAfuAfcUfcUfgsUfsg |
| AD-53117.1 | A-108670.1 | GfaGfuAfuGfuGfUfAfaAfaAfuCfuGfuAfL96 | A-108671.1 | uAfcAfgAfuUfuUfuacAfcAfuAfcUfcsUfsg |
| AD-52985.1 | A-108348.1 | UfcAfgUfuGfgGfAfCfaUfgGfuCfuUfaAfL96 | A-108349.1 | uUfaAfgAfcCfaUfgucCfcAfaCfuGfasAfsg |
| AD-52962.1 | A-108356.1 | GfgUfcUfuUfaAfAfGfAfcUfuUfgUfcCfaUfL96 | A-108357.1 | aUfgGfaCfaAfaGfucuUfuAfaGfaCfcsAfsu |
| AD-52974.1 | A-108360.1 | UfcUfuAfaAfgAfCfUfuUfgUfcCfaUfAfL96 | A-108361.1 | uUfaUfgGfaCfaAfaguCfuUfuAfaGfasCfsc |
| AD-52979.1 | A-108346.1 | UfuCfaGfuUfgGfGfAfcAfuGfgUfcUfuAfL96 | A-108347.1 | uAfaGfaCfcAfuGfuccCfaAfcUfgAfasGfsg |

Lowercase nucleotides (a, u, g, c) are 2'-O-methyl nucleotides; Nf (e.g., Af) is a 2'-fluoro nucleotide; s is aphosphothiorate linkage; L96 indicates a GalNAc ligand.

TABLE 9

Unmodified Sense and antisense strand sequences of ANGPTL3 dsRNAs without GalNal conjugation
These sequences are the same as the sequences listed in Table 7 except that they do not contain GalNal conjugation.

| Duplex Name | Sense OligoName | Sense Sequence (SEQ ID NOS 1004-1184, respectively, in order of appearance) | Antisense OligoName | Antisense Sequence (SEQ ID NOS 1185-1365, respectively, in order of appearance) | Position in NM_014495.2 |
|---|---|---|---|---|---|
| AD-52637.1 | A-108817.1 | UCACAAUUAAGCUCCUUCUUU | A-108307.2 | AAAGAAGGAGCUUAAUUGUGAAC | 54-76 |
| AD-52638.1 | A-108825.1 | UUAUUGUUCCUCUAGUUAUUU | A-108323.2 | AAAUAACUAGAGGAACAAUAAAA | 75-97 |
| AD-52639.1 | A-108833.1 | GCUAUGUUAGACGAUGUAAAA | A-108339.2 | UUUUACAUCGUCUAACAUAGCAA | 161-183 |
| AD-52640.1 | A-108841.1 | GGACAUGGUCUUAAAGACUUU | A-108355.2 | AAAGUCUUUAAGACCAUGUCCCA | 209-231 |
| AD-52641.1 | A-108849.1 | CAAAAACUCAACAUAUUUGAU | A-108371.2 | AUCAAAUAUGUUGAGUUUUUGAA | 266-288 |
| AD-52642.1 | A-108857.1 | ACCAGUGAAAUCAAAGAAGAA | A-108387.2 | UUCUUCUUUGAUUUCACUGGUUU | 314-336 |
| AD-52643.1 | A-108818.1 | CACAAUUAAGCUCCUUCUUUU | A-108309.2 | AAAAGAAGGAGCUUAAUUGUGAA | 55-77 |
| AD-52645.1 | A-108834.1 | CUAUGUUAGACGAUGUAAAAA | A-108341.2 | UUUUUACAUCGUCUAACAUAGCA | 162-184 |
| AD-52647.1 | A-108850.1 | UCAACAUAUUUGAUCAGUCUU | A-108373.2 | AAGACUGAUCAAAUAUGUUGAGU | 273-295 |
| AD-52648.1 | A-108858.1 | AACUGAGAAGAACUACAUAUA | A-108389.2 | UAUAUGUAGUUCUUCUCAGUUCC | 342-364 |
| AD-52649.1 | A-108819.1 | ACAAUUAAGCUCCUUCUUUUU | A-108311.2 | AAAAAGAAGGAGCUUAAUUGUGA | 56-78 |

TABLE 9-continued

Unmodified Sense and antisense strand sequences of ANGPTL3 dsRNAs
without GalNa1 conjugation
These sequences are the same as the sequences listed in Table 7 except that
they do not contain GalNa1 conjugation.

| Duplex Name | Sense OligoName | Sense Sequence (SEQ ID NOS 1004-1184, respectively, in order of appearance) | Antisense OligoName | Antisense Sequence (SEQ ID NOS 1185-1365, respectively, in order of appearance) | Position in NM_014495.2 |
|---|---|---|---|---|---|
| AD-52650.1 | A-108827.1 | CUCCAGAGCCAAAAUCAAGAU | A-108327.2 | AUCUUGAUUUUGGCUCUGGAGAU | 138-160 |
| AD-52651.1 | A-108835.1 | CGAUGUAAAAAUUUUAGCCAA | A-108343.2 | UUGGCUAAAAUUUUUACAUCGUC | 172-194 |
| AD-52652.1 | A-108843.1 | GUCUUAAAGACUUUGUCCAUA | A-108359.2 | UAUGGACAAAGUCUUUAAGACCA | 216-238 |
| AD-52653.1 | A-108851.1 | CAACAUAUUUGAUCAGUCUUU | A-108375.2 | AAAGACUGAUCAAAUAUGUUGAG | 274-296 |
| AD-52654.1 | A-108859.1 | ACUGAGAAGAACUACAUAUAA | A-108391.2 | UUAUAUGUAGUUCUUCUCAGUUC | 343-365 |
| AD-52656.1 | A-108828.1 | CCAGAGCCAAAAUCAAGAUUU | A-108329.2 | AAAUCUUGAUUUUGGCUCUGGAG | 140-162 |
| AD-52657.1 | A-108836.1 | GAUGUAAAAAUUUUAGCCAAU | A-108345.2 | AUUGGCUAAAAUUUUUACAUCGU | 173-195 |
| AD-52658.1 | A-108844.1 | UCUUAAAGACUUUGUCCAUAA | A-108361.2 | UUAUGGACAAAGUCUUUAAGACC | 217-239 |
| AD-52659.1 | A-108852.1 | AACAUAUUUGAUCAGUCUUUU | A-108377.2 | AAAAGACUGAUCAAAUAUGUUGA | 275-297 |
| AD-52660.1 | A-108860.1 | CUGAGAAGAACUACAUAUAAA | A-108393.2 | UUUAUAUGUAGUUCUUCUCAGUU | 344-366 |
| AD-52661.1 | A-108821.1 | AAUUAAGCUCCUUCUUUUUAU | A-108315.2 | AUAAAAAGAAGGAGCUUAAUUGU | 58-80 |
| AD-52662.1 | A-108829.1 | AAAUCAAGAUUUGCUAUGUUA | A-108331.2 | UAACAUAGCAAAUCUUGAUUUUG | 149-171 |
| AD-52663.1 | A-108837.1 | UUCAGUUGGGACAUGGUCUUA | A-108347.2 | UAAGACCAUGUCCCAACUGAAGG | 201-223 |
| AD-52664.1 | A-108845.1 | GGGCCAAAUUAAUGACAUAUU | A-108363.2 | AAUAUGUCAUUAAUUUGGCCCUU | 244-266 |
| AD-52665.1 | A-108853.1 | ACAUAUUUGAUCAGUCUUUUU | A-108379.2 | AAAAAGACUGAUCAAAUAUGUUG | 276-298 |
| AD-52666.1 | A-108861.1 | AGAACUACAUAUAAACUACAA | A-108395.2 | UUGUAGUUUAUAUGUAGUUCUUC | 350-372 |
| AD-52667.1 | A-108822.1 | AUUAAGCUCCUUCUUUUUAUU | A-108317.2 | AAUAAAAAGAAGGAGCUUAAUUG | 59-81 |
| AD-52668.1 | A-108830.1 | AGAUUUGCUAUGUUAGACGAU | A-108333.2 | AUCGUCUAACAUAGCAAAUCUUG | 155-177 |
| AD-52669.1 | A-108838.1 | UCAGUUGGGACAUGGUCUUAA | A-108349.2 | UUAAGACCAUGUCCCAACUGAAG | 202-224 |
| AD-52670.1 | A-108846.1 | GGCCAAAUUAAUGACAUAUUU | A-108365.2 | AAAUAUGUCAUUAAUUUGGCCCU | 245-267 |
| AD-52671.1 | A-108854.1 | CAUAUUUGAUCAGUCUUUUUA | A-108381.2 | UAAAAGACUGAUCAAAUAUGUU | 277-299 |
| AD-52672.1 | A-108862.1 | UACAUAUAAACUACAAGUCAA | A-108397.2 | UUGACUUGUAGUUUAUAUGUAGU | 355-377 |
| AD-52673.1 | A-108823.1 | UUUUAUUGUUCCUCUAGUUAU | A-108319.2 | AUAACUAGAGGAACAAUAAAAAG | 73-95 |
| AD-52674.1 | A-108831.1 | UUGCUAUGUUAGACGAUGUAA | A-108335.2 | UUACAUCGUCUAACAUAGCAAAU | 159-181 |
| AD-52675.1 | A-108839.1 | CAGUUGGGACAUGGUCUUAAA | A-108351.2 | UUUAAGACCAUGUCCCAACUGAA | 203-225 |
| AD-52676.1 | A-108847.1 | AAAUUAAUGACAUAUUUCAAA | A-108367.2 | UUUGAAAUAUGUCAUUAAUUUGG | 249-271 |
| AD-52677.1 | A-108855.1 | GAUCAGUCUUUUUAUGAUCUA | A-108383.2 | UAGAUCAUAAAAAGACUGAUCAA | 284-306 |
| AD-52678.1 | A-108863.1 | ACAUAUAAACUACAAGUCAAA | A-108399.2 | UUUGACUUGUAGUUUAUAUGUAG | 356-378 |
| AD-52679.1 | A-108824.1 | UUUAUUGUUCCUCUAGUUAUU | A-108321.2 | AAUAACUAGAGGAACAAUAAAAA | 74-96 |
| AD-52680.1 | A-108832.1 | UGCUAUGUUAGACGAUGUAAA | A-108337.2 | UUUACAUCGUCUAACAUAGCAAA | 160-182 |
| AD-52681.1 | A-108840.1 | GGGACAUGGUCUUAAAGACUU | A-108353.2 | AAGUCUUUAAGACCAUGUCCCAA | 208-230 |
| AD-52682.1 | A-108848.1 | UGACAUAUUUCAAAAACUCAA | A-108369.2 | UUGAGUUUUUGAAAUAUGUCAUU | 256-278 |
| AD-52683.1 | A-108856.1 | AUCAGUCUUUUUAUGAUCUAU | A-108385.2 | AUAGAUCAUAAAAAGACUGAUCA | 285-307 |
| AD-52684.1 | A-108864.1 | CAUAUAAACUACAAGUCAAAA | A-108401.2 | UUUUGACUUGUAGUUUAUAUGUA | 357-379 |
| AD-52685.1 | A-108872.1 | CUUGAACUCAACUCAAAACUU | A-108417.2 | AAGUUUUGAGUUGAGUUCAAGUG | 401-423 |

TABLE 9-continued

Unmodified Sense and antisense strand sequences of ANGPTL3 dsRNAs without GalNa1 conjugation
These sequences are the same as the sequences listed in Table 7 except that they do not contain GalNa1 conjugation.

| Duplex Name | Sense OligoName | Sense Sequence (SEQ ID NOS 1004-1184, respectively, in order of appearance) | Antisense OligoName | Antisense Sequence (SEQ ID NOS 1185-1365, respectively, in order of appearance) | Position in NM_014495.2 |
|---|---|---|---|---|---|
| AD-52686.1 | A-108880.1 | CUACUUCAACAAAAAGUGAAA | A-108433.2 | UUUCACUUUUUGUUGAAGUAGAA | 446-468 |
| AD-52687.1 | A-108888.1 | AAGAGCAACUAACUAACUUAA | A-108449.2 | UUAAGUUAGUUAGUUGCUCUUCU | 474-496 |
| AD-52688.1 | A-108896.1 | AAACAAGAUAAUAGCAUCAAA | A-108465.2 | UUUGAUGCUAUUAUCUUGUUUUU | 557-579 |
| AD-52689.1 | A-108904.1 | GCAUAGUCAAAUAAAGAAAU | A-108481.2 | AUUUCUUUUAUUUGACUAUGCUG | 625-647 |
| AD-52690.1 | A-108865.1 | AUAUAAACUACAAGUCAAAA | A-108403.2 | UUUUUGACUUGUAGUUUAUAUGU | 358-380 |
| AD-52691.1 | A-108873.1 | GAACUCAACUCAAAACUUGAA | A-108419.2 | UUCAAGUUUUGAGUUGAGUUCAA | 404-426 |
| AD-52692.1 | A-108881.1 | UACUUCAACAAAAAGUGAAAU | A-108435.2 | AUUUCACUUUUUGUUGAAGUAGA | 447-469 |
| AD-52693.1 | A-108889.1 | AGAGCAACUAACUAACUUAUU | A-108451.2 | AUUAAGUUAGUUAGUUGCUCUUC | 475-497 |
| AD-52694.1 | A-108897.1 | GAUAAUAGCAUCAAAGACCUU | A-108467.2 | AAGGUCUUUGAUGCUAUUAUCUU | 563-585 |
| AD-52695.1 | A-108905.1 | CAUAGUCAAAUAAAGAAAUA | A-108483.2 | UAUUUCUUUUAUUUGACUAUGCU | 626-648 |
| AD-52696.1 | A-108866.1 | UAUAAACUACAAGUCAAAAU | A-108405.2 | AUUUUGACUUGUAGUUUAUAUG | 359-381 |
| AD-52697.1 | A-108874.1 | AACUCAACUCAAAACUUGAAA | A-108421.2 | UUCAAGUUUUGAGUUGAGUUCA | 405-427 |
| AD-52698.1 | A-108882.1 | ACUUCAACAAAAAGUGAAAUA | A-108437.2 | UAUUUCACUUUUUGUUGAAGUAG | 448-470 |
| AD-52699.1 | A-108890.1 | GAGCAACUAACUAACUUAUU | A-108453.2 | AAUUAAGUUAGUUAGUUGCUCUU | 476-498 |
| AD-52700.1 | A-108898.1 | AACCAACAGCAUAGUCAAAUA | A-108469.2 | UAUUUGACUAUGCUGUUGGUUUA | 617-639 |
| AD-52701.1 | A-108906.1 | AGUCAAAUAAAGAAAUAGAA | A-108485.2 | UUCUAUUUCUUUUAUUUGACUAU | 629-651 |
| AD-52702.1 | A-108867.1 | AGUCAAAAAUGAAGAGGUAAA | A-108407.2 | UUUACCUCUUCAUUUUUGACUUG | 370-392 |
| AD-52703.1 | A-108875.1 | CUUGAAAGCCUCCUAGAAGAA | A-108423.2 | UUCUUCUAGGAGGCUUUCAAGUU | 419-441 |
| AD-52704.1 | A-108883.1 | CUUCAACAAAAAGUGAAAUAU | A-108439.2 | AUAUUUCACUUUUUGUUGAAGUA | 449-471 |
| AD-52705.1 | A-108891.1 | CAACUAACUAACUUAAUUCAA | A-108455.2 | UUGAAUUAAGUUAGUUAGUUGCU | 479-501 |
| AD-52706.1 | A-108899.1 | ACCAACAGCAUAGUCAAAUAA | A-108471.2 | UUAUUUGACUAUGCUGUUGGUUU | 618-640 |
| AD-52707.1 | A-108907.1 | GAACCCACAGAAAUUUCUCUA | A-108487.2 | UAGAGAAAUUUCUGUGGGUUCUU | 677-699 |
| AD-52708.1 | A-108868.1 | GAAUAUGUCACUUGAACUCAA | A-108409.2 | UUGAGUUCAAGUGACAUAUUCUU | 391-413 |
| AD-52709.1 | A-108876.1 | UGAAAGCCUCCUAGAAGAAAA | A-108425.2 | UUUUCUUCUAGGAGGCUUUCAAG | 421-443 |
| AD-52710.1 | A-108884.1 | UUCAACAAAAAGUGAAAUAUU | A-108441.2 | AAUAUUUCACUUUUUGUUGAAGU | 450-472 |
| AD-52711.1 | A-108892.1 | AACUAACUAACUUAAUUCAAA | A-108457.2 | UUUGAAUUAAGUUAGUUAGUUGC | 480-502 |
| AD-52712.1 | A-108900.1 | CCAACAGCAUAGUCAAAUAAA | A-108473.2 | UUUAUUUGACUAUGCUGUUGGUU | 619-641 |
| AD-52713.1 | A-108908.1 | AACCCACAGAAAUUUCUCUAU | A-108489.2 | AUAGAGAAAUUUCUGUGGGUUCU | 678-700 |
| AD-52714.1 | A-108869.1 | UGUCACUUGAACUCAACUCAA | A-108411.2 | UUGAGUUGAGUUCAAGUGACAUA | 396-418 |
| AD-52715.1 | A-108877.1 | GAAAGCCUCCUAGAAGAAAAA | A-108427.2 | UUUUUCUUCUAGGAGGCUUUCA | 422-444 |
| AD-52716.1 | A-108885.1 | AAUAUUUAGAAGAGCAACUAA | A-108443.2 | UUAGUUGCUCUUCUAAAUAUUUC | 465-487 |
| AD-52717.1 | A-108893.1 | ACUAACUAACUUAAUUCAAAA | A-108459.2 | UUUUGAAUUAAGUUAGUUAGUUG | 481-503 |
| AD-52718.1 | A-108901.1 | CAACAGCAUAGUCAAAUAAAA | A-108475.2 | UUUUAUUUGACUAUGCUGUUGGU | 620-642 |
| AD-52719.1 | A-108909.1 | CCACAGAAAUUUCUCUAUCUU | A-108491.2 | AAGAUAGAGAAAUUUCUGUGGGU | 681-703 |
| AD-52720.1 | A-108870.1 | GUCACUUGAACUCAACUCAAA | A-108413.2 | UUUGAGUUGAGUUCAAGUGACAU | 397-419 |

TABLE 9-continued

Unmodified Sense and antisense strand sequences of ANGPTL3 dsRNAs without GalNal conjugation
These sequences are the same as the sequences listed in Table 7 except that they do not contain GalNal conjugation.

| Duplex Name | Sense OligoName | Sense Sequence (SEQ ID NOS 1004-1184, respectively, in order of appearance) | Antisense OligoName | Antisense Sequence (SEQ ID NOS 1185-1365, respectively, in order of appearance) | Position in NM_014495.2 |
|---|---|---|---|---|---|
| AD-52721.1 | A-108878.1 | CUCCUAGAAGAAAAAAUUCUA | A-108429.2 | UAGAAUUUUUCUUCUAGGAGGC | 428-450 |
| AD-52722.1 | A-108886.1 | AUUUAGAAGAGCAACUAACUA | A-108445.2 | UAGUUAGUUGCUCUUCUAAAUAU | 468-490 |
| AD-52723.1 | A-108894.1 | CUAACUAACUUAAUUCAAAAU | A-108461.2 | AUUUUGAAUUAAGUUAGUUAGUU | 482-504 |
| AD-52724.1 | A-108902.1 | CAGCAUAGUCAAAUAAAAGAA | A-108477.2 | UUCUUUUAUUUGACUAUGCUGUU | 623-645 |
| AD-52725.1 | A-108910.1 | GAAAUAAGAAAUGUAAAACAU | A-108493.2 | AUGUUUUACAUUUCUUAUUUCAU | 746-768 |
| AD-52726.1 | A-108871.1 | UCACUUGAACUCAACUCAAAA | A-108415.2 | UUUUGAGUUGAGUUCAAGUGACA | 398-420 |
| AD-52727.1 | A-108879.1 | UCUACUUCAACAAAAAGUGAA | A-108431.2 | UUCACUUUUGUUGAAGUAGAAU | 445-467 |
| AD-52728.1 | A-108887.1 | UUUAGAAGAGCAACUAACUAA | A-108447.2 | UUAGUUAGUUGCUCUUCUAAAUA | 469-491 |
| AD-52729.1 | A-108895.1 | AAAACAAGAUAAUAGCAUCAA | A-108463.2 | UUGAUGCUAUUAUCUUGUUUUUC | 556-578 |
| AD-52730.1 | A-108903.1 | AGCAUAGUCAAAUAAAAGAAA | A-108479.2 | UUUCUUUUAUUUGACUAUGCUGU | 624-646 |
| AD-52731.1 | A-108958.1 | AGACCCAGCAACUCUCAAGUU | A-108495.2 | AACUUGAGAGUUGCUGGGUCUGA | 836-858 |
| AD-52732.1 | A-108966.1 | AGUCCAUGGACAUUAAUUCAA | A-108511.2 | UUGAAUUAAUGUCCAUGGACUAC | 887-909 |
| AD-52733.1 | A-108974.1 | GAUGGAUCACAAAACUUCAAU | A-108527.2 | AUUGAAGUUUUGUGAUCCAUCUA | 917-939 |
| AD-52734.1 | A-108982.1 | CUAGAGAAGAUAUACUCCAUA | A-108543.2 | UAUGGAGUAUAUCUUCUCUAGGC | 998-1020 |
| AD-52735.1 | A-108990.1 | AAAGACAACAAACAUUAUAUU | A-108559.2 | AAUAUAAUGUUUGUUGUCUUUCC | 1064-1086 |
| AD-52736.1 | A-108998.1 | CAUUAUAUUGAAUAUUCUUUU | A-108575.2 | AAAAGAAUAUUCAAUAUAAUGUU | 1076-1098 |
| AD-52737.1 | A-108959.1 | GACCCAGCAACUCUCAAGUUU | A-108497.2 | AAACUUGAGAGUUGCUGGGUCUG | 837-859 |
| AD-52739.1 | A-108975.1 | GGAUCACAAAACUUCAAUGAA | A-108529.2 | UUCAUUGAAGUUUUGUGAUCCAU | 920-942 |
| AD-52740.1 | A-108983.1 | GAAGAUAUACUCCAUAGUGAA | A-108545.2 | UUCACUAUGGAGUAUAUCUUCUC | 1003-1025 |
| AD-52741.1 | A-108991.1 | GACAACAAACAUUAUAUUGAA | A-108561.2 | UUCAAUAUAAUGUUUGUUGUCUU | 1067-1089 |
| AD-52742.1 | A-108999.1 | GGGAAAUCACGAAACCAACUA | A-108577.2 | UAGUUGGUUUCGUGAUUUCCAA | 1102-1124 |
| AD-52743.1 | A-108960.1 | ACCCAGCAACUCUCAAGUUUU | A-108499.2 | AAAACUUGAGAGUUGCUGGGUCU | 838-860 |
| AD-52744.1 | A-108968.1 | GGACAUUAAUUCAACAUCGAA | A-108515.2 | UUCGAUGUUGAAUUAAUGUCCAU | 894-916 |
| AD-52745.1 | A-108976.1 | GAUCACAAAACUUCAAUGAAA | A-108531.2 | UUUCAUUGAAGUUUUGUGAUCCA | 921-943 |
| AD-52746.1 | A-108984.1 | ACUCCAUAGUGAAGCAAUCUA | A-108547.2 | UAGAUUGCUUCACUAUGGAGUAU | 1011-1033 |
| AD-52747.1 | A-108992.1 | ACAACAAACAUUAUAUUGAAU | A-108563.2 | AUUCAAUAUAAUGUUUGUUGUCU | 1068-1090 |
| AD-52748.1 | A-109000.1 | GGAAAUCACGAAACCAACUAU | A-108579.2 | AUAGUUGGUUUCGUGAUUUCCCA | 1103-1125 |
| AD-52749.1 | A-108961.1 | CCCAGCAACUCUCAAGUUUUU | A-108501.2 | AAAAACUUGAGAGUUGCUGGGUC | 839-861 |
| AD-52750.1 | A-108969.1 | GACAUUAAUUCAACAUCGAAU | A-108517.2 | AUUCGAUGUUGAAUUAAUGUCCA | 895-917 |
| AD-52751.1 | A-108977.1 | AACGUGGGAGAACUACAAAUA | A-108533.2 | UAUUUGUAGUUCUCCCACGUUUC | 940-962 |
| AD-52752.1 | A-108985.1 | CUCCAUAGUGAAGCAAUCUAA | A-108549.2 | UUAGAUUGCUUCACUAUGGAGUA | 1012-1034 |
| AD-52753.1 | A-108993.1 | CAACAAACAUUAUAUUGAAUA | A-108565.2 | UAUUCAAUAUAAUGUUUGUUGUC | 1069-1091 |
| AD-52754.1 | A-109001.1 | GAAAUCACGAAACCAACUAUA | A-108581.2 | UAUAGUUGGUUUCGUGAUUUCCC | 1104-1126 |
| AD-52755.1 | A-108962.1 | CUCUCAAGUUUUUCAUGUCUA | A-108503.2 | UAGACAUGAAAAACUUGAGAGUU | 847-869 |

TABLE 9-continued

Unmodified Sense and antisense strand sequences of ANGPTL3 dsRNAs without GalNaI conjugation
These sequences are the same as the sequences listed in Table 7 except that they do not contain GalNaI conjugation.

| Duplex Name | Sense OligoName | Sense Sequence (SEQ ID NOS 1004-1184, respectively, in order of appearance) | Antisense OligoName | Antisense Sequence (SEQ ID NOS 1185-1365, respectively, in order of appearance) | Position in NM_014495.2 |
|---|---|---|---|---|---|
| AD-52756.1 | A-108970.1 | ACAUUAAUUCAACAUCGAAUA | A-108519.2 | UAUUCGAUGUUGAAUUAAUGUCC | 896-918 |
| AD-52757.1 | A-108978.1 | GGGAGAACUACAAAUAUGGUU | A-108535.2 | AACCAUAUUUGUAGUUCUCCCAC | 945-967 |
| AD-52758.1 | A-108986.1 | UCCAUAGUGAAGCAAUCUAAU | A-108551.2 | AUUAGAUUGCUUCACUAUGGAGU | 1013-1035 |
| AD-52759.1 | A-108994.1 | AACAAACAUUAUAUUGAAUAU | A-108567.2 | AUAUUCAAUAUAAUGUUUGUUGU | 1070-1092 |
| AD-52760.1 | A-109002.1 | UGGCAAUGUCCCCAAUGCAAU | A-108583.2 | AUUGCAUUGGGGACAUUGCCAGU | 1147-1169 |
| AD-52761.1 | A-108963.1 | UCAGGUAGUCCAUGGACAUUA | A-108505.2 | UAAUGUCCAUGGACUACCUGAUA | 881-903 |
| AD-52762.1 | A-108971.1 | UUAAUUCAACAUCGAAUAGAU | A-108521.2 | AUCUAUUCGAUGUUGAAUUAAUG | 899-921 |
| AD-52763.1 | A-108979.1 | GGAGAACUACAAAUAUGGUUU | A-108537.2 | AAACCAUAUUUGUAGUUCUCCCA | 946-968 |
| AD-52764.1 | A-108987.1 | CCAUAGUGAAGCAAUCUAAUU | A-108553.2 | AAUUAGAUUGCUUCACUAUGGAG | 1014-1036 |
| AD-52765.1 | A-108995.1 | ACAAACAUUAUAUUGAAUAUU | A-108569.2 | AAUAUUCAAUAUAAUGUUUGUUG | 1071-1093 |
| AD-52766.1 | A-109003.1 | AAUGCAAUCCCGGAAAACAAA | A-108585.2 | UUUGUUUUCCGGGAUUGCAUUGG | 1160-1182 |
| AD-52767.1 | A-108964.1 | CAGGUAGUCCAUGGACAUUAA | A-108507.2 | UUAAUGUCCAUGGACUACCUGAU | 882-904 |
| AD-52768.1 | A-108972.1 | UUCAACAUCGAAUAGAUGGAU | A-108523.2 | AUCCAUCUAUUCGAUGUUGAAUU | 903-925 |
| AD-52769.1 | A-108980.1 | GUUGGGCCUAGAGAAGAUAUA | A-108539.2 | UAUAUCUUCUCUAGGCCCAACCA | 991-1013 |
| AD-52770.1 | A-108988.1 | CAUAGUGAAGCAAUCUAAUUA | A-108555.2 | UAAUUAGAUUGCUUCACUAUGGA | 1015-1037 |
| AD-52771.1 | A-108996.1 | AACAUUAUAUUGAAUAUUCUU | A-108571.2 | AAGAAUAUUCAAUAUAAUGUUUG | 1074-1096 |
| AD-52772.1 | A-109004.1 | GCAAUCCCGGAAAACAAAGAU | A-108587.2 | AUCUUUGUUUUCCGGGAUUGCAU | 1163-1185 |
| AD-52773.1 | A-108965.1 | GGUAGUCCAUGGACAUUAAUU | A-108509.2 | AAUUAAUGUCCAUGGACUACCUG | 884-906 |
| AD-52774.1 | A-108973.1 | AUCGAAUAGAUGGAUCACAAA | A-108525.2 | UUUGUGAUCCAUCUAUUCGAUGU | 909-931 |
| AD-52775.1 | A-108981.1 | CCUAGAGAAGAUAUACUCCAU | A-108541.2 | AUGGAGUAUAUCUUCUCUAGGCC | 997-1019 |
| AD-52776.1 | A-108989.1 | GUUGAAGACUGGAAAGACAA | A-108557.2 | UUGUCUUUCCAGUCUUCCAACUC | 1051-1073 |
| AD-52777.1 | A-108997.1 | ACAUUAUAUUGAAUAUUCUUU | A-108573.2 | AAAGAAUAUUCAAUAUAAUGUUU | 1075-1097 |
| AD-52778.1 | A-109005.1 | CAAUCCCGGAAAACAAAGAUU | A-108589.2 | AAUCUUUGUUUUCCGGGAUUGCA | 1164-1186 |
| AD-52779.1 | A-109013.1 | CUACUUGGGAUCACAAAGCAA | A-108605.2 | UUGCUUUGUGAUCCCAAGUAGAA | 1194-1216 |
| AD-52780.1 | A-109021.1 | ACAACCUAAUGGUAAAUAUA | A-108621.2 | UAUAUUUACCAUUAGGUUGUUU | 1281-1303 |
| AD-52781.1 | A-109029.1 | AUCCAUCCAACAGAUUCAGAA | A-108637.2 | UUCUGAAUCUGUUGGAUGGAUCA | 1400-1422 |
| AD-52782.1 | A-109037.1 | AACUGAGGCAAAUUUAAAAGA | A-108653.2 | UCUUUUAAAUUUGCCUCAGUUCA | 1432-1454_G21A |
| AD-52783.1 | A-109045.1 | AGAGUAUGUGUAAAAAUCUGU | A-108669.2 | ACAGAUUUUUACACAUACUCUGU | 1913-1935 |
| AD-52784.1 | A-109006.1 | AAUCCCGGAAAACAAAGAUUU | A-108591.2 | AAAUCUUUGUUUUCCGGGAUUGC | 1165-1187 |
| AD-52785.1 | A-109014.1 | UACUUGGGAUCACAAAGCAAA | A-108607.2 | UUUGCUUUGUGAUCCCAAGUAGA | 1195-1217 |
| AD-52786.1 | A-109022.1 | CAACCUAAUGGUAAAUAUAA | A-108623.2 | UUAUAUUUACCAUUAGGUUGUUU | 1282-1304 |
| AD-52787.1 | A-109030.1 | UUGAAUGAACUGAGGCAAAUU | A-108639.2 | AAUUUGCCUCAGUUCAUUCAAAG | 1425-1447 |
| AD-52788.1 | A-109038.1 | ACUGAGGCAAAUUUAAAAGGA | A-108655.2 | UCCUUUUAAAUUUGCCUCAGUUC | 1433-1455_C21A |
| AD-52789.1 | A-109046.1 | GAGUAUGUGUAAAAAUCUGUA | A-108671.2 | UACAGAUUUUUACACAUACUCUG | 1914-1936 |
| AD-52791.1 | A-109015.1 | ACUUGGGAUCACAAAGCAAAA | A-108609.2 | UUUUGCUUUGUGAUCCCAAGUAG | 1196-1218 |

TABLE 9-continued

Unmodified Sense and antisense strand sequences of ANGPTL3 dsRNAs without GalNal conjugation
These sequences are the same as the sequences listed in Table 7 except that they do not contain GalNal conjugation.

| Duplex Name | Sense OligoName | Sense Sequence (SEQ ID NOS 1004-1184, respectively, in order of appearance) | Antisense OligoName | Antisense Sequence (SEQ ID NOS 1185-1365, respectively, in order of appearance) | Position in NM_014495.2 |
|---|---|---|---|---|---|
| AD-52792.1 | A-109023.1 | AUGGUAAAUAUAACAAACCAA | A-108625.2 | UUGGUUUGUUAUAUUUACCAUUU | 1290-1312 |
| AD-52793.1 | A-109031.1 | UGAAUGAACUGAGGCAAAUUU | A-108641.2 | AAAUUUGCCUCAGUUCAUUCAA | 1426-1448 |
| AD-52794.1 | A-109039.1 | CUGAGGCAAAUUUAAAAGGCA | A-108657.2 | UGCCUUUUAAAUUUGCCUCAGUU | 1434-1456 |
| AD-52795.1 | A-109047.1 | AGUAUGUGUAAAAAUCUGUAA | A-108673.2 | UUACAGAUUUUUACACAUACUCU | 1915-1937 |
| AD-52796.1 | A-109008.1 | GAAAACAAAGAUUUGGUGUUU | A-108595.2 | AAACACCAAAUCUUUGUUUUCCG | 1172-1194 |
| AD-52797.1 | A-109016.1 | AGUGUGGAGAAAACAACCUAA | A-108611.2 | UUAGGUUGUUUUCUCCACACUCA | 1269-1291 |
| AD-52798.1 | A-109024.1 | GUCUCAAAAUGGAAGGUUAUA | A-108627.2 | UAUAACCUUCCAUUUUGAGACUU | 1354-1376 |
| AD-52799.1 | A-109032.1 | GAAUGAACUGAGGCAAAUUUA | A-108643.2 | UAAAUUUGCCUCAGUUCAUUCAA | 1427-1449 |
| AD-52800.1 | A-109040.1 | UGAGGCAAAUUUAAAAGGCAA | A-108659.2 | UUGCCUUUUAAAUUUGCCUCAGU | 1435-1457 |
| AD-52801.1 | A-109048.1 | GUAUGUGUAAAAAUCUGUAAU | A-108675.2 | AUUACAGAUUUUUACACAUACUC | 1916-1938 |
| AD-52802.1 | A-109009.1 | AAAACAAAGAUUUGGUGUUUU | A-108597.2 | AAAACACCAAAUCUUUGUUUUCC | 1173-1195 |
| AD-52803.1 | A-109017.1 | GUGUGGAGAAAACAACCUAAA | A-108613.2 | UUUAGGUUGUUUUCUCCACACUC | 1270-1292 |
| AD-52804.1 | A-109025.1 | AUGGAAGGUUAUACUCUAUAA | A-108629.2 | UUAUAGAGUAUAACCUUCCAUUU | 1362-1384 |
| AD-52805.1 | A-109033.1 | AAUGAACUGAGGCAAAUUUAA | A-108645.2 | UUAAAUUUGCCUCAGUUCAUUCA | 1428-1450 |
| AD-52806.1 | A-109041.1 | GAGGCAAAUUUAAAAGGCAAU | A-108661.2 | AUUGCCUUUUAAAUUUGCCUCAG | 1436-1458 |
| AD-52807.1 | A-109049.1 | UAUGUGUAAAAAUCUGUAAUA | A-108677.2 | UAUUACAGAUUUUUACACAUACU | 1917-1939 |
| AD-52808.1 | A-109010.1 | ACAAAGAUUUGGUGUUUUCUA | A-108599.2 | UAGAAAACACCAAAUCUUUGUUU | 1176-1198 |
| AD-52809.1 | A-109018.1 | UGUGGAGAAAACAACCUAAAU | A-108615.2 | AUUUAGGUUGUUUUCUCCACACU | 1271-1293 |
| AD-52810.1 | A-109026.1 | UGGAAGGUUAUACUCUAUAAA | A-108631.2 | UUUAUAGAGUAUAACCUUCCAUU | 1363-1385 |
| AD-52811.1 | A-109034.1 | AUGAACUGAGGCAAAUUUAAA | A-108647.2 | UUUAAAUUUGCCUCAGUUCAUUC | 1429-1451 |
| AD-52812.1 | A-109042.1 | AGGCAAAUUUAAAAGGCAAUA | A-108663.2 | UAUUGCCUUUUAAAUUUGCCUCA | 1437-1459 |
| AD-52813.1 | A-109011.1 | AAGAUUUGGUGUUUUCUACUU | A-108601.2 | AAGUAGAAAACACCAAAUCUUUG | 1179-1201 |
| AD-52814.1 | A-109019.1 | AAACAACCUAAAUGGUAAAUA | A-108617.2 | UAUUUACCAUUUAGGUUGUUUUC | 1279-1301 |
| AD-52815.1 | A-109027.1 | AUACUCUAUAAAAUCAACCAA | A-108633.2 | UUGGUUGAUUUUAUAGAGUAUAA | 1372-1394 |
| AD-52816.1 | A-109035.1 | UGAACUGAGGCAAAUUUAAAA | A-108649.2 | UUUUAAAUUUGCCUCAGUUCAUU | 1430-1452 |
| AD-52817.1 | A-109043.1 | GGCAAAUUUAAAAGGCAAUAA | A-108665.2 | UUAUUGCCUUUUAAAUUUGCCUC | 1438-1460 |
| AD-52818.1 | A-109012.1 | UUUUCUACUUGGGAUCACAAA | A-108603.2 | UUUGUGAUCCCAAGUAGAAAACA | 1190-1212 |
| AD-52819.1 | A-109020.1 | AACAACCUAAAUGGUAAAUAU | A-108619.2 | AUAUUUACCAUUUAGGUUGUUUU | 1280-1302 |
| AD-52820.1 | A-109028.1 | UACUCUAUAAAAUCAACCAAA | A-108635.2 | UUUGGUUGAUUUUAUAGAGUAUA | 1373-1395 |
| AD-52821.1 | A-109036.1 | GAACUGAGGCAAAUUUAAAAA | A-108651.2 | UUUUUAAAUUUGCCUCAGUUCAU | 1431-1453_G21A |
| AD-52822.1 | A-109044.1 | CAGAGUAUGUGUAAAAAUCUU | A-108667.2 | AAGAUUUUUACACAUACUCUGUG | 1912-1934_G21U |

TABLE 10

Modified Sense and antisense strand sequences of ANGPTL3 dsRNAs without GalNal conjugation
These sequences are the same as the sequences listed in Table 8 except that they do not contain GalNal conjugation.

| Duplex Name | Sense Oligo Name | Sense Sequence (SEQ ID NOS 1366-1546, respectively, in order of appearance) | Antisense OligoName | Antisense Oligo Sequence (SEQ ID NOS 1547-1727, respectively, in order of appearance) |
|---|---|---|---|---|
| AD-52637.1 | A-108817.1 | UfcAfcAfaUfuAfAfGfcUfcCfuUfcUfuUf | A-108307.2 | aAfaGfaAfgGfaGfcuuAfaUfuGfuGfasAfsc |
| AD-52638.1 | A-108825.1 | UfuAfuUfgUfuCfCfUfcUfaGfuUfaUfuUf | A-108323.2 | aAfaUfaAfcUfaGfaggAfaCfaAfuAfasAfsa |
| AD-52639.1 | A-108833.1 | GfcUfaUfgUfuAfGfAfcGfaUfgUfaAfaAf | A-108339.2 | uUfuUfaCfaUfcGfucuAfaCfaUfaGfcsAfsa |
| AD-52640.1 | A-108841.1 | GfgAfcAfuGfgUfCfUfuAfaAfgAfcUfuUf | A-108355.2 | aAfaGfuCfuUfuAfagaCfcAfuGfuCfcsCfsa |
| AD-52641.1 | A-108849.1 | CfaAfaAfaCfuCfAfAfcAfuAfuUfgGfaUf | A-108371.2 | aUfcAfaAfuAfuGfuugAfgUfuUfuUfgsAfsa |
| AD-52642.1 | A-108857.1 | AfcCfaGfuGfaAfAfUfcAfaAfgAfaGfaAf | A-108387.2 | uUfcUfuCfuUfuGfauuUfcAfcUfgGfusUfsu |
| AD-52643.1 | A-108818.1 | CfaCfaAfuUfaAfGfCfuCfcUfuCfuUfuUf | A-108309.2 | aAfaAfgAfaGfgAfgcuUfaAfuUfgUfgsAfsa |
| AD-52645.1 | A-108834.1 | CfuAfuGfuUfaGfAfCfgAfuGfuAfaAfaAf | A-108341.2 | uUfuUfaAfcAfuCfgucUfaAfcAfuAfgsCfsa |
| AD-52647.1 | A-108850.1 | UfcAfaCfaUfaUfUfUfgAfuCfaGfuCfuUf | A-108373.2 | aAfgAfcUfgAfuCfaaaUfaUfgUfuGfasGfsu |
| AD-52648.1 | A-108858.1 | AfaCfuGfaGfaAfGfAfaCfuAfcAfuAfuAf | A-108389.2 | uAfuAfuGfuAfgUfucuUfcUfcAfgUfusCfsc |
| AD-52649.1 | A-108819.1 | AfcAfaUfaAfgCfUfUfcCfuUfcUfuUfuUf | A-108311.2 | aAfaAfaGfaAfgGfagcUfaAfuUfgUfusGfsa |
| AD-52650.1 | A-108827.1 | CfuCfcAfgAfgCfCfAfaAfaUfcAfaGfaUf | A-108327.2 | aUfcUfuGfaUfuUfuggCfuCfuGfgAfgsAfsu |
| AD-52651.1 | A-108835.1 | CfgAfuGfuAfaAfAfUfuUfaGfcCfaAfaAf | A-108343.2 | uUfgGfcUfaAfaAfuuuUfuAfcAfuCfgsUfsc |
| AD-52652.1 | A-108843.1 | GfuCfuUfaAfaGfAfCfuUfuGfuCfcAfuAf | A-108359.2 | uAfuGfgAfcAfaAfgucUfuUfaAfgAfcsCfsa |
| AD-52653.1 | A-108851.1 | CfaAfcAfuAfuUfUfGfaUfcAfgUfcUfuUf | A-108375.2 | aAfaGfaCfuGfaUfcaaAfuAfuGfuUfgsAfsg |
| AD-52654.1 | A-108859.1 | AfcUfgAfgAfaGfAfaCfuAfcAfuAfuAfaAf | A-108391.2 | uUfaUfaUfgUfaGfuucUfcUfcAfgUfusCfsc |
| AD-52656.1 | A-108828.1 | CfcAfgAfgCfcAfAfaAfaUfcAfaGfaUfuUf | A-108329.2 | aAfaUfcUfuGfaUfuuuGfgCfuCfuGfgsAfsg |
| AD-52657.1 | A-108836.1 | GfaUfgUfaAfaAfUfuUfaGfcCfaAfaUfaAf | A-108345.2 | aUfuGfgCfuAfaAfauuUfuAfcAfuCfgsGfsu |
| AD-52658.1 | A-108844.1 | UfcUfuAfaAfgAfCfUfuUfgUfccAfaUfaAf | A-108361.2 | uUfaUfgGfaCfaAfaguCfuUfuAfaGfasCfsc |
| AD-52659.1 | A-108852.1 | AfaCfaUfaUfuUfGfAfuCfaGfuCfuUfuUf | A-108377.2 | aAfaAfgAfcUfgAfucaAfaUfaUfgUfusGfsa |
| AD-52660.1 | A-108860.1 | CfuGfaGfaAfgAfAfCfuAfcAfuAfuAfaAf | A-108393.2 | uUfuAfuAfuGfuAfguuCfuUfcUfcAfgsUfsu |
| AD-52661.1 | A-108821.1 | AfaUfuAfaGfcUfCfCfuUfcUfuUfuUfaUf | A-108315.2 | aUfaAfaAfaGfaAfggaGfcUfuAfaUfusGfsu |
| AD-52662.1 | A-108829.1 | AfaAfuCfaAfgAfUfUfuGfcUfaUfgUfuAf | A-108331.2 | uAfaCfaUfaGfcAfaauCfuUfgAfuUfusUfsg |
| AD-52663.1 | A-108837.1 | UfuCfaGfuUfgGfGffAfcAfuGfgUfcUfuAf | A-108347.2 | uAfaGfaCfcAfuGfuccCfaAfcUfgAfasGfsg |
| AD-52664.1 | A-108845.1 | GfgGfcCfaAfaUfUfAfaUfgAfcAfuAfuUf | A-108363.2 | aAfuAfuGfuCfaUfuaaUfuUfgGfcCfcsUfsu |
| AD-52665.1 | A-108853.1 | AfcAfuAfuUfgAfUfcAfgUfcUfuUfuUf | A-108379.2 | aAfaAfgAfcUfgAfucAfaAfuAfuGfusUfsg |
| AD-52666.1 | A-108861.1 | AfgAfaCfuAfcAfuAfuAfaAfcUfaCfaAf | A-108395.2 | uUfgUfaGfuUfuAfuauGfuAfgUfuCfusUfsc |
| AD-52667.1 | A-108822.1 | AfuUfaAfgCfuCfCfUfuCfuUfuUfaUfuUf | A-108317.2 | aAfuAfaAfaAfgAfaggAfgCfuUfaAfusUfsg |
| AD-52668.1 | A-108830.1 | AfgAfuUfuGfcUfAfuUfgUfuAfgAfcGfaUf | A-108333.2 | uUfcGfuCfuAfaCfauaGfcAfaAfuCfusUfsg |
| AD-52669.1 | A-108838.1 | UfcAfgUfuGfgGfAfcAfuGfgUfcUfuAfaAf | A-108349.2 | uUfaAfgAfcCfaUfgucCfcAfaCfuGfasAfsg |
| AD-52670.1 | A-108846.1 | GfgCfcAfaAfuUfAfAfuGfaCfaUfaUfuUf | A-108365.2 | aAfaUfaUfgUfcAfuuaAfuUfuGfgCfcsCfsu |
| AD-52671.1 | A-108854.1 | CfaUfaUfuGfaUfcfaGfuCfuUfuUfuAf | A-108381.2 | uAfaAfaAfgAfcUfgauCfaAfaUfaUfgsUfsu |
| AD-52672.1 | A-108862.1 | UfaCfaUfaUfaAfAfCfuAfcAfaGfuCfaAf | A-108397.2 | uUfgAfcUfuGfuAfguuUfaUfaUfgUfasGfsu |
| AD-52673.1 | A-108823.1 | UfuUfaAfuUfgUfUfCfcUfcUfaGfuUfaUf | A-108319.2 | aUfaAfcUfaGfaGfgaaCfaAfuUfaAfasAfsg |
| AD-52674.1 | A-108831.1 | UfuGfcUfaUfgUfUfAfgAfcGfaUfgUfaAf | A-108335.2 | uUfaCfaUfcGfuCfuaaCfaUfaGfcAfasUfsu |

TABLE 10-continued

Modified Sense and antisense strand sequences of ANGPTL3
dsRNAs without GalNA1 conjugation
These sequences are the same as the sequences listed in Table 8 except that
they do not contain GalNA1 conjugation.

| Duplex Name | Sense Oligo Name | Sense Sequence (SEQ ID NOS 1366-1546, respectively, in order of appearance) | Antisense OligoName | Antisense Oligo Sequence (SEQ ID NOS 1547-1727, respectively, in order of appearance) |
|---|---|---|---|---|
| AD-52675.1 | A-108839.1 | CfaGfuUfgGfgAfCfAfuGfgUfcUfuAfaAf | A-108351.2 | uUfuAfaGfaCfcAfuguCfcCfaAfcUfgsAfsa |
| AD-52676.1 | A-108847.1 | AfaAfuUfaAfuGfAfCfaUfaUfuUfcAfaAf | A-108367.2 | uUfuGfaAfaUfaUfgucAfuUfaAfuUfusGfsg |
| AD-52677.1 | A-108855.1 | GfaUfcAfgUfcUfUfuUfaUfgAfuCfuAf | A-108383.2 | uAfgAfuCfaUfaAfaaGfaCfuGfaUfcsAfsa |
| AD-52678.1 | A-108863.1 | AfcAfuAfuAfaAfCfUfaCfaAfgUfcAfaAf | A-108399.2 | uUfuGfaCfuUfgUfaguUfuAfuAfuGfusAfsg |
| AD-52679.1 | A-108824.1 | UfuUfaUfuGfuUfCfCfuCfuAfgUfaAfuUf | A-108321.2 | aAfuAfaCfuAfgAfggaAfcAfaUfaAfasAfsa |
| AD-52680.1 | A-108832.1 | UfgCfuAfuGfuUfAfGfaCfgAfuGfuAfaAf | A-108337.2 | uUfuAfcAfuCfgUfcuaAfcAfuAfgCfasAfsa |
| AD-52681.1 | A-108840.1 | GfgGfaCfaUfgGfUfCfuUfaAfaGfaCfuUf | A-108353.2 | aAfgUfcUfuUfaAfgacCfaUfgUfcCfcsAfsa |
| AD-52682.1 | A-108848.1 | UfgAfcAfuAfuUfUfCfaAfaAfaCfuCfaAf | A-108369.2 | uUfgAfgUfuUfuUfgaaAfuAfuGfuCfasUfsu |
| AD-52683.1 | A-108856.1 | AfuCfaGfuCfuUfUfUfuAfuGfaUfcUfaUf | A-108385.2 | aUfaGfaUfcAfuAfaaaAfgAfcUfgAfusCfsa |
| AD-52684.1 | A-108864.1 | CfaUfaUfaAfaCfUfAfcAfaGfuCfaAfaAf | A-108401.2 | uUfuUfgAfcUfuGfuagUfuUfaUfaUfgsUfsa |
| AD-52685.1 | A-108872.1 | CfuUfgAfaCfuCfAfAfcAfcAfaAfaCfuUf | A-108417.2 | aAfgUfuUfuGfuuGfaGfuUfcAfaAfgsUfsg |
| AD-52686.1 | A-108880.1 | CfuAfcUfuCfaAfCfAfaAfaUfgAfaAf | A-108433.2 | uUfcAfcAfuUfuUfuguUfgAfaGfuAfgsAfsa |
| AD-52687.1 | A-108888.1 | AfaGfaGfcAfaCfUfAfaCfuAfaCfuUfaAf | A-108449.2 | uUfaAfgUfuAfgUfuagUfuGfcUfcUfusCfsu |
| AD-52688.1 | A-108896.1 | AfaAfcAfaGfaUfAfAfuAfgCfaUfcAfaAf | A-108465.2 | uUfuGfaUfgCfuAfuuaUfcUfuGfuUfusUfsu |
| AD-52689.1 | A-108904.1 | GfcAfuAfgUfcAfAfAfuAfaAfaGfaAfaUf | A-108481.2 | aUfuUfcUfuUfuAfuuuGfaCfuAfuGfcsUfsg |
| AD-52690.1 | A-108865.1 | AfuAfuAfaAfcUfAfCfaAfgUfcAfaAfaAf | A-108403.2 | uUfuUfgAfcUfuGfuaGfuUfuAfuAfusGfsu |
| AD-52691.1 | A-108873.1 | GfaAfcUfcAfaCfUfCfaAfaAfcUfuGfaAf | A-108419.2 | uUfcAfaGfuUfuUfgagUfuGfaGfuUfcsAfsa |
| AD-52692.1 | A-108881.1 | UfaCfuUfcAfaCfAfAfaAfaGfuGfaAfaUf | A-108435.2 | aUfuUfcAfcUfuUfuugUfuGfaAfgUfasGfsa |
| AD-52693.1 | A-108889.1 | AfgAfgCfaAfcUfAfAfcUfaAfcUfuAfaUf | A-108451.2 | aUfuAfaGfuUfaGfuuaGfuUfgCfuCfusUfsc |
| AD-52694.1 | A-108897.1 | GfaUfaAfuAfgCfAfAfUfcAfaAfgAfcCfuUf | A-108467.2 | aAfgGfuCfuUfuGfaugCfuAfuUfaUfcsUfsu |
| AD-52695.1 | A-108905.1 | CfaUfaGfuCfaAfAfUfaAfaAfgAfaAfuAf | A-108483.2 | uAfuUfcUfuUfuAfuuuGfaCfuAfuGfsCfsu |
| AD-52696.1 | A-108866.1 | UfaUfaAfaCfuAfCfAfaGfuCfaAfaAfuUf | A-108405.2 | aUfuUfuUfgAfcUfuguAfgUfuUfaUfasUfsg |
| AD-52697.1 | A-108874.1 | AfaCfuCfaAfcUfCfAfaAfaCfuUfgAfaAf | A-108421.2 | uUfuCfaAfgUfuUfugaGfuUfgAfgUfusCfsa |
| AD-52698.1 | A-108882.1 | AfcUfuCfaAfcAfAfaAfgUfgAfaAfuAf | A-108437.2 | uAfuUfuCfaCfuUfuuuGfuUfgAfaGfusAfsg |
| AD-52699.1 | A-108890.1 | GfaGfcAfaCfUfAfAfcUfaAfcUfuAfaUf | A-108453.2 | aAfuUfaAfgUfuAfguuAfgUfuGfcUfcsUfsu |
| AD-52700.1 | A-108898.1 | AfaCfcAfaCfaGfCfAfuAfgUfcAfaAfuAf | A-108469.2 | uAfuUfuGfaCfuAfugcUfgUfuGfgUfusUfsa |
| AD-52701.1 | A-108906.1 | AfgUfcAfaAfuAfAfAfaGfaAfaUfaGfaAf | A-108485.2 | uUfcUfaUfuUfcUfuuuAfuUfuGfaCfusAfsu |
| AD-52702.1 | A-108867.1 | AfgUfcAfaAfaAfUfGfaAfgAfgGfuAfaAf | A-108407.2 | uUfuAfcCfuCfuUfcauUfuUfuGfaCfusUfsg |
| AD-52703.1 | A-108875.1 | CfuUfgAfaAfgCfCfUfcCfuAfgAfaAf | A-108423.2 | uUfcUfuCfuAfgGfaggCfuUfuCfaAfgsUfsu |
| AD-52704.1 | A-108883.1 | CfuUfcAfaCfaAfAfAfaGfuGfaAfaUfaUf | A-108439.2 | aUfaUfuUfcAfcUfuuuGfuUfgAfaGfusAfsa |
| AD-52705.1 | A-108891.1 | CfaAfcUfaAfcUfAfAfcUfuAfaUfcUfaAf | A-108455.2 | uUfgAfaUfuAfaGfuuaGfuUfaGfuUfgsCfsu |
| AD-52706.1 | A-108899.1 | AfcCfaAfcAfgCfAfUfaGfuCfaAfaUfaAf | A-108471.2 | uUfaUfuUfgAfcUfaugCfuGfuUfgGfusUfsu |
| AD-52707.1 | A-108907.1 | GfaAfcCfcAfcAfGfAfaAfuUfcCfuCfuAf | A-108487.2 | aAfgAfgGfaAfuUfucuGfuGfgGfuUfcsUfsu |
| AD-52708.1 | A-108868.1 | GfaAfuAfuGfuCfAfCfuUfgAfaCfuAfaAf | A-108409.2 | uUfgAfgUfuCfaAfgugAfcAfuAfuUfcsUfsu |
| AD-52709.1 | A-108876.1 | UfgAfaAfgCfcUfCfCfuAfgAfaGfaAfaAf | A-108425.2 | uUfuUfcUfuCfuAfggaGfgCfuUfuCfasAfsg |

TABLE 10-continued

Modified Sense and antisense strand sequences of ANGPTL3
dsRNAs without GalNAl conjugation
These sequences are the same as the sequences listed in Table 8 except that
they do not contain GalNAl conjugation.

| Duplex Name | Sense Oligo Name | Sense Sequence (SEQ ID NOS 1366-1546, respectively, in order of appearance) | Antisense OligoName | Antisense Oligo Sequence (SEQ ID NOS 1547-1727, respectively, in order of appearance) |
|---|---|---|---|---|
| AD-52710.1 | A-108884.1 | UfuCfaAfcAfaAfAfAfgUfgAfaAfuAfuUf | A-108441.2 | aAfuAfuUfuCfaCfuuuUfuGfuUfgAfasGfsu |
| AD-52711.1 | A-108892.1 | AfaCfuAfaCfuAfAfCfuUfaAfuUfcAfaAf | A-108457.2 | uFuGfaAfuUfaAfguuAfgUfuAfgUfusGfsc |
| AD-52712.1 | A-108900.1 | CfcAfaCfaGfcAfUfAfgUfcAfaAfuAfaAf | A-108473.2 | uFuAfuUfuGfaCfuauGfcUfgUfuGfgsUfsu |
| AD-52713.1 | A-108908.1 | AfaCfcCfaCfaGfAfAfaUfuUfcUfcUfaUf | A-108489.2 | aUfaGfaGfaAfaUfuucUfgUfgGfgUfusCfsu |
| AD-52714.1 | A-108869.1 | UfgUfcAfcUfuGfAfAfcUfcAfaCfuCfaAf | A-108411.2 | uUfgAfgUfuGfaGfuucAfaGfuGfaCfasUfsa |
| AD-52715.1 | A-108877.1 | GfaAfaGfcCfuCfCfCfUfaGfaAfgAfaAfAf | A-108427.2 | uUfuUfcCfuUfcUfaggAfgGfcUfuUfcsAfsa |
| AD-52716.1 | A-108885.1 | AfaUfaUfuUfaGfAfAfgAfgCfaAfcUfaAf | A-108443.2 | uUfaGfuUfgCfuCfuucUfaAfaUfaUfusUfsc |
| AD-52717.1 | A-108893.1 | AfcUfaAfcUfaAfCfUfuAfaUfcCfaAfaAf | A-108459.2 | uUfuUfgAfaUfuAfaguUfaGfuUfaGfusUfsg |
| AD-52718.1 | A-108901.1 | CfaAfcAfgCfaUfAfGfuCfaAfaUfaAfaAf | A-108475.2 | uUfuUfaUfuUfgAfcuaUfgCfuGfuUfgsGfsu |
| AD-52719.1 | A-108909.1 | CfcAfcAfgAfaAfUfUfuCfuCfuAfuCfuUf | A-108491.2 | aAfgAfuAfgAfgAfaauUfcUfuGfuGfgsSfsu |
| AD-52720.1 | A-108870.1 | GfuCfaCfuUfgAfAfCfuCfaAfcUfcAfaAf | A-108413.2 | uUfuGfaGfuUfgAfguuCfaAfgUfgAfcsAfsu |
| AD-52721.1 | A-108878.1 | CfuCfcUfaGfaAfGfAfaAfaUfuCfuUfaAf | A-108429.2 | uAfgAfaUfuUfuUfucuUfcUfaGfgAfgsGfsc |
| AD-52722.1 | A-108886.1 | AfuUfuAfgAfaGfAfGfcAfaCfuAfcUfaAf | A-108445.2 | uAfgUfaGfuUfgCfucUfcUfaAfaUfusAfsu |
| AD-52723.1 | A-108894.1 | CfuAfaCfuAfaCfUfUfaAfuUfcAfaAfaUf | A-108461.2 | aUfuUfuGfaAfuUfaagUfuAfgUfuAfgsUfsu |
| AD-52724.1 | A-108902.1 | CfaGfcAfuAfgUfCfAfaAfuAfaAfaGfaAf | A-108477.2 | uUfcUfuUfuAfuUfugaCfuAfuGfcUfgsUfsu |
| AD-52725.1 | A-108910.1 | GfaAfaUfaAfgAfAfAfuGfuAfaAfaCfaUf | A-108493.2 | aUfgUfuUfuAfcAfuuuCfuUfaUfuUfcsAfsu |
| AD-52726.1 | A-108871.1 | UfcAfcUfuGfaAfCfUfcAfaCfuCfaAfaAf | A-108415.2 | uUfuUfgAfgUfuGfaguUfcAfaGfuGfasCfsa |
| AD-52727.1 | A-108879.1 | UfcUfaCfuUfcAfAfCfaAfaAfaGfuGfaAf | A-108431.2 | uUfcAfcUfuUfuUfguuGfaAfgUfaGfasAfsu |
| AD-52728.1 | A-108887.1 | UfuUfaGfaAfgAfGfCfaAfcUfaAfcUfaAf | A-108447.2 | uUfaGfuUfaGfuUfgcuCfuUfcUfaAfasUfsa |
| AD-52729.1 | A-108895.1 | AfaAfaCfaAfgAfUfAfaUfaGfcAfuCfaAf | A-108463.2 | uUfgAfuGfcUfaUfuauCfuUfgUfuUfusUfsc |
| AD-52730.1 | A-108903.1 | AfgCfaUfaGfuCfAfAfaUfaAfaAfgAfaAf | A-108479.2 | uUfuCfuUfuUfaUfuugAfcUfaUfgCfusGfsu |
| AD-52731.1 | A-108958.1 | AfgAfcCfcAfgCfAfAfcUfcUfcAfaGfuUf | A-108495.2 | aAfcUfuGfaGfaGfuuGfcUfgGfgUfcUfusGfsa |
| AD-52732.1 | A-108966.1 | AfgUfcCfaUfgGfAfCfaUfuAfaUfuCfaAf | A-108511.2 | uUfgAfaUfuAfaUfgucCfaUfgGfaCfusAfsc |
| AD-52733.1 | A-108974.1 | GfaUfgGfaUfcAfCffaAfaCfuUfcAfaUf | A-108527.2 | aUfuGfaAfgUfuUfuguGfaUfcCfaUfcsUfsa |
| AD-52734.1 | A-108982.1 | CfuAfgAfgAfGfAfUfaUfaCfuCfcAfuAf | A-108543.2 | uAfuGfgAfgUfaUfaucUfcUfcUfaAfgsGfsc |
| AD-52735.1 | A-108990.1 | AfaAfgAfcAfaCfAfAfaCfaUfuAfuUfuUf | A-108559.2 | aAfuAfaUfgUfuGfuuGfuCfuUfusCfsc |
| AD-52736.1 | A-108998.1 | CfaUfuAfuUfGfAfaUfaUfuCfuUfuUf | A-108575.2 | aAfaAfgAfaUfaUfucaAfuAfuAfaUfgsUfsu |
| AD-52737.1 | A-108959.1 | GfaCfcCfaGfcAfAfCfuCfuCfaAfgUfuUf | A-108497.2 | aAfaCfuUfgAfgAfguuGfcUfgGfgUfcsUfsg |
| AD-52739.1 | A-108975.1 | GfgAfuCfaCfaAfAfAfcUfuCfaAfuGfaAf | A-108529.2 | uUfcAfuUfgAfaGfuuuUfgUfgAfuCfcsAfsu |
| AD-52740.1 | A-108983.1 | GfaAfgAfuAfuAfcUfcCfaUfaGfuGfaAf | A-108545.2 | uUfcAfcUfaUfgGfaguAfuAfuCfuUfcsUfsc |
| AD-52741.1 | A-108991.1 | GfaCfaAfcAfaAfcAfUfuAfuUfuGfaAf | A-108561.2 | uUfcAfaUfaUfaAfuguUfuGfuUfgUfcsUfsu |
| AD-52742.1 | A-108999.1 | GfgGfaAfaUfcAfcCfgAfaAfcCfaCfuAf | A-108577.2 | uAfgUfgGfuUfuUfcguAfuUfuCfcCfcsAfsa |
| AD-52743.1 | A-108960.1 | AfcCfcAfgCfaAfCfUfcUfcAfaGfuUfuUf | A-108499.2 | aAfaAfcUfuGfaGfaguUfgCfuGfgGfuscCfsu |
| AD-52744.1 | A-108968.1 | GfgAfcAfuUfaAfUfUfcAfuUfaUfcGfaAf | A-108515.2 | uUfcGfaUfgUfuGfaauUfaAfuGfuCfcsAfsu |
| AD-52745.1 | A-108976.1 | GfaUfcAfcAfaAfAfCfuUfcAfaUfgAfaAf | A-108531.2 | uUfuCfaUfuGfaAfguuUfuGfuGfaUfcsCfsa |

TABLE 10-continued

Modified Sense and antisense strand sequences of ANGPTL3
dsRNAs without GalNa1 conjugation
These sequences are the same as the sequences listed in Table 8 except that
they do not contain GalNa1 conjugation.

| Duplex Name | Sense Oligo Name | Sense Sequence (SEQ ID NOS 1366-1546, respectively, in order of appearance) | Antisense OligoName | Antisense Oligo Sequence (SEQ ID NOS 1547-1727, respectively, in order of appearance) |
|---|---|---|---|---|
| AD-52746.1 | A-108984.1 | AfcUfcCfaUfaGfUfGfaAfgCfaAfuCfuAf | A-108547.2 | uAfgAfuUfgCfuUfcacUfaUfgGfaGfusAfsu |
| AD-52747.1 | A-108992.1 | AfcAfaCfaAfaCfAfUfuAfuAfuUfgAfaUf | A-108563.2 | aUfuCfaAfuAfuAfaugUfuUfgUfuGfusCfsu |
| AD-52748.1 | A-109000.1 | GfgAfaAfuCfaCfGfAfaAfcCfaAfcUfaUf | A-108579.2 | aUfaGfuUfgGfuUfucgUfgAfuUfcCfcsCfsa |
| AD-52749.1 | A-108961.1 | CfcCfaGfcAfaCfUfCfuCfaAfgUfuUfuUf | A-108501.2 | aAfaAfaCfuUfgAfgagUfuGfcUfgGfgsUfsc |
| AD-52750.1 | A-108969.1 | GfaCfaUfaAfaUfUfCfaAfcAfuCfgAfaUf | A-108517.2 | aUfuCfgAfuGfuUfgaaUfuAfaUfgUfcsCfsa |
| AD-52751.1 | A-108977.1 | AfaCfgUfgGfgAfGfAfaCfuAfcAfaAfuAf | A-108533.2 | uAfuUfuGfuAfgUfucuCfcCfaCfgUfusUfsc |
| AD-52752.1 | A-108985.1 | CfuCfcAfuAfgUfGfAfaGfcAfaUfcUfaAf | A-108549.2 | uUfaGfaUfuGfcUfucaCfuAfuGfgAfgsUfsa |
| AD-52753.1 | A-108993.1 | CfaAfcAfaAfcAfUfUfaUfaUfuGfaAfuAf | A-108565.2 | uAfuUfcAfaUfaUfaauGfuUfuGfuUfgsUfsc |
| AD-52754.1 | A-109001.1 | GfaAfaUfcAfcGfAfAfaCfcAfaCfuAfuAf | A-108581.2 | uAfuAfgUfuGfgUfuucGfuGfaUfuUfcsCfsc |
| AD-52755.1 | A-108962.1 | CfuCfuCfaAfgUfUfUfuUfcAfuGfuCfuAf | A-108503.2 | uAfgAfcAfuGfaAfaaaCfuUfgAfgAfgsUfsu |
| AD-52756.1 | A-108970.1 | AfcAfuUfaAfuUfcCfAfaCfaUfcGfaAfuAf | A-108519.2 | uAfuUfcGfaUfgUfugaAfuUfaAfuGfusCfsc |
| AD-52757.1 | A-108978.1 | GfgGfaGfaAfcUfAfCfaAfaUfaUfgGfuUf | A-108535.2 | aAfcCfaUfaUfuUfguaGfuUfcUfcCfcsAfsc |
| AD-52758.1 | A-108986.1 | UfcCfaUfaGfuGfAfAfgCfaAfuCfuAfaUf | A-108551.2 | aUfuAfgAfuUfgCfuucAfcUfaUfgGfasGfsu |
| AD-52759.1 | A-108994.1 | AfaCfaAfaCfaUfUfAfuAfuUfgAfaUfaUf | A-108567.2 | aUfaUfuCfaAfuAfuaaUfgUfuUfgUfusGfsu |
| AD-52760.1 | A-109002.1 | UfgGfcAfaUfgUfCfCfcCfaAfuGfcAfaUf | A-108583.2 | aUfuGfcAfuUfgGfggaCfaUfuGfcCfasGfsu |
| AD-52761.1 | A-108963.1 | UfcAfgGfuAfgUfCfCfaUfgGfaCfaUfuAf | A-108505.2 | uAfaUfgUfcCfaUfggaCfuAfcCfuGfasUfsa |
| AD-52762.1 | A-108971.1 | UfuAfaUfuCfaAfcCfAfuCfgAfaUfaGfaUf | A-108521.2 | aUfcUfaUfuCfgAfuguUfgAfaUfuAfasUfsg |
| AD-52763.1 | A-108979.1 | GfgAfgAfaCfuAfcCfAfaAfuAfuGfgUfuUf | A-108537.2 | aAfaCfcAfuAfuUfuguAfgUfuCfuCfcsCfsa |
| AD-52764.1 | A-108987.1 | CfcAfuAfgUfgAfAfGfcAfaUfcUfaAfuUf | A-108553.2 | aAfuUfaGfaUfuGfcuuCfaCfuAfuGfgsAfsg |
| AD-52765.1 | A-108995.1 | AfcAfaAfcAfuUfAfUfaUfuGfaAfuAfuUf | A-108569.2 | aAfuAfuUfcAfaUfauaAfuGfuUfuGfusUfsg |
| AD-52766.1 | A-109003.1 | AfaUfgCfaAfuCfCfCfgGfaAfaAfcAfaAf | A-108585.2 | uUfuGfuUfuUfcCfgggAfuUfgCfaUfusGfsg |
| AD-52767.1 | A-108964.1 | CfaGfgUfaGfuCfCfAfuGfgAfcAfuUfaAf | A-108507.2 | uUfaAfuGfuCfcAfuggAfcUfaCfcUfgsAfsu |
| AD-52768.1 | A-108972.1 | UfuCfaAfcAfuCfGfAfaUfaGfaUfgGfaUf | A-108523.2 | aUfcCfaUfcUfaUfucgAfuGfuUfgAfasUfsu |
| AD-52769.1 | A-108980.1 | GfuUfgGfgCfcUfAfGfaGfaAfgAfuAfuAf | A-108539.2 | uAfuAfuCfuUfcUfcuaGfcCfcAfaCfsCfsa |
| AD-52770.1 | A-108988.1 | CfaUfaGfuGfaAfGfCfaAfuCfuAfaUfaUf | A-108555.2 | uAfaUfuAfgAfuUfgcuUfcAfcUfaUfgsGfsa |
| AD-52771.1 | A-108996.1 | AfaCfaUfuAfuAfUfUfgAfaUfaUfuCfuUf | A-108571.2 | aAfgAfaUfaUfuCfaauAfuAfaUfgUfusUfsg |
| AD-52772.1 | A-109004.1 | GfcAfaUfcCfcGfGfaAfaAfcAfaAfaGfaUf | A-108587.2 | aUfcUfuUfgUfuUfuccGfgGfaUfuGfcsAfsu |
| AD-52773.1 | A-108965.1 | GfgUfaGfuCfcAfUfGfgAfcAfuUfaAfuUf | A-108509.2 | aAfuUfaAfuGfuCfcauGfgAfcUfaCfcsUfsg |
| AD-52774.1 | A-108973.1 | AfuCfgAfaUfaGfAfUfgGfaUfcAfcAfaAf | A-108525.2 | uUfuGfuGfaUfcCfaucUfaUfuCfgAfusUfsu |
| AD-52775.1 | A-108981.1 | CfcUfaGfaGfaAfGfAfuAfuAfcUfcCfaUf | A-108541.2 | aUfgGfaGfuAfuAfucuUfcUfcUfaGfgsCfsc |
| AD-52776.1 | A-108989.1 | GfuUfgGfaAfgAfCfUfgGfaAfaGfaCfaAf | A-108557.2 | uUfgUfcUfuUfcCfaguCfuUfcCfaAfcsUfsc |
| AD-52777.1 | A-108997.1 | AfcAfuUfaUfaUfUfGfaAfuAfuUfcUfuUf | A-108573.2 | aAfaGfaAfuAfuUfcaaUfaUfaAfuGfusUfsu |
| AD-52778.1 | A-109005.1 | CfaAfuCfcCfgGfAfAfaAfcAfaAfgAfuUf | A-108589.2 | aAfuCfuUfuGfuUfuucCfgGfgAfuUfgsCfsa |
| AD-52779.1 | A-109013.1 | CfuAfcUfuGfgGfAfUfcAfcAfaAfgCfaAf | A-108605.2 | uUfgCfuUfuGfuGfaucCfcAfaGfuAfgsAfsa |
| AD-52780.1 | A-109021.1 | AfcAfaCfcUfaAfAfUfgGfuAfaAfuAfaAf | A-108621.2 | uAfuUfuAfcUfuAfccAfauuUfaGfgUfuGfusUfsu |

TABLE 10-continued

Modified Sense and antisense strand sequences of ANGPTL3 dsRNAs without GalNa1 conjugation
These sequences are the same as the sequences listed in Table 8 except that they do not contain GalNa1 conjugation.

| Duplex Name | Sense Oligo Name | Sense Sequence (SEQ ID NOS 1366-1546, respectively, in order of appearance) | Antisense OligoName | Antisense Oligo Sequence (SEQ ID NOS 1547-1727, respectively, in order of appearance) |
|---|---|---|---|---|
| AD-52781.1 | A-109029.1 | AfuCfcAfuCfcAfAfCfaGfaUfuCfaGfaAf | A-108637.2 | uUfcUfgAfaUfcUfguuGfgAfuGfgAfusCfsa |
| AD-52782.1 | A-109037.1 | AfaCfuGfaGfgCfAfAfaUfuUfaAfaAfgAf | A-108653.2 | uCfuUfuUfaAfaUfuugCfcUfcAfgUfusCfsa |
| AD-52783.1 | A-109045.1 | AfgAfgUfaUfgUfGfUfaAfaAfaUfcUfgUf | A-108669.2 | aCfaGfaUfuUfuUfacaCfaUfaCfuCfusGfsu |
| AD-52784.1 | A-109006.1 | AfaUfcCfcGfgAfAfAfaCfaAfaGfaUfuUf | A-108591.2 | aAfaUfcUfuUfgUfuuuCfcGfgGfaUfusGfsc |
| AD-52785.1 | A-109014.1 | UfaCfuUfgGfgAfUfCfaCfaAfaGfcAfaAf | A-108607.2 | uUfuGfcUfuUfgUfgauCfcCfaAfgUfasGfsa |
| AD-52786.1 | A-109022.1 | CfaAfcCfuAfaAfUfGfgUfaAfaUfaUfaAf | A-108623.2 | uUfaUfaUfuUfaCfcauUfuAfgGfuUfgsUfsu |
| AD-52787.1 | A-109030.1 | UfuGfaAfuGfaAfCfUfgAfgGfcAfaAfuUf | A-108639.2 | aAfuUfuGfcCfuCfaguUfcAfuUfcAfasAfsg |
| AD-52788.1 | A-109038.1 | AfcUfgAfgGfcAfAfAfuUfuAfaAfaGfgAf | A-108655.2 | uCfcUfuUfuAfaAfuuuGfcCfuCfaGfusUfsc |
| AD-52789.1 | A-109046.1 | GfaGfuAfuGfuGfUfAfaAfaAfuCfuGfuAf | A-108671.2 | uAfcAfgAfuUfuUfuacAfcAfuAfcUfcsUfsg |
| AD-52791.1 | A-109015.1 | AfcUfuGfgGfaUfCfAfcAfaAfgCfaAfaAf | A-108609.2 | uUfuUfgCfuUfuGfugaUfcCfcAfaGfusAfsg |
| AD-52792.1 | A-109023.1 | AfuGfgUfaAfaUfAfUfaAfcAfaAfcCfaAf | A-108625.2 | uUfgGfuUfuGfuUfauaUfuUfaCfcAfusUfsu |
| AD-52793.1 | A-109031.1 | UfgAfaUfgAfaCfUfGfaGfgCfaAfaUfuUf | A-108641.2 | aAfaUfuUfgCfcUfcagUfuCfaUfuCfasAfsa |
| AD-52794.1 | A-109039.1 | CfuGfaGfgCfaAfAfUfuUfaAfaAfgGfcAf | A-108657.2 | uGfcCfuUfuUfaAfauuUfgCfcUfcAfgsUfsu |
| AD-52795.1 | A-109047.1 | AfgUfaUfgUfgUfAfAfaAfaUfcUfgUfaAf | A-108673.2 | uUfaCfaGfaUfuUfuuaCfaCfaUfaCfusCfsu |
| AD-52796.1 | A-109008.1 | GfaAfaAfcAfaAfgAfUfuGfgUfgUfuUfuUf | A-108595.2 | aAfaCfaCfcAfaAfucuUfuGfuUfuUfcsCfsg |
| AD-52797.1 | A-109016.1 | AfgUfgUfgGfaGfAfAfaAfcAfaCffcUfaAf | A-108611.2 | uUfaGfgUfuGfuUfuucUfcCfaCfaCfusCfsa |
| AD-52798.1 | A-109024.1 | GfuCfuCfaAfaAfUfGfgAfaGfgUfuAfuAf | A-108627.2 | uAfuAfaCfcUfuCfcauUfuUfgAfgAfcsUfsu |
| AD-52799.1 | A-109032.1 | GfaAfuGfaAfcUfGffAfgGfcAfaAfuUfuAf | A-108643.2 | uAfaUfuUfgCfcUfucaGfuUfcAfuUfcsAfsa |
| AD-52800.1 | A-109040.1 | UfgAfgGfcAfaAfuUfUfaAfaAfgGfcAfaAf | A-108659.2 | uUfgCfcUfuUfuAfaauUfuGfcCfuCfasGfsu |
| AD-52801.1 | A-109048.1 | GfuAfuGfuGfuAfAfAfaAfuCfuGfuAfuAf | A-108675.2 | aUfuAfcAfgAfuUfuuuAfcAfcAfuAfcsUfsc |
| AD-52802.1 | A-109009.1 | AfaAfaCfaAfaGfAfUfuGfgUfgUfuUfuUf | A-108597.2 | aAfaAfcAfcCfaAfaucUfuUfgUfuUfusCfsc |
| AD-52803.1 | A-109017.1 | GfuGfuGfgAfgAfAfAfaCfaAfcCfuAfaAf | A-108613.2 | uUfaGfgGfuUfgUfuuuCfuCfcAfcAfcsUfsc |
| AD-52804.1 | A-109025.1 | AfuGfgAfgGfuUfUfAfuAfcUfcUfaUfaAf | A-108629.2 | uUfaUfaGfaGfuAfuaaCfcUfuCfcAfusUfsu |
| AD-52805.1 | A-109033.1 | AfaUfgAfaCfuGfAfgGfCfaAfaUfuUfaAf | A-108645.2 | uUfaAfaUfuUfgCfcucAfgUfuCfaUfusCfsa |
| AD-52806.1 | A-109041.1 | GfaGfgCfaAfaUfUfUfaAfaAfgGfcAfaUf | A-108661.2 | aUfuGfcCfuUfuUfaaaUfuUfgCfcUfcsAfsg |
| AD-52807.1 | A-109049.1 | UfaUfgUfgUfaAfAfAfaUfcUfgUfaAfuAf | A-108677.2 | uAfuUfaCfaGfaUfuuuUfaCfaCfaUfasCfsu |
| AD-52808.1 | A-109010.1 | AfcAfaAfgAfuUfGfgUfgUfuUfuCfuAfAf | A-108599.2 | uAfgAfaAfaCfaCfcaaAfuCfuUfuGfusUfsu |
| AD-52809.1 | A-109018.1 | UfgUfgGfaGfaAfAfAfcAfaCfcUfaAfaUf | A-108615.2 | aUfuUfaGfgUfuGfuuuUfcUfcCfaCfasCfsu |
| AD-52810.1 | A-109026.1 | UfgGfaAfgGfuUfAfUfaCfuCfuAfuAfaAf | A-108631.2 | uUfuAfuAfgAfgUfauaAfcCfuUfcCfasUfsu |
| AD-52811.1 | A-109034.1 | AfuGfaAfcUfgAfGfGfcAfaAfuUfuAfaAf | A-108647.2 | uUfuAfaAfuUfuGfccuCfaGfuUfcAfusUfsc |
| AD-52812.1 | A-109042.1 | AfgGfcAfaAfuUfUfAfaAfaGfgCfaAfuAf | A-108663.2 | uAfuUfgCfcUfuUfuaaAfuUfuGfcCfusCfsa |
| AD-52813.1 | A-109011.1 | AfaGfaUfuUfgGfUfgUfuUfuCfuaCfuUf | A-108601.2 | aAfgUfaGfaAfaAfcacCfaAfaUfcUfusUfsg |
| AD-52814.1 | A-109019.1 | AfaAfcAfaCfcUfAfAfaUfgGfuAfaAfuAf | A-108617.2 | uAfuUfuAfcCfaUfuuaGfgUfuGfuUfusUfsc |
| AD-52815.1 | A-109027.1 | AfuAfcUfcUfaUfAfAfaAfuCfaAfcCfaAf | A-108633.2 | uUfgGfuUfgAfuUfuuaUfaGfaGfuAfusAfsa |
| AD-52816.1 | A-109035.1 | UfgAfaCfuGfaGfGfCfaAfaUfuUfaAfaAf | A-108649.2 | uUfuUfaAfaUfuUfgccUfcAfgUfuCfasUfsu |

TABLE 10-continued

Modified Sense and antisense strand sequences of ANGPTL3
dsRNAs without GalNa1 conjugation
These sequences are the same as the sequences listed in Table 8 except that
they do not contain GalNa1 conjugation.

| Duplex Name | Sense Oligo Name | Sense Sequence (SEQ ID NOS 1366-1546, respectively, in order of appearance) | Antisense OligoName | Antisense Oligo Sequence (SEQ ID NOS 1547-1727, respectively, in order of appearance) |
|---|---|---|---|---|
| AD-52817.1 | A-109043.1 | GfgCfaAfaUfuUfAfAfaAfgGfcAfaUfaAf | A-108665.2 | uUfaUfuGfcCfuUfuuaAfaUfuUfgCfcsUfsc |
| AD-52818.1 | A-109012.1 | UfuUfuCfuAfcUfUfGfgGfaUfcAfcAfaAf | A-108603.2 | uUfuGfuGfaUfcCfcaaGfuAfgAfaAfasCfsa |
| AD-52819.1 | A-109020.1 | AfaCfaAfcCfuAfAfAfuGfgUfaAfaUfaUf | A-108619.2 | aUfaUfuUfaCfcAfuuuAfgGfuUfgUfusUfsu |
| AD-52820.1 | A-109028.1 | UfaCfuCfuAfuAfAfAfaUfcAfaCfcAfaAf | A-108635.2 | uUfuGfgUfuGfaUfuuuAfuAfgAfgUfasUfsa |
| AD-52821.1 | A-109036.1 | GfaAfcUfgAfgGfCfAfaAfuUfuAfaAfaAf | A-108651.2 | uUfuUfuAfaAfuUfugcCfuCfaGfuUfcsAfsu |
| AD-52822.1 | A-109044.1 | CfaGfaGfuAfuGfUfGfuAfaAfaAfuCfuUf | A-108667.2 | aAfgAfuUfuUfuAfcacAfuAfcUfcUfgsUfsg |

TABLE 11

Results of single dose screen using ANGPTL3 GalNac-conjugated dsRNA
Modified siRNAs were tested by transfection in Hep3b cells and by free-
uptake in primary cynomolgus monkey (PCH) cells at the above-stated doses.

| DUPLEX ID | 10 nM (RNAimax) | 0.1 nM (RNAimax) | 500 nM PCH Celsis (FU) | 100 nM PCH Celsis (FU) | 10 nM PCH Celsis (FU) | STDEV 10 nM (RNAimax) | STDEV 0.1 nM (RNAimax) | STDEV 500 nM (FU) | STDEV 100 nM (FU) | STDEV 10 nM (FU) |
|---|---|---|---|---|---|---|---|---|---|---|
| AD1955/naïve FU | 0.93 | 0.93 | 1.01 | 0.91 | 1.17 | 0.02 | 0.08 | 0.09 | 0.00 | 0.07 |
| AD1955/naïve FU | 1.02 | 1.09 | 1.07 | 1.07 | 0.92 | 0.06 | 0.04 | 0.02 | 0.00 | 0.03 |
| AD1955/naïve FU | 1.06 | 0.99 | 0.93 | 1.02 | 0.93 | 0.03 | 0.00 | 0.09 | 0.01 | 0.02 |
| AD1955/naïve FU | 1.05 | 0.90 | 1.05 | 1.03 | 1.03 | 0.04 | 0.02 | 0.01 | 0.05 | 0.01 |
| AD1955/naïve FU | 1.06 | 1.08 | 0.90 | 0.97 | 1.03 | 0.02 | 0.01 | 0.02 | 0.04 | 0.09 |
| AD1955/naïve FU | 0.90 | 1.03 | 1.05 | 1.00 | 0.94 | 0.04 | 0.03 | 0.01 | 0.04 | 0.05 |
| AD-45165 (TTR) | 0.91 | 0.98 | 1.06 | 0.98 | 0.96 | 0.05 | 0.01 | 0.05 | 0.00 | 0.00 |
| AD-52953.1 | 0.06 | 0.34 | 0.15 | 0.17 | 0.46 | 0.00 | 0.01 | 0.00 | 0.01 | 0.01 |
| AD-52954.1 | 0.09 | 0.39 | 0.17 | 0.20 | 0.55 | 0.00 | 0.01 | 0.00 | 0.01 | 0.00 |
| AD-52955.1 | 0.11 | 0.59 | 0.38 | 0.41 | 0.75 | 0.01 | 0.04 | 0.02 | 0.01 | 0.12 |
| AD-52956.1 | 0.31 | 0.94 | 0.79 | 0.94 | 1.17 | 0.01 | 0.00 | 0.02 | 0.06 | 0.02 |
| AD-52957.1 | 0.13 | 0.61 | 0.35 | 0.38 | 0.73 | 0.01 | 0.00 | 0.01 | 0.00 | 0.04 |
| AD-52958.1 | 0.19 | 0.74 | 0.66 | 0.71 | 0.97 | 0.01 | 0.01 | 0.02 | 0.07 | 0.06 |
| AD-52960.1 | 0.14 | 0.59 | 0.31 | 0.32 | 0.55 | 0.01 | 0.01 | 0.00 | 0.02 | 0.02 |
| AD-52961.1 | 0.05 | 0.66 | 0.27 | 0.24 | 0.49 | 0.00 | 0.00 | 0.00 | 0.02 | 0.02 |
| AD-52962.1 | 0.83 | 0.89 | 1.03 | 1.02 | 1.26 | 0.02 | 0.05 | 0.07 | 0.07 | 0.07 |
| AD-52963.1 | 0.07 | 0.72 | 0.46 | 0.56 | 0.91 | 0.00 | 0.00 | 0.00 | 0.00 | 0.06 |
| AD-52964.1 | 0.13 | 0.73 | 0.41 | 0.47 | 0.68 | 0.01 | 0.03 | 0.02 | 0.03 | 0.01 |
| AD-52965.1 | 0.07 | 0.44 | 0.16 | 0.18 | 0.43 | 0.00 | 0.01 | 0.00 | 0.01 | 0.01 |
| AD-52966.1 | 0.12 | 0.76 | 0.67 | 0.72 | 0.96 | 0.00 | 0.02 | 0.05 | 0.01 | 0.01 |
| AD-52967.1 | 0.10 | 0.75 | 0.44 | 0.58 | 0.89 | 0.01 | 0.04 | 0.02 | 0.03 | 0.04 |
| AD-52968.1 | 1.01 | 0.96 | 0.87 | 0.91 | 1.15 | 0.00 | 0.01 | 0.09 | 0.03 | 0.02 |
| AD-52969.1 | 0.04 | 0.46 | 0.22 | 0.29 | 0.59 | 0.00 | 0.00 | 0.01 | 0.02 | 0.04 |
| AD-52970.1 | 0.06 | 0.45 | 0.27 | 0.30 | 0.51 | 0.00 | 0.00 | 0.01 | 0.02 | 0.00 |
| AD-52971.1 | 0.08 | 0.55 | 0.20 | 0.22 | 0.45 | 0.00 | 0.00 | 0.01 | 0.02 | 0.05 |
| AD-52972.1 | 0.10 | 0.73 | 0.41 | 0.49 | 0.81 | 0.00 | 0.01 | 0.01 | 0.02 | 0.01 |
| AD-52973.1 | 0.11 | 0.73 | 0.36 | 0.46 | 0.75 | 0.01 | 0.01 | 0.03 | 0.02 | 0.02 |
| AD-52974.1 | 1.00 | 0.95 | 1.00 | 1.09 | 1.27 | 0.01 | 0.01 | 0.08 | 0.05 | 0.06 |
| AD-52975.1 | 0.07 | 0.54 | 0.25 | 0.34 | 0.66 | 0.00 | 0.01 | 0.01 | 0.01 | 0.03 |
| AD-52976.1 | 0.17 | 0.59 | 0.35 | 0.41 | 0.65 | 0.00 | 0.02 | 0.04 | 0.01 | 0.01 |
| AD-52977.1 | 0.07 | 0.45 | 0.16 | 0.25 | 0.50 | 0.01 | 0.02 | 0.00 | 0.02 | 0.03 |
| AD-52978.1 | 0.10 | 0.72 | 0.39 | 0.53 | 0.77 | 0.00 | 0.02 | 0.00 | 0.08 | 0.03 |
| AD-52979.1 | 0.54 | 0.92 | 0.99 | 1.12 | 1.28 | 0.01 | 0.02 | 0.02 | 0.04 | 0.05 |
| AD-52980.1 | 0.29 | 0.85 | 0.67 | 0.85 | 1.03 | 0.01 | 0.01 | 0.05 | 0.05 | 0.04 |
| AD-52981.1 | 0.07 | 0.44 | 0.20 | 0.26 | 0.59 | 0.01 | 0.02 | 0.00 | 0.00 | 0.03 |
| AD-52982.1 | 0.28 | 0.87 | 0.67 | 0.99 | 1.14 | 0.01 | 0.01 | 0.04 | 0.00 | 0.01 |
| AD-52983.1 | 0.06 | 0.40 | 0.14 | 0.40 | 0.46 | 0.00 | 0.00 | 0.01 | 0.05 | 0.02 |
| AD-52984.1 | 0.29 | 0.87 | 0.66 | 0.74 | 1.09 | 0.01 | 0.02 | 0.01 | 0.00 | 0.00 |
| AD-52985.1 | 0.72 | 0.87 | 0.89 | 1.18 | 1.22 | 0.03 | 0.00 | 0.05 | 0.03 | 0.16 |
| AD-52986.1 | 0.08 | 0.47 | 0.24 | 0.30 | 0.48 | 0.00 | 0.02 | 0.02 | 0.00 | 0.02 |
| AD-52987.1 | 0.16 | 0.83 | 0.42 | 0.73 | 1.09 | 0.00 | 0.00 | 0.01 | 0.02 | 0.02 |
| AD-52988.1 | 0.11 | 0.73 | 0.42 | 0.60 | 0.96 | 0.01 | 0.04 | 0.00 | 0.00 | 0.10 |
| AD-52989.1 | 0.05 | 0.48 | 0.15 | 0.42 | 0.46 | 0.00 | 0.02 | 0.00 | 0.02 | 0.00 |
| AD-52990.1 | 0.14 | 0.86 | 0.33 | 0.45 | 0.77 | 0.00 | 0.01 | 0.00 | 0.02 | 0.05 |

TABLE 11-continued

Results of single dose screen using ANGPTL3 GalNac-conjugated dsRNA
Modified siRNAs were tested by transfection in Hep3b cells and by free-
uptake in primary cynomolgus monkey (PCH) cells at the above-stated doses.

| DUPLEX ID | 10 nM (RNAimax) | 0.1 nM (RNAimax) | 500 nM PCH Celsis (FU) | 100 nM PCH Celsis (FU) | 10 nM PCH Celsis (FU) | STDEV 10 nM (RNAimax) | STDEV 0.1 nM (RNAimax) | STDEV 500 nM (FU) | STDEV 100 nM (FU) | STDEV 10 nM (FU) |
|---|---|---|---|---|---|---|---|---|---|---|
| AD-52991.1 | 0.16 | 0.86 | 0.58 | 0.69 | 1.05 | 0.00 | 0.00 | 0.02 | 0.00 | 0.02 |
| AD-52992.1 | 0.08 | 0.65 | 0.42 | 0.56 | 0.90 | 0.00 | 0.01 | 0.02 | 0.01 | 0.00 |
| AD-52993.1 | 0.13 | 0.87 | 0.53 | 0.76 | 1.08 | 0.02 | 0.03 | 0.04 | 0.04 | 0.00 |
| AD-52994.1 | 0.10 | 0.52 | 0.28 | 0.33 | 0.53 | 0.01 | 0.00 | 0.02 | 0.00 | 0.01 |
| AD-52995.1 | 0.06 | 0.56 | 0.19 | 0.41 | 0.60 | 0.00 | 0.01 | 0.04 | 0.02 | 0.05 |
| AD-52996.1 | 0.09 | 0.68 | 0.26 | 0.47 | 0.68 | 0.00 | 0.03 | 0.01 | 0.04 | 0.01 |
| AD-52997.1 | 0.59 | 1.03 | 0.87 | 0.51 | 1.25 | 0.05 | 0.01 | 0.00 | 0.01 | 0.01 |
| AD-52998.1 | 0.09 | 0.79 | 0.44 | 0.55 | 0.85 | 0.00 | 0.00 | 0.04 | 0.03 | 0.10 |
| AD-52999.1 | 0.08 | 0.57 | 0.17 | 0.36 | 0.84 | 0.01 | 0.00 | 0.01 | 0.02 | 0.00 |
| AD-53000.1 | 0.38 | 0.94 | 0.58 | 0.67 | 0.85 | 0.01 | 0.02 | 0.03 | 0.03 | 0.02 |
| AD-53001.1 | 0.05 | 0.48 | 0.21 | 0.18 | 0.40 | 0.00 | 0.00 | 0.01 | 0.00 | 0.05 |
| AD-53002.1 | 0.07 | 0.65 | 0.43 | 0.48 | 0.80 | 0.00 | 0.05 | 0.04 | 0.01 | 0.02 |
| AD-53003.1 | 0.05 | 0.46 | 0.31 | 0.34 | 0.56 | 0.01 | 0.01 | 0.00 | 0.02 | 0.05 |
| AD-53004.1 | 0.05 | 0.36 | 0.29 | 0.66 | 0.57 | 0.00 | 0.01 | 0.03 | 0.35 | 0.02 |
| AD-53005.1 | 0.05 | 0.72 | 0.32 | 0.58 | 0.83 | 0.01 | 0.00 | 0.01 | 0.29 | 0.00 |
| AD-53006.1 | 0.21 | 0.82 | 0.66 | 0.77 | 1.03 | 0.01 | 0.00 | 0.02 | 0.07 | 0.02 |
| AD-53007.1 | 0.12 | 0.76 | 0.55 | 0.73 | 0.74 | 0.01 | 0.00 | 0.00 | 0.08 | 0.20 |
| AD-53008.1 | 0.07 | 0.68 | 0.28 | 0.36 | 0.84 | 0.00 | 0.02 | 0.01 | 0.05 | 0.03 |
| AD-53009.1 | 0.10 | 0.61 | 0.48 | 0.60 | 0.91 | 0.00 | 0.02 | 0.01 | 0.01 | 0.06 |
| AD-53010.1 | 0.05 | 0.58 | 0.47 | 0.54 | 0.84 | 0.00 | 0.02 | 0.00 | 0.02 | 0.03 |
| AD-53011.1 | 0.07 | 0.65 | 0.29 | 0.34 | 0.84 | 0.00 | 0.03 | 0.07 | 0.01 | 0.04 |
| AD-53012.1 | 0.06 | 0.55 | 0.36 | 0.45 | 0.70 | 0.00 | 0.03 | 0.02 | 0.02 | 0.00 |
| AD-53013.1 | 0.11 | 0.85 | 0.59 | 0.70 | 1.01 | 0.00 | 0.00 | 0.03 | 0.03 | 0.02 |
| AD-53014.1 | 0.16 | 0.78 | 0.61 | 0.78 | 1.11 | 0.00 | 0.02 | 0.01 | 0.05 | 0.00 |
| AD-53015.1 | 0.03 | 0.35 | 0.25 | 0.37 | 0.46 | 0.01 | 0.01 | 0.01 | 0.00 | 0.01 |
| AD-53016.1 | 0.03 | 0.56 | 0.40 | 0.58 | 1.01 | 0.00 | 0.01 | 0.02 | 0.06 | 0.09 |
| AD-53017.1 | 0.07 | 0.71 | 0.64 | 0.78 | 0.98 | 0.00 | 0.01 | 0.01 | 0.05 | 0.00 |
| AD-53018.1 | 0.30 | 0.96 | 0.75 | 0.97 | 1.14 | 0.00 | 0.02 | 0.02 | 0.03 | 0.05 |
| AD-53019.1 | 0.27 | 0.99 | 0.77 | 1.05 | 1.31 | 0.00 | 0.01 | 0.01 | 0.04 | 0.00 |
| AD-53020.1 | 0.04 | 0.64 | 0.32 | 0.45 | 0.69 | 0.00 | 0.00 | 0.03 | 0.02 | 0.03 |
| AD-53021.1 | 0.04 | 0.68 | 0.36 | 0.48 | 0.70 | 0.01 | 0.01 | 0.02 | 0.07 | 0.00 |
| AD-53022.1 | 0.05 | 0.76 | 0.36 | 0.59 | 1.04 | 0.01 | 0.01 | 0.02 | 0.03 | 0.06 |
| AD-53023.1 | 0.10 | 0.83 | 0.69 | 0.84 | 0.97 | 0.01 | 0.01 | 0.06 | 0.02 | 0.01 |
| AD-53024.1 | 0.09 | 0.44 | 0.23 | 0.23 | 0.44 | 0.00 | 0.00 | 0.03 | 0.01 | 0.02 |
| AD-53025.1 | 0.09 | 0.87 | 0.58 | 0.80 | 1.09 | 0.00 | 0.03 | 0.01 | 0.04 | 0.04 |
| AD-53026.1 | 0.05 | 0.60 | 0.35 | 0.46 | 0.77 | 0.01 | 0.01 | 0.02 | 0.05 | 0.03 |
| AD-53027.1 | 0.02 | 0.32 | 0.26 | 0.30 | 0.45 | 0.00 | 0.01 | 0.02 | 0.03 | 0.02 |
| AD-53028.1 | 0.19 | 0.82 | 0.77 | 0.95 | 1.04 | 0.01 | 0.04 | 0.05 | 0.01 | 0.03 |
| AD-53029.1 | 0.02 | 0.52 | 0.32 | 0.41 | 0.72 | 0.00 | 0.00 | 0.01 | 0.02 | 0.07 |
| AD-53030.1 | 0.09 | 0.42 | 0.15 | 0.16 | 0.46 | 0.00 | 0.00 | 0.00 | 0.00 | 0.02 |
| AD-53031.1 | 0.12 | 0.79 | 0.63 | 0.73 | 1.04 | 0.01 | 0.02 | 0.05 | 0.02 | 0.04 | 0.03 |
| AD-53032.1 | 0.12 | 0.71 | 0.41 | 0.59 | 0.90 | 0.01 | 0.00 | 0.02 | 0.04 | 0.00 |
| AD-53033.1 | 0.02 | 0.48 | 0.20 | 0.21 | 0.51 | 0.00 | 0.02 | 0.02 | 0.01 | 0.00 |
| AD-53034.1 | 0.04 | 0.52 | 0.31 | 0.36 | 0.71 | 0.00 | 0.01 | 0.07 | 0.02 | 0.01 |
| AD-53035.1 | 0.02 | 0.63 | 0.34 | 0.50 | 0.85 | 0.00 | 0.02 | 0.03 | 0.00 | 0.03 |
| AD-53036.1 | 0.10 | 0.57 | 0.31 | 0.35 | 0.65 | 0.01 | 0.01 | 0.03 | 0.03 | 0.01 |
| AD-53037.1 | 0.08 | 0.47 | 0.27 | 0.36 | 0.60 | 0.00 | 0.02 | 0.01 | 0.03 | 0.01 |
| AD-53038.1 | 0.05 | 0.85 | 0.48 | 0.63 | 1.08 | 0.00 | 0.05 | 0.00 | 0.02 | 0.05 |
| AD-53039.1 | 0.08 | 0.82 | 0.45 | 0.64 | 0.97 | 0.00 | 0.01 | 0.01 | 0.03 | 0.00 |
| AD-53040.1 | 0.05 | 0.79 | 0.46 | 0.62 | 0.97 | 0.01 | 0.01 | 0.01 | 0.05 | 0.06 |
| AD-53041.1 | 0.06 | 0.72 | 0.59 | 0.61 | 0.86 | 0.00 | 0.01 | 0.05 | 0.06 | 0.03 |
| AD-53042.1 | 0.08 | 0.85 | 0.30 | 0.35 | 0.81 | 0.01 | 0.00 | 0.00 | 0.03 | 0.03 |
| AD-53043.1 | 0.63 | 1.00 | 0.92 | 1.04 | 1.07 | 0.03 | 0.00 | 0.06 | 0.03 | 0.07 |
| AD-53044.1 | 0.05 | 0.91 | 0.35 | 0.49 | 0.97 | 0.01 | 0.01 | 0.01 | 0.04 | 0.02 |
| AD-53045.1 | 0.20 | 1.00 | 0.85 | 1.00 | 0.98 | 0.00 | 0.03 | 0.04 | 0.01 | 0.04 |
| AD-53046.1 | 0.07 | 0.70 | 0.44 | 0.62 | 1.12 | 0.00 | 0.01 | 0.03 | 0.00 | 0.09 |
| AD-53059.1 | 0.35 | 1.04 | 0.75 | 0.85 | 0.86 | 0.01 | 0.01 | 0.03 | 0.02 | 0.04 |
| AD-53060.1 | 0.34 | 0.85 | 0.72 | 0.96 | 0.82 | 0.00 | 0.01 | 0.02 | 0.01 | 0.02 |
| AD-53061.1 | 0.17 | 0.94 | 0.36 | 0.37 | 0.59 | 0.00 | 0.00 | 0.02 | 0.00 | 0.02 |
| AD-53062.1 | 0.09 | 0.76 | 0.43 | 0.47 | 0.69 | 0.01 | 0.01 | 0.01 | 0.03 | 0.01 |
| AD-53063.1 | 0.06 | 0.48 | 0.18 | 0.16 | 0.25 | 0.00 | 0.01 | 0.01 | 0.01 | 0.02 |
| AD-53064.1 | 0.07 | 0.59 | 0.22 | 0.22 | 0.48 | 0.01 | 0.02 | 0.01 | 0.02 | 0.06 |
| AD-53065.1 | 0.08 | 0.97 | 0.45 | 0.39 | 0.64 | 0.01 | 0.01 | 0.02 | 0.01 | 0.01 |
| AD-53066.1 | 0.12 | 0.99 | 0.73 | 0.67 | 0.88 | 0.01 | 0.03 | 0.01 | 0.01 | 0.05 |
| AD-53067.1 | 0.12 | 1.08 | 0.59 | 0.60 | 0.79 | 0.00 | 0.12 | 0.01 | 0.01 | 0.03 |
| AD-53068.1 | 0.09 | 0.98 | 0.46 | 0.59 | 0.83 | 0.00 | 0.03 | 0.04 | 0.07 | 0.05 |
| AD-53069.1 | 0.04 | 0.69 | 0.35 | 0.43 | 0.59 | 0.00 | 0.01 | 0.01 | 0.04 | 0.01 |
| AD-53070.1 | 0.17 | 1.12 | 0.88 | 0.83 | 0.98 | 0.00 | 0.01 | 0.04 | 0.00 | 0.01 |
| AD-53071.1 | 0.07 | 0.70 | 0.23 | 0.23 | 0.43 | 0.00 | 0.00 | 0.02 | 0.00 | 0.01 |
| AD-53072.1 | 0.10 | 0.90 | 0.49 | 0.48 | 0.75 | 0.01 | 0.05 | 0.00 | 0.01 | 0.02 |
| AD-53073.1 | 0.07 | 0.63 | 0.27 | 0.30 | 0.43 | 0.00 | 0.00 | 0.01 | 0.01 | 0.00 |

TABLE 11-continued

Results of single dose screen using ANGPTL3 GalNac-conjugated dsRNA
Modified siRNAs were tested by transfection in Hep3b cells and by free-
uptake in primary cynomolgus monkey (PCH) cells at the above-stated doses.

| DUPLEX ID | 10 nM (RNAimax) | 0.1 nM (RNAimax) | 500 nM PCH Celsis (FU) | 100 nM PCH Celsis (FU) | 10 nM PCH Celsis (FU) | STDEV 10 nM (RNAimax) | STDEV 0.1 nM (RNAimax) | STDEV 500 nM (FU) | STDEV 100 nM (FU) | STDEV 10 nM (FU) |
|---|---|---|---|---|---|---|---|---|---|---|
| AD-53074.1 | 0.07 | 0.88 | 0.46 | 0.49 | 0.62 | 0.01 | 0.08 | 0.01 | 0.06 | 0.03 |
| AD-53075.1 | 0.05 | 0.76 | 0.29 | 0.35 | 0.50 | 0.01 | 0.01 | 0.00 | 0.02 | 0.03 |
| AD-53076.1 | 0.09 | 0.80 | 0.31 | 0.40 | 0.54 | 0.01 | 0.01 | 0.02 | 0.05 | 0.02 |
| AD-53077.1 | 0.07 | 0.96 | 0.29 | 0.28 | 0.49 | 0.00 | 0.03 | 0.00 | 0.01 | 0.01 |
| AD-53078.1 | 0.16 | 0.95 | 0.51 | 0.51 | 0.70 | 0.00 | 0.04 | 0.01 | 0.01 | 0.06 |
| AD-53079.1 | 0.08 | 0.96 | 0.59 | 0.67 | 0.83 | 0.00 | 0.02 | 0.01 | 0.03 | 0.01 |
| AD-53080.1 | 0.04 | 0.63 | 0.20 | 0.22 | 0.43 | 0.00 | 0.01 | 0.00 | 0.01 | 0.01 |
| AD-53081.1 | 0.16 | 1.02 | 0.63 | 0.75 | 0.87 | 0.00 | 0.09 | 0.00 | 0.02 | 0.05 |
| AD-53082.1 | 0.06 | 0.94 | 0.50 | 0.52 | 0.66 | 0.01 | 0.06 | 0.02 | 0.03 | 0.03 |
| AD-53083.1 | 0.14 | 0.87 | 0.48 | 0.50 | 0.80 | 0.01 | 0.02 | 0.04 | 0.06 | 0.01 |
| AD-53084.1 | 0.12 | 0.95 | 0.50 | 0.47 | 0.72 | 0.01 | 0.03 | 0.04 | 0.00 | 0.00 |
| AD-53085.1 | 0.27 | 1.02 | 0.68 | 0.81 | 0.99 | 0.01 | 0.01 | 0.01 | 0.05 | 0.02 |
| AD-53086.1 | 0.05 | 0.60 | 0.26 | 0.25 | 0.48 | 0.00 | 0.01 | 0.03 | 0.00 | 0.01 |
| AD-53087.1 | 0.05 | 0.56 | 0.32 | 0.39 | 0.53 | 0.00 | 0.01 | 0.01 | 0.03 | 0.02 |
| AD-53088.1 | 0.09 | 0.89 | 0.53 | 0.69 | 0.87 | 0.00 | 0.01 | 0.02 | 0.04 | 0.02 |
| AD-53089.1 | 0.29 | 0.97 | 0.58 | 0.57 | 0.78 | 0.01 | 0.00 | 0.02 | 0.02 | 0.02 |
| AD-53090.1 | 0.13 | 0.86 | 0.56 | 0.55 | 0.73 | 0.00 | 0.01 | 0.01 | 0.03 | 0.00 |
| AD-53091.1 | 0.12 | 0.82 | 0.27 | 0.35 | 0.66 | 0.00 | 0.03 | 0.03 | 0.01 | 0.07 |
| AD-53092.1 | 0.05 | 0.66 | 0.26 | 0.29 | 0.42 | 0.00 | 0.01 | 0.02 | 0.04 | 0.02 |
| AD-53093.1 | 0.08 | 0.68 | 0.36 | 0.44 | 0.55 | 0.00 | 0.02 | 0.03 | 0.04 | 0.10 |
| AD-53094.1 | 0.32 | 1.00 | 1.05 | 0.92 | 1.11 | 0.02 | 0.01 | 0.01 | 0.00 | 0.03 |
| AD-53095.1 | 0.14 | 0.77 | 0.29 | 0.29 | 0.49 | 0.00 | 0.02 | 0.00 | 0.01 | 0.01 |
| AD-53096.1 | 0.30 | 0.96 | 0.61 | 0.57 | 0.73 | 0.03 | 0.01 | 0.02 | 0.02 | 0.01 |
| AD-53097.1 | 0.37 | 0.97 | 0.67 | 0.82 | 0.86 | 0.01 | 0.01 | 0.01 | 0.02 | 0.01 |
| AD-53098.1 | 0.06 | 0.65 | 0.22 | 0.30 | 0.43 | 0.00 | 0.03 | 0.03 | 0.00 | 0.01 |
| AD-53099.1 | 0.34 | 0.99 | 0.61 | 0.81 | 0.91 | 0.00 | 0.00 | 0.04 | 0.02 | 0.06 |
| AD-53100.1 | 0.31 | 1.04 | 0.95 | 1.03 | 1.00 | 0.02 | 0.01 | 0.06 | 0.02 | 0.17 |
| AD-53101.1 | 0.46 | 0.93 | 0.63 | 0.69 | 0.78 | 0.00 | 0.01 | 0.04 | 0.03 | 0.04 |
| AD-53102.1 | 0.23 | 0.80 | 0.60 | 0.55 | 0.66 | 0.00 | 0.03 | 0.01 | 0.02 | 0.03 |
| AD-53103.1 | 0.05 | 0.61 | 0.27 | 0.32 | 0.50 | 0.01 | 0.02 | 0.00 | 0.01 | 0.00 |
| AD-53104.1 | 0.13 | 0.80 | 0.64 | 0.68 | 0.77 | 0.00 | 0.02 | 0.03 | 0.01 | 0.05 |
| AD-53105.1 | 0.15 | 0.77 | 0.43 | 0.65 | 0.77 | 0.01 | 0.03 | 0.02 | 0.02 | 0.05 |
| AD-53106.1 | 0.16 | 0.87 | 0.72 | 0.70 | 0.83 | 0.01 | 0.02 | 0.00 | 0.00 | 0.04 |
| AD-53107.1 | 0.19 | 0.95 | 0.62 | 0.65 | 0.90 | 0.00 | 0.02 | 0.01 | 0.03 | 0.04 |
| AD-53108.1 | 0.22 | 0.94 | 0.60 | 0.68 | 0.81 | 0.00 | 0.01 | 0.00 | 0.03 | 0.04 |
| AD-53109.1 | 0.16 | 1.01 | 0.82 | 0.78 | 0.96 | 0.01 | 0.08 | 0.04 | 0.01 | 0.07 |
| AD-53110.1 | 0.10 | 0.86 | 0.79 | 0.77 | 0.94 | 0.00 | 0.05 | 0.03 | 0.01 | 0.05 |
| AD-53111.1 | 0.22 | 0.78 | 0.94 | 0.85 | 1.04 | 0.01 | 0.01 | 0.01 | 0.01 | 0.07 |
| AD-53112.1 | 0.09 | 0.96 | 0.64 | 0.65 | 0.86 | 0.01 | 0.02 | 0.07 | 0.07 | 0.00 |
| AD-53113.1 | 0.10 | 0.97 | 0.71 | 0.77 | 0.88 | 0.01 | 0.05 | 0.01 | 0.02 | 0.01 |
| AD-53114.1 | 0.19 | 0.83 | 0.48 | 0.52 | 0.66 | 0.01 | 0.01 | 0.02 | 0.01 | 0.00 |
| AD-53115.1 | 0.10 | 0.59 | 0.42 | 0.44 | 0.66 | 0.01 | 0.03 | 0.04 | 0.00 | 0.02 |
| AD-53116.1 | 0.11 | 0.87 | 0.82 | 0.85 | 0.95 | 0.00 | 0.05 | 0.05 | 0.05 | 0.05 |
| AD-53117.1 | 0.52 | 0.64 | 1.21 | 1.00 | 1.08 | 0.01 | 0.03 | 0.09 | 0.04 | 0.07 |
| AD-53118.1 | 0.19 | 1.04 | 0.60 | 0.72 | 0.94 | 0.00 | 0.07 | 0.02 | 0.05 | 0.06 |
| AD-53119.1 | 0.06 | 0.77 | 0.44 | 0.47 | 0.64 | 0.01 | 0.03 | 0.00 | 0.01 | 0.01 |
| AD-53120.1 | 0.10 | 0.97 | 0.78 | 0.89 | 1.01 | 0.01 | 0.04 | 0.05 | 0.01 | 0.04 |
| AD-53121.1 | 0.23 | 0.80 | 0.58 | 0.69 | 0.90 | 0.01 | 0.02 | 0.04 | 0.02 | 0.06 |
| AD-53122.1 | 0.09 | 0.80 | 0.90 | 0.94 | 1.09 | 0.01 | 0.07 | 0.02 | 0.04 | 0.10 |
| AD-53123.1 | 0.27 | 0.74 | 0.95 | 0.93 | 0.97 | 0.00 | 0.01 | 0.03 | 0.01 | 0.08 |
| AD-53124.1 | 0.08 | 0.81 | 0.33 | 0.34 | 0.61 | 0.01 | 0.02 | 0.00 | 0.01 | 0.01 |
| AD-53125.1 | 0.08 | 0.82 | 0.34 | 0.38 | 0.58 | 0.00 | 0.02 | 0.00 | 0.01 | 0.07 |
| AD-53126.1 | 0.15 | 0.95 | 0.70 | 0.86 | 1.06 | 0.01 | 0.04 | 0.05 | 0.02 | 0.00 |
| AD-53127.1 | 0.21 | 0.81 | 0.62 | 0.75 | 0.91 | 0.02 | 0.04 | 0.01 | 0.03 | 0.00 |
| AD-53128.1 | 0.08 | 0.79 | 0.80 | 1.14 | 1.09 | 0.00 | 0.06 | 0.04 | 0.01 | 0.03 |
| AD-53129.1 | 0.48 | 0.78 | 1.05 | 1.00 | 1.10 | 0.00 | 0.01 | 0.06 | 0.01 | 0.03 |
| AD-53130.1 | 0.25 | 1.08 | 0.63 | 0.72 | 0.88 | 0.01 | 0.02 | 0.00 | 0.01 | 0.00 |
| AD-53131.1 | 0.14 | 0.96 | 0.54 | 0.57 | 0.81 | 0.02 | 0.02 | 0.05 | 0.01 | 0.04 |
| AD-53132.1 | 0.03 | 0.54 | 0.24 | 0.27 | 0.49 | 0.00 | 0.02 | 0.02 | 0.00 | 0.01 |
| AD-53133.1 | 0.12 | 0.76 | 0.50 | 0.67 | 0.93 | 0.00 | 0.03 | 0.01 | 0.01 | 0.06 |
| AD-53134.1 | 0.28 | 0.86 | 1.14 | 0.81 | 0.97 | 0.01 | 0.04 | 0.05 | 0.02 | 0.04 |
| AD-53135.1 | 0.47 | 0.74 | 1.03 | 0.94 | 1.09 | 0.01 | 0.03 | 0.04 | 0.07 | 0.04 |
| AD-53136.1 | 0.09 | 0.99 | 0.64 | 0.69 | 0.94 | 0.01 | 0.05 | 0.01 | 0.05 | 0.02 |
| AD-53137.1 | 0.08 | 0.75 | 0.39 | 0.39 | 0.59 | 0.01 | 0.03 | 0.00 | 0.00 | 0.00 |
| AD-53138.1 | 0.04 | 0.71 | 0.33 | 0.34 | 0.60 | 0.00 | 0.02 | 0.00 | 0.03 | 0.00 |
| AD-53139.1 | 0.11 | 0.76 | 0.55 | 0.66 | 0.84 | 0.01 | 0.01 | 0.06 | 0.01 | 0.02 |
| AD-53140.1 | 0.09 | 0.71 | 0.64 | 0.71 | 0.86 | 0.00 | 0.04 | 0.01 | 0.02 | 0.02 |
| AD-53141.1 | 0.24 | 1.09 | 0.77 | 0.91 | 0.93 | 0.00 | 0.01 | 0.00 | 0.06 | 0.00 |
| AD-53142.1 | 0.13 | 0.95 | 0.55 | 0.70 | 0.82 | 0.01 | 0.03 | 0.03 | 0.04 | 0.02 |
| AD-53143.1 | 0.13 | 0.91 | 0.67 | 0.83 | 0.94 | 0.01 | 0.00 | 0.03 | 0.03 | 0.07 |
| AD-53144.1 | 0.10 | 0.72 | 0.54 | 0.69 | 0.84 | 0.01 | 0.03 | 0.01 | 0.03 | 0.00 |

TABLE 11-continued

Results of single dose screen using ANGPTL3 GalNac-conjugated dsRNA
Modified siRNAs were tested by transfection in Hep3b cells and by free-
uptake in primary cynomolgus monkey (PCH) cells at the above-stated doses.

| DUPLEX ID | 10 nM (RNAimax) | 0.1 nM (RNAimax) | 500 nM PCH Celsis (FU) | 100 nM PCH Celsis (FU) | 10 nM PCH Celsis (FU) | STDEV 10 nM (RNAimax) | STDEV 0.1 nM (RNAimax) | STDEV 500 nM (FU) | STDEV 100 nM (FU) | STDEV 10 nM (FU) |
|---|---|---|---|---|---|---|---|---|---|---|
| AD-53145.1 | 0.08 | 0.72 | 0.70 | 0.78 | 0.88 | 0.01 | 0.03 | 0.01 | 0.08 | 0.02 |
| AD-53146.1 | 0.83 | 1.07 | 0.85 | 0.96 | 0.98 | 0.01 | 0.06 | 0.00 | 0.05 | 0.00 |
| AD-53147.1 | 0.08 | 0.56 | 0.27 | 0.34 | 0.47 | 0.00 | 0.01 | 0.01 | 0.01 | 0.01 |
| AD-53148.1 | 0.06 | 0.81 | 0.61 | 0.68 | 0.74 | 0.01 | 0.00 | 0.03 | 0.06 | 0.05 |
| AD-53149.1 | 0.23 | 0.86 | 0.71 | 0.83 | 0.92 | 0.01 | 0.02 | 0.06 | 0.02 | 0.03 |
| AD-53150.1 | 0.41 | 0.70 | 1.03 | 1.09 | 1.03 | 0.03 | 0.06 | 0.03 | 0.04 | 0.01 |

TABLE 12

Dose response screen results for ANGPTL3
GalNac-conjugated dsRNA sequences
A subset of active siRNAs from the single dose screen (refer to
data in Table 11) was tested in a dose response experiment by
free uptake in PCH cells. A subset of these active siRNAs was
also tested in dose response in Hep3B cells by transfection.

| | IC$_{50}$ (nM) | |
|---|---|---|
| | Free uptake | Transfection (RNAiMax) |
| AD-53063.1 | 1.60 | 0.03 |
| AD-53001.1 | 2.27 | 0.01 |
| AD-53015.1 | 2.90 | 0.02 |
| AD-52953.1 | 2.94 | 0.03 |
| AD-52986.1 | 3.30 | 0.03 |
| AD-53024.1 | 3.42 | 0.02 |
| AD-53033.1 | 3.42 | 0.02 |
| AD-53027.1 | 3.84 | 0.01 |
| AD-53030.1 | 3.90 | 0.03 |
| AD-53080.1 | 4.08 | 0.04 |
| AD-53073.1 | 4.20 | 0.05 |
| AD-52965.1 | 4.63 | ND |
| AD-53092.1 | 5.37 | ND |
| AD-53132.1 | 5.54 | ND |
| AD-52983.1 | 5.55 | ND |
| AD-52954.1 | 5.67 | ND |
| AD-52961.1 | 6.37 | ND |
| AD-52994.1 | 6.43 | ND |
| AD-53098.1 | 6.58 | ND |
| AD-52970.1 | 6.71 | ND |
| AD-53075.1 | 6.74 | ND |
| AD-53086.1 | 7.08 | ND |
| AD-52971.1 | 7.50 | ND |
| AD-53064.1 | 8.33 | ND |
| AD-53147.1 | 8.34 | ND |
| AD-52969.1 | 8.86 | ND |
| AD-53077.1 | 8.98 | ND |
| AD-52981.1 | 9.44 | ND |
| AD-52977.1 | 10.45 | ND |
| AD-53071.1 | 11.19 | ND |
| AD-52960.1 | 13.03 | ND |
| AD-53095.1 | 21.31 | ND |
| AD-53103.1 | 21.92 | ND |

TABLE 13

Results of single dose screen using sequences listed in Table 10.

| Duplex | 10 nM | 0.1 nM | 0.025 nM | STDEV 10 nM | STDEV 0.1 nM | STDEV 0.025 nM |
|---|---|---|---|---|---|---|
| AD-52719.1 | 0.01 | 0.60 | 0.35 | 0.000 | 0.093 | 0.002 |
| AD-52717.1 | 0.02 | 0.31 | 0.32 | 0.001 | 0.014 | 0.008 |
| AD-52713.1 | 0.02 | 0.37 | 0.36 | 0.001 | 0.011 | 0.007 |
| AD-52711.1 | 0.03 | 0.22 | 0.23 | 0.005 | 0.011 | 0.009 |
| AD-52718.1 | 0.03 | 0.31 | 0.39 | 0.000 | 0.025 | 0.023 |
| AD-52687.1 | 0.03 | 0.37 | 0.38 | 0.005 | 0.020 | 0.002 |
| AD-52699.1 | 0.03 | 0.25 | 0.21 | 0.002 | 0.011 | 0.002 |
| AD-52679.1 | 0.03 | 0.51 | 0.24 | | 0.345 | 0.008 |
| AD-52689.1 | 0.03 | 0.44 | 0.42 | 0.000 | 0.039 | 0.002 |
| AD-52700.1 | 0.03 | 0.56 | 0.57 | 0.005 | 0.044 | 0.020 |
| AD-52637.1 | 0.04 | 0.27 | 0.23 | 0.001 | 0.003 | 0.005 |
| AD-52730.1 | 0.04 | 0.61 | 0.59 | 0.005 | 0.053 | 0.014 |
| AD-52725.1 | 0.04 | 0.62 | 0.61 | 0.002 | 0.027 | 0.012 |
| AD-52688.1 | 0.04 | 0.23 | 0.20 | 0.006 | 0.012 | 0.011 |
| AD-52661.1 | 0.04 | 0.61 | 0.25 | 0.001 | 0.449 | 0.009 |
| AD-52667.1 | 0.04 | 0.28 | 0.22 | 0.004 | 0.018 | 0.013 |
| AD-52665.1 | 0.04 | 0.43 | 0.48 | 0.007 | 0.019 | 0.009 |
| AD-52638.1 | 0.04 | 0.28 | 0.25 | 0.000 | 0.016 | 0.027 |
| AD-52724.1 | 0.05 | 0.86 | 0.76 | 0.001 | 0.055 | 0.011 |
| AD-52705.1 | 0.05 | 0.74 | 0.65 | 0.004 | 0.022 | 0.016 |
| AD-52708.1 | 0.05 | 0.53 | 0.52 | 0.001 | 0.034 | 0.013 |
| AD-52659.1 | 0.05 | 0.56 | 0.48 | 0.000 | 0.000 | 0.033 |
| AD-52678.1 | 0.05 | 0.53 | 0.53 | 0.002 | 0.034 | 0.000 |
| AD-52670.1 | 0.05 | 0.35 | 0.33 | 0.002 | 0.009 | 0.003 |
| AD-52695.1 | 0.05 | 0.63 | 0.67 | 0.001 | 0.012 | 0.013 |
| AD-52704.1 | 0.05 | 0.55 | 0.53 | 0.002 | 0.005 | 0.034 |
| AD-52683.1 | 0.05 | 0.36 | 0.28 | 0.002 | 0.021 | 0.011 |
| AD-52673.1 | 0.05 | 0.22 | 0.19 | 0.023 | 0.010 | 0.002 |
| AD-52721.1 | 0.05 | 0.60 | 0.53 | 0.003 | 0.006 | 0.029 |
| AD-52710.1 | 0.05 | 0.56 | 0.40 | 0.007 | 0.073 | 0.000 |
| AD-52714.1 | 0.05 | 0.40 | 0.51 | 0.000 | 0.016 | 0.003 |
| AD-52686.1 | 0.05 | 0.57 | 0.60 | 0.003 | 0.014 | 0.000 |
| AD-52645.1 | 0.05 | 0.62 | 0.59 | 0.004 | 0.030 | 0.003 |
| AD-52662.1 | 0.05 | 0.55 | 0.52 | 0.002 | 0.030 | 0.008 |
| AD-52720.1 | 0.05 | 0.50 | 0.46 | 0.003 | 0.007 | 0.011 |
| AD-52654.1 | 0.05 | 0.29 | 0.36 | 0.008 | 0.037 | 0.014 |
| AD-52680.1 | 0.06 | 0.48 | 0.41 | 0.001 | 0.019 | 0.026 |
| AD-52723.1 | 0.06 | 0.84 | 0.76 | 0.001 | 0.041 | 0.004 |
| AD-52726.1 | 0.06 | 0.72 | 0.66 | 0.003 | 0.028 | 0.016 |
| AD-52701.1 | 0.06 | 0.67 | 0.39 | 0.001 | 0.003 | 0.002 |
| AD-52694.1 | 0.06 | 0.68 | 0.59 | 0.004 | 0.040 | 0.012 |
| AD-52685.1 | 0.06 | 0.30 | 0.25 | 0.002 | 0.013 | 0.016 |
| AD-52728.1 | 0.06 | 0.80 | 0.79 | 0.005 | 0.043 | 0.015 |
| AD-52676.1 | 0.06 | 0.68 | 0.67 | 0.002 | 0.023 | 0.029 |
| AD-52639.1 | 0.06 | 0.47 | 0.45 | 0.000 | 0.005 | 0.007 |
| AD-52722.1 | 0.06 | 0.81 | 0.93 | 0.005 | 0.004 | 0.027 |
| AD-52682.1 | 0.06 | 0.87 | 0.73 | 0.009 | 0.038 | 0.014 |
| AD-52660.1 | 0.07 | 0.69 | 0.68 | 0.002 | 0.014 | 0.017 |
| AD-52709.1 | 0.07 | 0.89 | 0.82 | 0.001 | 0.013 | 0.020 |
| AD-52643.1 | 0.07 | 0.27 | 0.24 | 0.006 | 0.016 | 0.012 |
| AD-52696.1 | 0.07 | 0.53 | 0.46 | 0.003 | 0.026 | 0.007 |
| AD-52657.1 | 0.08 | 0.60 | 0.58 | 0.008 | 0.030 | 0.006 |
| AD-52706.1 | 0.08 | 0.84 | 0.78 | 0.001 | 0.021 | 0.019 |
| AD-52653.1 | 0.08 | 0.41 | 0.45 | 0.057 | 0.004 | 0.029 |
| AD-52656.1 | 0.08 | 0.65 | 0.50 | 0.004 | 0.022 | 0.012 |
| AD-52693.1 | 0.09 | 0.61 | 0.62 | 0.007 | 0.021 | 0.018 |
| AD-52692.1 | 0.09 | 0.54 | 0.52 | 0.023 | 0.018 | 0.033 |
| AD-52674.1 | 0.10 | 0.79 | 0.64 | 0.001 | 0.008 | 0.028 |
| AD-52648.1 | 0.10 | 0.67 | 0.53 | 0.002 | 0.013 | 0.028 |

TABLE 13-continued

Results of single dose screen using sequences listed in Table 10.

| Duplex | 10 nM | 0.1 nM | 0.025 nM | STDEV 10 nM | STDEV 0.1 nM | STDEV 0.025 nM |
|---|---|---|---|---|---|---|
| AD-52651.1 | 0.10 | 0.84 | 0.73 | 0.000 | 0.000 | 0.007 |
| AD-52641.1 | 0.10 | 0.62 | 0.50 | 0.004 | 0.172 | 0.002 |
| AD-52707.1 | 0.10 | 0.92 | 0.81 | 0.001 | 0.018 | 0.032 |
| AD-52671.1 | 0.11 | 0.87 | 0.84 | 0.005 | 0.034 | 0.025 |
| AD-52650.1 | 0.12 | 0.88 | 0.94 | 0.007 | 0.013 | 0.041 |
| AD-52642.1 | 0.12 | 0.90 | 0.76 | 0.015 | 0.022 | 0.004 |
| AD-52675.1 | 0.13 | 0.94 | 0.89 | 0.001 | 0.018 | 0.044 |
| AD-52647.1 | 0.13 | 0.80 | 0.79 | 0.031 | 0.008 | 0.023 |
| AD-52716.1 | 0.14 | 0.61 | 0.69 | 0.010 | 0.060 | 0.013 |
| AD-52649.1 | 0.14 | 0.31 | 0.29 | 0.136 | 0.020 | 0.006 |
| AD-52677.1 | 0.16 | 1.01 | 0.72 | 0.059 | 0.040 | 0.007 |
| AD-52697.1 | 0.16 | 0.86 | 0.77 | 0.012 | 0.021 | 0.015 |
| AD-52715.1 | 0.17 | 0.90 | 0.89 | 0.005 | 0.009 | 0.022 |
| AD-52691.1 | 0.18 | 0.93 | 0.88 | 0.004 | 0.036 | 0.017 |
| AD-52698.1 | 0.20 | 0.97 | 0.87 | 0.010 | 0.028 | 0.000 |
| AD-52672.1 | 0.20 | 0.70 | 0.66 | 0.170 | 0.014 | 0.019 |
| AD-52712.1 | 0.29 | 0.92 | 0.90 | 0.007 | 0.036 | 0.004 |
| AD-52690.1 | 0.30 | 0.95 | 0.85 | 0.115 | 0.032 | 0.004 |
| AD-52640.1 | 0.30 | 1.04 | 0.91 | 0.018 | 0.046 | 0.013 |
| AD-52684.1 | 0.31 | 0.90 | 0.94 | 0.014 | 0.018 | 0.014 |
| AD-52666.1 | 0.32 | 1.04 | 0.91 | 0.013 | 0.005 | 0.004 |
| AD-52703.1 | 0.32 | 1.02 | 0.96 | 0.016 | 0.015 | 0.005 |
| AD-52729.1 | 0.33 | 1.02 | 0.87 | 0.032 | 0.020 | 0.008 |
| AD-52668.1 | 0.35 | 0.94 | 0.90 | 0.029 | 0.046 | 0.026 |
| AD-52681.1 | 0.57 | 1.00 | 0.99 | 0.003 | 0.034 | 0.039 |
| AD-52702.1 | 0.72 | 1.02 | 0.92 | 0.658 | 0.060 | 0.014 |
| AD-52727.1 | 0.73 | 1.03 | 0.91 | 0.004 | 0.065 | 0.027 |
| AD-52663.1 | 0.78 | 1.05 | 0.96 | 0.027 | 0.010 | 0.005 |
| AD-52669.1 | 0.91 | 0.91 | 0.94 | 0.004 | 0.049 | 0.032 |
| AD-1955 | 0.95 | 0.84 | 0.95 | 0.005 | 0.021 | 0.019 |
| AD-1955 | 0.97 | 1.07 | 1.03 | 0.000 | 0.021 | 0.015 |
| AD-1955 | 1.01 | 1.08 | 1.01 | 0.035 | 0.011 | 0.005 |
| mock | 1.02 | 0.96 | 0.97 | 0.030 | 0.037 | 0.005 |
| AD-1955 | 1.08 | 1.03 | 1.02 | 0.032 | 0.051 | 0.005 |
| AD-52652.1 | 1.13 | 1.11 | 1.02 | 0.028 | 0.043 | 0.020 |
| AD-52658.1 | 1.33 | 1.10 | 0.93 | 0.091 | 0.043 | 0.018 |
| AD-52664.1 | 1.49 | 0.95 | 0.88 | 0.438 | 0.019 | 0.009 |
| AD-52752.1 | 0.03 | 0.43 | 0.69 | 0.002 | 0.015 | 0.017 |
| AD-52741.1 | 0.03 | 0.56 | 0.86 | 0.001 | 0.044 | 0.021 |
| AD-52804.1 | 0.03 | 0.49 | 0.89 | 0.001 | 0.002 | 0.017 |
| AD-52764.1 | 0.03 | 0.54 | 0.79 | 0.005 | 0.016 | 0.078 |
| AD-52770.1 | 0.03 | 0.58 | 0.78 | 0.000 | 0.006 | 0.027 |
| AD-52735.1 | 0.03 | 0.31 | 0.46 | 0.003 | 0.031 | 0.009 |
| AD-52810.1 | 0.03 | 0.67 | 0.86 | 0.001 | 0.013 | 0.025 |
| AD-52759.1 | 0.03 | 0.54 | 0.79 | 0.000 | 0.018 | 0.023 |
| AD-52736.1 | 0.03 | 0.51 | 0.60 | 0.004 | 0.012 | 0.023 |
| AD-52775.1 | 0.03 | 0.54 | 0.73 | 0.005 | 0.024 | 0.022 |
| AD-52758.1 | 0.03 | 0.57 | 0.78 | 0.001 | 0.014 | 0.050 |
| AD-52743.1 | 0.03 | 0.45 | 0.67 | 0.002 | 0.018 | 0.033 |
| AD-52747.1 | 0.04 | 0.57 | 0.84 | 0.002 | 0.061 | 0.058 |
| AD-52819.1 | 0.04 | 0.26 | 0.45 | 0.005 | 0.001 | 0.022 |
| AD-52765.1 | 0.04 | 0.68 | 0.83 | 0.000 | 0.013 | 0.053 |
| AD-52754.1 | 0.04 | 0.76 | 1.00 | 0.000 | 0.007 | 0.015 |
| AD-52787.1 | 0.05 | 0.55 | 0.68 | 0.001 | 0.043 | 0.060 |
| AD-52791.1 | 0.05 | 0.70 | 0.91 | 0.001 | 0.014 | 0.084 |
| AD-52811.1 | 0.05 | 0.73 | 0.84 | 0.002 | 0.014 | 0.058 |
| AD-52817.1 | 0.05 | 0.77 | 0.92 | 0.003 | 0.011 | 0.031 |
| AD-52745.1 | 0.06 | 0.62 | 0.77 | 0.007 | 0.021 | 0.000 |
| AD-52749.1 | 0.06 | 0.63 | 0.88 | 0.005 | 0.037 | 0.043 |
| AD-52740.1 | 0.06 | 0.83 | 0.94 | 0.007 | 0.012 | 0.051 |
| AD-52796.1 | 0.06 | 0.72 | 0.92 | 0.003 | 0.021 | 0.054 |
| AD-52820.1 | 0.06 | 0.90 | 0.87 | 0.001 | 0.026 | 0.064 |
| AD-52809.1 | 0.06 | 0.76 | 0.90 | 0.001 | 0.037 | 0.027 |
| AD-52760.1 | 0.06 | 0.81 | 0.97 | 0.001 | 0.056 | 0.047 |
| AD-52767.1 | 0.07 | 0.55 | 0.55 | 0.001 | 0.016 | 0.013 |
| AD-52734.1 | 0.07 | 0.61 | 0.64 | 0.004 | 0.003 | 0.003 |
| AD-52794.1 | 0.07 | 0.94 | 0.87 | 0.007 | 0.014 | 0.051 |
| AD-52797.1 | 0.07 | 0.69 | 0.87 | 0.004 | 0.000 | 0.038 |
| AD-52737.1 | 0.08 | 0.70 | 0.84 | 0.004 | 0.031 | 0.012 |
| AD-52812.1 | 0.08 | 0.75 | 0.88 | 0.004 | 0.000 | 0.056 |
| AD-52748.1 | 0.08 | 0.70 | 0.89 | 0.001 | 0.010 | 0.009 |
| AD-52782.1 | 0.08 | 0.68 | 0.78 | 0.004 | 0.023 | 0.011 |
| AD-52816.1 | 0.08 | 0.71 | 0.88 | 0.003 | 0.042 | 0.060 |
| AD-52763.1 | 0.08 | 0.68 | 0.77 | 0.002 | 0.013 | 0.026 |
| AD-52788.1 | 0.08 | 0.89 | 1.00 | 0.004 | 0.017 | 0.034 |
| AD-52762.1 | 0.08 | 0.78 | 0.91 | 0.007 | 0.046 | 0.009 |
| AD-52785.1 | 0.08 | 0.88 | 0.95 | 0.002 | 0.004 | 0.019 |
| AD-52800.1 | 0.09 | 0.82 | 0.94 | 0.001 | 0.040 | 0.005 |
| AD-52792.1 | 0.09 | 0.93 | 0.94 | 0.002 | 0.018 | 0.037 |
| AD-52784.1 | 0.10 | 0.84 | 0.92 | 0.000 | 0.066 | 0.032 |
| AD-52746.1 | 0.10 | 0.82 | 0.93 | 0.002 | 0.060 | 0.059 |
| AD-52814.1 | 0.10 | 0.85 | 0.88 | 0.002 | 0.042 | 0.013 |
| AD-52751.1 | 0.10 | 0.88 | 0.98 | 0.005 | 0.030 | 0.067 |
| AD-52786.1 | 0.10 | 0.81 | 0.81 | 0.006 | 0.028 | 0.048 |
| AD-52755.1 | 0.10 | 0.93 | 0.99 | 0.003 | 0.032 | 0.048 |
| AD-52808.1 | 0.11 | 0.98 | 0.92 | 0.000 | 0.038 | 0.032 |
| AD-52815.1 | 0.11 | 0.96 | 0.96 | 0.002 | 0.009 | 0.000 |
| AD-52805.1 | 0.11 | 0.79 | 0.86 | 0.003 | 0.050 | 0.008 |
| AD-52777.1 | 0.11 | 0.88 | 0.94 | 0.001 | 0.065 | 0.000 |
| AD-52756.1 | 0.11 | 0.92 | 0.91 | 0.003 | 0.032 | 0.004 |
| AD-52733.1 | 0.12 | 0.66 | 0.65 | 0.005 | 0.071 | 0.022 |
| AD-52739.1 | 0.13 | 0.83 | 0.95 | 0.002 | 0.008 | 0.061 |
| AD-52780.1 | 0.13 | 0.70 | 0.67 | 0.012 | 0.021 | 0.059 |
| AD-52798.1 | 0.13 | 0.64 | 0.97 | 0.001 | 0.006 | 0.038 |
| AD-52776.1 | 0.14 | 0.97 | 0.94 | 0.011 | 0.029 | 0.023 |
| AD-52753.1 | 0.15 | 0.88 | 1.09 | 0.001 | 0.048 | 0.005 |
| AD-52778.1 | 0.16 | 0.76 | 0.69 | 0.003 | 0.067 | 0.003 |
| AD-52744.1 | 0.16 | 0.90 | 0.91 | 0.002 | 0.000 | 0.049 |
| AD-52750.1 | 0.16 | 0.87 | 1.01 | 0.000 | 0.060 | 0.055 |
| AD-52774.1 | 0.17 | 0.71 | 0.89 | 0.002 | 0.010 | 0.017 |
| AD-52803.1 | 0.18 | 0.87 | 0.92 | 0.015 | 0.026 | 0.040 |
| AD-52821.1 | 0.18 | 0.86 | 0.87 | 0.005 | 0.046 | 0.055 |
| AD-52781.1 | 0.18 | 0.78 | 0.66 | 0.008 | 0.000 | 0.023 |
| AD-52779.1 | 0.20 | 0.83 | 0.66 | 0.002 | 0.024 | 0.016 |
| AD-52793.1 | 0.20 | 0.74 | 0.88 | 0.010 | 0.025 | 0.069 |
| AD-52799.1 | 0.20 | 0.75 | 1.01 | 0.005 | 0.018 | 0.010 |
| AD-52761.1 | 0.22 | 0.83 | 0.92 | 0.000 | 0.024 | 0.023 |
| AD-52768.1 | 0.22 | 0.96 | 0.97 | 0.001 | ND | 0.028 |
| AD-52757.1 | 0.23 | 1.02 | 0.95 | 0.018 | 0.040 | 0.042 |
| AD-52806.1 | 0.24 | 0.96 | 0.87 | 0.011 | 0.084 | 0.055 |
| AD-52771.1 | 0.25 | 0.92 | 0.98 | 0.010 | 0.018 | 0.048 |
| AD-52802.1 | 0.30 | 0.95 | 1.00 | 0.010 | 0.019 | 0.005 |
| AD-52731.1 | 0.30 | 0.85 | 0.75 | 0.001 | 0.067 | 0.022 |
| AD-52813.1 | 0.30 | 1.07 | 0.98 | 0.001 | 0.109 | 0.014 |
| AD-52742.1 | 0.31 | 0.95 | 1.03 | 0.005 | 0.028 | 0.056 |
| AD-52766.1 | 0.35 | 0.97 | 1.00 | 0.010 | 0.024 | 0.044 |
| AD-52732.1 | 0.41 | 0.79 | 0.73 | 0.004 | 0.016 | 0.039 |
| AD-52773.1 | 0.43 | 0.99 | 0.92 | 0.004 | 0.029 | 0.022 |
| AD-52772.1 | 0.43 | 1.00 | 1.02 | 0.006 | 0.000 | 0.065 |
| AD-52822.1 | 0.44 | 0.68 | 0.81 | 0.004 | 0.010 | 0.016 |
| AD-52783.1 | 0.45 | 0.66 | 0.76 | 0.009 | 0.036 | 0.019 |
| AD-52789.1 | 0.50 | 0.68 | 0.78 | 0.010 | 0.053 | 0.004 |
| AD-52795.1 | 0.50 | 0.82 | 0.69 | 0.000 | 0.080 | 0.054 |
| AD-52801.1 | 0.54 | 0.70 | 0.79 | 0.018 | 0.038 | 0.035 |
| AD-52807.1 | 0.57 | 0.76 | 0.93 | 0.006 | 0.011 | 0.032 |
| AD-52769.1 | 0.76 | 0.97 | 0.92 | 0.015 | 0.085 | 0.045 |
| AD-1955 | 0.90 | 0.96 | 1.04 | 0.018 | 0.165 | 0.010 |
| AD-52818.1 | 0.92 | 1.03 | 0.92 | 0.009 | 0.010 | 0.063 |
| AD-1955 | 1.01 | 0.90 | 0.96 | 0.005 | 0.031 | 0.019 |
| AD-1955 | 1.05 | 1.09 | 1.00 | 0.046 | 0.085 | 0.005 |
| AD-1955 | 1.05 | 1.07 | 1.00 | 0.010 | 0.031 | 0.039 |
| mock | 1.20 | 0.98 | 0.92 | 0.000 | 0.014 | 0.005 |
| mock | 1.25 | 0.99 | 1.00 | 0.006 | 0.005 | 0.034 |

TABLE 14

Results of a dose response screen using a subset of sequences from Table 13. A subset of active ANGPTL3 siRNAs from Table 10 were tested by transfection in Hep3B cells in dose response screens.

| Duplex | IC50 (nM) |
|---|---|
| AD-52819.1 | 0.0036 |
| AD-52667.1 | 0.0037 |
| AD-52638.1 | 0.0048 |
| AD-52673.1 | 0.0049 |

TABLE 14-continued

Results of a dose response screen using
a subset of sequences from Table 13.
A subset of active ANGPTL3 siRNAs from Table 10 were
tested by transfection in Hep3B cells in dose response screens.

| Duplex | IC50 (nM) |
|---|---|
| AD-52711.1 | 0.0050 |
| AD-52661.1 | 0.0054 |
| AD-52654.1 | 0.0058 |
| AD-52637.1 | 0.0058 |
| AD-52643.1 | 0.0060 |
| AD-52685.1 | 0.0062 |
| AD-52670.1 | 0.0064 |
| AD-52679.1 | 0.0064 |
| AD-52649.1 | 0.0066 |
| AD-52683.1 | 0.0069 |
| AD-52688.1 | 0.0071 |
| AD-52717.1 | 0.0072 |
| AD-52699.1 | 0.0073 |
| AD-52714.1 | 0.0086 |
| AD-52718.1 | 0.0088 |
| AD-52735.1 | 0.0093 |
| AD-52653.1 | 0.0102 |
| AD-52687.1 | 0.0109 |
| AD-52680.1 | 0.0120 |
| AD-52713.1 | 0.0133 |
| AD-52720.1 | 0.0143 |
| AD-52639.1 | 0.0161 |
| AD-52696.1 | 0.0163 |
| AD-52662.1 | 0.0179 |
| AD-52659.1 | 0.0180 |
| AD-52710.1 | 0.0195 |
| AD-52689.1 | 0.0216 |
| AD-52787.1 | 0.0242 |
| AD-52765.1 | 0.0318 |

TABLE 15

IDs of duplex pairs for which both an unconjuaged and a
GalNac-conjugated version were synthesized and tested
These duplexes have the same sequence and modification pattern.

| Unconjugated duplex ID | GalNac conjugated duplex ID |
|---|---|
| AD-52637.1 | AD-52953.1 |
| AD-52638.1 | AD-52954.1 |
| AD-52639.1 | AD-52955.1 |
| AD-52640.1 | AD-52956.1 |
| AD-52641.1 | AD-52957.1 |
| AD-52642.1 | AD-52958.1 |
| AD-52643.1 | None |
| None | AD-52960.1 |
| None | AD-52961.1 |
| AD-52645.1 | AD-52962.1 |
| AD-52647.1 | AD-52963.1 |
| AD-52648.1 | AD-52964.1 |
| AD-52649.1 | AD-52965.1 |
| AD-52650.1 | AD-52966.1 |
| AD-52651.1 | AD-52967.1 |
| AD-52652.1 | AD-52968.1 |
| AD-52653.1 | AD-52969.1 |
| AD-52654.1 | AD-52970.1 |
| None | AD-52971.1 |
| AD-52656.1 | AD-52972.1 |
| AD-52657.1 | AD-52973.1 |
| AD-52658.1 | AD-52974.1 |
| AD-52659.1 | AD-52975.1 |
| AD-52660.1 | AD-52976.1 |
| AD-52661.1 | AD-52977.1 |
| AD-52662.1 | AD-52978.1 |
| AD-52663.1 | AD-52979.1 |
| AD-52664.1 | AD-52980.1 |
| AD-52665.1 | AD-52981.1 |
| AD-52666.1 | AD-52982.1 |
| AD-52667.1 | AD-52983.1 |
| AD-52668.1 | AD-52984.1 |
| AD-52669.1 | AD-52985.1 |
| AD-52670.1 | AD-52986.1 |
| AD-52671.1 | AD-52987.1 |
| AD-52672.1 | AD-52988.1 |
| AD-52673.1 | AD-52989.1 |
| AD-52674.1 | AD-52990.1 |
| AD-52675.1 | AD-52991.1 |
| AD-52676.1 | AD-52992.1 |
| AD-52677.1 | AD-52993.1 |
| AD-52678.1 | AD-52994.1 |
| AD-52679.1 | AD-52995.1 |
| AD-52680.1 | AD-52996.1 |
| AD-52681.1 | AD-52997.1 |
| AD-52682.1 | AD-52998.1 |
| AD-52683.1 | AD-52999.1 |
| AD-52684.1 | AD-53000.1 |
| AD-52685.1 | AD-53001.1 |
| AD-52686.1 | AD-53002.1 |
| AD-52687.1 | AD-53003.1 |
| AD-52688.1 | AD-53004.1 |
| AD-52689.1 | AD-53005.1 |
| AD-52690.1 | AD-53006.1 |
| AD-52691.1 | AD-53007.1 |
| AD-52692.1 | AD-53008.1 |
| AD-52693.1 | AD-53009.1 |
| AD-52694.1 | AD-53010.1 |
| AD-52695.1 | AD-53011.1 |
| AD-52696.1 | AD-53012.1 |
| AD-52697.1 | AD-53013.1 |
| AD-52698.1 | AD-53014.1 |
| AD-52699.1 | AD-53015.1 |
| AD-52700.1 | AD-53016.1 |
| AD-52701.1 | AD-53017.1 |
| AD-52702.1 | AD-53018.1 |
| AD-52703.1 | AD-53019.1 |
| AD-52704.1 | AD-53020.1 |
| AD-52705.1 | AD-53021.1 |
| AD-52706.1 | AD-53022.1 |
| AD-52707.1 | AD-53023.1 |
| AD-52708.1 | AD-53024.1 |
| AD-52709.1 | AD-53025.1 |
| AD-52710.1 | AD-53026.1 |
| AD-52711.1 | AD-53027.1 |
| AD-52712.1 | AD-53028.1 |
| AD-52713.1 | AD-53029.1 |
| AD-52714.1 | AD-53030.1 |
| AD-52715.1 | AD-53031.1 |
| AD-52716.1 | AD-53032.1 |
| AD-52717.1 | AD-53033.1 |
| AD-52718.1 | AD-53034.1 |
| AD-52719.1 | AD-53035.1 |
| AD-52720.1 | AD-53036.1 |
| AD-52721.1 | AD-53037.1 |
| AD-52722.1 | AD-53038.1 |
| AD-52723.1 | AD-53039.1 |
| AD-52724.1 | AD-53040.1 |
| AD-52725.1 | AD-53041.1 |
| AD-52726.1 | AD-53042.1 |
| AD-52727.1 | AD-53043.1 |
| AD-52728.1 | AD-53044.1 |
| AD-52729.1 | AD-53045.1 |
| AD-52730.1 | AD-53046.1 |
| AD-52731.1 | AD-53059.1 |
| AD-52732.1 | AD-53060.1 |
| AD-52733.1 | AD-53061.1 |
| AD-52734.1 | AD-53062.1 |
| AD-52735.1 | AD-53063.1 |
| AD-52736.1 | AD-53064.1 |
| AD-52737.1 | AD-53065.1 |
| None | AD-53066.1 |
| AD-52739.1 | AD-53067.1 |
| AD-52740.1 | AD-53068.1 |
| AD-52741.1 | AD-53069.1 |
| AD-52742.1 | AD-53070.1 |

TABLE 15-continued

IDs of duplex pairs for which both an unconjuaged and a
GalNac-conjugated version were synthesized and tested
These duplexes have the same sequence and modification pattern.

| Unconjugated duplex ID | GalNac conjugated duplex ID |
|---|---|
| AD-52743.1 | AD-53071.1 |
| AD-52744.1 | AD-53072.1 |
| AD-52745.1 | AD-53073.1 |
| AD-52746.1 | AD-53074.1 |
| AD-52747.1 | AD-53075.1 |
| AD-52748.1 | AD-53076.1 |
| AD-52749.1 | AD-53077.1 |
| AD-52750.1 | AD-53078.1 |
| AD-52751.1 | AD-53079.1 |
| AD-52752.1 | AD-53080.1 |
| AD-52753.1 | AD-53081.1 |
| AD-52754.1 | AD-53082.1 |
| AD-52755.1 | AD-53083.1 |
| AD-52756.1 | AD-53084.1 |
| AD-52757.1 | AD-53085.1 |
| AD-52758.1 | AD-53086.1 |
| AD-52759.1 | AD-53087.1 |
| AD-52760.1 | AD-53088.1 |
| AD-52761.1 | AD-53089.1 |
| AD-52762.1 | AD-53090.1 |
| AD-52763.1 | AD-53091.1 |
| AD-52764.1 | AD-53092.1 |
| AD-52765.1 | AD-53093.1 |
| AD-52766.1 | AD-53094.1 |
| AD-52767.1 | AD-53095.1 |
| AD-52768.1 | AD-53096.1 |
| AD-52769.1 | AD-53097.1 |
| AD-52770.1 | AD-53098.1 |
| AD-52771.1 | AD-53099.1 |
| AD-52772.1 | AD-53100.1 |
| AD-52773.1 | AD-53101.1 |
| AD-52774.1 | AD-53102.1 |
| AD-52775.1 | AD-53103.1 |
| AD-52776.1 | AD-53104.1 |
| AD-52777.1 | AD-53105.1 |
| AD-52778.1 | AD-53106.1 |
| AD-52779.1 | AD-53107.1 |
| AD-52780.1 | AD-53108.1 |
| AD-52781.1 | AD-53109.1 |
| AD-52782.1 | AD-53110.1 |
| AD-52783.1 | AD-53111.1 |
| AD-52784.1 | AD-53112.1 |
| AD-52785.1 | AD-53113.1 |
| AD-52786.1 | AD-53114.1 |
| AD-52787.1 | AD-53115.1 |
| AD-52788.1 | AD-53116.1 |
| AD-52789.1 | AD-53117.1 |
| None | AD-53118.1 |
| AD-52791.1 | AD-53119.1 |
| AD-52792.1 | AD-53120.1 |
| AD-52793.1 | AD-53121.1 |
| AD-52794.1 | AD-53122.1 |
| AD-52795.1 | AD-53123.1 |
| AD-52796.1 | AD-53124.1 |
| AD-52797.1 | AD-53125.1 |
| AD-52798.1 | AD-53126.1 |
| AD-52799.1 | AD-53127.1 |
| AD-52800.1 | AD-53128.1 |
| AD-52801.1 | AD-53129.1 |
| AD-52802.1 | AD-53130.1 |
| AD-52803.1 | AD-53131.1 |
| AD-52804.1 | AD-53132.1 |
| AD-52805.1 | AD-53133.1 |
| AD-52806.1 | AD-53134.1 |
| AD-52807.1 | AD-53135.1 |
| AD-52808.1 | AD-53136.1 |
| AD-52809.1 | AD-53137.1 |
| AD-52810.1 | AD-53138.1 |
| AD-52811.1 | AD-53139.1 |
| AD-52812.1 | AD-53140.1 |
| AD-52813.1 | AD-53141.1 |
| AD-52814.1 | AD-53142.1 |
| AD-52815.1 | AD-53143.1 |
| AD-52816.1 | AD-53144.1 |
| AD-52817.1 | AD-53145.1 |
| AD-52818.1 | AD-53146.1 |
| AD-52819.1 | AD-53147.1 |
| AD-52820.1 | AD-53148.1 |
| AD-52821.1 | AD-53149.1 |
| AD-52822.1 | AD-53150.1 |

In Vivo Tests

Example 3

Test Articles

In vivo experiments were conducted using dsRNA sequences of the invention. The dsRNA sequence used in the experiments was GalNac-conjugated AD-52981 ("ANG", sense sequence: AfcAfuAfuUfuGfAfUfcAfgUfcUfuU-fuUfL96 (SEQ ID NO: 657); antisense sequence: aAfaAf-aGfaCfuGfaucAfaAfuAfuGfusUfsg (SEQ ID NO: 842)). The dsRNA sequence used as a negative control was luciferase-conjugated AD-48399B1 ("Luc", sense sequence: CfaCfuUfaCfgCfuGfaGfuAfcUfuCfgAfL96 (SEQ ID NO: 1728), antisense sequence: uCfgAfaGfuAfcUfcAfgCfgU-faAfgUfgsAfsu (SEQ ID NO: 1729)). Also used as a negative control was GalNal-conjugated AD-1955 containing alternating 2'-methyl and 2' fluoro modifications.

Experimental Procedure

The dsRNA sequences were tested in C57BL/6 (WT) and ob/ob mice. WT mice received five daily doses of dsRNAs in PBS, Luc at 20 mg/kg, or ANG at 5 or 20 mg/kg; and ob/ob mice received five daily doses of NPLs formulated with Luc at 20 mg/kg or ANG at 20 mg/kg. All test articles were administered by subcutaneous injection according to the procedure shown in FIG. 1. Specifically, five daily doses of the test articles were administered on five consecutive days (day 0, 1, 2, 3 and 4), and blood samples were collected 5, 3 or 1 day prior to administration, as well as on days 0, 1, 2, 3, 4, 7, 9, 11, 15, 18, 21, 25, 30, 37, 45 and 50 post-administration. The collected blood samples were used to measure the expression of ANGPTL3 protein using an ELISA assay. Levels of serum triglycerides (TGs), low density lipoprotein cholesterol (LDLc), high density lipoprotein cholesterol (HDLc) and total cholesterol (TC) were also measured using an Olympus Analyzer.

Results

Figure 2A:
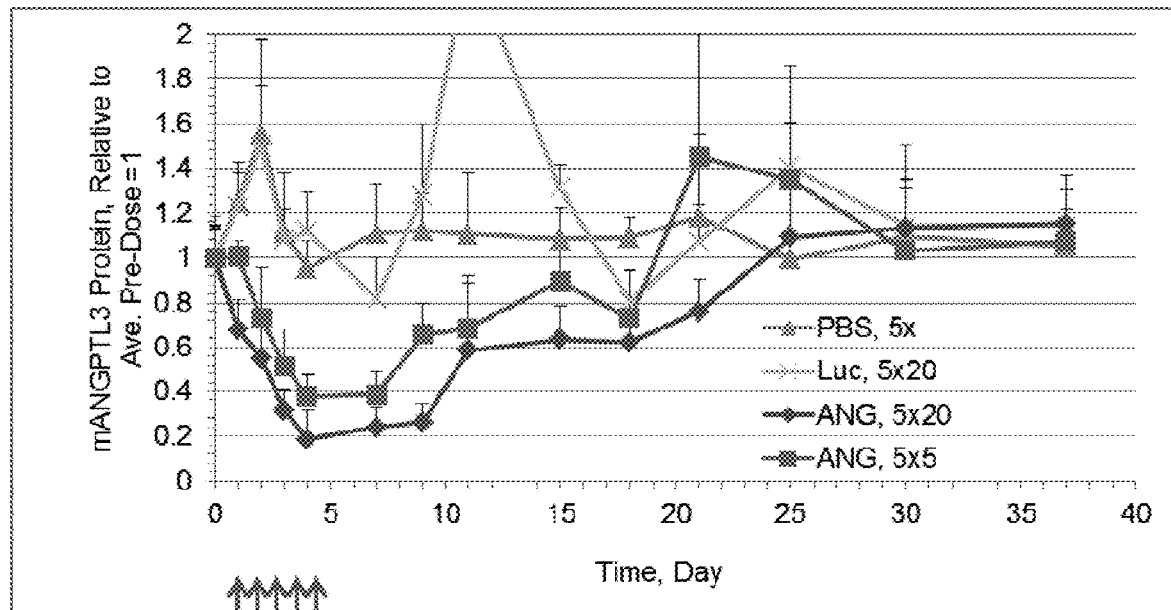
FIG. 2A is a graph showing measured levels of ANGPTL3 protein in WT mice after treatment with the indicated iRNA or a control.
Figure 2B:
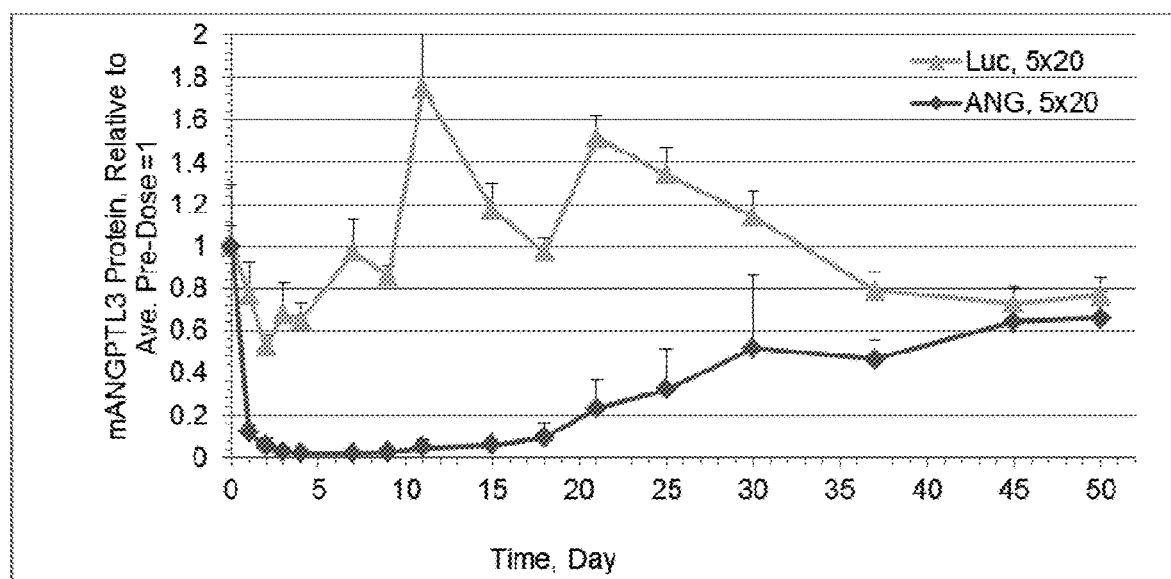
FIG. 2B is a graph showing measured levels of ANGPTL3 proten in ob/ob mice after treatment with the indicated iRNA or a control.

Shown in FIG. 2, Panel A, are levels of murine ANGPTL3 (mANGPTL3, protein measured in WT mice after administration of control or ANG at 5 or 20 mg/kg. Also shown in FIG. 2, Panel B are levels of mANGPTL3 protein measured in ob/ob mice after administration of control or ANG at 20 mg/kg. The data indicates that, for both WT and ob/ob mice, administration of ANG results in decreased levels of mANGPTL3 protein, as compared to controls.

Figure 3A:
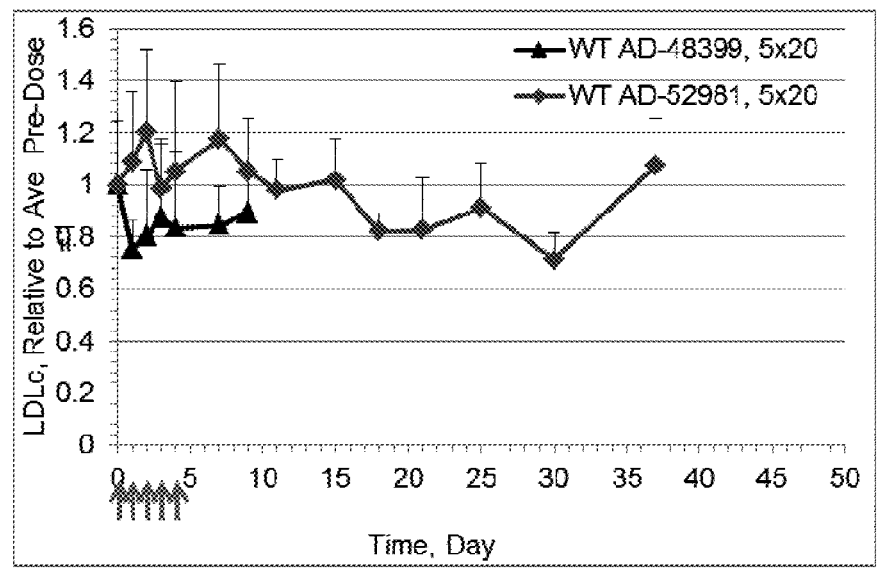
FIG. 3A is a graph showing measured levels of LDL-c in WT mice after treatment with the indicated iRNA or a control.
Figure 3B:
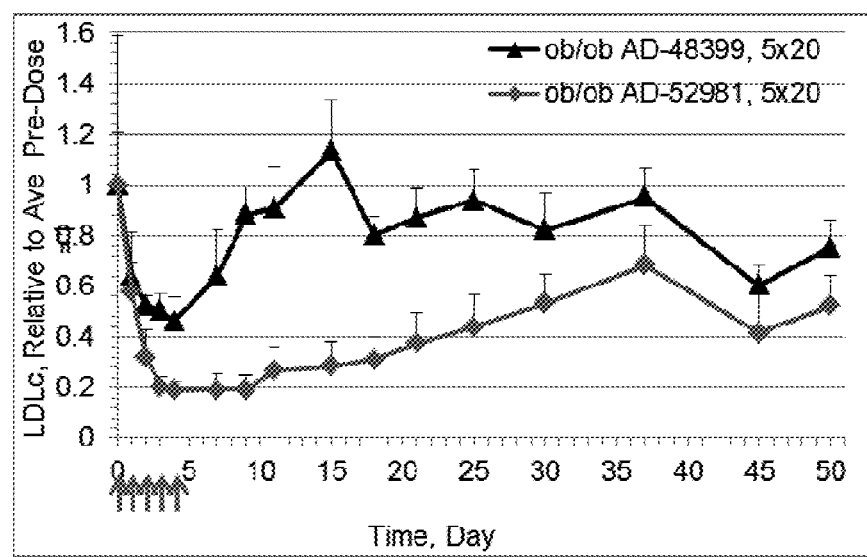
FIG. 3B is a graph showing measured levels of LDL-c in ob/ob mice after treatment with the indicated iRNA or a control.

Shown in FIG. 3, Panel A, are levels of LDL-c measured in WT mice after administration of control or ANG at 20 mg/kg. Shown in FIG. 3, Panel B are levels of LDL-c measured in ob/ob mice after administration of control or ANG at 20 mg/kg. The data indicates that administration of ANG causes decreased levels of LDL-c, particularly in ob/ob mice, as compared to controls.

Figure 4A:
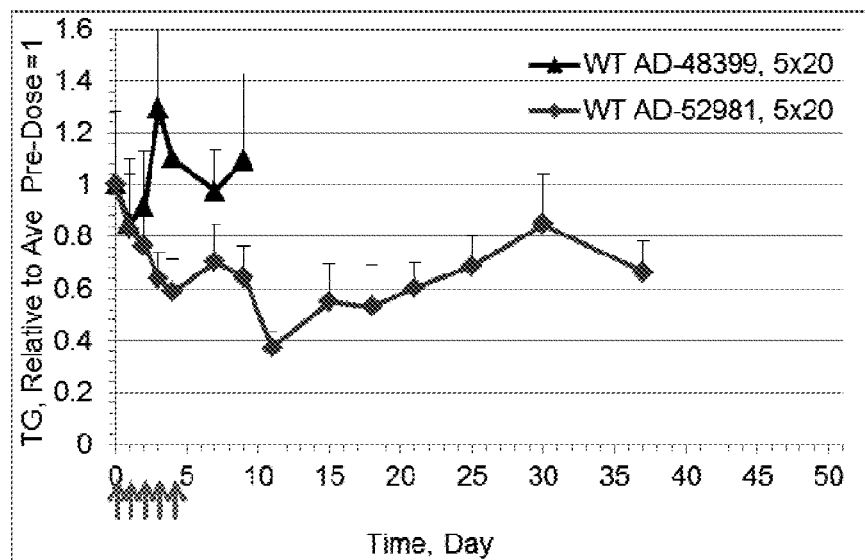
FIG. 4A is a graph showing measured levels of triglycerides in WT mice after treatment with the indicated iRNA or a control.
Figure 4B:
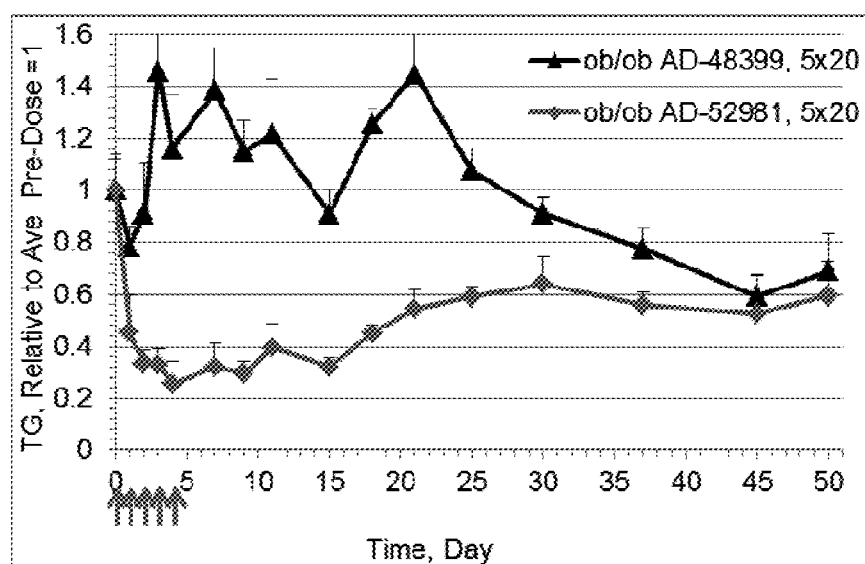
FIG. 4B is a graph showing measured levels of triglycerides in ob/ob mice after treatment with the indicated iRNA or a control.

Shown in FIG. 4, Panel A, are levels of triglycerides measured in WT mice after administration of control or ANG at 20 mg/kg. Shown in FIG. 4, Panel B are levels of triglycerides measured in ob/ob mice after administration of control or ANG at 20 mg/kg. The data indicates that administration of ANG causes decreased levels of tryglycerides, particularly, in ob/ob mice, as compared to controls.

Figure 5A:
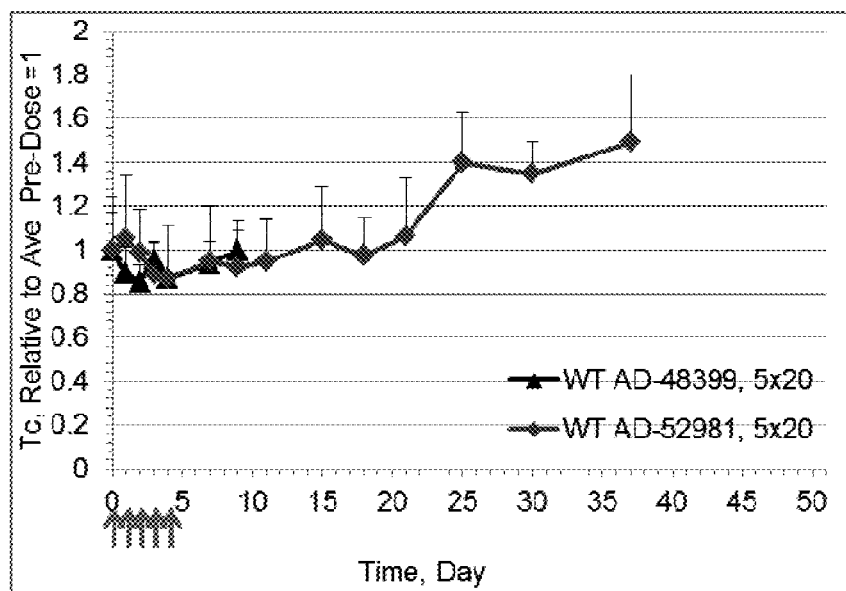
FIG. 5A is a graph showing measured levels of total cholesterol (TC) in WT mice after treatment with the indicated iRNA or a control.
Figure 5B:
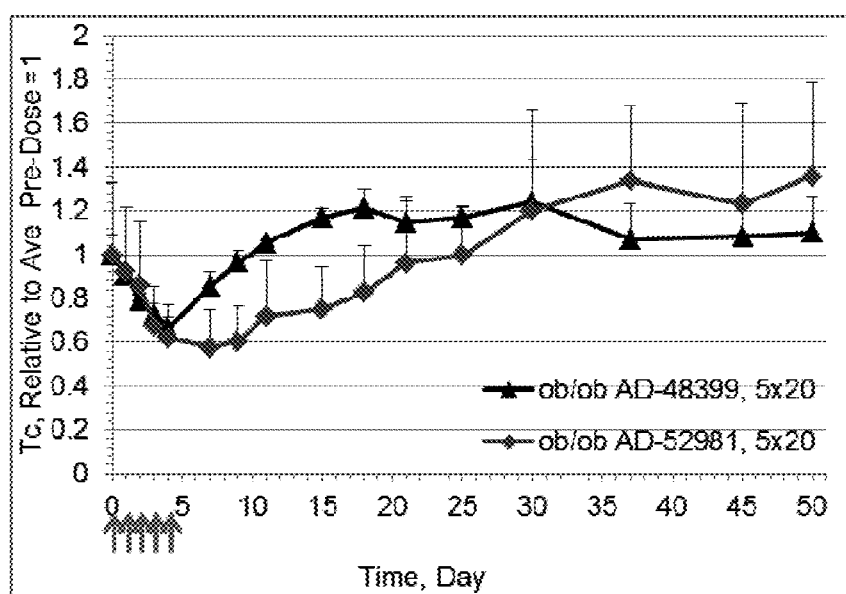
FIG. 5B is a graph showing measured levels of total cholesterol (TC) in ob/ob mice after treatment with the indicated iRNA or a control.
Figure 6A:
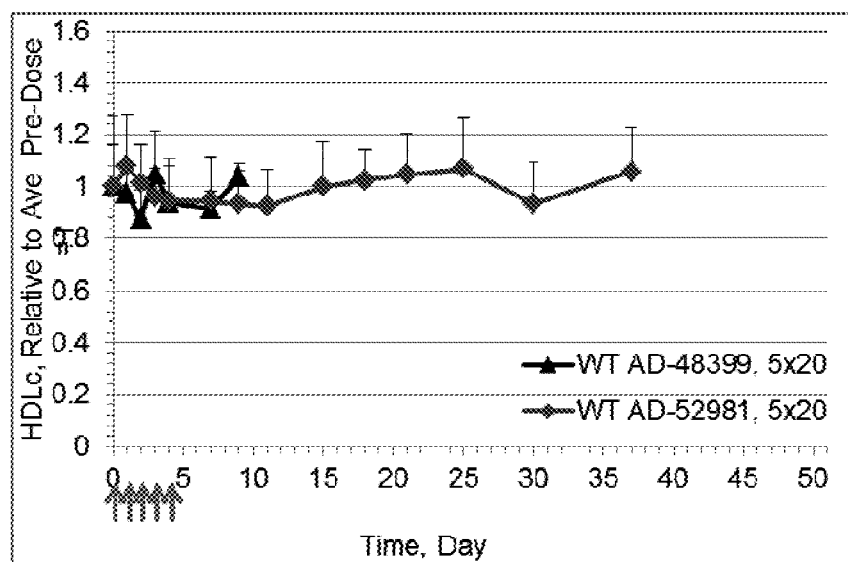
FIG. 6A is a graph showing measured levels of HDL-c in WT mice after treatment with the indicated iRNA or a control.
Figure 6B:
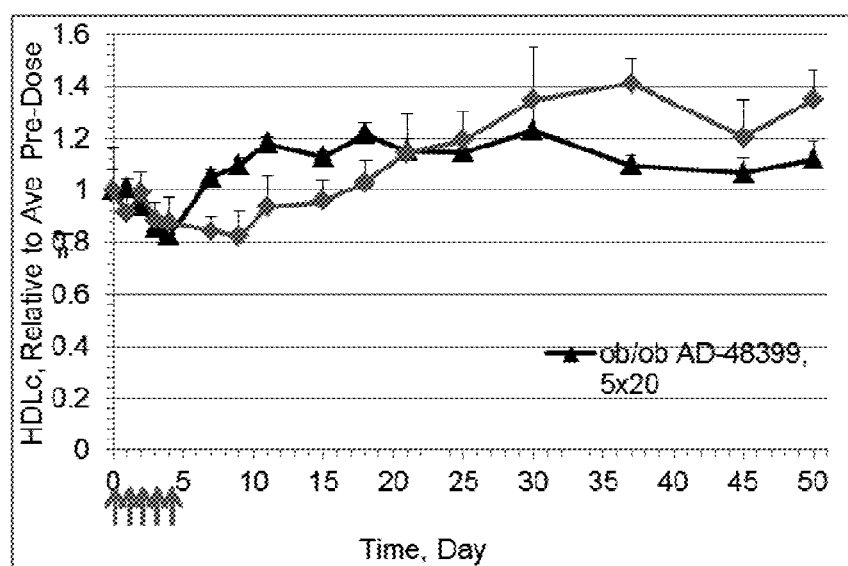
FIG. 6B is a graph showing measured levels of HDL-c in ob/ob mice after treatment with the indicated iRNA or a control.

Shown in FIG. 5, Panel A and B are levels of total cholesterol (TC) measured in WT and ob/ob mice, respectively, after administration of control or ANG at 20 mg/kg. The data indicates that administration of ANG causes a moderate decrease in TC levels in ob/ob mice, but not in WT mice. Similarly, administration of ANG causes a moderate decrease in HDL-c levels in ob/ob mice, but not in WT mice, as is shown in the graphs in FIG. 6.

Example 4

Test Article

The effect of a single injection of dsRNA sequence of the invention on the level of ANGPTL3 protein was tested. The dsRNA sequence used in the experiments was GalNac-conjugated AD-52981 ("ANG", sense sequence: AfcAfuAfuUfuGfAfUfcAfgUfcUfuUfuUfL96 (SEQ ID NO: 657); antisense sequence: aAfaAfaGfaCfuGfaucAfaAfuAfuGfusUfsg (SEQ ID NO: 842)). PBS was used as a negative control.

Experimental Procedure

The dsRNA sequences were tested in Human PCS Transgenic mouse characterized by liver-specific expression of full-length human PCSK9 gene. Human PCS transgenic mice were dosed with the AD-52981 or PBS using a single subcutaneous injection. The mice were divided into four groups, each group consisting of two males and two females. Each group received an injection of PBS or a 5 mg/kg, 20 mg/kg or 60 mg/kg dose of AD-52981. Blood samples were collected at day 1 and day 0 prior to dosing, and at 72 hours post dosing. ANGPTL3 protein levels were measured by ELISA and compared to levels at day 1 and day 0 prior to dosing.

Results

Figure 7:
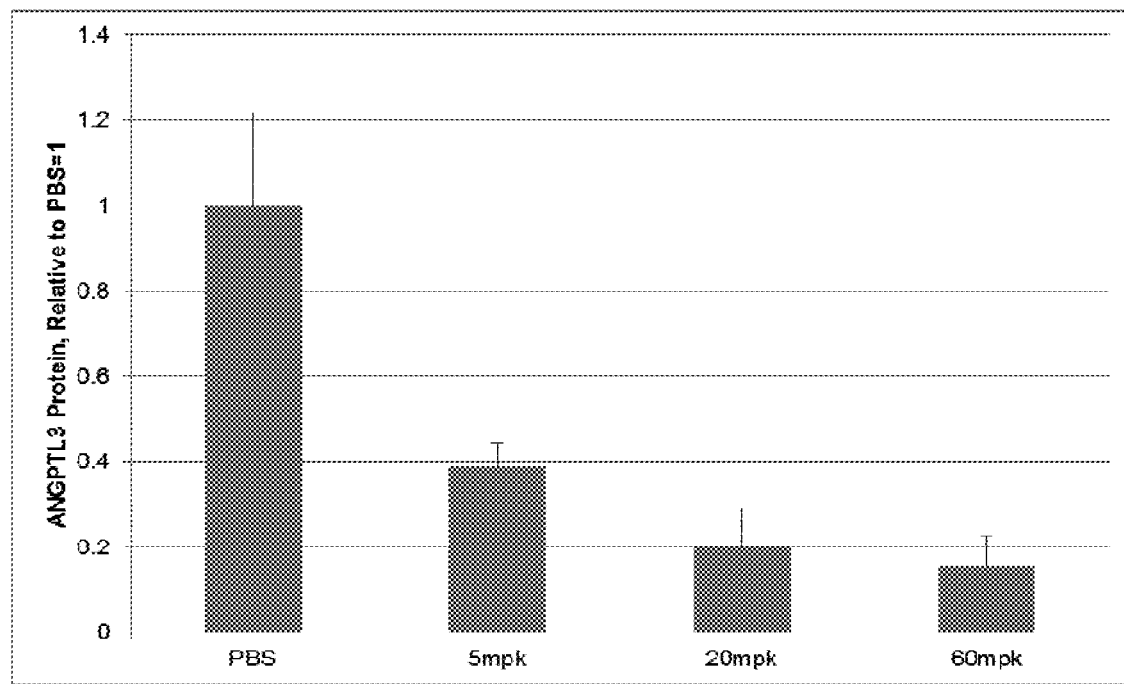
FIG. 7 is a graph showing measured levels of ANGPTL3 protein in human PCS transgenic mice after treatment with a single dose of the indicated iRNA or a control.

Shown in FIG. 7, are levels of murine ANGPTL3 protein (mANGPTL3) measured in Human PCS transgenic mice. The data shown is expressed relative to PBS control and represents an average for 2 males and 2 females in each group. Error bars represent standard deviation. The data indicates that administration of a single injection of AD-52981 reduces the levels of ANGPTL3 protein in the mice in a dose-dependent manner, with the dose of 60 mg/kg decreasing the levels of ANGPTL3 protein more than five-fold (see FIG. 7).

```
SEQUENCES
>gi|41327750|ref|NM_014495.2| Homo sapiens angiopoietin-like 3
(ANGPTL3), mRNA
                                                        SEQ ID NO: 1
TTCCAGAAGAAAACAGTTCCACGTTGCTTGAAATTGAAAATCAAGATAAAAATGTTCACAATTAAGCTCCT

TCTTTTTATTGTTCCTCTAGTTATTTCCTCCAGAATTGATCAAGACAATTCATCATTTGATTCTCTATCTC

CAGAGCCAAAATCAAGATTTGCTATGTTAGACGATGTAAAAATTTTAGCCAATGGCCTCCTTCAGTTGGGA

CATGGTCTTAAAGACTTTGTCCATAAGACGAAGGGCCAAATTAATGACATATTTCAAAAACTCAACATATT

TGATCAGTCTTTTTATGATCTATCGCTGCAAACCAGTGAAATCAAAGAAGAAGAAAAGGAACTGAGAAGAA

CTACATATAAACTACAAGTCAAAAATGAAGAGGTAAAGAATATGTCACTTGAACTCAACTCAAAACTTGAA

AGCCTCCTAGAAGAAAAAATTCTACTTCAACAAAAAGTGAAATATTTAGAAGAGCAACTAACTAACTTAAT

TCAAAATCAACCTGAAACTCCAGAACACCCAGAAGTAACTTCACTTAAAACTTTTGTAGAAAAACAAGATA

ATAGCATCAAAGACCTTCTCCAGACCGTGGAAGACCAATATAAACAATTAAACCAACAGCATAGTCAAATA

AAAGAAATAGAAATCAGCTCAGAAGGACTAGTATTCAAGAACCCACAGAAATTTCTCTATCTTCCAAGCC

AAGAGCACCAAGAACTACTCCCTTTCTTCAGTTGAATGAAATAAGAAATGTAAAACATGATGGCATTCCTG

CTGAATGTACCACCATTTATAACAGAGGTGAACATACAAGTGGCATGTATGCCATCAGACCCAGCAACTCT

CAAGTTTTTCATGTCTACTGTGATGTTATATCAGGTAGTCCATGGACATTAATTCAACATCGAATAGATGG

ATCACAAAACTTCAATGAAACGTGGGAGAACTACAAATATGGTTTTGGGAGGCTTGATGGAGAATTTTGGT

TGGGCCTAGAGAAGATATACTCCATAGTGAAGCAATCTAATTATGTTTTACGAATTGAGTTGGAAGACTGG

AAAGACAACAAACATTATATTGAATATTCTTTTTACTTGGGAAATCACGAAACCAACTATACGCTACATCT

AGTTGCGATTACTGGCAATGTCCCCAATGCAATCCCGGAAAACAAAGATTTGGTGTTTTCTACTTGGGATC

ACAAAGCAAAGGACACTTCAACTGTCCAGAGGGTTATTCAGGAGGCTGGTGGTGGCATGATGAGTGTGGA

GAAAACAACCTAAATGGTAAATATAACAAACCAAGAGCAAAATCTAAGCCAGAGAGGAGAAGAGGATTATC

TTGGAAGTCTCAAAATGGAAGGTTATACTCTATAAAATCAACCAAAATGTTGATCCATCCAACAGATTCAG

AAAGCTTTGAATGAACTGAGGCAAATTTAAAAGGCAATAATTTAAACATTAACCTCATTCCAAGTTAATGT

GGTCTAATAATCTGGTATTAAATCCTTAAGAGAAAGCTTGAGAAATAGATTTTTTTATCTTAAAGTCACT
```

-continued

```
GTCTATTTAAGATTAAACATACAATCACATAACCTTAAAGAATACCGTTTACATTTCTCAATCAAAATTCT
TATAATACTATTTGTTTTAAATTTTGTGATGTGGGAATCAATTTTAGATGGTCACAATCTAGATTATAATC
AATAGGTGAACTTATTAAATAACTTTTCTAAATAAAAAATTTAGAGACTTTTATTTTAAAAGGCATCATAT
GAGCTAATATCACAACTTTCCCAGTTTAAAAAACTAGTACTCTTGTTAAAACTCTAAACTTGACTAAATAC
AGAGGACTGGTAATTGTACAGTTCTTAAATGTTGTAGTATTAATTTCAAAACTAAAAATCGTCAGCACAGA
GTATGTGTAAAAATCTGTAATACAAATTTTTAAACTGATGCTTCATTTTGCTACAAAATAATTTGGAGTAA
ATGTTTGATATGATTTATTTATGAAACCTAATGAAGCAGAATTAAATACTGTATTAAAATAAGTTCGCTGT
CTTTAAACAAATGGAGATGACTACTAAGTCACATTGACTTTAACATGAGGTATCACTATACCTTATT
```

>gi|297278846|ref|XM_001086114.2| PREDICTED: Macaca mulatta
angiopoietin-like 3 (ANGPTL3), mRNA

SEQ ID NO: 2

```
ATATATAGAGTTAAGAAGTCTAGGTCTGCTTCCAGAAGAACACAGTTCCACGTTGCTTGAAATTGAAATC
AGGATAAAAATGTTCACAATTAAGCTCCTTCTTTTTATTGTTCCTCTAGTTATTTCCTCCAGAATTGACCA
AGACAATTCATCATTTGATTCTGTATCTCCAGAGCCAAAATCAAGATTTGCTATGTTAGACGATGTAAAA
TTTTAGCCAATGGCCTCCTTCAGTTGGGACATGGTCTTAAAGACTTTGTCCATAAGACTAAGGGCCAAATT
AATGACATATTTCAAAAACTCAACATATTTGATCAGTCTTTTTATGATCTATCACTGCAAACCAGTGAAAT
CAAAGAAGAAGAAAAGGAACTGAGAAGAACTACATATAAACTACAAGTCAAAAATGAAGAGGTAAAGAATA
TGTCACTTGAACTCAACTCAAAACTTGAAAGCCTCCTAGAAGAAAAAATTCTACTTCAACAAAAAGTGAAA
TATTTAGAAGAGCAACTAACTAACTTAATTCAAAATCAACCTGAAACTCCAGAACATCCAGAAGTAACTTC
ACTTAAAAGTTTTGTAGAAAAACAAGATAATAGCATCAAAGACCTTCTCCAGACTGTGGAAGAACAATATA
AGCAATTAAACCAACAGCACAGTCAAATAAAAGAAATAGAAAATCAGCTCAGAATGACTAATATTCAAGAA
CCCACAGAAATTTCTCTATCTTCCAAGCCAAGAGCACCAAGAACTACTCCCTTTCTTCAGCTGAATGAAAT
AAGAAATGTAAAACATGATGGCATTCCTGCTGATTGTACCACCATTTACAATAGAGGTGAACATATAAGTG
GCATGTATGCCATCAGACCCAGCAACTCTCAAGTTTTTCATGTCTACTGTGATGTTGTATCAGGTAAAACC
TGTCTAAGGAGAATAGATGGATCACAAAACTTCAATGAAACGTGGGAGAACTACAAATATGGTTTCGGGAG
GCTTGATGGAGAATTCTGGTTGGGCCTAGAGAAGATATACTCCATAGTGAAGCAATCTAATTACGTTTTAC
GAATTGAGTTGGAAGACTGGAAAGACAACAAACATTATATTGAATATTCTTTTTACTTGGGAAATCACGAA
ACCAACTATACGCTACATGTAGTTAAGATTACTGGCAATGTCCCCAATGCAATCCCGGAAAACAAAGATTT
GGTGTTTTCTACTTGGGATCACAAAGCAAAAGGACACTTCAGCTGTCCAGAGAGTTATTCAGGAGGCTGGT
GGTGGCATGATGAGTGTGGAGAAAACAACCTAAATGGTAAATATAACAAACCAAGAACAAAATCTAAGCCA
GAGCGGAGAAGAGGATTATCCTGGAAGTCTCAAAATGGAAGGTTATACTCTATAAAATCAACCAAAATGTT
GATCCATCCAACAGATTCAGAAAGCTTTGAATGAACTGAGGCAAATTTAAAAGGCAATAAATTAAACATTA
AACTCATTCCAAGTTAATGTGGTTTAATAATCTGGTATTAAATCCTTAAGAGAAGGCTTGAGAAATAGATT
TTTTTATCTTAAAGTCACTGTCAATTTAAGATTAAACATACAATCACATAACCTTAAAGAATACCATTTAC
ATTTCTCAATCAAAATTCCTACAACACTATTTGTTTTATATTTTGTGATGTGGGAATCAATTTTAGATGGT
CGCAATCTAAATTATAATCAACAGGTGAACTTACTAAATAACTTTTCTAAATAAAAAACTTAGAGACTTTA
ATTTTAAAAGTCATCATATGAGCTAATATCACAATTTTCCCAGTTTAAAAAACTAGTTTTCTTGTTAAAAC
TCTAAACTTGACTAAATAAAGAGGACTGATAATTATACAGTTCTTAAATTTGTTGTAATATTAATTTCAAA
ACTAAAAATTGTCAGCACAGAGTATGTGTAAAAATCTGTAATATAAATTTTTAAACTGATGCCTCATTTTG
CTACAAAATAATCTGGAGTAAATTTTTGATAGGATTTATTTATGAAACCTAATGAAGCAGGATTAAATACT
GTATTAAAATAGGTTCGCTGTCTTTTAAACAAATGGAGATGATGATTACTAAGTCACATTGACTTTAATAT
GAGGTATCACTATACCTTA
```

-continued

\>gi|142388354|ref|NM_013913.3| Mus musculus angiopoietin-like 3 (Angptl3), mRNA

SEQ ID NO: 3

```
CAGGAGGGAGAAGTTCCAAATTGCTTAAAATTGAATAATTGAGACAAAAAATGCACACAATTAAATTATTC

CTTTTTGTTGTTCCTTTAGTAATTGCATCCAGAGTGGATCCAGACCTTTCATCATTTGATTCTGCACCTTC

AGAGCCAAAATCAAGATTTGCTATGTTGGATGATGTCAAAATTTTAGCGAATGGCCTCCTGCAGCTGGGTC

ATGGACTTAAAGATTTTGTCCATAAGACTAAGGGACAAATTAACGACATATTTCAGAAGCTCAACATATTT

GATCAGTCTTTTTATGACCTATCACTTCGAACCAATGAAATCAAAGAAGAGGAAAAGGAGCTAAGAAGAAC

TACATCTACACTACAAGTTAAAAACGAGGAGGTGAAGAACATGTCAGTAGAACTGAACTCAAAGCTTGAGA

GTCTGCTGGAAGAGAAGACAGCCCTTCAACACAAGGTCAGGGCTTTGGAGGAGCAGCTAACCAACTTAATT

CTAAGCCCAGCTGGGGCTCAGGAGCACCCAGAAGTAACATCACTCAAAAGTTTTGTAGAACAGCAAGACAA

CAGCATAAGAGAACTCCTCCAGAGTGTGGAAGAACAGTATAAACAATTAAGTCAACAGCACATGCAGATAA

AAGAAATAGAAAAGCAGCTCAGAAAGACTGGTATTCAAGAACCCTCAGAAAATTCTCTTTCTTCTAAATCA

AGAGCACCAAGAACTACTCCCCCTCTTCAACTGAACGAAACAGAAAATACAGAACAAGATGACCTTCCTGC

CGACTGCTCTGCCGTTTATAACAGAGGCGAACATACAAGTGGCGTGTACACTATTAAACCAAGAAACTCCC

AAGGGTTTAATGTCTACTGTGATACCCAATCAGGCAGTCCATGGACATTAATTCAACACCGGAAAGATGGC

TCACAGGACTTCAACGAAACATGGGAAAACTACGAAAAGGGCTTTGGGAGGCTCGATGGAGAATTTTGGTT

GGGCCTAGAGAAGATCTATGCTATAGTCCAACAGTCTAACTACATTTTACGACTCGAGCTACAAGACTGGA

AAGACAGCAAGCACTACGTTGAATACTCCTTTCACCTGGGCAGTCACGAAACCAACTACACGCTACATGTG

GCTGAGATTGCTGGCAATATCCCTGGGGCCCTCCCAGAGCACACAGACCTGATGTTTTCTACATGGAATCA

CAGAGCAAAGGGACAGCTCTACTGTCCAGAAAAGTTACTCAGGTGGCTGGTGGTGGAATGACATATGTGGAG

AAAACAACCTAAATGGAAAATACAACAAACCCAGAACCAAATCCAGACCAGAGAGAAGAAGAGGGATCTAC

TGGAGACCTCAGAGCAGAAAGCTCTATGCTATCAAATCATCCAAAATGATGCTCCAGCCCACCACCTAAGA

AGCTTCAACTGAACTGAGACAAAATAAAAGATCAATAAATTAAATATTTAAAGTCCTCCCGATCACTGTAGT

AATCTGGTATTAAAATTTTAATGGAAAGCTTGAGAATTGAATTTCAATTAGGTTTAAACTCATTGTTAAGA

TCAGATATCACCGAATCAACGTAAACAAAATTTATC
```

\>gi|68163568|ref|NM_001025065.1| Rattus norvegicus angiopoietin-like 3 (Angptl3), mRNA

SEQ ID NO: 4

```
GACGTTCCAAATTGCTTGAAATTGAATAATTGAAACAAAAATGCACACAATTAAGCTGCTCCTTTTGTTG

TTCCTCTAGTAATTTCGTCCAGAGTTGATCCAGACCTTTCGCCATTTGATTCTGTACCGTCAGAGCCAAAA

TCAAGATTTGCTATGTTGGATGATGTCAAAATTTTAGCCAATGGCCTCCTGCAGCTGGGTCATGGTCTTAA

AGATTTTGTCCATAAGACAAAGGGACAAATTAATGACATATTTCAGAAGCTCAACATATTTGATCAGTGTT

TTTATGACCTATCACTTCAAACCAATGAAATCAAAGAAGAGGAAAAGGAGCTAAGAAGAACCACATCTAAA

CTACAAGTTAAAAACGAAGAGGTGAAGAATATGTCACTTGAACTGAACTCAAAGCTTGAAAGTCTACTGGA

GGAGAAGATGGCGCTCCAACACAGAGTCAGGGCTTTGGAGGAACAGCTGACCAGCTTGGTTCAGAACCCGC

CTGGGGCTCGGGAGCACCCAGAGGTAACGTCACTTAAAAGTTTTGTAGAACAGCAAGATAACAGCATAAGA

GAACTCCTCCAGAGTGTGGAAGAACAATATAAACAACTAAGTCAACAGCACATTCAGATAAAAGAAATAGA

AAATCAGCTCAGAAAGACTGGCATTCAAGAACCCACTGAAAATTCTCTTTATTCTAAACCAAGAGCACCAA

GAACTACTCCCCCTCTTCATCTGAAGGAAGCAAAAATATAGAACAAGATGATCTGCCTGCTGACTGCTCT

GCCATTTATAACAGAGGTGAACATACAAGTGGCGTGTATACTATTAGACCAAGCAGCTCTCAAGTGTTTAA

TGTCTACTGTGACACCCAATCAGGCACTCCACGGACATTAATTCAACACCGGAAAGATGGCTCTCAAAACT

TCAACCAAACGTGGGAAAACTACGAAAAGGGTTTTGGGAGGCTTGATGGTAAAGTGATTTCCTTGCATCAC
```

-continued

```
TCACTTATCTGTTGATTTAATAGTATTAGTTGGGTGTGTTGACACAGGCCTGAGACCATAGCGCTTTTGGG

CAAGGGGGAGGAGGAGCAGCAGGTGAATTGAAAGTTCAAGACCAGTCTGGGCCACACATTGATACTCCTT

CTCGACATTAAGAATTATAAATTAAGCAGCAATTATAAAATGGGCTGTGGAAATGTAACAATAAGCAAAG

CAGACCCCAGTCTTCATAAAACTGATTGGTAAATATTATCCATGATAGCAACTGCAATGATCTCATTGTAC

TTATCACTACTGCATGCCTGCAGTATGCTTGTTGAAACTTAATTCTATAGTTCATGGTTATCATAAGTCTT

ATTAAGGAACATAGTATACGCCATTGGCTCTAGTGAGGGGCCATGCTACAAATGAGCTGCAAAGATAGCAG

TATAGAGCTCTTTCAGTGATATCCTAAGCACAACGTAACACAGGTGAAATGGGCTGGAGGCACAGTTGTGG

TGGAACACGCGGCCAGCAGGACACTGGGACTGATCCCCAGCAGCACAAAGAAAGTGATAGGAACACAGAGC

GAGAGTTAGAAGGGACAGGGTCACCGTCAGAGATACGGTGTCTAACTCCTGCAACCCTACCTGTAATTATT

CCATATTATAAACATATACTATATAACTGTGGGTCTCTGCATGTTCTAGAATATGAATTCTATTTGATTGT

AAAACAAAACTATAAAAATAAGTAAAAAAATAAAAAATAAACAGATACTTAAAATCAAAAAAAAAAAAAAA

AAAAAAAAA
```

Reverse Complement of SEQ ID NO: 1

SEQ ID NO: 5

```
AATAAGGTATAGTGATACCTCATGTTAAAGTCAATGTGACTTAGTAGTCATCTCCATTTGTTTAAAGACAG

CGAACTTATTTTAATACAGTATTTAATTCTGCTTCATTAGGTTTCATAAATAAATCATATCAAACATTTAC

TCCAAATTATTTTGTAGCAAAATGAAGCATCAGTTTAAAAATTTGTATTACAGATTTTTACACATACTCTG

TGCTGACGATTTTTAGTTTTGAAATTAATACTACAACATTTAAGAACTGTACAATTACCAGTCCTCTGTAT

TTAGTCAAGTTTAGAGTTTTAACAAGAGTACTAGTTTTTTAAACTGGGAAAGTTGTGATATTAGCTCATAT

GATGCCTTTTAAAATAAAAGTCTCTAAATTTTTTATTTAGAAAAGTTATTTAATAAGTTCACCTATTGATT

ATAATCTAGATTGTGACCATCTAAAATTGATTCCCACATCACAAAATTTAAAACAAATAGTATTATAAGAA

TTTTGATTGAGAAATGTAAACGGTATTCTTTAAGGTTATGTGATTGTATGTTTAATCTTAAATAGACAGTG

ACTTTAAGATAAAAAAATCTATTTCTCAAGCTTTCTCTTAAGGATTTAATACCAGATTATTAGACCACAT

TAACTTGGAATGAGGTTAATGTTTAAATTATTGCCTTTTAAATTTGCCTCAGTTCATTCAAAGCTTTCTGA

ATCTGTTGGATGGATCAACATTTTGGTTGATTTTATAGAGTATAACCTTCCATTTTGAGACTTCCAAGATA

ATCCTCTTCTCCTCTCTGGCTTAGATTTTGCTCTTGGTTTGTTATATTTACCATTTAGGTTGTTTTCTCCA

CACTCATCATGCCACCACCAGCCTCCTGAATAACCCTCTGGACAGTTGAAGTGTCCTTTTGCTTTGTGATC

CCAAGTAGAAAACACCAAATCTTTGTTTTCCGGGATTGCATTGGGGACATTGCCAGTAATCGCAACTAGAT

GTAGCGTATAGTTGGTTTCGTGATTTCCCAAGTAAAAGAATATTCAATATAATGTTTGTTGTCTTTCCAG

TCTTCCAACTCAATTCGTAAAACATAATTAGATTGCTTCACTATGGAGTATATCTTCTCTAGGCCCAACCA

AAATTCTCCATCAAGCCTCCCAAAACCATATTTGTAGTTCTCCCACGTTTCATTGAAGTTTTGTGATCCAT

CTATTCGATGTTGAATTAATGTCCATGGACTACCTGATATAACATCACAGTAGACATGAAAAACTTGAGAG

TTGCTGGGTCTGATGGCATACATGCCACTTGTATGTTCACCTCTGTTATAAATGGTGGTACATTCAGCAGG

AATGCCATCATGTTTTACATTTCTTATTTCATTCAACTGAAGAAAGGGAGTAGTTCTTGGTGCTCTTGGCT

TGGAAGATAGAGAAATTTCTGTGGGTTCTTGAATACTAGTCCTTCTGAGCTGATTTTCTATTTCTTTTATT

TGACTATGCTGTTGGTTTAATTGTTTATATTGGTCTTCCACGGTCTGGAGAAGGTCTTTGATGCTATTATC

TTGTTTTTCTACAAAAGTTTTAAGTGAAGTTACTTCTGGGTGTTCTGGAGTTTCAGGTTGATTTGAATTA

AGTTAGTTAGTTGCTCTTCTAAATATTTCACTTTTTGTTGAAGTAGAATTTTTTCTTCTAGGAGGCTTTCA

AGTTTTGAGTTGAGTTCAAGTGACATATTCTTTACCTCTTCATTTTTGACTTGTAGTTTATATGTAGTTCT

TCTCAGTTCCTTTTCTTCTTCTTTGATTTCACTGGTTTGCAGCGATAGATCATAAAAAGACTGATCAAATA

TGTTGAGTTTTTGAAATATGTCATTAATTTGGCCCTTCGTCTTATGGACAAAGTCTTTAAGACCATGTCCC

AACTGAAGGAGGCCATTGGCTAAAATTTTTACATCGTCTAACATAGCAAATCTTGATTTTGGCTCTGGAGA
```

-continued

TAGAGAATCAAATGATGAATTGTCTTGATCAATTCTGGAGGAAATAACTAGAGGAACAATAAAAAGAAGGA

GCTTAATTGTGAACATTTTTATCTTGATTTTCAATTTCAAGCAACGTGGAACTGTTTTCTTCTGGAA

Reverse Complement of SEQ ID NO: 2

SEQ ID NO: 6
TAAGGTATAGTGATACCTCATATTAAAGTCAATGTGACTTAGTAATCATCATCTCCATTTGTTTAAAAGAC

AGCGAACCTATTTTAATACAGTATTTAATCCTGCTTCATTAGGTTTCATAAATAAATCCTATCAAAAATTT

ACTCCAGATTATTTTGTAGCAAAATGAGGCATCAGTTTAAAAATTTATATTACAGATTTTTACACATACTC

TGTGCTGACAATTTTTAGTTTTGAAATTAATATTACAACAAATTTAAGAACTGTATAATTATCAGTCCTCT

TTATTTAGTCAAGTTTAGAGTTTTAACAAGAAAACTAGTTTTTTAAACTGGGAAAATTGTGATATTAGCTC

ATATGATGACTTTTAAAATTAAAGTCTCTAAGTTTTTTATTTAGAAAAGTTATTTAGTAAGTTCACCTGTT

GATTATAATTTAGATTGCGACCATCTAAAATTGATTCCCACATCACAAAATATAAAACAAATAGTGTTGTA

GGAATTTTGATTGAGAAATGTAAATGGTATTCTTTAAGGTTATGTGATTGTATGTTTAATCTTAAATTGAC

AGTGACTTTAAGATAAAAAAATCTATTTCTCAAGCCTTCTCTTAAGGATTTAATACCAGATTATTAAACCA

CATTAACTTGGAATGAGTTTAATGTTTAATTTATTGCCTTTTAAATTTGCCTCAGTTCATTCAAAGCTTTC

TGAATCTGTTGGATGGATCAACATTTTGGTTGATTTTATAGAGTATAACCTTCCATTTTGAGACTTCCAGG

ATAATCCTCTTCTCCGCTCTGGCTTAGATTTTGTTCTTGGTTTGTTATATTTACCATTTAGGTTGTTTTCT

CCACACTCATCATGCCACCACCAGCCTCCTGAATAACTCTCTGGACAGCTGAAGTGTCCTTTTGCTTTGTG

ATCCCAAGTAGAAAACACCAAATCTTTGTTTTCCGGGATTGCATTGGGGACATTGCCAGTAATCTTAACTA

CATGTAGCGTATAGTTGGTTTCGTGATTTCCCAAGTAAAAAGAATATTCAATATAATGTTTGTTGTCTTTC

CAGTCTTCCAACTCAATTCGTAAAACGTAATTAGATTGCTTCACTATGGAGTATATCTTCTCTAGGCCCAA

CCAGAATTCTCCATCAAGCCTCCCGAAACCATATTTGTAGTTCTCCCACGTTTCATTGAAGTTTTGTGATC

CATCTATTCTCCTTAGACAGGTTTTACCTGATACAACATCACAGTAGACATGAAAAACTTGAGAGTTGCTG

GGTCTGATGGCATACATGCCACTTATATGTTCACCTCTATTGTAAATGGTGGTACAATCAGCAGGAATGCC

ATCATGTTTTACATTTCTTATTTCATTCAGCTGAAGAAAGGGAGTAGTTCTTGGTGCTCTTGGCTTGGAAG

ATAGAGAAATTTCTGTGGGTTCTTGAATATTAGTCATTCTGAGCTGATTTTCTATTTCTTTTATTTGACTG

TGCTGTTGGTTTAATTGCTTATATTGTTCTTCCACAGTCTGGAGAAGGTCTTTGATGCTATTATCTTGTTT

TTCTACAAAACTTTTAAGTGAAGTTACTTCTGGATGTTCTGGAGTTTCAGGTTGATTTTGAATTAAGTTAG

TTAGTTGCTCTTCTAAATATTTCACTTTTTGTTGAAGTAGAATTTTTTCTTCTAGGAGGCTTTCAAGTTTT

GAGTTGAGTTCAAGTGACATATTCTTTACCTCTTCATTTTTGACTTGTAGTTTATATGTAGTTCTTCTCAG

TTCCTTTTCTTCTTCTTTGATTTCACTGGTTTGCAGTGATAGATCATAAAAAGACTGATCAAATATGTTGA

GTTTTTGAAATATGTCATTAATTTGGCCCTTAGTCTTATGGACAAAGTCTTTAAGACCATGTCCCAACTGA

AGGAGGCCATTGGCTAAAATTTTTACATCGTCTAACATAGCAAATCTTGATTTTGGCTCTGGAGATACAGA

ATCAAATGATGAATTGTCTTGGTCAATTCTGGAGGAAATAACTAGAGGAACAATAAAAAGAAGGAGCTTAA

TTGTGAACATTTTTATCCTGATTTTCAATTTCAAGCAACGTGGAACTGTGTTCTTCTGGAAGCAGACCTAG

ACTTCTTAACTCTATATAT

Reverse Complement of SEQ ID NO: 3

SEQ ID NO: 7
CAGGAGGGAGAAGTTCCAAATTGCTTAAAATTGAATAATTGAGACAAAAAATGCACACAATTAAATTATTC

CTTTTTGTTGTTCCTTTAGTAATTGCATCCAGAGTGGATCCAGACCTTTCATCATTTGATTCTGCACCTTC

AGAGCCAAAATCAAGATTTGCTATGTTGGATGATGTCAAAATTTTAGCGAATGGCCTCCTGCAGCTGGGTC

ATGGACTTAAAGATTTTGTCCATAAGACTAAGGGACAAATTAACGACATATTTCAGAAGCTCAACATATTT

GATCAGTCTTTTTATGACCTATCACTTCGAACCAATGAAATCAAAGAAGAGGAAAAGGAGCTAAGAAGAAC

-continued

```
TACATCTACACTACAAGTTAAAAACGAGGAGGTGAAGAACATGTCAGTAGAACTGAACTCAAAGCTTGAGA

GTCTGCTGGAAGAGAAGACAGCCCTTCAACACAAGGTCAGGGCTTTGGAGGAGCAGCTAACCAACTTAATT

CTAAGCCCAGCTGGGGCTCAGGAGCACCCAGAAGTAACATCACTCAAAAGTTTTGTAGAACAGCAAGACAA

CAGCATAAGAGAACTCCTCCAGAGTGTGGAAGAACAGTATAAACAATTAAGTCAACAGCACATGCAGATAA

AAGAAATAGAAAAGCAGCTCAGAAAGACTGGTATTCAAGAACCCTCAGAAAATTCTCTTTCTTCTAAATCA

AGAGCACCAAGAACTACTCCCCCTCTTCAACTGAACGAAACAGAAAATACAGAACAAGATGACCTTCCTGC

CGACTGCTCTGCCGTTTATAACAGAGGCGAACATACAAGTGGCGTGTACACTATTAAACCAAGAAACTCCC

AAGGGTTTAATGTCTACTGTGATACCCAATCAGGCAGTCCATGGACATTAATTCAACACCGGAAAGATGGC

TCACAGGACTTCAACGAAACATGGGAAAACTACGAAAAGGGCTTTGGGAGGCTCGATGGAGAATTTTGGTT

GGGCCTAGAGAAGATCTATGCTATAGTCCAACAGTCTAACTACATTTTACGACTCGAGCTACAAGACTGGA

AAGACAGCAAGCACTACGTTGAATACTCCTTTCACCTGGGCAGTCACGAAACCAACTACACGCTACATGTG

GCTGAGATTGCTGGCAATATCCCTGGGGCCCTCCCAGAGCACACAGACCTGATGTTTTCTACATGGAATCA

CAGAGCAAAGGGACAGCTCTACTGTCCAGAAAGTTACTCAGGTGGCTGGTGGTGGAATGACATATGTGGAG

AAAACAACCTAAATGGAAAATACAACAAACCCAGAACCAAATCCAGACCAGAGAGAAGAAGAGGGATCTAC

TGGAGACCTCAGAGCAGAAAGCTCTATGCTATCAAATCATCCAAAATGATGCTCCAGCCCACCACCTAAGA

AGCTTCAACTGAACTGAGACAAAATAAAAGATCAATAAATTAAATATTAAAGTCCTCCCGATCACTGTAGT

AATCTGGTATTAAAATTTTAATGGAAAGCTTGAGAATTGAATTTCAATTAGGTTTAAACTCATTGTTAAGA

TCAGATATCACCGAATCAACGTAAACAAAATTTATC
```

Reverse Complement of SEQ ID NO: 4

SEQ ID NO: 8

```
TTTTTTTTTTTTTTTTTTTTTTTTGATTTTAAGTATCTGTTTATTTTTATTTTTTACTTATTTTTATA

GTTTTGTTTTACAATCAAATAGAATTCATATTCTAGAACATGCAGAGACCCACAGTTATATAGTATATGTT

TATAATATGGAATAATTACAGGTAGGGTTGCAGGAGTTAGACACCGTATCTCTGACGGTGACCCTGTCCCT

TCTAACTCTCGCTCTGTGTTCCTATCACTTTCTTTGTGCTGCTGGGGATCAGTCCCAGTGTCCTGCTGGCC

GCGTGTTCCACCACAACTGTGCCTCCAGCCCATTTCACCTGTGTTACGTTGTGCTTAGGATATCACTGAAA

GAGCTCTATACTGCTATCTTTGCAGCTCATTTGTAGCATGGCCCCTCACTAGAGCCAATGGCGTATACTAT

GTTCCTTAATAAGACTTATGATAACCATGAACTATAGAATTAAGTTTCAACAAGCATACTGCAGGCATGCA

GTAGTGATAAGTACAATGAGATCATTGCAGTTGCTATCATGGATAATATTTACCAATCAGTTTTATGAAGA

CTGGGGTCTGCTTTTGCTTATTGTTACATTTCCACAGCCCATTTTATAATTGCTGCTTAATTTATAATTCT

TAATGTCGAGAAGGAGTATCAATGTGTGGCCCAGACTGGTCTTGAACTTTCAATTCACCTGCTGCTCCTCC

TCCCCCCTTGCCCAAAAGCGCTATGGTCTCAGGCCTGTGTCAACACACCCAACTAATACTATTAAATCAAC

AGATAAGTGAGTGATGCAAGGAAATCACTTTACCATCAAGCCTCCCAAAACCCTTTTCGTAGTTTTCCCAC

GTTTGGTTGAAGTTTTGAGAGCCATCTTTCCGGTGTTGAATTAATGTCCGTGGAGTGCCTGATTGGGTGTC

ACAGTAGACATTAAACACTTGAGAGCTGCTTGGTCTAATAGTATACACGCCACTTGTATGTTCACCTCTGT

TATAAATGGCAGAGCAGTCAGCAGGCAGATCATCTTGTTCTATATTTTTGCTTCCTTCAGATGAAGAGGG

GGAGTAGTTCTTGGTGCTCTTGGTTTAGAATAAAGAGAATTTTCAGTGGGTTCTTGAATGCCAGTCTTTCT

GAGCTGATTTTCTATTTCTTTTATCTGAATGTGCTGTTGACTTAGTTGTTTATATTGTTCTTCCACACTCT

GGAGGAGTTCTCTTATGCTGTTATCTTGCTGTTCTACAAAACTTTTAAGTGACGTTACCTCTGGGTGCTCC

CGAGCCCCAGGCGGGTTCTGAACCAAGCTGGTCAGCTGTTCCTCCAAAGCCCTGACTCTGTGTTGGAGCGC

CATCTTCTCCTCCAGTAGACTTTCAAGCTTTGAGTTCAGTTCAAGTGACATATTCTTCACCTCTTCGTTTT

TAACTTGTAGTTTAGATGTGGTTCTTCTTAGCTCCTTTTCCTCTTCTTTGATTTCATTGGTTTGAAGTGAT

AGGTCATAAAAACACTGATCAAATATGTTGAGCTTCTGAAATATGTCATTAATTTGTCCCTTTGTCTTATG
```

```
GACAAAATCTTTAAGACCATGACCCAGCTGCAGGAGGCCATTGGCTAAAATTTTGACATCATCCAACATAG

CAAATCTTGATTTTGGCTCTGACGGTACAGAATCAAATGGCGAAAGGTCTGGATCAACTCTGGACGAAATT

ACTAGAGGAACAACAAAAAGGAGCAGCTTAATTGTGTGCATTTTTGTTTCAATTATTCAATTTCAAGCAAT

TTGGAACGTC
```

Macaca fascicularis angiopoietin-like 3 (Angptl3), mRNA
SEQ ID NO: 9

```
GGGTAGTATATAGAGTTAAGAAGTCTAGGTCTGCTTCCAGAAGAACACAGTTCCACGCTGCTTGAAATTGA

AAATCAGGATAAAAATGTTCACAATTAAGCTCCTTCTTTTTATTGTTCCTCTAGTTATTTCCTCCAGAATT

GACCAAGACAATTCATCATTTGATTCTGTATCTCCAGAGCCAAAATCAAGATTTGCTATGTTAGACGATGT

AAAAATTTTAGCCAATGGCCTCCTTCAGTTGGGACATGGTCTTAAAGACTTTGTCCATAAGACTAAGGGCC

AAATTAATGACATATTTCAAAAACTCAACATATTTGATCAGTCTTTTTATGATCTATCACTGCAAACCAGT

GAAATCAAAGAAGAAGAAAAGGAACTGAGAAGAACTACATATAAACTACAAGTCAAAAATGAAGAGGTAAA

GAATATGTCACTTGAACTCAACTCAAAACTTGAAAGCCTCCTAGAAGAAAAAATTCTACTTCAACAAAAAG

TGAAATATTTAGAAGAGCAACTAACTAACTTAATTCAAAATCAACCTGCAACTCCAGAACATCCAGAAGTA

ACTTCACTTAAAAGTTTTGTAGAAAAACAAGATAATAGCATCAAAGACCTTCTCCAGACTGTGGAAGAACA

ATATAAGCAATTAAACCAACAGCATAGTCAAATAAAAGAAATAGAAAATCAGCTCAGAATGACTAATATTC

AAGAACCCACAGAAATTTCTCTATCTTCCAAGCCAAGAGCACCAAGAACTACTCCCTTTCTTCAGCTGAAT

GAAATAAGAAATGTAAAACATGATGGCATTCCTGCTGATTGTACCACCATTTACAATAGAGGTGAACATAT

AAGTGGCACGTATGCCATCAGACCCAGCAACTCTCAAGTTTTTCATGTCTACTGTGATGTTGTATCAGGTA

GTCCATGGACATTAATTCAACATCGAATAGATGGATCACAAAACTTCAATGAAACGTGGGAGAACTACAAA

TATGGTTTCGGGAGGCTTGATGGAGAATTCTGGTTGGGCCTAGAGAAGATATACTCCATAGTGAAGCAATC

TAATTACGTTTTACGAATTGAGTTGGAAGACTGGAAAGACAACAAACATTATATTGAATATTCTTTTTACT

TGGGAAATCACGAAACCAACTATACGCTACATGTAGTTAAGATTACTGGCAATGTCCCCAATGCAATCCCG

GAAAACAAAGATTTGGTGTTTTCTACTTGGGATCACAAAGCAAAAGGACACTTCAGCTGTCCAGAGAGTTA

TTCAGGAGGCTGGTGGTGGCATGATGAGTGTGGAGAAAACAACCTAAATGGTAAATATAACAAACCAAGAA

CAAAATCTAAGCCAGAGCGGAGAAGAGGATTATCCTGGAAGTCTCAAAATGGAAGGTTATACTCTATAAAA

TCAACCAAAATGTTGATCCATCCAACAGATTCAGAAAGCTTTGAATGAACTGAGGCAAATTTAAAAGGCAA

TAAATTAAACATTAAACTCATTCCAAGTTAATGTGGTTTAATAATCTGGTATTAAATCCTTAAGAGAAGGC

TTGAGAAATAGATTTTTTTATCTTAAAGTCACTGTCAATTTAAGATTAAACATACAATCACATAACCTTAA

AGAATACCATTTACATTTCTCAATCAAAATTCTTACAACACTATTTGTTTTATATTTTGTGATGTGGGAAT

CAATTTTAGATGGTCGCAATCTAAATTATAATCAACAGGTGAACTTACTAAATAACTTTTCTAAATAAAAA

ACTTAGAGACTTTAATTTTAAAAGTCATCATATGAGCTAATGTCACAATTTTCCCAGTTTAAAAAACTAGT

TTTCTTGTTAAAACTCTAAACTTGACTAAATAAAGAGGACTGATAATTATACAGTTCTTAAATTTGTTGTA

ATATTAATTTCAAAACTAAAAATTGTCAGCACAGAGTATGTGTAAAAATCTGTAATATAAATTTTTAAACT

GATGCCTCATTTTGCTACAAAATAATCTGGAGTAAATTTTTGATAGGATTTATTTATGAAACCTAATGAAG

CAGGATTAAATACTGTATTAAAATAGGTTCGCTGTCTTTTAAACAAATGGAGATGATGATTACTAAGTCAC

ATTGACTTTAATATGAGGTATCACTATACCTTAACATATTTGTTAAAACGTATACTGTATACATTTTGTGT
```

We claim:

1. A double-stranded ribonucleic acid (dsRNA) agent for inhibiting expression of Angiopoietin-like 3 (ANGPTL3),
   wherein said dsRNA agent comprises a sense strand and an antisense strand forming a double stranded region,
   wherein said antisense strand comprises at least 15 contiguous nucleotides differing by no more than 3 nucleotides from the nucleotide sequence of the complement of nucleotides 881-943 of SEQ ID NO: 1.

2. The dsRNA agent of claim 1, wherein said dsRNA agent comprises at least one modified nucleotide.

3. The dsRNA agent of claim 2, wherein the at least one of said modified nucleotides is selected from the group consisting of a 2'-O-methyl modified nucleotide, a 2'-fluoro modified nucleotide, a 2'-deoxythymidine (dT) nucleotide, a nucleotide comprising a 5'-phosphorothioate group, and a terminal nucleotide linked to a cholesteryl derivative or a dodecanoic acid bisdecylamide group.

4. The dsRNA agent of claim 1, wherein each strand is no more than 30 nucleotides in length.

5. The dsRNA agent of claim 1, wherein at least one strand comprises a 3' overhang of at least 1 nucleotide.

6. The dsRNA agent of claim 1, further comprising a ligand.

7. A cell containing the dsRNA agent of claim 1.

8. A pharmaceutical composition for inhibiting expression of an ANGPTL3 gene comprising the dsRNA agent of claim 1.

9. A method of inhibiting ANGPTL3 expression in a cell, the method comprising:
   (a) contacting the cell with the dsRNA agent of claim 1 or a pharmaceutical composition of claim 8; and
   (b) maintaining the cell produced in step (a) for a time sufficient to obtain degradation of the mRNA transcript of an ANGPTL3 gene, thereby inhibiting expression of the ANGPTL3 gene in the cell.

10. The method of claim 9, wherein said cell is within a subject.

11. A method of treating a subject having a disorder that would benefit from reduction in ANGPTL3 expression, comprising administering to the subject a therapeutically effective amount of the dsRNA agent of claim 1 or a pharmaceutical composition of claim 8, thereby treating said subject.

12. The method of claim 11, wherein the disorder is a disorder of lipid metabolism.

13. A method of inhibiting the expression of ANGPTL3 in a subject, the method comprising administering to said subject a therapeutically effective amount of the dsRNA agent of claim 1 or a pharmaceutical composition of claim 8, thereby inhibiting the expression of ANGPTL3 in said subject.

14. A double-stranded ribonucleic acid (dsRNA) agent for inhibiting expression of Angiopoietin-like 3 (ANGPTL3),
    wherein said dsRNA agent comprises a sense strand and an antisense strand forming a double stranded region,
    wherein said antisense strand comprises at least 16 contiguous nucleotides differing by no more than 3 nucleotides from the nucleotide sequence of the complement of nucleotides 881-943 of SEQ ID NO: 1.

15. A double-stranded ribonucleic acid (dsRNA) agent for inhibiting expression of Angiopoietin-like 3 (ANGPTL3),
    wherein said dsRNA agent comprises a sense strand and an antisense strand forming a double stranded region,
    wherein said antisense strand comprises at least 17 contiguous nucleotides differing by no more than 3 nucleotides from the nucleotide sequence of the complement of nucleotides 881-943 of SEQ ID NO: 1.

16. The dsRNA agent of claim 1, wherein each strand is independently 17-25 nucleotides in length.

17. The dsRNA agent of claim 1, wherein each strand is independently 19-25 nucleotides in length.

18. The dsRNA agent of claim 1, wherein each strand is independently 19-23 nucleotides in length.

19. The dsRNA agent of claim 1, wherein the sense strand is 21 nucleotides in length and the antisense strand is 23 nucleotides in length.

20. The dsRNA agent of claim 1, wherein the sense strand is 19 nucleotides in length and the antisense strand is 19 nucleotides in length.

21. The dsRNA agent of claim 1, wherein at least one strand comprises a 3' overhang of at least 2 nucleotides.

22. The dsRNA agent of claim 1, wherein the antisense strand comprises a nucleotide sequence selected from the group consisting of

```
5'-AAUUAAUGUCCAUGGACUACCUG-3';  (SEQ ID NO: 1317)
5'-UUAAUGUCCAUGGACUACCUGAU-3';  (SEQ ID NO: 1311)
5'-AUCCAUCUAUUCGAUGUUGAAUU-3';  (SEQ ID NO: 1312)
5'-AUCUAUUCGAUGUUGAAUUAAUG-3';  (SEQ ID NO: 1306)
5'-UAUUCGAUGUUGAAUUAAUGUCC-3';  (SEQ ID NO: 1300)
5'-AUUCGAUGUUGAAUUAAUGUCCA-3';  (SEQ ID NO: 1294)
5'-UUGAAUUAAUGUCCAUGGACUAC-3';  (SEQ ID NO: 1277)
5'-UUCGAUGUUGAAUUAAUGUCCAU-3';  (SEQ ID NO: 1288)
5'-UAAUGUCCAUGGACUACCUGAUA-3';  (SEQ ID NO: 1305)
5'-UUUGUGAUCCAUCUAUUCGAUGU-3';  (SEQ ID NO: 1318)
5'-UUUCAUUGAAGUUUUGUGAUCCA-3';  (SEQ ID NO: 1289)
5'-UUCAUUGAAGUUUUGUGAUCCAU-3';  (SEQ ID NO: 1283)
5'-AUUGAAGUUUUGUGAUCCAUCUA-3';  (SEQ ID NO: 1278)
5'-AUCCAUCUAUUCGAUGUUG-3';      (SEQ ID NO: 136)
5'-UUGAAUUAAUGUCCAUGGA-3';      (SEQ ID NO: 124)
5'-UGUUGAAUUAAUGUCCAUG-3';      (SEQ ID NO: 118)
5'-UCGAUGUUGAAUUAAUGUC-3';      (SEQ ID NO: 95)
5'-AUUCGAUGUUGAAUUAAUG-3';      (SEQ ID NO: 89)
5'-UGAAUUAAUGUCCAUGGAC-3';      (SEQ ID NO: 84) and
5'-UUUGUGAUCCAUCUAUUCG-3';      (SEQ ID NO: 121).
```

23. The dsRNA agent of claim 1, wherein the sense and antisense strands comprise nucleotide sequences selected from the group consisting of

```
5'-GGUAGUCCAUGGACAUUAAUU-3'    (SEQ ID NO: 1136) and
5'-AAUUAAUGUCCAUGGACUACCUG-3'; (SEQ ID NO: 1317)
5'-CAGGUAGUCCAUGGACAUUAA-3'    (SEQ ID NO: 1130) and
5'-UUAAUGUCCAUGGACUACCUGAU-3'; (SEQ ID NO: 1311)
5'-UUCAACAUCGAAUAGAUGGAU-3'    (SEQ ID NO: 1131) and
5'-AUCCAUCUAUUCGAUGUUGAAUU-3'; (SEQ ID NO: 1312)
5'-UUAAUUCAACAUCGAAUAGAU-3'    (SEQ ID NO: 1125) and
5'-AUCUAUUCGAUGUUGAAUUAAUG-3'; (SEQ ID NO: 1306)
5'-ACAUUAAUUCAACAUCGAAUA-3'    (SEQ ID NO: 1119) and
5'-UAUUCGAUGUUGAAUUAAUGUCC-3'; (SEQ ID NO: 1300)
5'-GACAUUAAUUCAACAUCGAAU-3'    (SEQ ID NO: 1116) and
5'-AUUCGAUGUUGAAUUAAUGUCCA-3'; (SEQ ID NO: 1294)
5'-AGUCCAUGGACAUUAAUUCAA-3'    (SEQ ID NO: 1096) and
5'-UUGAAUUAAUGUCCAUGGACUAC-3'; (SEQ ID NO: 1277)
5'-GGACAUUAAUUCAACAUCGAA-3'    (SEQ ID NO: 1107) and
5'-UUCGAUGUUGAAUUAAUGUCCAU-3'; (SEQ ID NO: 1288)
5'-UCAGGUAGUCCAUGGACAUUA-3'    (SEQ ID NO: 1124) and
5'-UAAUGUCCAUGGACUACCUGAUA-3'; (SEQ ID NO: 1305)
5'-AUCGAAUAGAUGGAUCACAAA-3'    (SEQ ID NO: 1137) and
5'-UUUGUGAUCCAUCUAUUCGAUGU-3'; (SEQ ID NO: 1318)
5'-GAUCACAAAACUUCAAUGAAA-3'    (SEQ ID NO: 1108) and
5'-UUUCAUUGAAGUUUUGUGAUCCA-3'; (SEQ ID NO: 1289)
5'-GGAUCACAAAACUUCAAUGAA-3'    (SEQ ID NO: 1102) and
5'-UUCAUUGAAGUUUUGUGAUCCAU-3'; (SEQ ID NO: 1283)
5'-GAUGGAUCACAAAACUUCAAU-3'    (SEQ ID NO: 1097) and
5'-AUUGAAGUUUUGUGAUCCAUCUA-3'; (SEQ ID NO: 1278)
5'-CAACAUCGAAUAGAUGGAU-3'      (SEQ ID NO: 74) and
5'-AUCCAUCUAUUCGAUGUUG-3';     (SEQ ID NO: 136)
5'-UCCAUGGACAUUAAUUCAA-3'      (SEQ ID NO: 62) and
5'-UUGAAUUAAUGUCCAUGGA-3';     (SEQ ID NO: 124)
5'-CAUGGACAUUAAUUCAACA-3'      (SEQ ID NO: 56) and
5'-UGUUGAAUUAAUGUCCAUG-3';     (SEQ ID NO: 118)
5'-GACAUUAAUUCAACAUCGA-3'      (SEQ ID NO: 33) and
5'-UCGAUGUUGAAUUAAUGUC-3';     (SEQ ID NO: 95)
5'-CAUUAAUUCAACAUCGAAU-3'      (SEQ ID NO: 27) and
5'-AUUCGAUGUUGAAUUAAUG-3';     (SEQ ID NO: 89)
5'-GUCCAUGGACAUUAAUUCA-3'      (SEQ ID NO: 22) and
5'-UGAAUUAAUGUCCAUGGAC-3';     (SEQ ID NO: 84) and
5'-CGAAUAGAUGGAUCACAAA-3'      (SEQ ID NO: 59) and
5'-UUUGUGAUCCAUCUAUUCG-3';     (SEQ ID NO: 121).
```

24. The dsRNA agent of claim 6, wherein the ligand is one or more GalNAc derivatives attached through a bivalent or trivalent branched linker.

25. The dsRNA agent of claim 24, wherein the ligand is
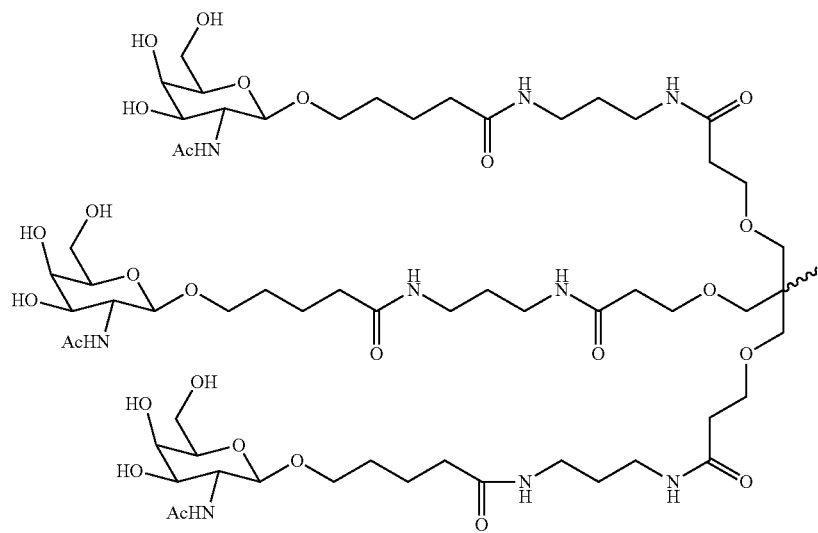
26. The dsRNA agent of claim 1, wherein said dsRNA agent further comprises at least one phosphorothioate or methylphosphonate internucleotide linkage.
* * * * *